(12) United States Patent
Woodley et al.

(10) Patent No.: US 10,702,209 B2
(45) Date of Patent: Jul. 7, 2020

(54) GRAPHICAL USER INTERFACE FOR LASER EYE SURGERY SYSTEM

(71) Applicant: AMO Development, LLC, Santa Ana, CA (US)

(72) Inventors: Bruce Woodley, Sunnyvale, CA (US); Javier Gonzalez, Sunnyvale, CA (US); Katrina Bell Sheehy, Sunnyvale, CA (US); Daniel Oliveira Santos, San Francisco, CA (US); Darrel Q. Pham, San Jose, CA (US); Paul Daniel Gallagher, Menlo Park, CA (US); Lawrence Edward Miller, Scotts Valley, CA (US)

(73) Assignee: AMO Development, LLC, Santa Ana, CA (US)

( * ) Notice: Subject to any disclaimer, the term of this patent is extended or adjusted under 35 U.S.C. 154(b) by 1640 days.

(21) Appl. No.: 14/062,448

(22) Filed: Oct. 24, 2013

(65) Prior Publication Data
US 2014/0114297 A1 Apr. 24, 2014

Related U.S. Application Data

(60) Provisional application No. 61/718,156, filed on Oct. 24, 2012, provisional application No. 61/722,037, filed on Nov. 2, 2012.

(51) Int. Cl.
*A61N 5/06* (2006.01)
*A61B 5/00* (2006.01)
(Continued)

(52) U.S. Cl.
CPC .......... *A61B 5/4836* (2013.01); *A61B 3/0008* (2013.01); *A61B 3/102* (2013.01); *A61B 5/748* (2013.01); *A61B 5/7425* (2013.01); *A61B 34/25* (2016.02); *A61F 9/008* (2013.01); *A61F 9/009* (2013.01); *A61F 9/00736* (2013.01); *A61F 9/00754* (2013.01); *A61B 3/1005* (2013.01);
(Continued)

(58) Field of Classification Search
CPC ..... A61B 5/4836; A61B 34/25; A61B 3/0008; A61B 5/7425; A61B 5/748; A61B 3/1005; A61B 2034/107; A61B 2034/258; A61B 2090/3735; A61F 9/00736; A61F 9/00754; A61F 9/008
USPC .......................................................... 606/6
See application file for complete search history.

(56) References Cited

U.S. PATENT DOCUMENTS 5,098,426 A * 3/1992 Sklar .................. A61F 9/008
219/121.6
5,459,570 A 10/1995 Swanson et al.
(Continued)

*Primary Examiner* — Aaron F Roane
(74) *Attorney, Agent, or Firm* — Johnson & Johnson Surgical Vision, Inc.

(57) ABSTRACT

Methods and systems for planning and forming incisions in a cornea, lens capsule, and/or crystalline lens nucleus are disclosed. A method includes measuring spatial dispositions, relative to a laser surgery system, of at least portions of the corneal anterior and posterior surfaces. A spatial disposition of an incision of the cornea is generated based at least in part on the measured corneal anterior and posterior spatial dispositions and at least one corneal incision parameter. A composite image is displayed that includes an image representative of the measured corneal anterior and posterior surfaces and an image representing the corneal incision.

11 Claims, 90 Drawing Sheets

(51) Int. Cl.
  *A61B 3/00* (2006.01)
  *A61B 3/10* (2006.01)
  *A61F 9/009* (2006.01)
  *A61F 9/008* (2006.01)
  *A61F 9/007* (2006.01)
  *A61B 34/00* (2016.01)
  *A61B 90/00* (2016.01)
  *A61B 34/10* (2016.01)

(52) U.S. Cl.
  CPC ... *A61B 2034/107* (2016.02); *A61B 2034/258* (2016.02); *A61B 2090/3735* (2016.02)

(56) References Cited

U.S. PATENT DOCUMENTS

| | | |
|---|---|---|
| 5,720,894 A | 2/1998 | Neev et al. |
| 5,748,352 A | 5/1998 | Hattori |
| 5,748,898 A | 5/1998 | Ueda |
| 5,957,915 A | 9/1999 | Trost |
| 5,984,916 A | 11/1999 | Lai |
| 6,019,472 A | 2/2000 | Koester et al. |
| 6,053,613 A | 4/2000 | Wei et al. |
| 6,111,645 A | 8/2000 | Tearney et al. |
| 6,454,761 B1 | 9/2002 | Freedman |
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 2003/0223037 A1* | 12/2003 | Chernyak ............ A61B 3/1015 351/209 |
| 2007/0219543 A1* | 9/2007 | Yee ..................... A61F 9/00829 606/5 |
| 2011/0319873 A1 | 12/2011 | Raksi et al. |
| 2011/0319875 A1 | 12/2011 | Loesel et al. |

\* cited by examiner

FIG. 63

(PLEASE INDICATE THE RED SHADED AREA USING CROSSHATCHING)

GRAPHICAL USER INTERFACE FOR LASER EYE SURGERY SYSTEM

CROSS REFERENCE TO RELATED APPLICATIONS

This application claims the benefit of priority to U.S. Provisional Application No. 61/718,156, filed Oct. 24, 2012 and U.S. Provisional Application No. 61/722,037, filed Nov. 2, 2012.

BACKGROUND

Cataract extraction is one of the most commonly performed surgical procedures in the world. A cataract is formed by opacification of the crystalline lens or its envelope—the lens capsule—of the eye. The cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). Presently, an estimated 15 million cataract surgeries per year are performed worldwide. The cataract treatment market is composed of various segments including intraocular lenses for implantation, viscoelastic polymers to facilitate surgical procedures, and disposable instrumentation including ultrasonic phacoemulsification tips, tubing, various knives, and forceps.

Presently, cataract surgery is typically performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small (often round) hole is formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye. Typically, the IOL is held in place by the edges of the anterior capsule and the capsular bag. The IOL may also be held by the posterior capsule, either alone or in unison with the anterior capsule. This latter configuration is known in the field as a "Bag-in-Lens" implant.

One of the most technically challenging and critical steps in the cataract extraction procedure is providing access to the lens nucleus. The manual continuous curvilinear capsulorhexis (CCC) procedure evolved from an earlier technique termed can-opener capsulotomy in which a sharp needle was used to perforate the anterior lens capsule in a circular fashion followed by the removal of a circular fragment of lens capsule typically in the range of 5-8 mm in diameter. The smaller the capsulotomy, the more difficult it is to produce manually. The capsulotomy provides access for the next step of nuclear sculpting by phacoemulsification. Due to a variety of complications associated with the initial can-opener technique, attempts were made by leading experts in the field to develop a better technique for removal of the circular fragment of the anterior lens capsule prior to the emulsification step.

The desired outcome of the manual continuous curvilinear capsulorhexis is to provide a smooth continuous circular opening through which not only the phacoemulsification of the nucleus can be performed safely and easily, but also to provide for easy insertion of the intraocular lens. The resulting opening in the anterior lens capsule provides access for tool insertion during removal of the nucleus and for IOL insertion, a permanent aperture for transmission of the image to the retina of the patient, and also support of the IOL inside the remaining lens capsule that limits the potential for dislocation. The resulting reliance on the shape, symmetry, uniformity, and strength of the remaining lens capsule to contain, constrain, position, and maintain the IOL in the patient's eye limits the placement accuracy of the IOL, both initially and over time. Subsequently, a patient's refractive outcome and resultant visual acuity are less deterministic and intrinsically sub-optimal due to the IOL placement uncertainty. This is especially true for astigmatism correcting ("toric") and accommodating ("presbyopic") IOLs.

Problems may also develop related to inability of the surgeon to adequately visualize the lens capsule due to lack of red reflex, to grasp the lens capsule with sufficient security, and to tear a smooth circular opening in the lens capsule of the appropriate size and in the correct location without creating radial rips and extensions. Also present are technical difficulties related to maintenance of the depth of the anterior chamber depth after opening the lens capsule, small pupils, or the absence of a red reflex due to the lens opacity. Some of the problems with visualization can be minimized through the use of dyes such as methylene blue or indocyanine green. Additional complications may also arise in patients with weak zonules (typically older patients) and very young children that have very soft and elastic lens capsules, which are very difficult to controllably and reliably rupture and tear.

The implantation of a "Bag-in-Lens" IOL typically uses anterior and posterior openings in the lens capsule of the same size. Manually creating matching anterior and posterior capsulotomies for the "Bag-in-Lens" configuration, however, is particularly difficult.

Many cataract patients have astigmatic visual errors. Astigmatism can occur when the corneal curvature is unequal in all directions. An IOL can be used to correct for astigmatism but require precise rotational and central placement. Additionally, IOLs are not typically used for correction beyond 5D of astigmatism. Many patients, however, have astigmatic visual errors exceeding 5D. Higher correction beyond 5D typically requires reshaping the cornea to make it more spherical. There are numerous existing approaches for reshaping the cornea, including Corneaplasty, Astigmatic Keratotomy, Corneal Relaxing Incision (CRI), and Limbal Relaxing Incision (LRI). In Astigmatic Keratotomy, Corneal Relaxing Incision (CRI), and Limbal Relaxing Incision (LRI), corneal incisions are made in a well-defined manner and depth to allow the cornea to change shape to become more spherical. Presently, these corneal incisions are typically accomplished manually often with limited precision.

Thus, improved methods and systems for treating cataracts and/or creating corneal incisions are needed.

SUMMARY

Methods and systems related to laser eye surgery use a laser to form precise incisions in the cornea (e.g., one or more cataract access incisions and/or one or more arcuate incisions), in the lens capsule, and/or in the crystalline lens nucleus. Control of the laser eye surgery can include treatment planning prior to coupling a patient's eye to a laser surgery system, coupling of the patient's eye to the laser surgery system, imaging of the patient's eye to measure the spatial dispositions of the cornea and lens relative to the laser eye surgery system, treatment planning using the measured spatial dispositions of the cornea and lens, and control the laser to automatically form the planned incisions in the patient's eye in an accurate fashion relative to the measured structures of the patient's eye. In many embodiments, the laser eye surgery system includes graphical user interface (GUI) to facilitate user control of the treatment planning, patient coupling, and the treatment procedure.

In many embodiments, the laser eye surgery system automatically generates surface and curved line models corresponding to the anterior surface of the cornea, the posterior surface of the cornea, the anterior portion of the lens capsule, the posterior portion of the lens capsule, the iris, the pupil, and the limbus. The laser eye surgery system can display composite images that include representations of the measured eye structures and representations of the generated surface and/or curved line models for user verification of the accuracy of the automatically generated surface and/or curved line models. In many embodiments, the operator of the laser eye surgery system can selectively modify the generated surface and/or curved models if desired, for example, to better match the measured eye structure.

Thus, in one aspect, a method is provided for planning a laser surgery procedure on an eye having a cornea, a pupil, and a lens. The cornea has an anterior surface and a posterior surface. The lens is disposed within a lens capsule having an anterior portion and a posterior portion. The method includes coupling the eye to a laser surgery system operable to measure a spatial disposition of an internal structure of the eye relative to the laser surgery system. A spatial disposition of at least a portion of the corneal anterior surface is measured by using the laser surgery system. A spatial disposition of at least a portion of the corneal posterior surface is measured by using the laser surgery system. A spatial disposition of an incision of the cornea is generated based at least in part on the measured corneal anterior and posterior spatial dispositions and at least one corneal incision parameter. And a composite image is displayed that includes an image representative of the measured corneal anterior and posterior surfaces and an image representing the corneal incision.

Variations of the method for planning a laser surgery procedure can be performed. For example, the at least one corneal incision parameter can include a corneal incision line density parameter to control amount of overlap between adjacent lines of laser pulse focus points that will be used to form the corneal incision. The corneal incision can extend partially through the cornea so as to leave an uncut region of the cornea aligned with one or more cut portions of the corneal incision, the corneal incision and the uncut region of the cornea defining an access path for a cataract surgery instrument. The method can include altering the at least one corneal incision parameter in response to user input; generating a spatial disposition of an altered incision of the cornea based at least in part on the measured corneal anterior and posterior spatial dispositions and the altered corneal incision parameter; and displaying a second composite image that includes an image representative of the measured corneal anterior and posterior surfaces and an image representing the altered corneal incision. The method can include measuring a spatial disposition of at least a portion of the anterior portion of the lens capsule by using the laser surgery system; generating a spatial disposition of a capsulotomy incision of the anterior portion of the lens capsule based at least in part on the measured spatial disposition of the anterior portion of the lens capsule and at least one capsulotomy parameter; and displaying a third composite image that includes an image representative of the measured anterior portion of the lens capsule and an image representing the capsulotomy incision. The at least one capsulotomy parameter can include a capsulotomy line density parameter to control amount of overlap between adjacent lines of laser pulse focus points that will be used to form the capsulotomy incision. The method can include altering the at least one capsulotomy parameter in response to user input; generating a spatial disposition of an altered capsulotomy incision of the anterior portion of the lens capsule based at least in part on the measured corneal anterior and posterior spatial dispositions and the altered capsulotomy parameter; and displaying a fourth composite image that includes an image representative of the measured anterior portion of the lens capsule and an image representing the altered capsulotomy incision. The method can include measuring a spatial disposition of at least a portion of the posterior portion of the lens capsule by using the laser surgery system; generating a spatial disposition of a lens fragmentation incision pattern of the lens based at least in part on the measured spatial dispositions of the anterior and posterior portions of the lens capsule and at least one lens fragmentation parameter; and displaying a fifth composite image that includes an image representative of the measured anterior and posterior portions of the lens capsule and an image representing the lens fragmentation incision pattern. The at least one lens fragmentation parameter can include a lens fragmentation line density parameter to control amount of overlap between adjacent lines of laser pulse focus points that will be used to form the lens fragmentation incision pattern. The method can include altering the at least one lens fragmentation parameter in response to user input; generating a spatial disposition of an altered lens fragmentation incision pattern of the lens based at least in part on the measured spatial dispositions of the anterior and posterior portions of the lens capsule and the altered at least one lens fragmentation parameter; and displaying a sixth composite image that includes an image representative of the measured anterior and posterior portions of the lens capsule and an image representing the altered lens fragmentation incision pattern. The method can include generating a spatial disposition of a safety volume within the lens, the incision pattern not overlapping the safety volume, the safety volume separating the lens fragmentation incision pattern from the anterior and posterior portions of the lens capsule and separating the lens fragmentation pattern transverse to the pupil such that a maximum transverse width of the lens fragmentation pattern is less than a diameter of the pupil; and displaying a safety volume image that includes a representation of the safety volume. The method can include, prior to the coupling of the eye to the laser surgery system, displaying a seventh composite image that includes an image representative of the eye and at least one of an image representing an incision of the cornea corresponding to the at least one corneal incision parameter, an image representing an incision of the anterior portion of the lens capsule corresponding to the at least one capsulotomy parameter, or an image representing a lens fragmentation incision pattern corresponding to the at least one lens fragmentation parameter. The method can include, prior to the coupling of the eye to the laser surgery system, generating a spatial disposition of a safety volume within the lens, the incision pattern not overlapping the safety volume, the safety volume separating the lens fragmentation incision pattern from the anterior and posterior portions of the lens capsule and separating the lens fragmentation pattern transverse to the pupil such that a maximum transverse width of the lens fragmentation pattern is less than a diameter of the pupil; and displaying a safety volume image that includes a representation of the safety volume.

In another aspect, a method is provided for planning a laser surgery procedure of an eye having a cornea and a lens capsule. The method includes coupling the eye to a laser surgery system operable to measure spatial dispositions of, relative to the laser surgery system, the cornea and the lens capsule; generating and displaying a first cross-sectional image of the eye based at least in part on measured spatial dispositions of the cornea and lens capsule, the first cross-sectional image including at least one of a cross section of the cornea and a cross section of a central portion of the lens capsule; receiving user input designating a plurality of points in the first cross-sectional image corresponding to points on a boundary surface of the cornea or the lens capsule; generating and displaying a second cross-sectional image of the eye based at least in part on the measured spatial dispositions of the cornea and lens capsule, the second cross-sectional image being transverse to the first cross-sectional image and including at least one of a cross section of the cornea and a cross section of a central portion of the lens capsule; receiving user input designating a plurality of points in the second cross-sectional image corresponding to points on the boundary surface; generating a surface model of the boundary surface based on the user designated points; and generating a spatial disposition of an incision of the cornea or the lens capsule based at least in part on the surface model and at least one incision parameter.

In another aspect, a system is provided for planning and performing a laser surgery procedure on an eye having a cornea, a pupil, a limbus, and a lens. The cornea has an anterior surface and a posterior surface. The lens is disposed within a lens capsule having an anterior portion and a posterior portion. The system includes a laser source configured to produce a treatment beam that includes a plurality of laser pulses; an integrated optical system that includes an imaging assembly operatively coupled to a treatment laser delivery assembly for the treatment beam such that the imaging assembly and the treatment laser delivery system share at least one common optical element, the integrated optical system being configured to locate at least a portion of the corneal anterior surface and at least a portion of the corneal posterior surface; a patient interface configured to couple the eye with the integrated optical system so as to constrain the position of the eye relative to the integrated optical system; a display device; and a controller operatively coupled with the display device, the laser source, and the integrated optical system. The controller is configured to generate, relative to the integrated optical system, a spatial disposition of the corneal anterior surface and a spatial disposition of the corneal posterior surface by using the integrated optical system to locate at least portions of the corneal anterior and posterior surfaces; generate a spatial disposition of an incision of the cornea using the generated spatial dispositions of the corneal anterior and posterior surfaces and at least one corneal incision parameter; and display a composite image on the display device, the composite image including an image representative of the generated spatial dispositions of the corneal anterior and posterior surfaces and an image representing the corneal incision.

Variations of the system for planning and performing a laser surgery procedure on an eye are possible. For example, the at least one corneal incision parameter can include a corneal incision line density parameter to control amount of overlap between adjacent lines of laser pulse focus points that will be used to form the corneal incision. The corneal incision can extend partially through the cornea so as to leave an uncut region of the cornea aligned with one or more cut portions of the corneal incision, the corneal incision and the uncut region of the cornea defining an access path for a cataract surgery instrument. The system can include a user input device. The controller can be configured to alter the at least one corneal incision parameter in response to user input via the user input device; generate a spatial disposition of an altered incision of the cornea using the generated corneal anterior and posterior spatial dispositions and the altered corneal incision parameter; and display a second composite image on the display device, the second composite image including an image representative of the generated spatial dispositions of the corneal anterior and posterior surfaces and an image representing the altered corneal incision. The integrated optical system can be configured to locate at least a portion of the anterior portion of the lens capsule. The controller can be configured to generate a spatial disposition of at least a portion of the anterior portion of the lens capsule by using the integrated optical system to locate at least a portion of the anterior portion of the lens capsule; generate a spatial disposition of a capsulotomy incision of the anterior portion of the lens capsule using the generated spatial disposition of the anterior portion of the lens capsule and at least one capsulotomy parameter; and display a third composite image on the display device, the third composite image including an image representative of the generated spatial disposition of the anterior portion of the lens capsule and an image representing the capsulotomy incision. The at least one capsulotomy parameter can include a capsulotomy line density parameter to control amount of overlap between adjacent lines of laser pulse focus points that will be used to form the capsulotomy incision. The controller can be configured to alter the at least one capsulotomy parameter in response to user input via the user input device; generate a spatial disposition of an altered capsulotomy incision of the anterior portion of the lens capsule using the generated anterior lens capsule spatial disposition and the altered capsulotomy parameter; and display a fourth composite image on the display device, the fourth composite image including an image representative of the generated spatial disposition of the anterior portion of the lens capsule and an image representing the altered capsulotomy incision. The integrated optical system can be configured to locate at least a portion of the posterior portion of the lens capsule. The controller can be configured to generate a spatial disposition of at least a portion of the posterior portion of the lens capsule by using the integrated optical system to locate at least the portion of the posterior portion of the lens capsule; generate a spatial disposition of a lens fragmentation incision pattern of the lens using the generated spatial disposition of the posterior portion of the lens capsule and at least one lens fragmentation parameter; and display a fifth composite image on the display device, the fifth composite image including an image representative of the generated spatial dispositions of the anterior and posterior portions of the lens capsule and an image representing the lens fragmentation incision pattern. The at least one lens fragmentation parameter can include a lens fragmentation line density parameter to control amount of overlap between adjacent lines of laser pulse focus points that will be used to form the lens fragmentation incision pattern. The controller can be configured to alter the at least one lens fragmentation parameter in response to user input via the user input device; generate a spatial disposition of an altered lens fragmentation incision pattern using the generated spatial dispositions of the anterior and posterior portions of the lens capsule and the altered at least one lens fragmentation parameter; and display a sixth composite image on the display device, the sixth composite image including an image representative of the generated spatial dispositions of the corneal anterior and posterior surfaces and an image representing the altered lens fragmentation incision pattern. The controller being further configured to generate a spatial disposition of a safety volume within the lens, the incision pattern not overlapping the safety volume, the safety volume separating the lens fragmentation incision pattern from the anterior and posterior portions of the lens capsule and separating the lens fragmentation pattern transverse to the pupil such that a maximum transverse width of the lens fragmentation pattern is less than a diameter of the pupil; and display a safety volume image that includes a representation of the safety volume. The controller can be configured to, prior to coupling the eye to the integrated optical system, generate a spatial disposition of a safety volume within the lens, the incision pattern not overlapping the safety volume, the safety volume separating the lens fragmentation incision pattern from the anterior and posterior portions of the lens capsule and separating the lens fragmentation pattern transverse to the pupil such that a maximum transverse width of the lens fragmentation pattern is less than a diameter of the pupil; and display a safety volume image that includes a representation of the safety volume.

In another aspect, a system is provided for planning and performing a laser surgery procedure on an eye having a cornea, a pupil, and a lens. The cornea has an anterior surface and a posterior surface. The lens is disposed within a lens capsule having an anterior portion and a posterior portion. The system includes a laser source configured to produce a treatment beam that includes a plurality of laser pulses; an integrated optical system that includes an imaging assembly operatively coupled to a treatment laser delivery assembly for the treatment beam such that the imaging assembly and the treatment laser delivery system share at least one common optical element, the integrated optical system being configured to locate at least a portion of the corneal anterior surface and at least a portion of the corneal posterior surface; a patient interface configured to couple the eye with the integrated optical system so as to constrain the position of the eye relative to the integrated optical system; a display device; and a controller operatively coupled with the display device, the laser source, and the integrated optical system. The controller is configured to generate and display a first cross-sectional image of the eye based at least in part on spatial dispositions of the cornea and lens capsule measured by the integrated optics system, the first cross-sectional image including at least one of a cross section of the cornea and a cross section of a central portion of the lens capsule; receive user input designating a plurality of points in the first cross-sectional image corresponding to points on a boundary surface of the cornea or the lens capsule; generate and display a second cross-sectional image of the eye based at least in part on the measured spatial dispositions of the cornea and lens capsule, the second cross-sectional image being transverse to the first cross-sectional image and including at least one of a cross section of the cornea and a cross section of a central portion of the lens capsule; receive user input designating a plurality of points in the second cross-sectional image corresponding to points on the boundary surface; generate a surface model of the boundary surface based at least in part on the user designated points; and generate a spatial disposition of an incision of the cornea or the lens capsule based at least in part on the surface model and at least one incision parameter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
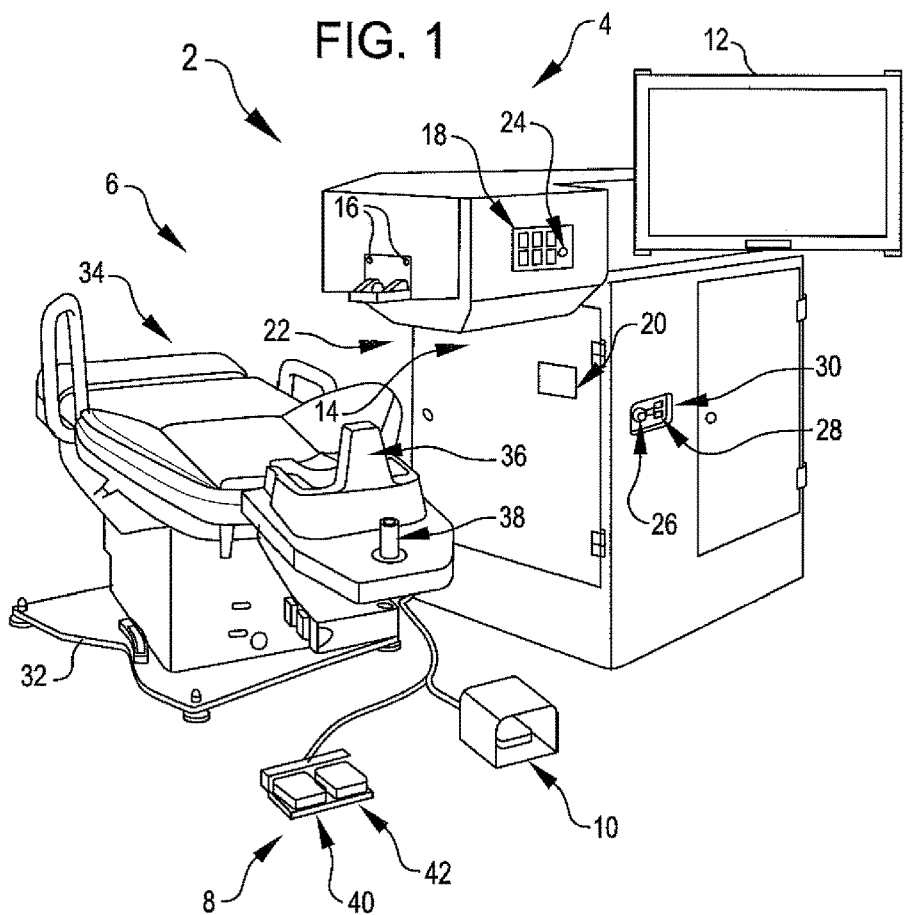
FIG. 1 is a perspective view showing a laser eye surgery system, in accordance with many embodiments.

Methods and systems related to laser eye surgery are disclosed. A laser is used to form precise incisions in the cornea, in the lens capsule, and/or in the crystalline lens nucleus. Control of the laser eye surgery can include treatment planning prior to coupling a patient's eye to a laser surgery system, coupling of the patient's eye to the laser surgery system, imaging of the patient's eye including the cornea and lens, treatment planning after the patient's eye has been coupled to the laser surgery system, and forming precise incisions in the cornea, in the lens capsule, and/or in the crystalline lens nucleus. In many embodiments, the laser eye surgery system includes graphical user interface (GUI) to facilitate user control of the treatment planning, patient coupling, and the treatment procedure.

Prior to coupling the patient's eye to the laser eye surgery system, the GUI can be used to plan one or more cataract incisions (both primary and secondary) in the cornea, one or more arcuate incisions in the cornea, a capsulotomy incision in the anterior portion of the lens capsule, and/or lens fragmentation incisions in the crystalline lens nucleus. Any desired combination of cataract incision(s), arcuate incision(s), capsulotomy incision, and lens fragmentation incisions can be selected and planned. In many embodiments, the GUI displays planning screens that display a composite image that includes an image of a model representation of an eye and an image representing the planned incision(s). For each type of incision (i.e., cataract incision(s), arcuate incision(s), capsulotomy incision, and lens fragmentation incisions), the GUI can display an anterior view of the composite image and/or a cross-sectional view of the composite image. The composite images are shown on planning screens on which associated incision parameters (e.g., length, depth, location, etc. . . . ) are displayed and through which a user can selectively modify the associated incision parameters. The composite images provide the user with visual feedback regarding the configuration of the incisions selected such that the user can adjust the associated incision parameters until desired incision configurations are achieved.

In many embodiments, the GUI displays docking screens that guide the user through docking a patient's eye to the laser eye surgery system. Such guidance can include guidance to install/replace a disposable lens, guidance to couple a suction ring to the patient's eye, guidance to add fluid to the suction ring and maneuver a patient chair to position the suction ring to be coupled with the laser eye surgery system, guidance to maneuver the patient chair to minimize forces exerted on the patient's eye and to position the patients eye correctly, and guidance to verify the patient interface has fluid present with no bubbles.

In many embodiments, the laser eye surgery system scans the patient's eye to measure the spatial disposition, relative to the laser eye surgery system, of structures of the patient's eye, including the anterior and posterior surfaces of the cornea, anterior and posterior portions of the lens capsule, the iris, and the limbus. The laser eye surgery system can automatically generate surface models corresponding to the anterior surface of the cornea, the posterior surface of the cornea, the anterior portion of the lens capsule, the posterior portion of the lens capsule, and the iris. The laser eye surgery system can also automatically generate curved line models corresponding to the limbus and the pupil. In many embodiments, the GUI displays composite images that include representations of the measured structures of the patient's eye and representations corresponding to the automatically generated surface models and/or curved line models. In many embodiments, the GUI provides the ability for the user to selectively modify the generated surface models and/or the curved line models. In many embodiments, the planned incisions are based on the surface models and curved line models, either as automatically generated or user modified.

System Configuration

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
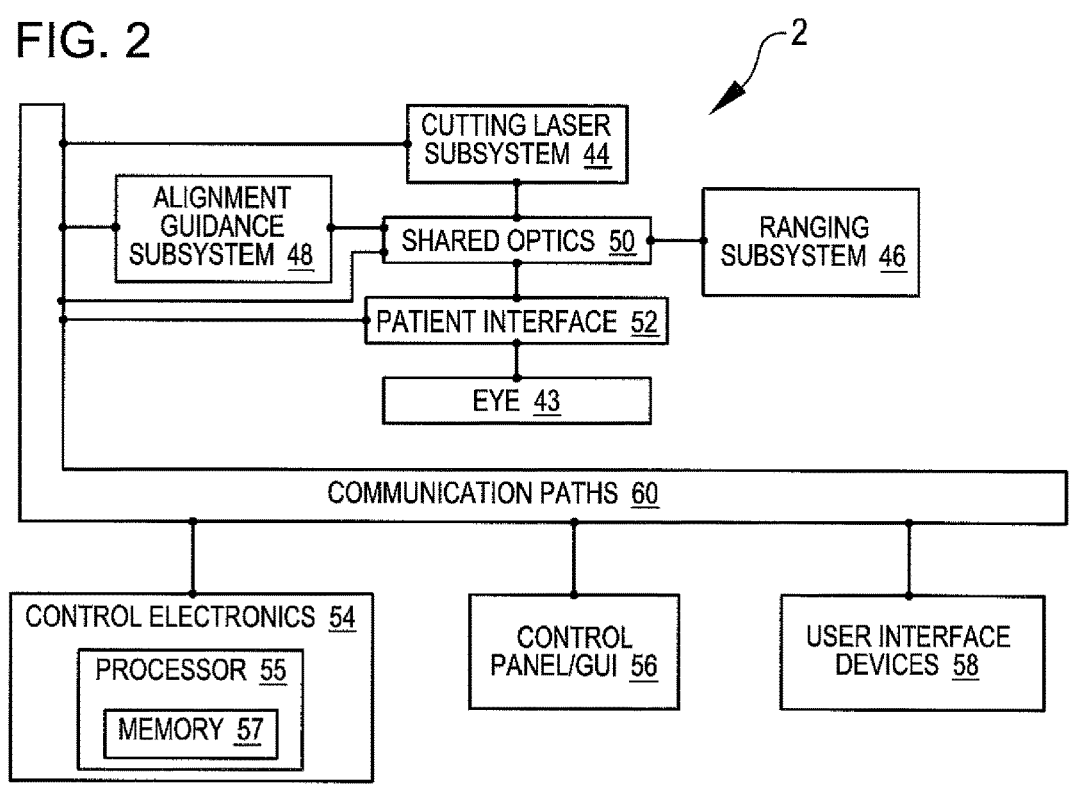
FIG. 2 is a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface and the patient's cornea and forms part of a transmission path between the shared optics 50 and the patient's eye 43. The optically transmissive structure may comprise a lens 96 having one or more curved surfaces. Alternatively, the patient interface 52 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The control electronics 54 may comprise a processor/controller 55 (referred to herein as a processor) that is used to perform calculations related to system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3:
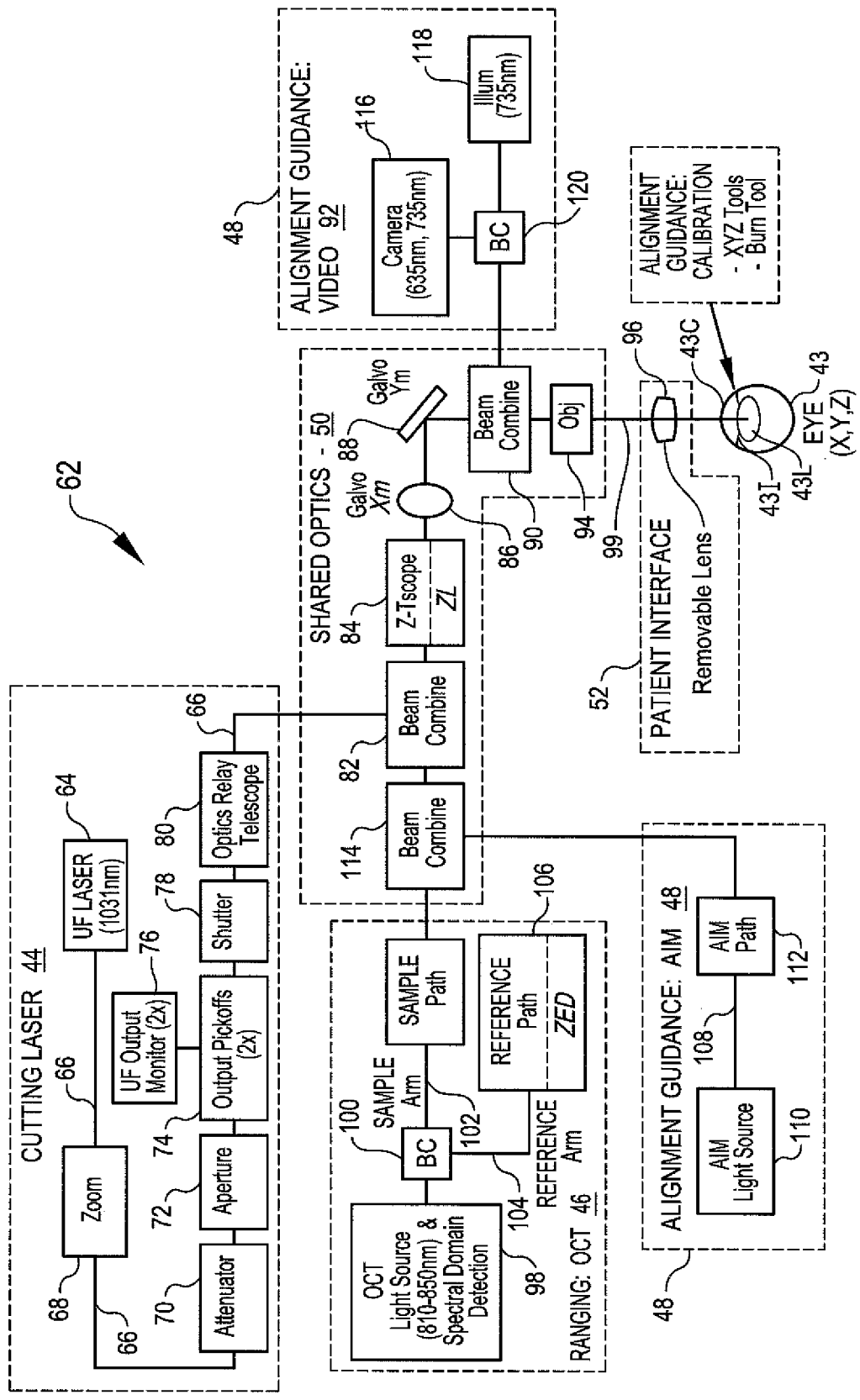
FIG. 3 is a simplified block diagram illustrating the configuration of an optical assembly of a laser eye surgery system, in accordance with many embodiments.

FIG. 3 is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as a Z-scan device for scanning the focus point of the laser-pulse beam 66 in the patient's eye 43. The Z-telescope 84 can be controlled automatically and dynamically by the control electronics 54 and selected to be independent or to interplay with the X- and Y-scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-scan device 86 and the Y-scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials placed on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others. Additionally the ranging subsystem such as an OCT can be used to detect features or aspects involved with the patient interface. Features can include fiducials placed on the docking structures and optical structures of the disposable lens such as the location of the anterior and posterior surfaces.

The ranging subsystem 46 in FIG. 3 includes an OCT light source and detection device 98. The OCT light source and detection device 98 includes a light source that generates and emits an OCT source beam with a suitable broad spectrum. For example, in many embodiments, the OCT light source and detection device 98 generates and emits the OCT source beam with a broad spectrum from 810 nm to 850 nm wavelength. The generated and emitted light is coupled to the device 98 by a single mode fiber optic connection.

The OCT source beam emitted from the OCT light source and detection device 98 is passed through a pickoff/combiner assembly 100, which divides the OCT source beam into a sample beam 102 and a reference portion 104. A significant portion of the sample beam 102 is transmitted through the shared optics 50. A relative small portion of the sample beam is reflected from the patient interface 52 and/or the patient's eye 43 and travels back through the shared optics 50, back through the pickoff/combiner assembly 100 and into the OCT light source and detection device 98. The reference portion 104 is transmitted along a reference path 106 having an adjustable path length. The reference path 106 is configured to receive the reference portion 104 from the pickoff/combiner assembly 100, propagate the reference portion 104 over an adjustable path length, and then return the reference portion 106 back to the pickoff/combiner assembly 100, which then directs the returned reference portion 104 back to the OCT light source and detection device 98. The OCT light source and detection device 98 then directs the returning small portion of the sample beam 102 and the returning reference portion 104 into a detection assembly, which employs a time domain detection technique, a frequency detection technique, or a single point detection technique. For example, a frequency domain technique can be used with an OCT wavelength of 830 nm and bandwidth of 100 nm.

Once combined with the UF laser pulse beam 66 subsequent to the beam combiner 82, the OCT sample beam 102 follows a shared path with the UF laser pulse beam 66 through the shared optics 50 and the patient interface 52. In this way, the OCT sample beam 102 is generally indicative of the location of the UF laser pulse beam 66. Similar to the UF laser beam, the OCT sample beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the pickoff/combiner assembly 100, and back into the OCT light source and detection device 98. The returning back reflections of the sample beam 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for an axially stationary surface in the eye of patient interface volume because the optical path length does not change as a function of different settings of the Z-telescope 84. The ranging subsystem 46 has an inherent Z range that is related to the light source and detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path via a stage ZED 106 within ranging subsystem 46. Passing the OCT sample beam 102 through the Z-telescope 84, while not impacting the sample path length, allows for optimization of the OCT signal strength. This is accomplished by focusing the OCT sample beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample beam 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber, and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim beam path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-field configuration such that the illumination sources are directed to the independent surfaces outside the capture numerical aperture of the image portion of the video system. Alternatively the illumination may also be in a bright field configuration. In both the dark and bright field configurations, the illumination light source maybe be used as a fixation beam for the patient. The illumination may also be used to illuminate the patients pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 52. The illumination light reflected and scattered off of various structures of the eye 43 and patient interface travel back through the patient interface 52, back through the objective lens assembly 94, and back to the beam combiner 90. At the beam combiner 90, the returning light is directed back to the beam combiner 120 where the returning light is redirected toward the camera 116. The beam combiner can be a cube, plate, or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be any suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

System Functionality Overview

The laser eye surgery system 2 is an integrated scanning laser system that can be used by cataract surgeons to create a precise anterior capsulotomy and/or subsequent lens fragmentation of the crystalline lens, with or without single plane and multi-plane arc cuts/incisions in the cornea. Treatment is accomplished through the use of ultrafast ($\tau \sim 10^{-13}$ s, or hundreds of femtoseconds [FS]) infrared laser pulses. The ranging subsystem 46 provides a three-dimensional image of the anterior segment of the eye and guides laser treatment. The shared optics 50 is used for both the ranging subsystem 46 and the cutting laser subsystem 44 to provide inherent co-registration of the two optical subsystems.

Each FS laser pulse creates a highly localized plasma and subsequent cavitation event that disrupts only microns of tissue per pulse. In many embodiments, treatment of the eye 43 consists of applying user-defined laser patterns to the crystalline lens, lens capsule, and cornea of the eye to create incisions by applying FS laser pulses, guided by data generated by the ranging subsystem 46.

Treatment planning can be used to verify incision patterns prior to treatment. For example, intended treatment patterns can be presented to the physician overlaid on cross-sectional images of the anterior segment (generated by using the ranging subsystem 46) for review/modification before initiation of treatment of the eye 43.

The laser eye surgery system 2 is configured such that it can be used by a single operator. A graphical user interface (GUI) allows for pretreatment planning prior to coupling the patient's eye 43 to the patient interface 52. The laser eye surgery system can be used in any suitable type/location of treatment, for example, for in-patient or out-patient treatments performed in a hospital or in an Ambulatory Surgery Center (ASC).

User Interface

Figure 4:
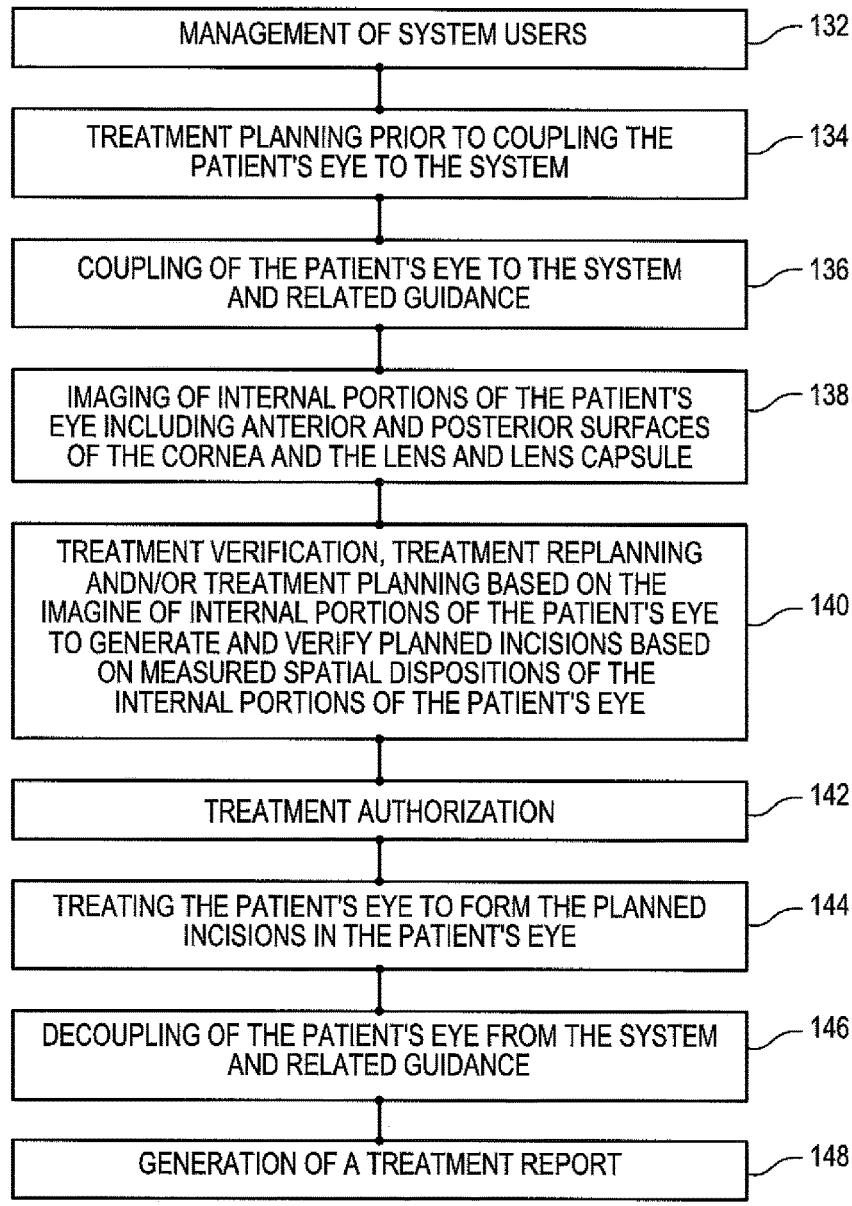
FIG. 4 is a simplified block diagram of functionality provided by a laser eye surgery system, in accordance with many embodiments.

FIG. 4 is a simplified chart illustrating top-level functionality of the laser eye surgery system 2 that is accessible to a user through the GUI. In many embodiments, the laser eye surgery system 2 is configured to enable management of system users (132); treatment planning prior to coupling the patient's eye to the system (134); coupling of the patient's eye to the system and related guidance (136); imaging of internal portions of the patient's eye including anterior and posterior surfaces of the cornea and the lens and lens capsule (138); treatment verification, treatment replanning, and/or treatment planning based on the imaging of internal portions of the patient's eye to generate and verify planned incisions based on measured spatial dispositions of the internal portions of the patient's eye (140); treatment authorization (142); treating the patient's eye to form the planned incisions in the patient's eye (144); decoupling of the patient's eye from the system and related guidance (146); and generation of a treatment report (148).

Figure 5:
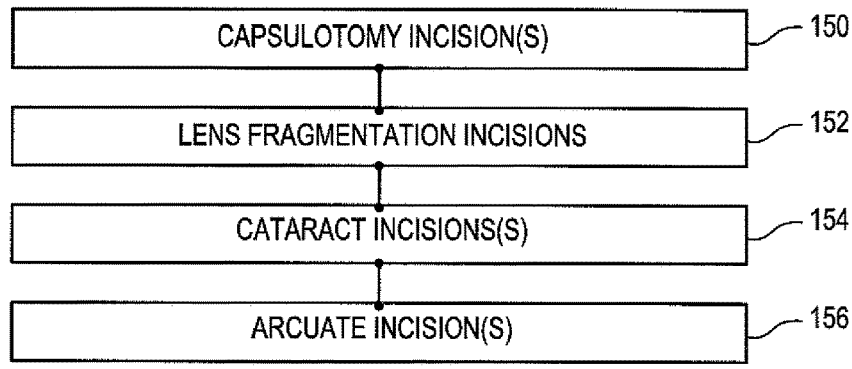
FIG. 5 is a simplified block diagram showing types of incisions that can be planned and formed by a laser eye surgery system, in accordance with many embodiments.

FIG. 5 is a top-level chart showing types of incisions that can be planned and formed by the laser eye surgery system 2. The incisions that can be planned and formed by the laser eye surgery system 2 include capsulotomy incisions (150), lens fragmentation incisions (152), cataract incisions (154), and arcuate incisions (156). A capsulotomy incision (150) is often formed in the anterior portion of the lens capsule so as to provide access to a cataractous lens nucleus for removal of the cataractous lens nucleus. The laser eye surgery system 2 is operable to form a smooth circular opening in the anterior portion of the lens capsule. The lens fragmentation incisions (152) are formed in the cataractous lens nucleus so as to fragment the lens into small portions to aid in the removal of the lens nucleus. The cataract incisions (154) are formed in the cornea to provide access for surgical tools used to remove the fragmented lens nucleus and through which an IOL can be passed for implantation to provide optical function compensating for the absence of the lens nucleus. The cataract incisions (154) are made in the cornea to provide access through the cornea for surgical instruments used during cataract replacement surgery. The cataract incision (154) can include primary incisions, which are typically large enough that an IOL can be inserted through the primary incision as well as surgical instruments used during cataract replacement surgery, and secondary (or "sideport") incisions, that are smaller than the primary incisions and through which surgical instruments used during cataract replacement surgery can be inserted. The arcuate incisions (156) are made in the cornea and used to reshape the cornea, thereby modifying the optical properties of the cornea.

The graphical user interface (GUI) is displayed on the touch-screen control panel 12 and features different types of control screens including administrative screens, planning screens, a surgical timeout screen, docking screens, treatment screens, and undocking screens. The GUI and the touch-screen control panel 12 enables the user to press a respective portion of the touch-screen control panel 12 to either navigate within the GUI or initiate the entry of data for the parameter listed at the selected portion of the touch-screen control panel 12.

The administrative screens can be used by a system administrator to manage system users and allow users to log into, log out of, and shut down the system. The planning screens can be used by users to create and edit treatment templates; to create, edit, and initiate treatment plans; to enable/disable the system; and to enable/disable the laser. The surgical timeout screen can be used to verify patient details and treatment parameters before proceeding to the docking screens. The docking screens guide a user through the process of positioning the suction ring, applying vacuum, and capturing the suction ring. The treatment screens allow a user to internally image the eye 43 using the ranging subsystem 46, to verify and customize treatment parameters prior to laser treatment, and to initiate and monitor laser treatment. The undocking screens guide a user through the process of releasing the patient, removing a disposable portion of the patient interface 52, and reviewing the treatment report.

All planning screens and most treatment screens have a Quick Navigation bar at the bottom of the screen that allows a user to easily navigate between screens. Refer to the following table 1 for a description of the icons in the Quick Navigation bar.

TABLE 1

Quick Navigation bar icons.

| Icon | Press to go to . . . |
|---|---|
|  | Plan a Treatment Screen |
|  | Capsulotomy (Basic) or Details Screen |
|  | Lens Fragmentation Basic or Details Screen |
|  | Arcuate Incisions (Basic) or Details Screen |
|  | Cataract Incisions (Basic) or Details Screen |
|  | Treatment Summary or Final Review Screen |
|  | Arcuate/Cataract Incisions Adjustment Screen |
|  | Lens Group Adjustment Screen |
|  | Scanning Summary Screen |
|  | Arcuate/Cataract Incisions Review Screen |

In addition to the icons in the Quick Navigation bar, there are two icons that provide treatment-related information. Refer to the following table 2 for a description of the informational icons.

TABLE 2

Information icons.

| Icon | Description |
|---|---|
|  | The compass icon represents the orientation of the selected eye: I = Inferior; S = Superior; T = Temporal; N = Nasal; A = Anterior; and P = Posterior. |
|  | The colored ring provides a visual indication of the forces exerted on the patient interface 52 by the eye 43. The ring is green when the forces exerted on the patient interface are within a range acceptable for locking the suction ring/disposable lens assembly to the system. The ring is yellow when the forces exerted on the patient interface rise to a level of concern. The ring is orange when the forces exerted on the patient interface rise to a level that will stop scanning of the eye 43 by the ranging subsystem 46 or a laser treatment. The ring is red when the forces exerted on the patient interface rise to an unacceptable level. In many embodiments, the system is configured to undock the patient after a suitable time period (e.g., three seconds) if the ring is red during the docking process. Likewise, the system can be configured to undock the patient after a suitable time period (e.g., immediately, 1 second) if the ring is red during laser treatment. |

Figure 6:
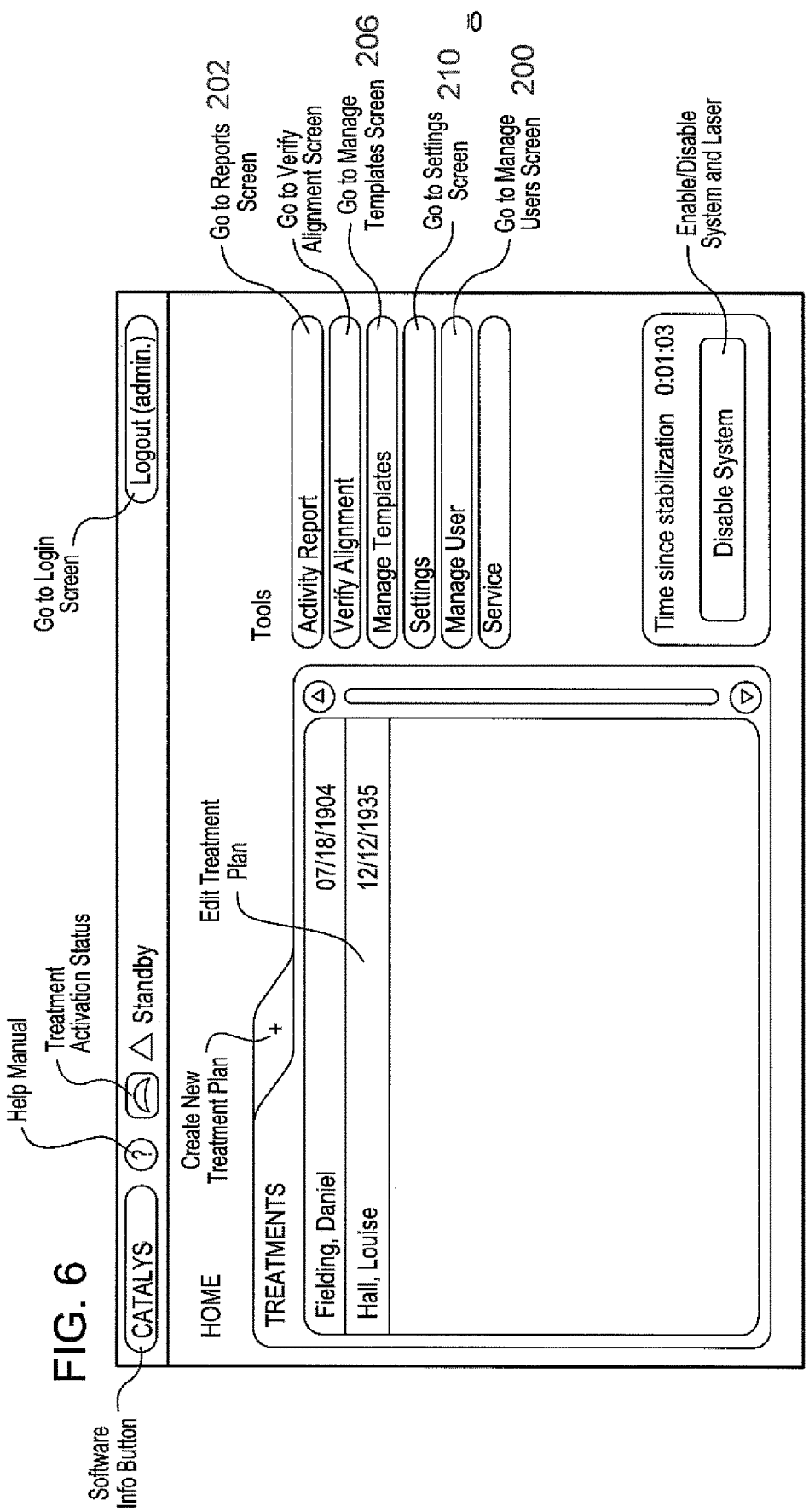
FIGS. 6 through 85 show example screens of graphical user interface (GUI) of a laser eye surgery system, in accordance with many embodiments.
Figure 8:
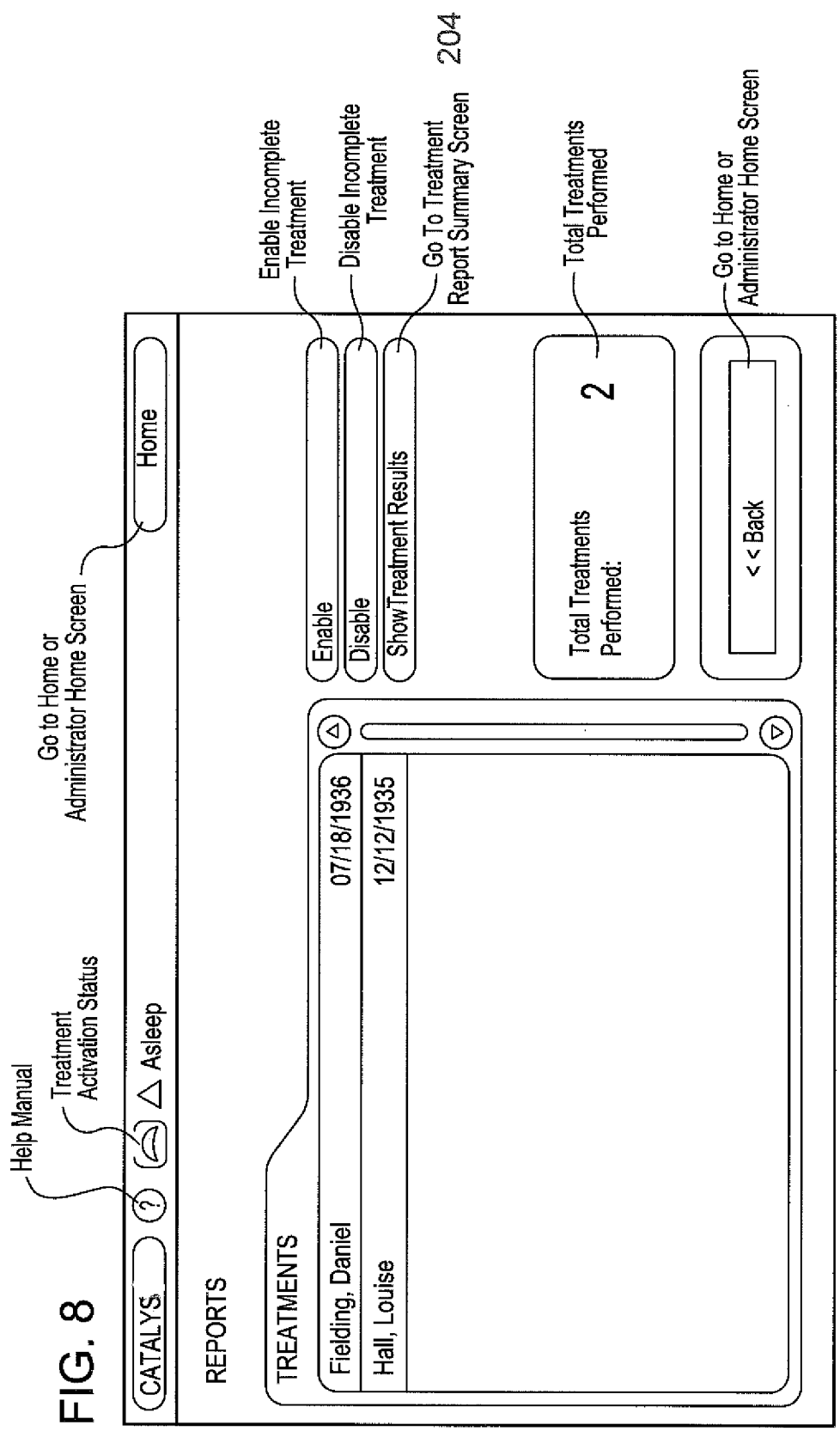
Figure 9:
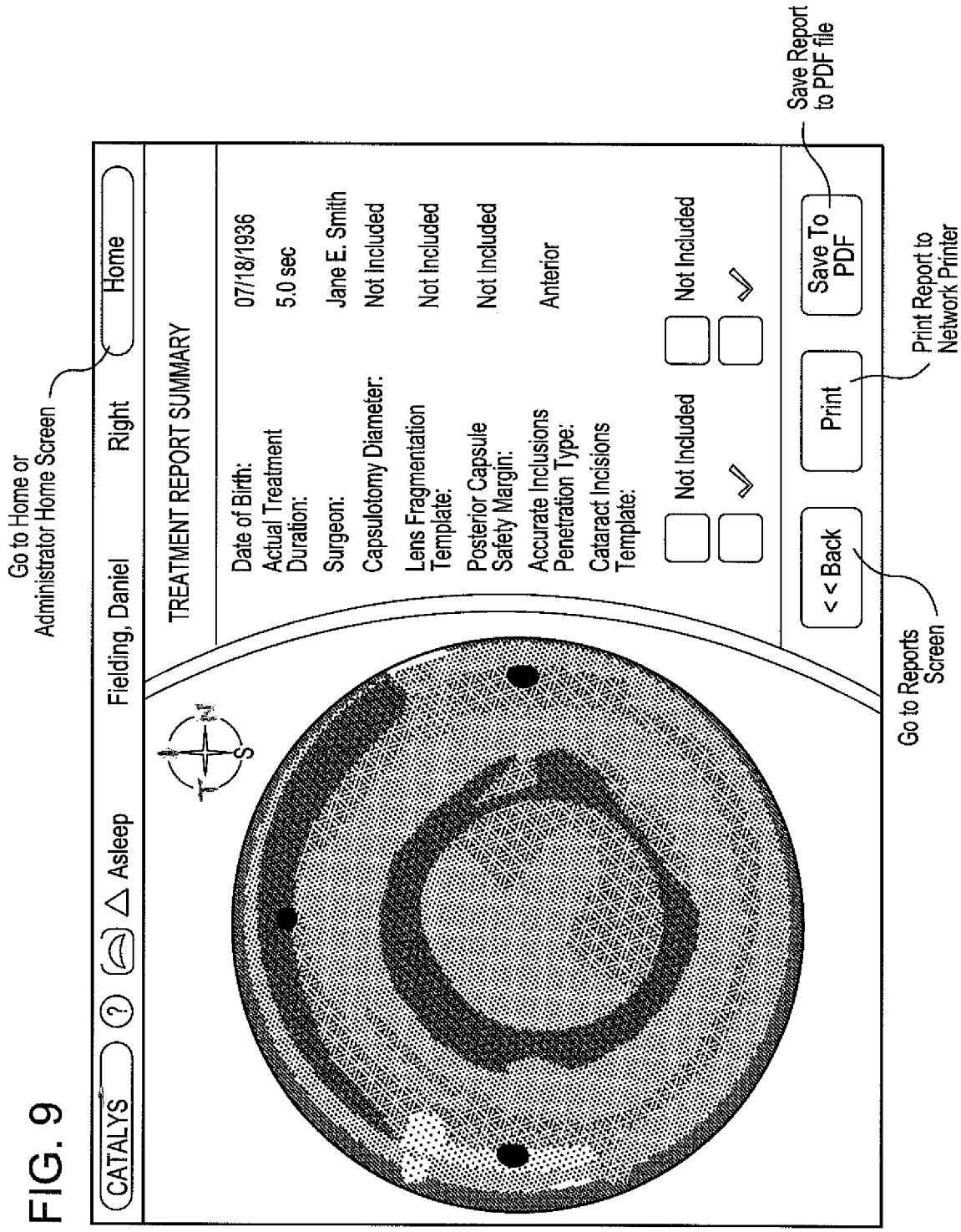

The GUI includes a home screen for a system administrator (referred to herein as "administrator home screen") and a home screen for general users (referred to herein as "home screen"). The administrator home screen provides the administrator access to several features that are not accessible to general users. From the administrator home screen, the administrator can go to a Manage Users Screen, a Reports Screen, Manage Templates Screen, and Settings Screen; verify system alignment; create new treatment plans and edit previously created treatment plans; initiate a treatment plan; enable/disable the system and laser; view treatment activation status; return to the Login Screen; open a Software Info window; and access a Help Manual. FIG. 6 shows an example administrator home screen. FIG. 8 shows an example Reports Screen. And FIG. 9 shows an example Treatment Report Screen, which is accessible from the Reports Screen, for a specific treatment.

Figure 7:
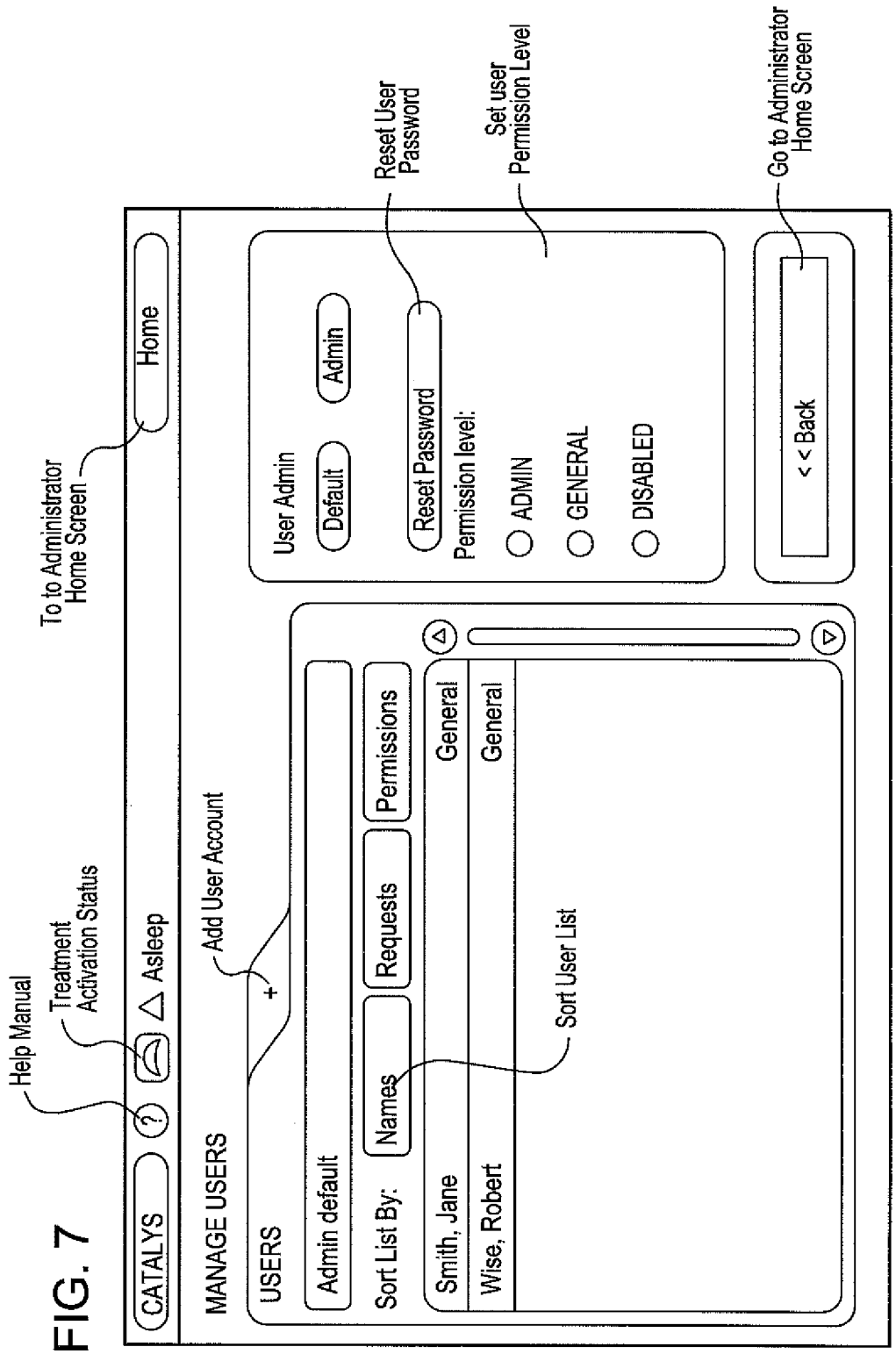

From the Administrator Home Screen, pressing the MANAGE USERS button 200 causes the Manage Users Screen shown in FIG. 7 to be displayed. From the Manage Users Screen, the administrator can add user accounts; assign user permission levels (e.g., Admin—user has administrator privileges, as described herein, General—user can plan and start treatments and perform system calibration and self-test, and Disabled—user has no permissions); reset user passwords; view requests for user accounts submitted from the Login Screen; sort users by name, requests, or permissions; return to the Administrator Home Screen, access the Help Manual, and view treatment activation status.

From the Home Screen or Administrator Home Screen, pressing the ACTIVITY REPORT button 202 causes the Reports Screen (example shown in FIG. 8) to be displayed. From the Reports Screen, a person can view a list of patients for whom there are incomplete, complete, and/or aborted treatments; view a list of treatments for each patient; enable or disable incomplete treatments; go to the Treatment Report Summary Screen for the selected treatment; view the total number of treatments performed; return to the Home Screen or Administrator Home Screen; access the Help Manual; and view treatment activation status.

From the Reports Screen, a specific patient can be selected to view a list of treatments for that patient. Selecting a specific treatment from the list, and then pressing the SHOW TREATMENT RESULTS 204 button causes the Treatment Report Summary Screen (example shown in FIG. 9) for that treatment to be displayed. From the Treatment Report Summary Screen, a user can view treatment results, save the treatment report as a PDF file, print the treatment report to a network printer, return to the Reports Screen, go to the Home Screen or Administrator Home Screen, access the Help Manual, and view treatment activation status.

Figure 10:
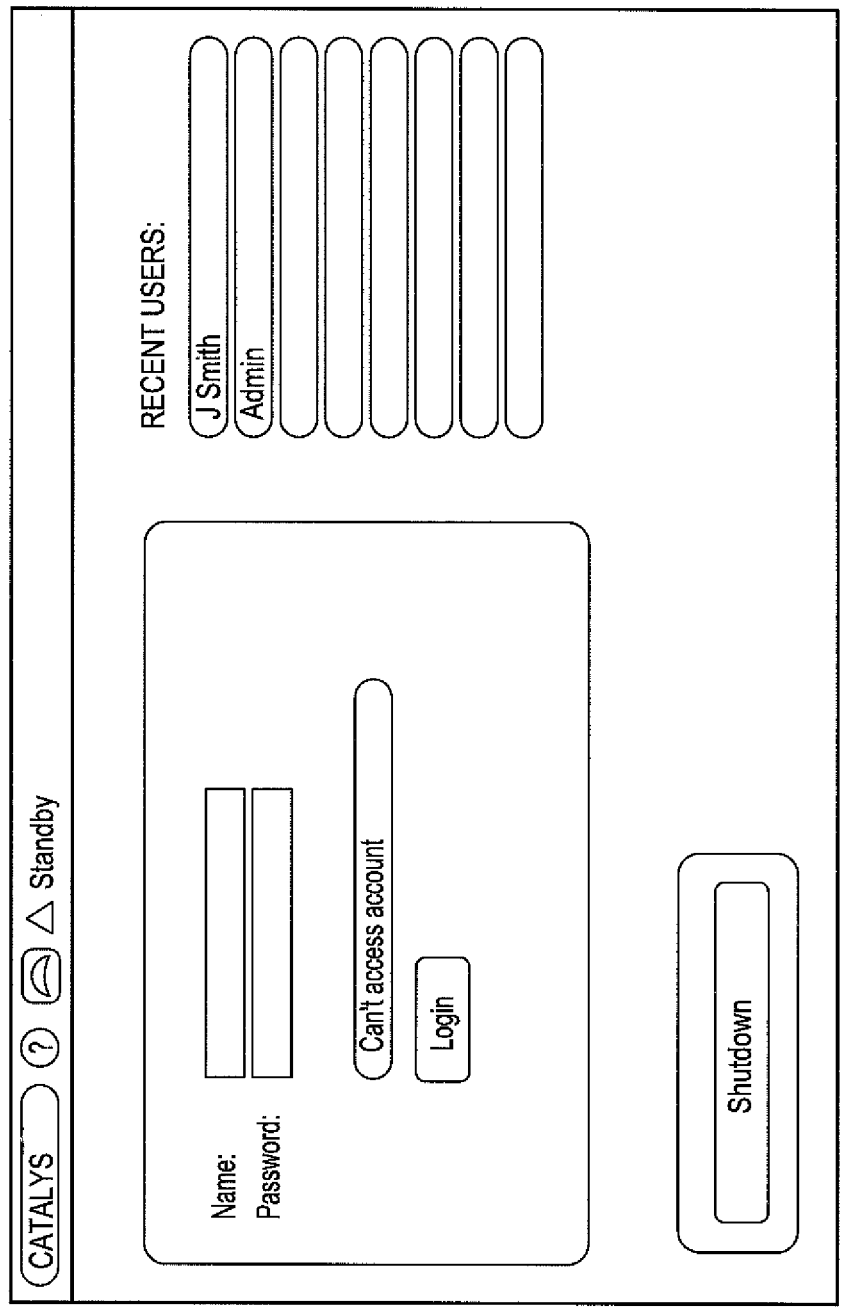
Figure 11:
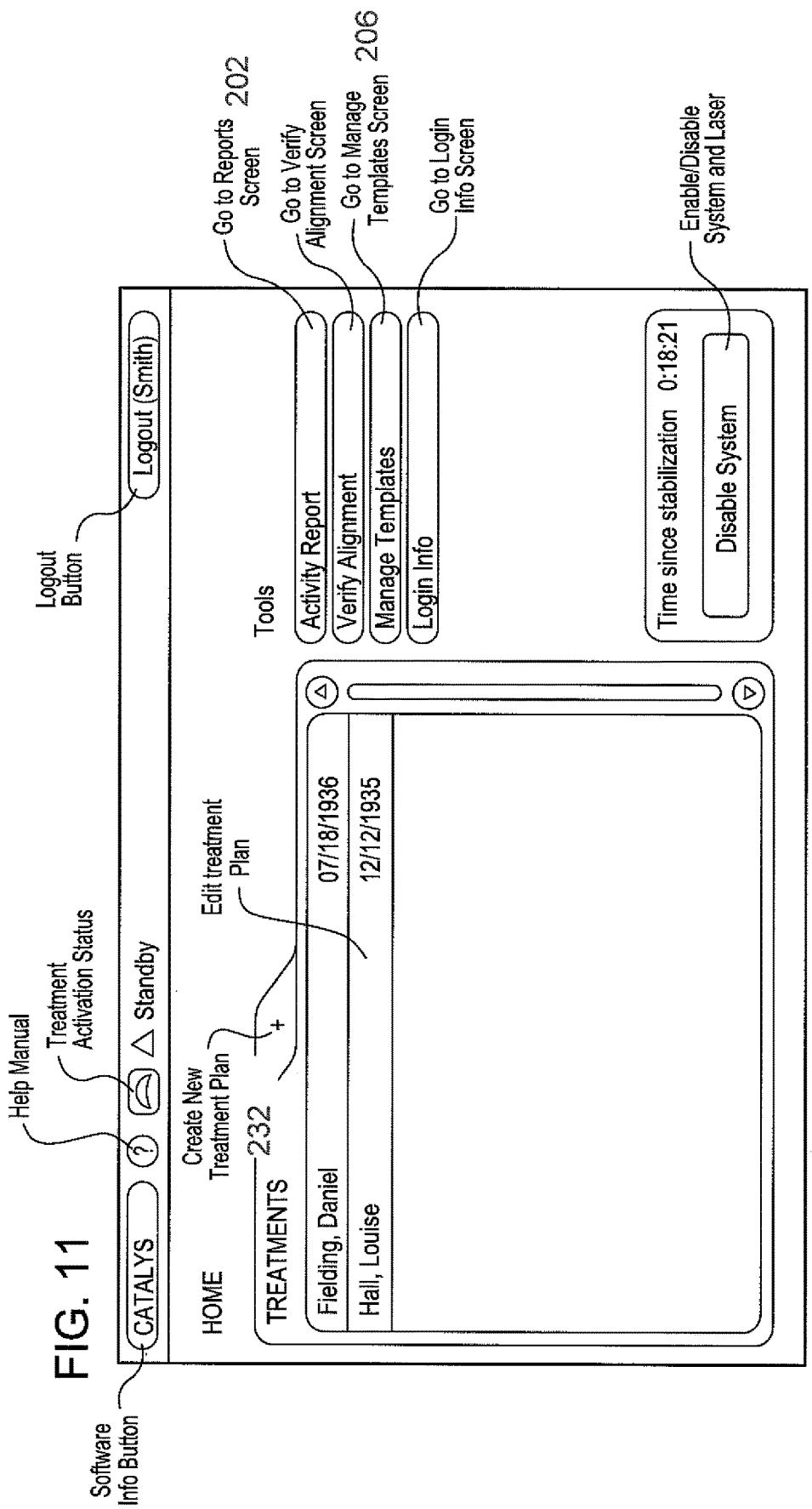

FIG. 10 shows a login screen for general users. After logging into the laser eye surgery system 2 as a general user, the home screen shown in FIG. 11 is displayed on the touch-screen control panel 12. From the home screen, the general user can create new treatment plans and edit previously created treatment plans; initiate a treatment plan; enable/disable the system and laser; go to the Login Info Screen, Reports Screen, and Manage Templates Screen; verify system alignment; view treatment activation status; return to the Login Screen; open a Software Info window; and access the Help Manual. During treatment planning, a user can return to the Home Screen at any time by pressing the HOME button in the upper right corner of the treatment planning screens.

Figure 12:
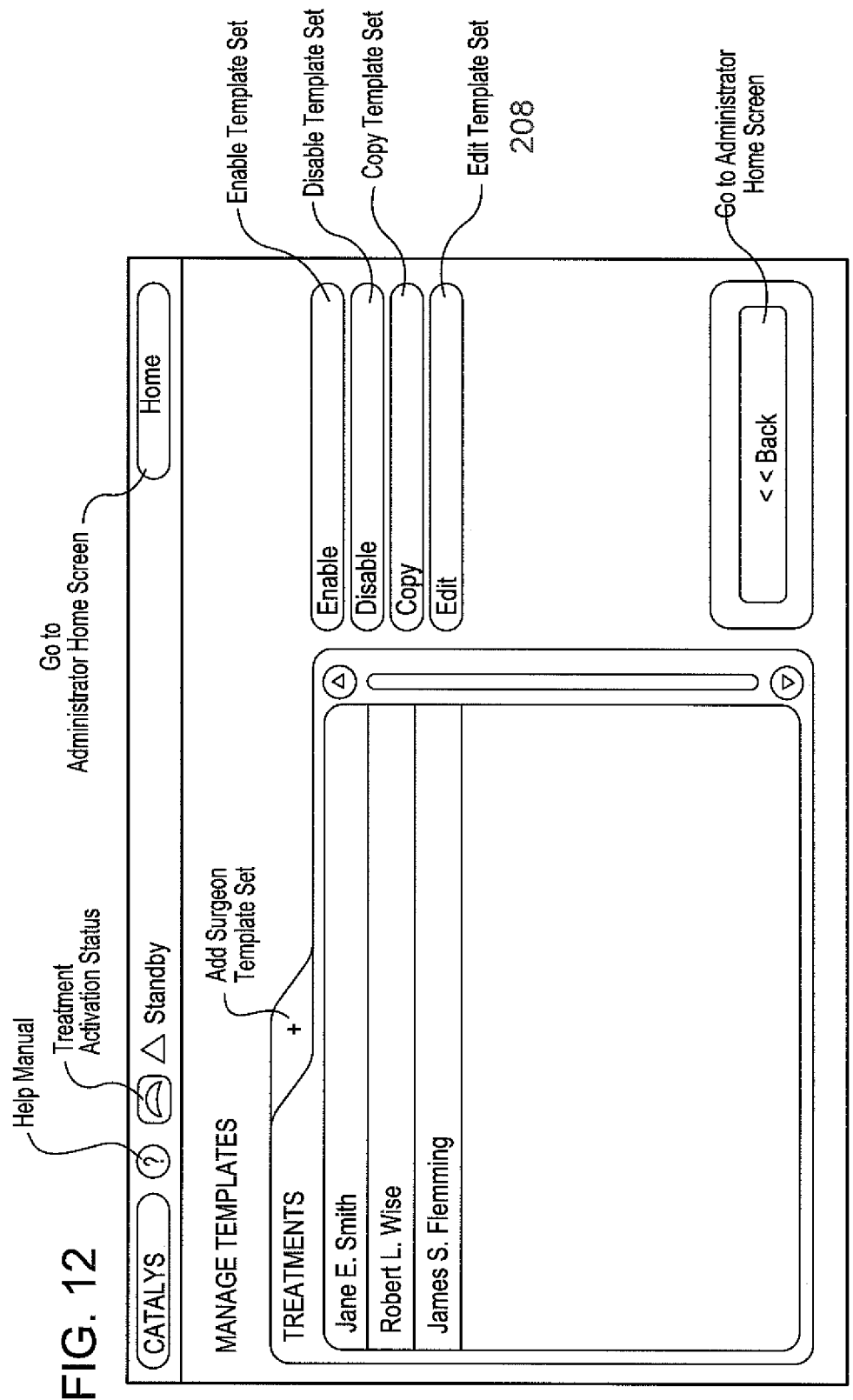
Figure 13:
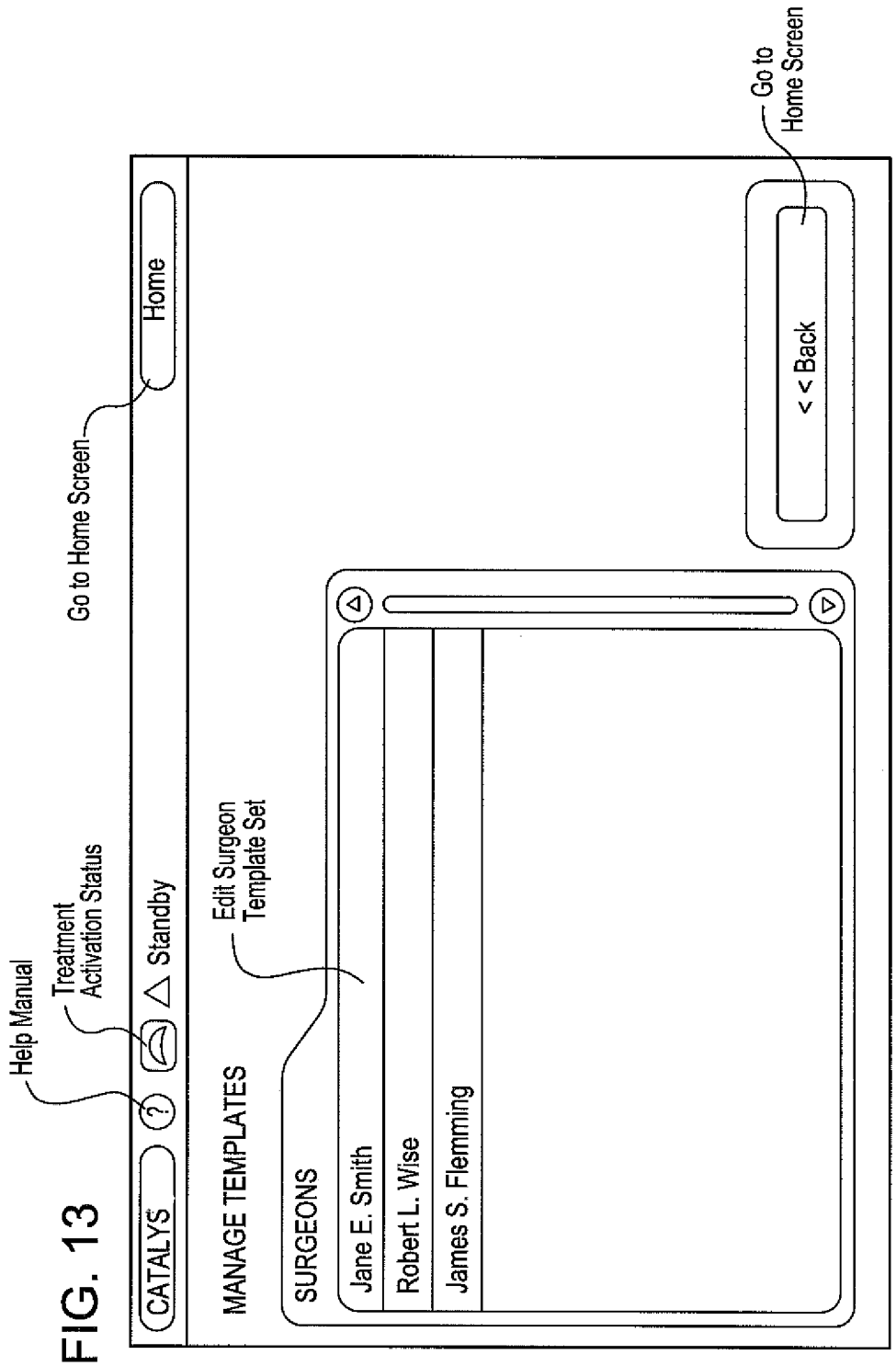

From the Home Screen or Administrator Home Screen, pressing the MANAGE TEMPLATES button 206 causes the Manage Templates Screen (example for administrators shown in FIG. 12 and example for general users shown in FIG. 13) to be displayed. From the Manage Templates Screen for administrators, a person can add new surgeon template sets and edit previously created surgeon template sets, enable or disable surgeon template sets, copy surgeon template sets, return to the Administrator Home Screen, access the Help Manual, and view treatment activation status. From the Manage Templates Screen for general users, a person can edit previously created surgeon template sets, return to the Home Screen, access the Help Manual, and view treatment activation status.

Figure 14:
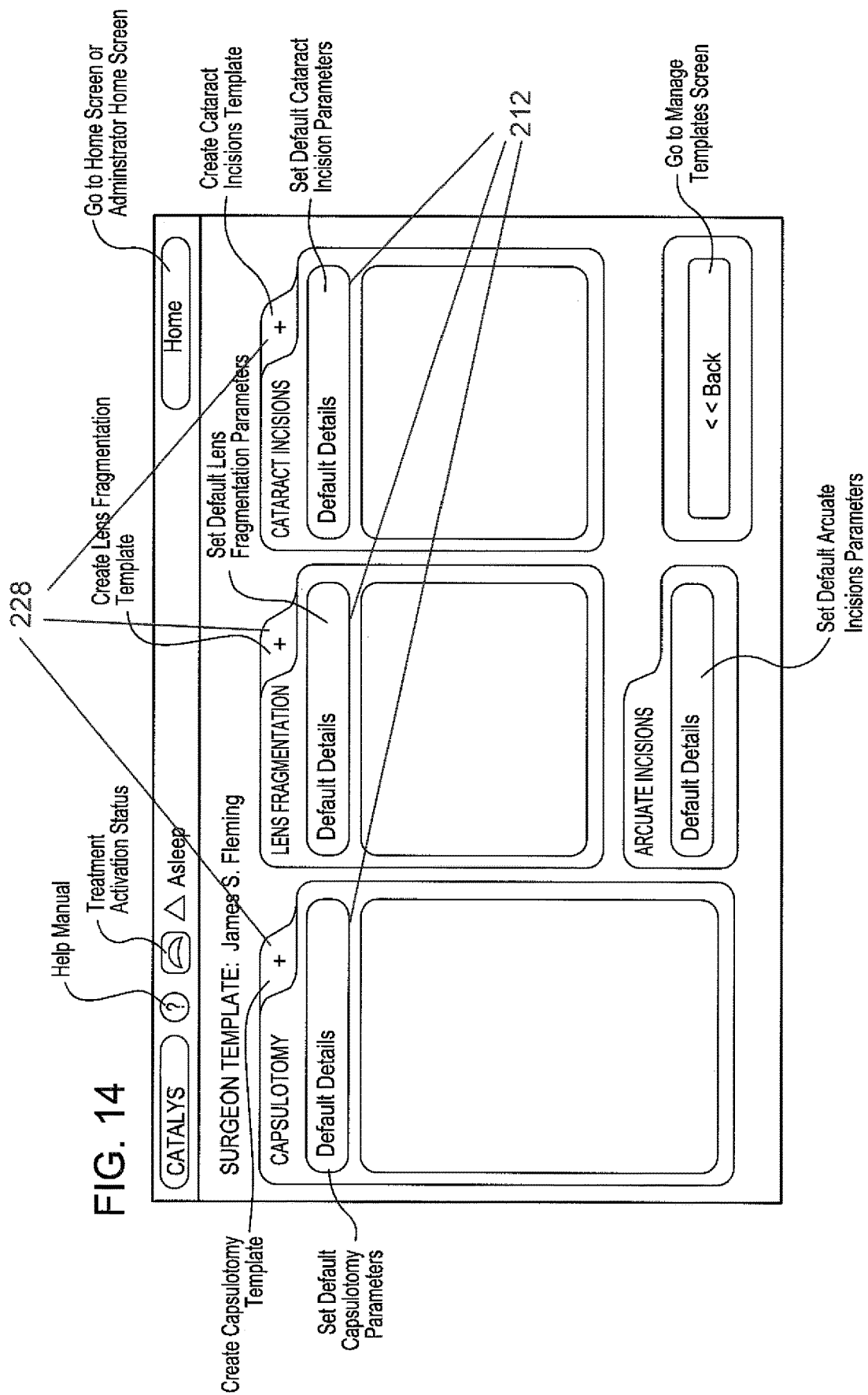

From the Manage Templates Screen for administrators or general users, selecting a surgeon name and pressing the EDIT button 208 causes the Surgeon Template Screen (such as shown in FIG. 14) for that surgeon to be displayed. From the Surgeon Template Screen, the administrator/user can create templates for the desired treatment(s) and edit previously created templates, set default parameters, go to the Home Screen or Administrator Home Screen, return to the Manage Templates Screen, access the Help Manual, and view treatment activation status.

From the Administrator Home Screen, pressing the SETTINGS button 210 causes the Settings Screen to be displayed. From the Settings Screen, the administrator can select the user language and country for software localization, adjust the touchscreen drag sensitivity, enable and disable graphic reports, enable and disable the network connection, return to the Administrator Home Screen, access the Help Manual, and view treatment activation status.

There are three main types of planning screens, all of which have a similar appearance but perform different functions. Default Details Screens allow a person to set default treatment parameters, which carry over to the Surgeon Template and Treatment Planning Screens. Surgeon Template Screens allow a person to create templates with preset treatment parameters, which can be recalled from the Treatment Planning Screens. Treatment Planning Screens allow a person to create an individual treatment plan for a given patient.

When a parameter field on a planning screen is selected by touching, an input keypad displays on the screen. The range of allowable settings is displayed at the top of the keypad. If a value outside of the displayed range is entered, an "out of range" error is displayed.

If a parameter value is entered that differs from the default value for any treatment parameter, an asterisk displays to the left of the treatment parameter value and a "return-to-default" button displays to the right. Pressing the "return-to-default" button causes the treatment parameter value to revert to the default value displayed on the "return-to-default" button.

Figure 15:
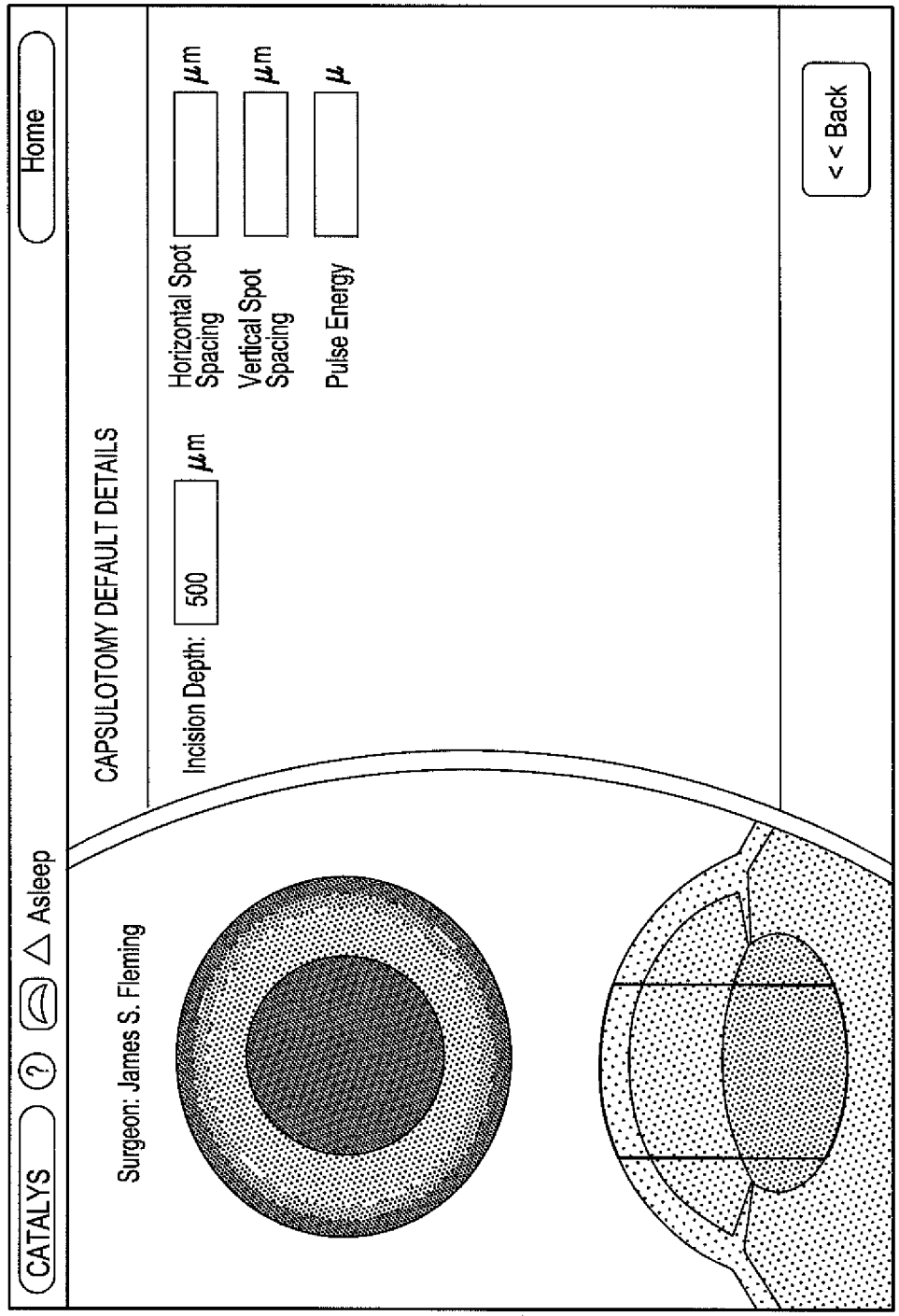
Figure 16:
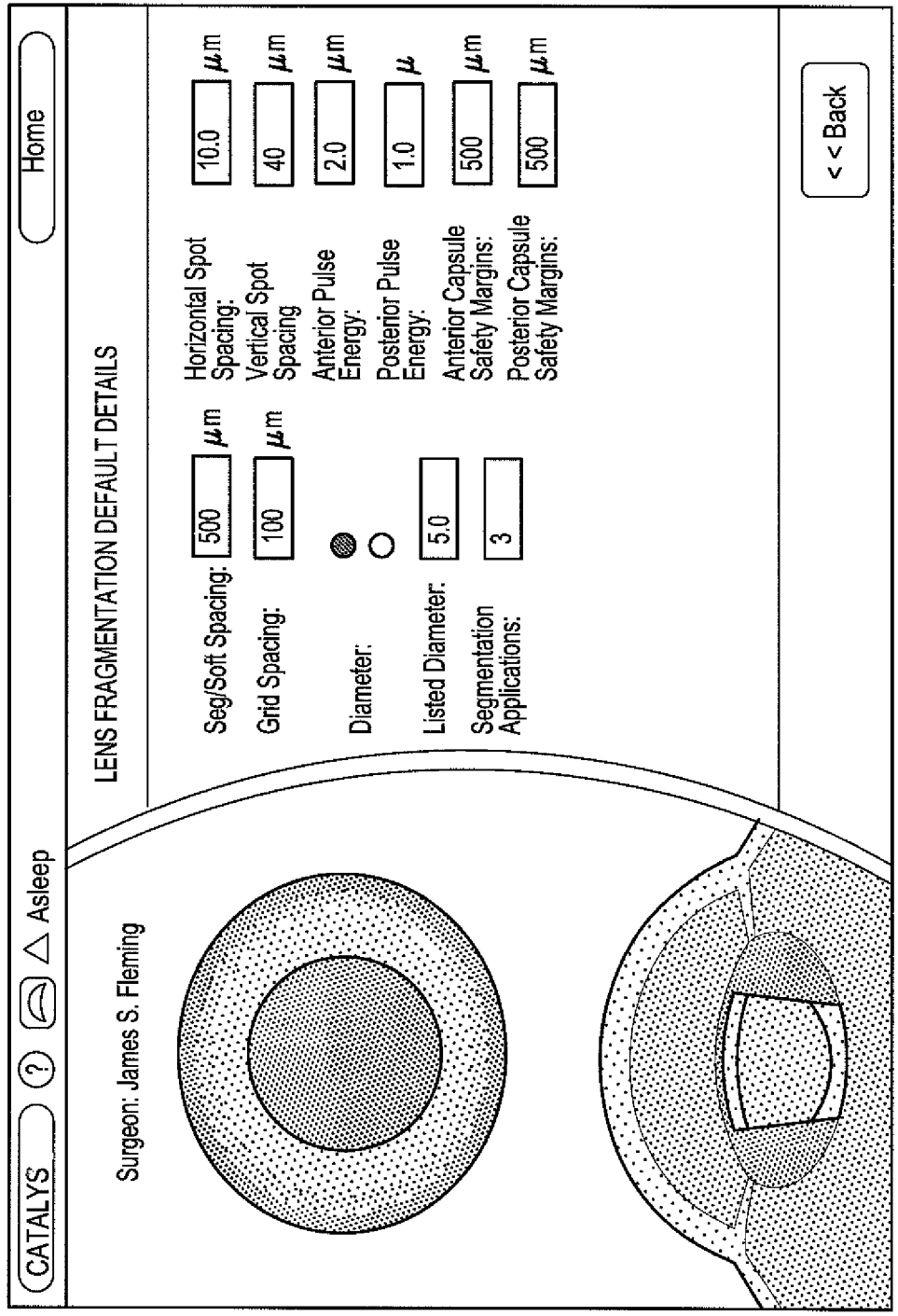
Figure 17:
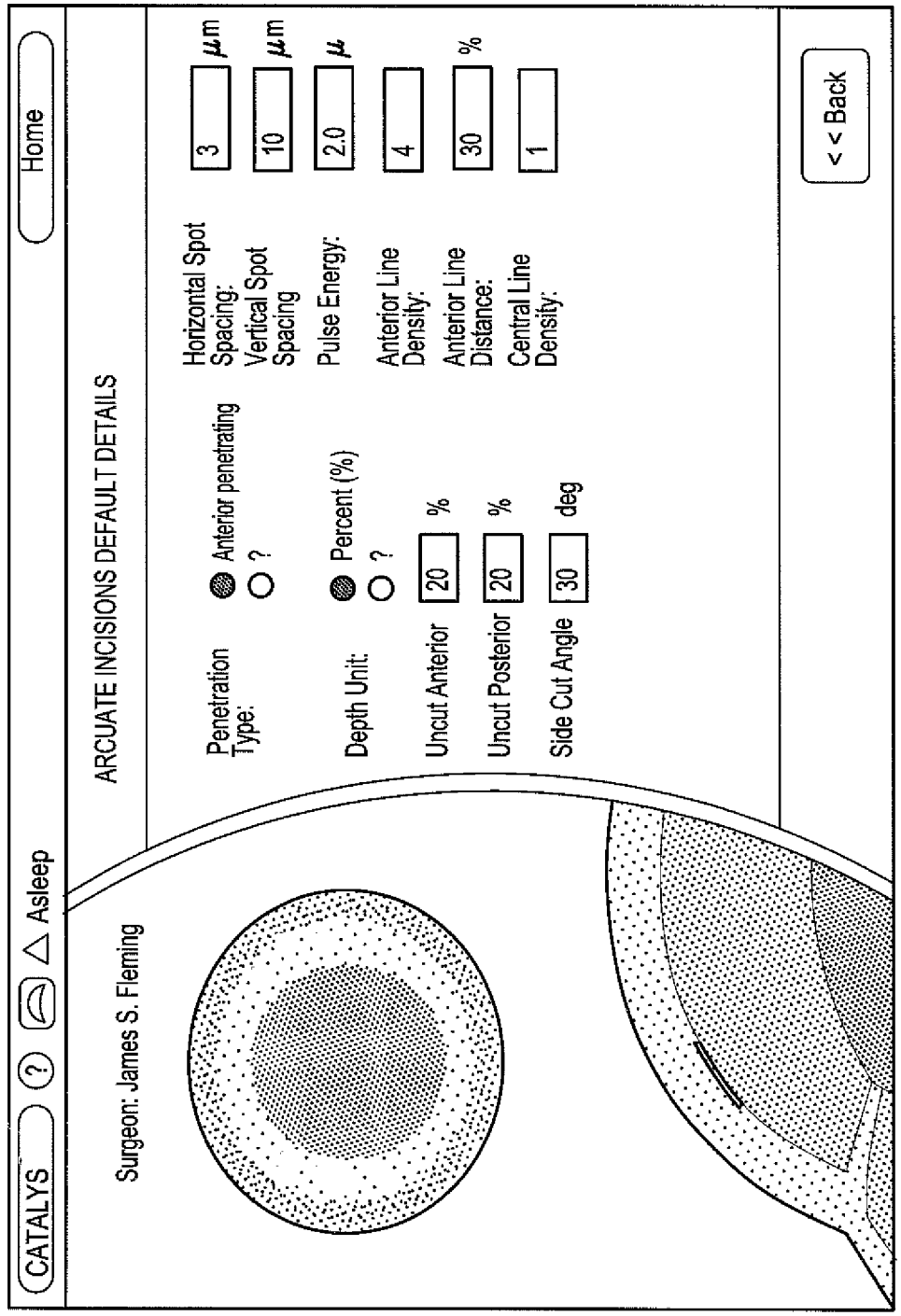
Figure 18:
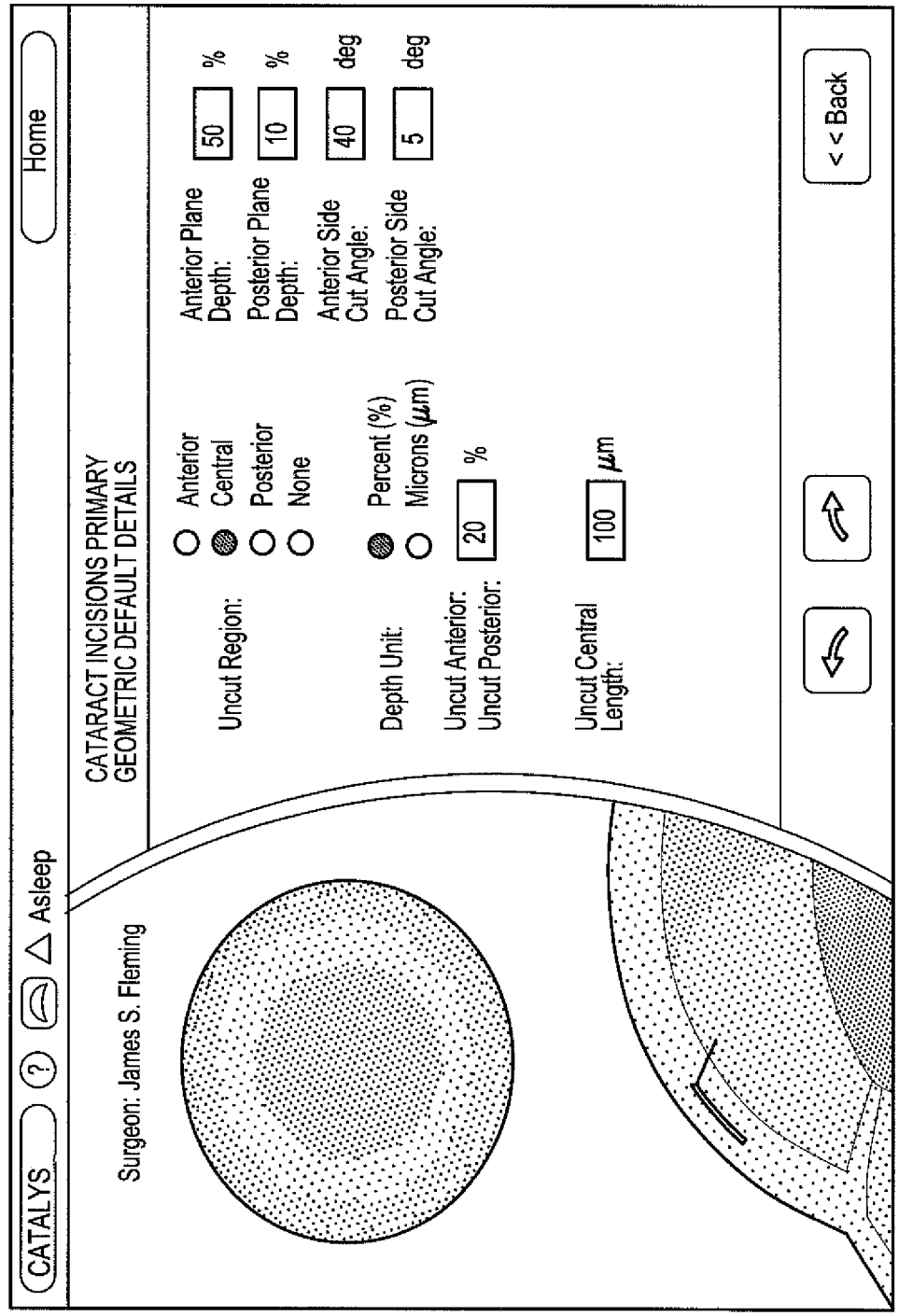
Figure 19:
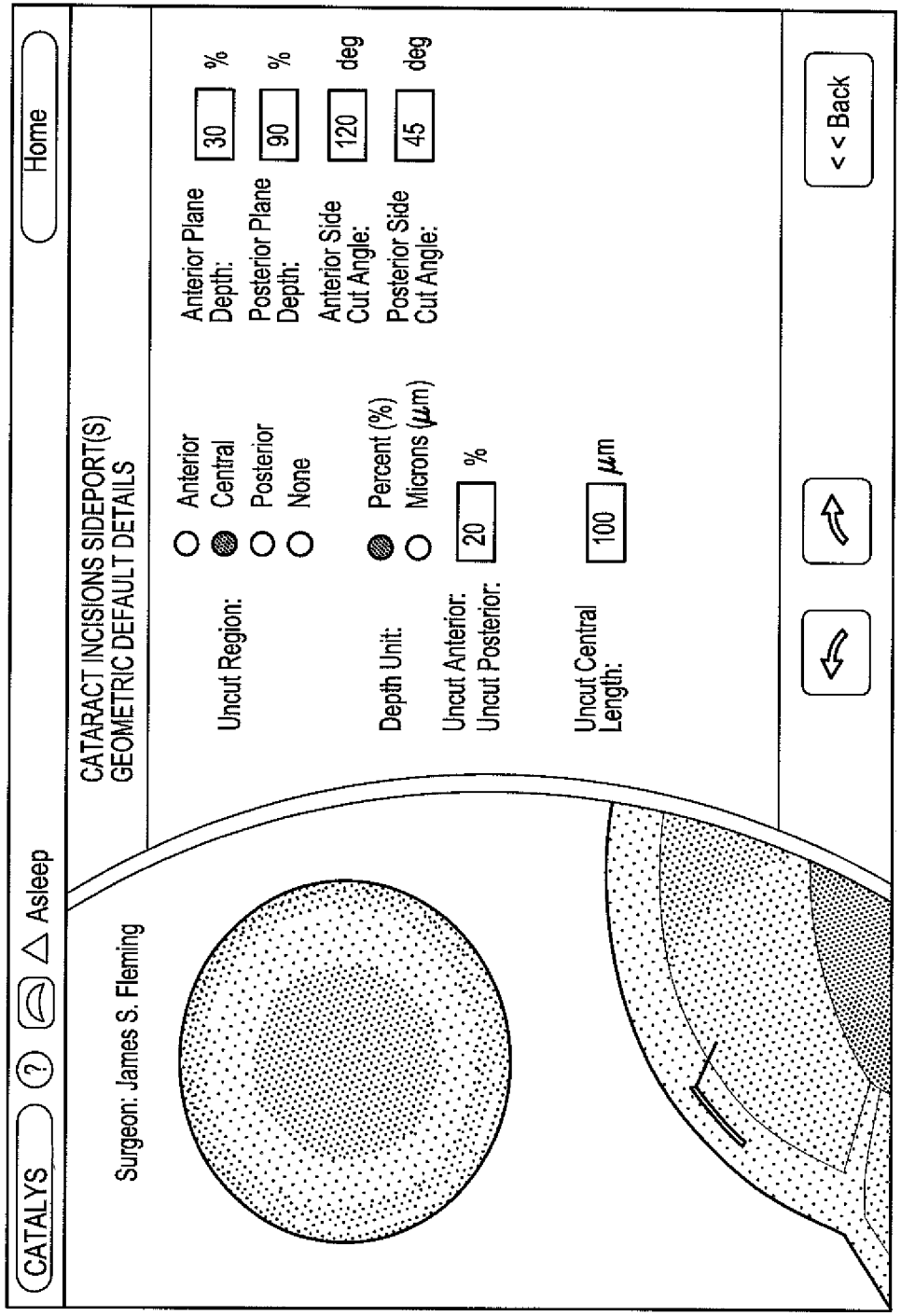
Figure 20:
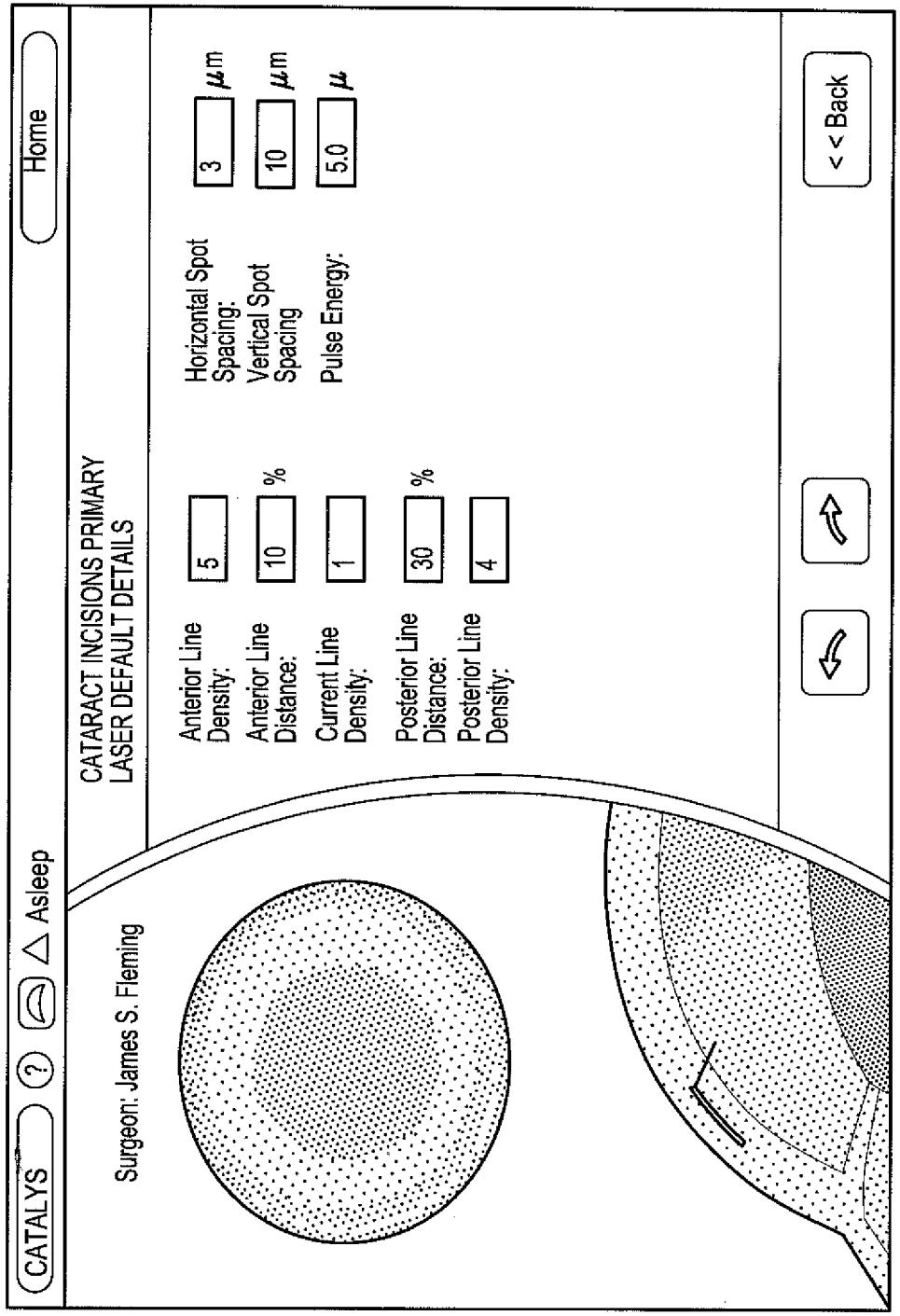
Figure 21:
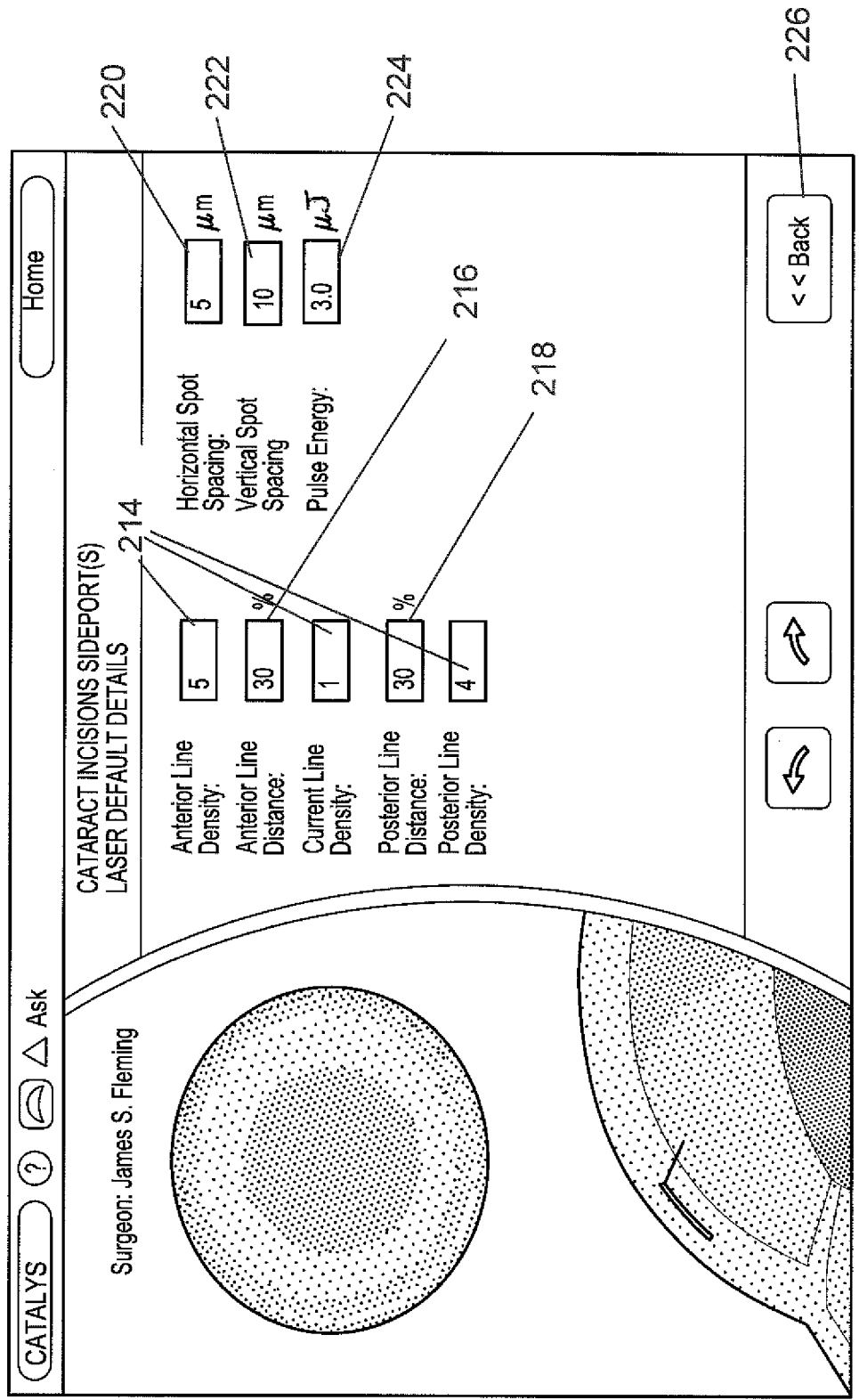

From the Surgeon Template Screen for the selected surgeon, pressing the DEFAULT DETAILS button 212 for the desired treatment causes the corresponding Default Details Screen to be displayed. The desired default parameter values can then be entered. FIG. 15 shows an example Capsulotomy Default Details Screen used to specify default parameter values used to form a capsulotomy incision in the anterior portion of the lens capsule. FIG. 16 shows an example Lens Fragmentation Default Details Screen used to specify default parameter values used to form incisions in the lens to fragment the lens. FIG. 17 shows an Arcuate Incisions Default Details Screen used to specify default parameter values used to form an arcuate incision in the cornea. FIG. 18 shows a Cataract Incisions Primary Geometric Default Details Screen used to specify default parameter values used to form access incision in the cornea for primary cataract surgical instruments (e.g., an instrument used to insert an IOL following removal of the fragmented crystalline lens nucleus). FIG. 19 shows a Cataract Incisions Sideport(s) Geometric Default Details Screen used to specify default parameter values used to form access incision in the cornea for sideport cataract surgical instruments (e.g., a cataract instrument that is not used to insert an IOL following removal of the fragmented crystalline lens nucleus). FIG. 20 shows a Cataract Incisions Primary Laser Default Details Screen used to specify default parameter values related to controlling the energy and placement of the laser pulse focus points used to create primary cataract incision in the cornea. FIG. 21 shows a Cataract Incisions Sideport(s) Laser Default Details Screen used to specify default parameter values related to controlling the energy and placement of the laser pulse focus points used to create sideport cataract incisions in the cornea. The "line density" parameters 214 control the amount of overlap between adjacent lines of laser pulse locations—a density of 1.0 or less results in no overlap and a density greater than 1.0 can be used to specify corresponding increasing levels of overlap. The GUI provides the ability to independently control aspects of the incision in an anterior portion of the cornea, in a posterior portion of the cornea, and between the anterior and posterior portions of the cornea. An Anterior Line Distance parameter 216 is used to specify a depth as a percentage of the thickness of the cornea that controls the depth in the cornea above which the anterior line density parameter applies and below which the central line density parameter applies. Similarly, the Posterior Line Distance parameter 218 is used to specify a depth as a percentage of the thickness of the cornea that controls the depth in the cornea above which the central line density parameter applies and below which the posterior line density parameter applies. The horizontal spot spacing parameter 220 controls the horizontal spacing between laser pulse focus locations. The vertical spot spacing parameter 222 controls the vertical spacing between laser pulse focus locations. And the pulse energy parameter 224 controls the pulse energy of the laser pulses. Pressing the BACK button 226 returns to the Surgeon Template Screen.

The values entered in the Default Details Screens carry over to the Surgeon Template and Treatment Planning Screens. If a user selects a value other than the default value for any parameter on a Surgeon Template or Treatment Planning Screen, an asterisk displays to the left of the value and a "return-to-default" button displays to the right.

Figure 22:
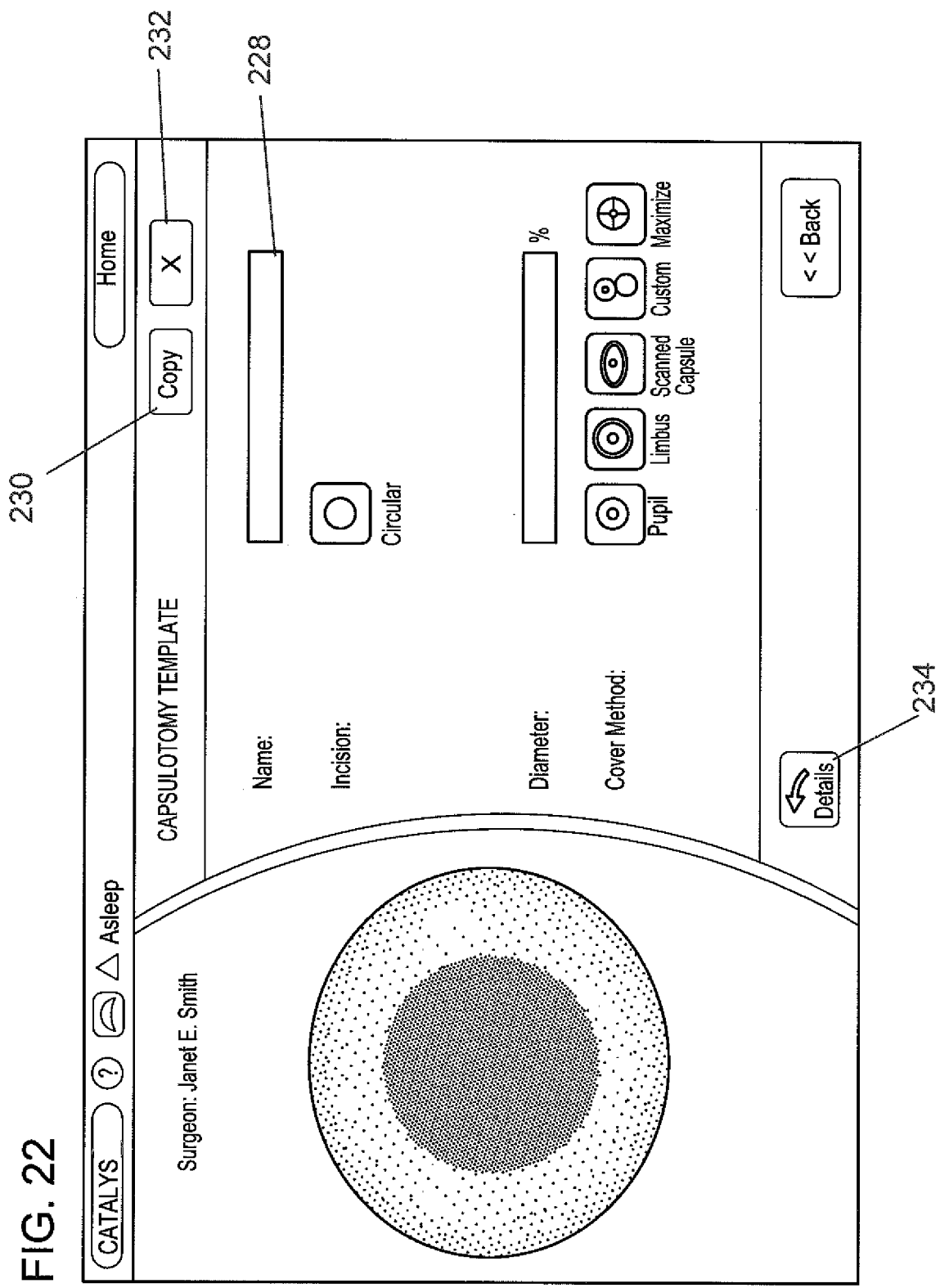
Figure 23:
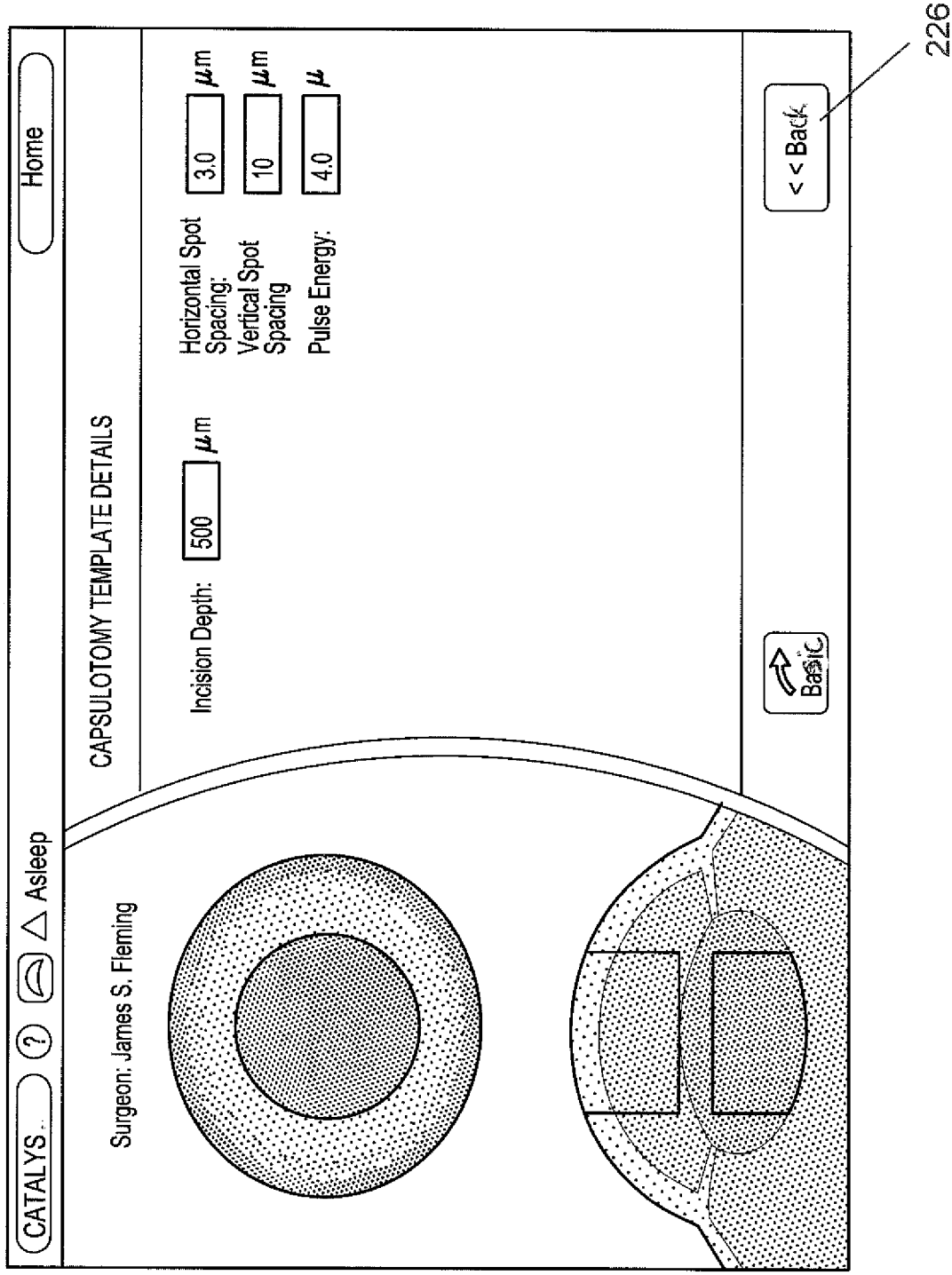
Figure 24:
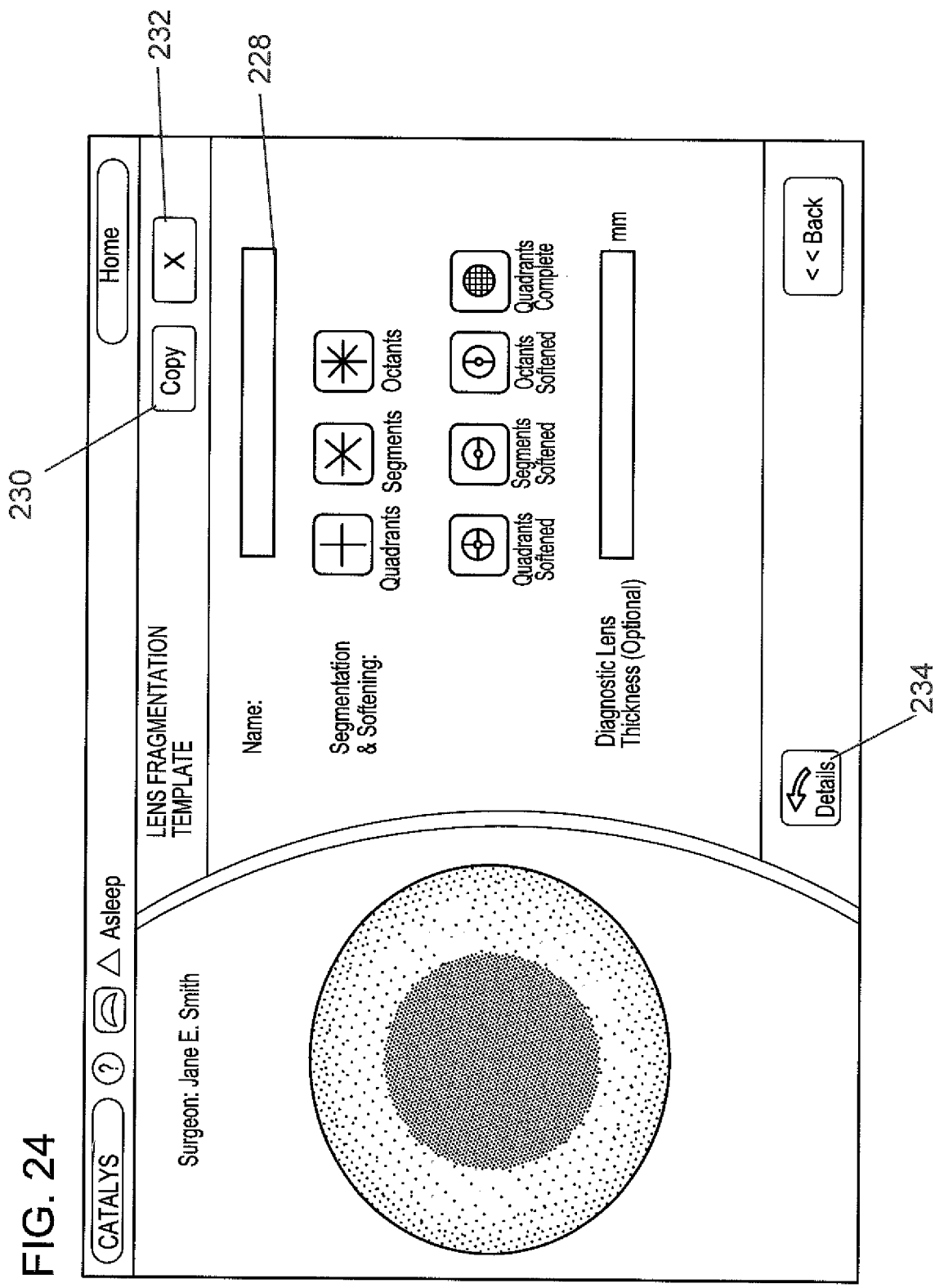
Figure 25:
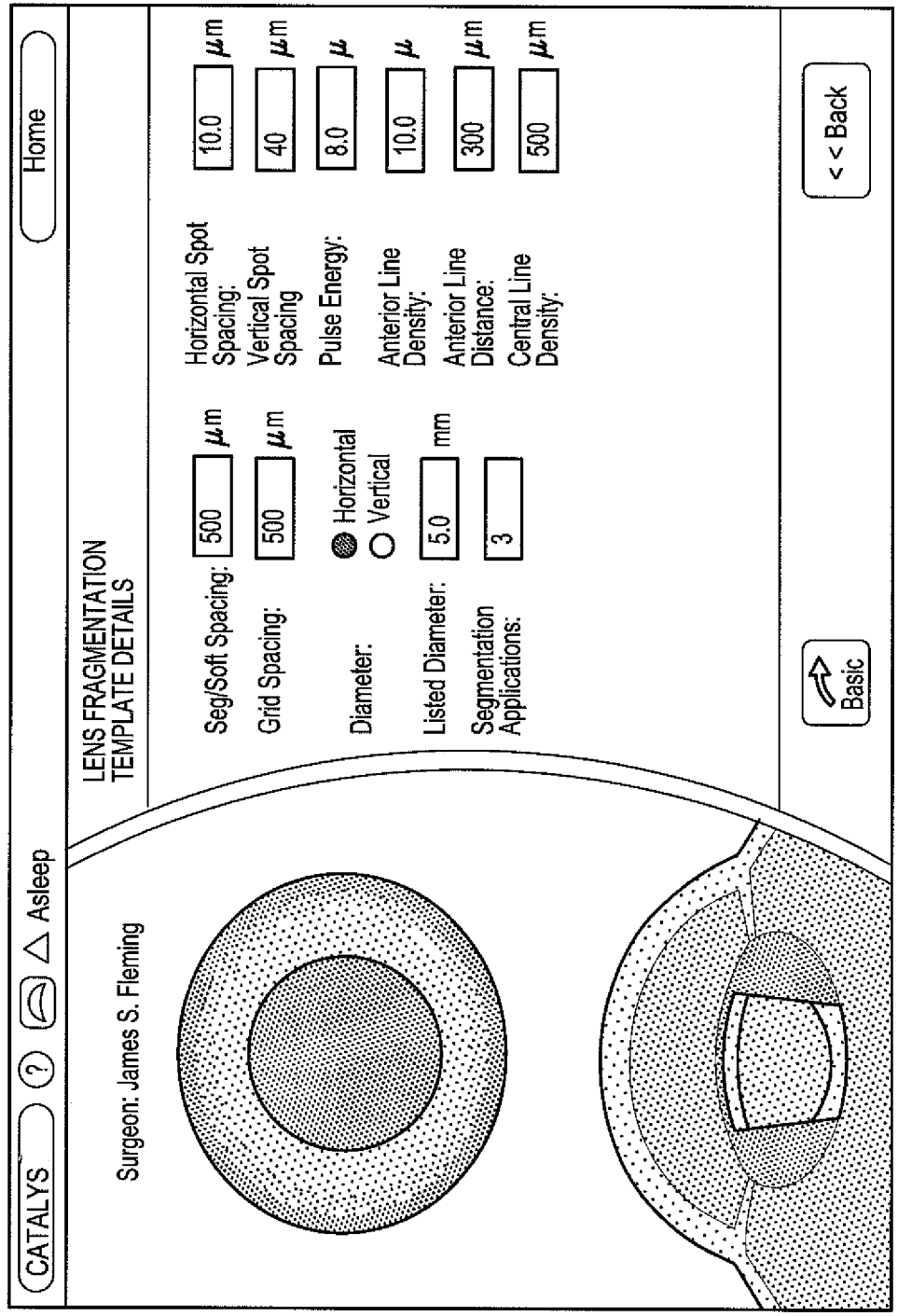
Figure 26:
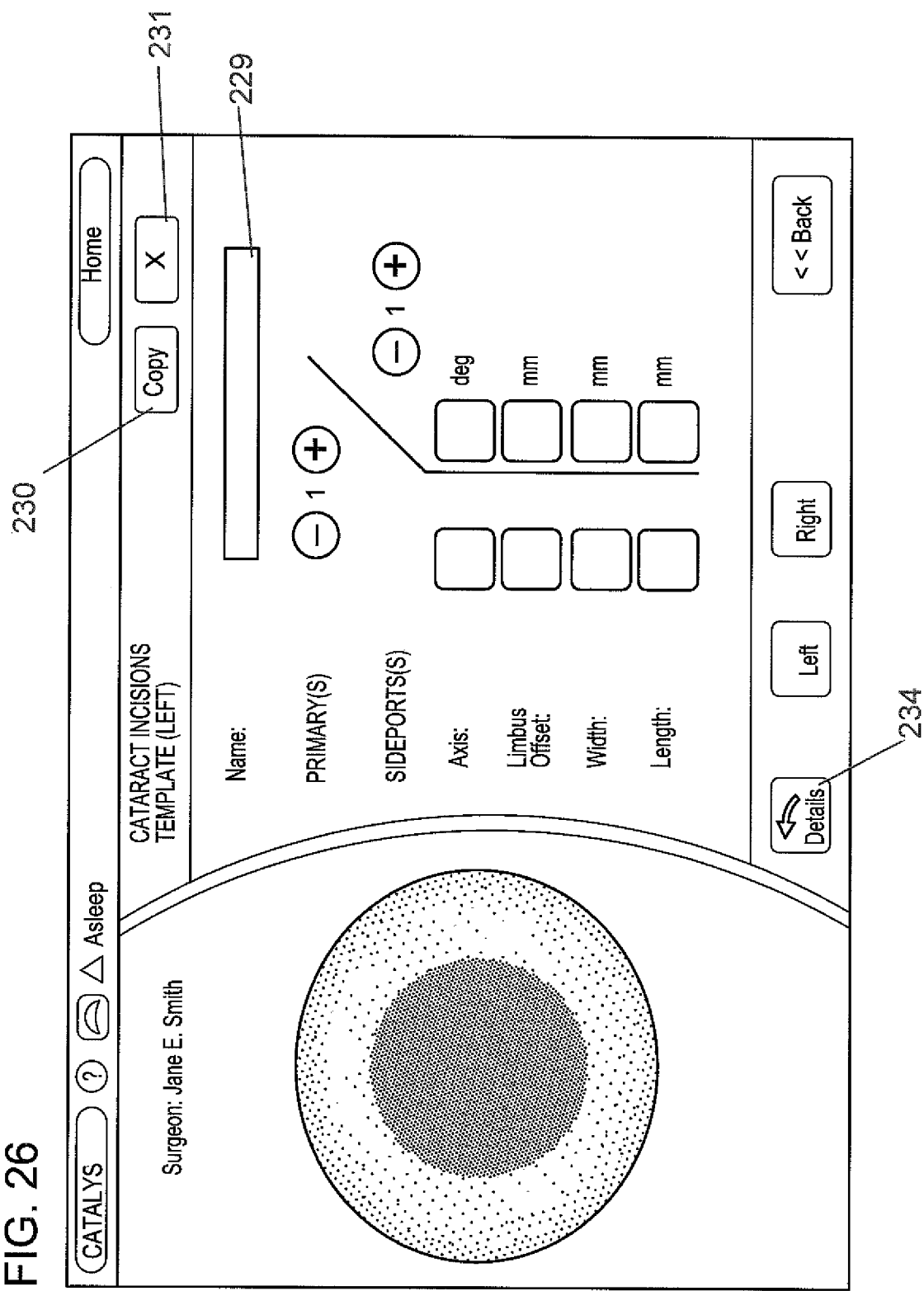
Figure 27:
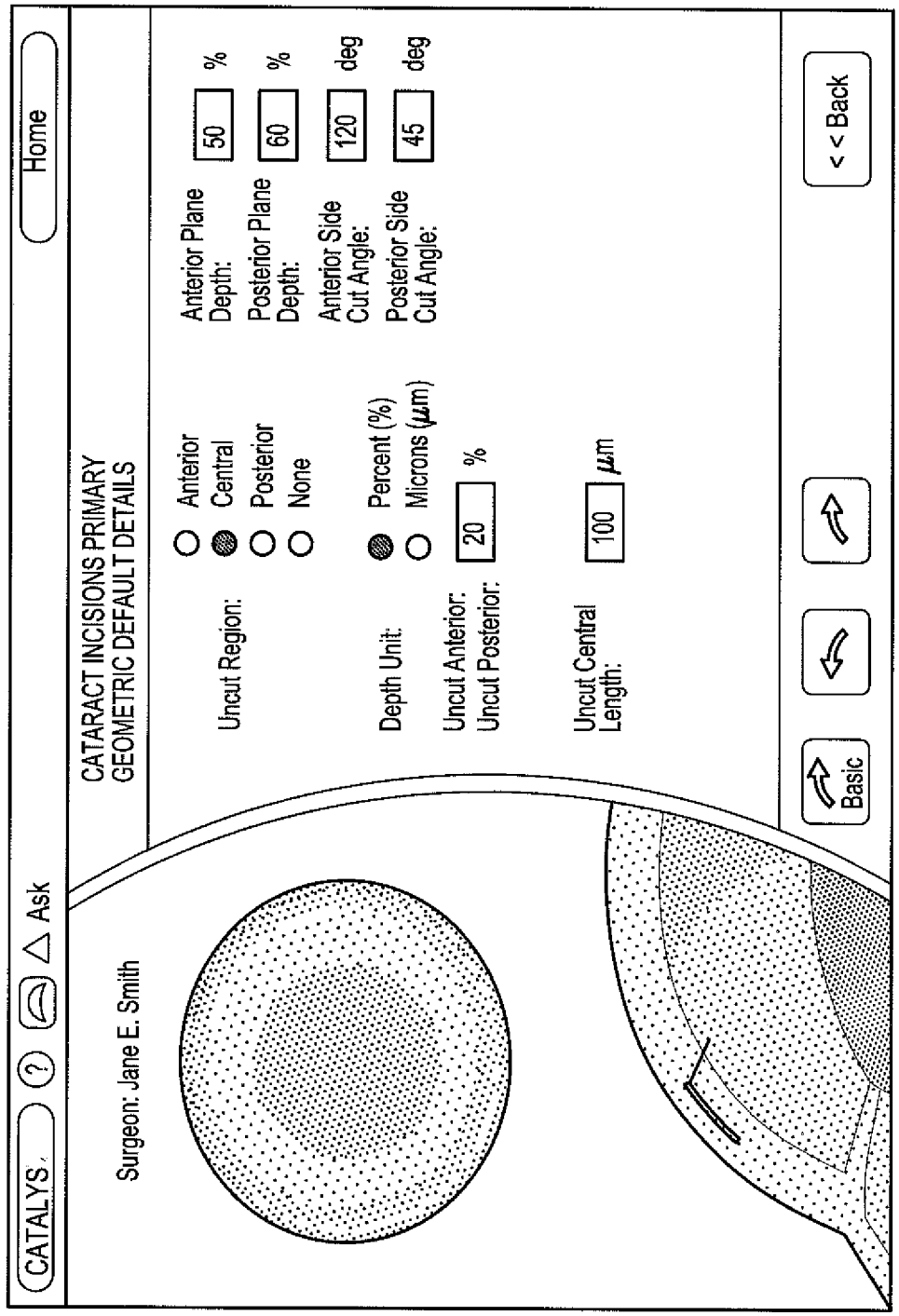
Figure 28:
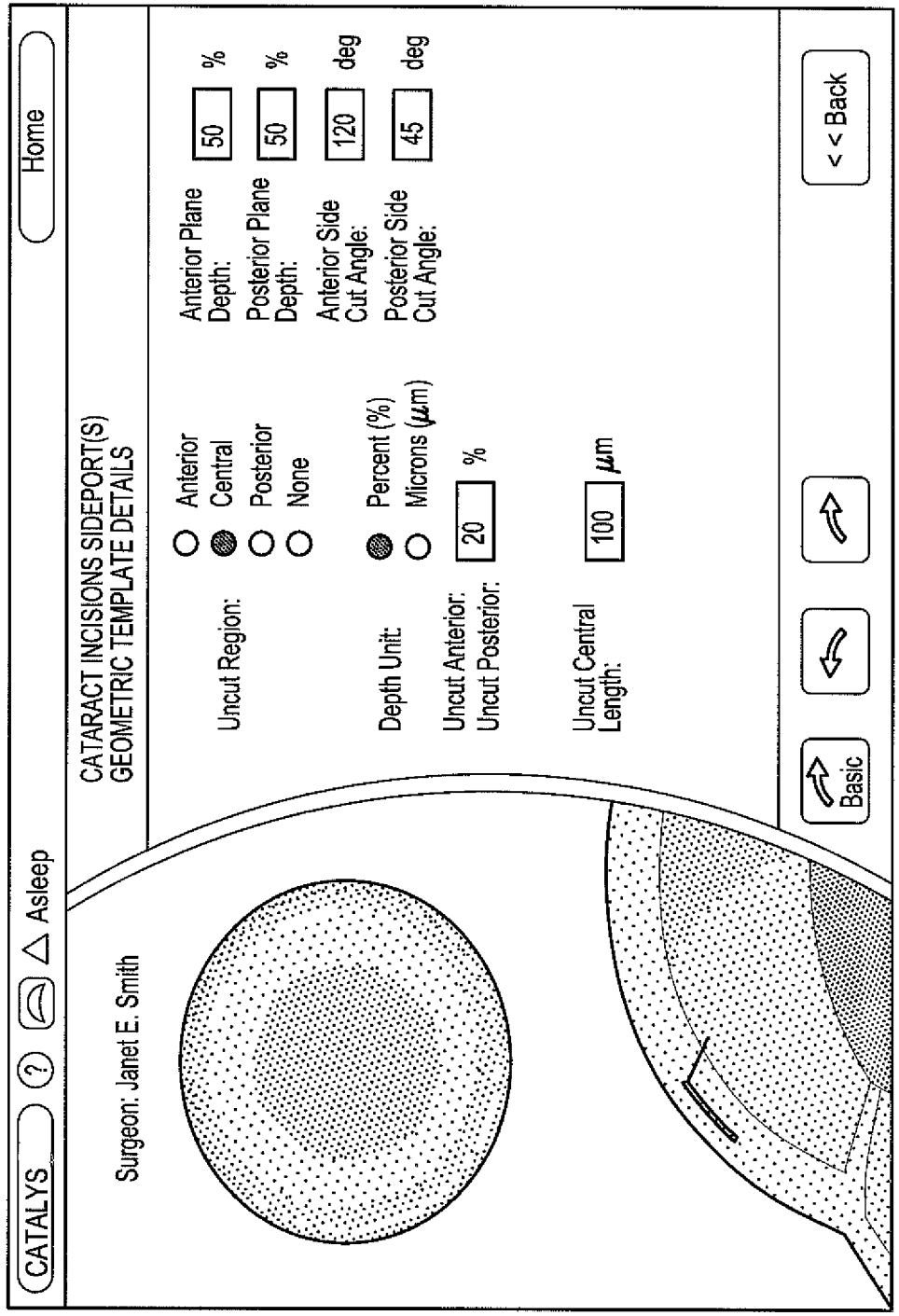
Figure 29:
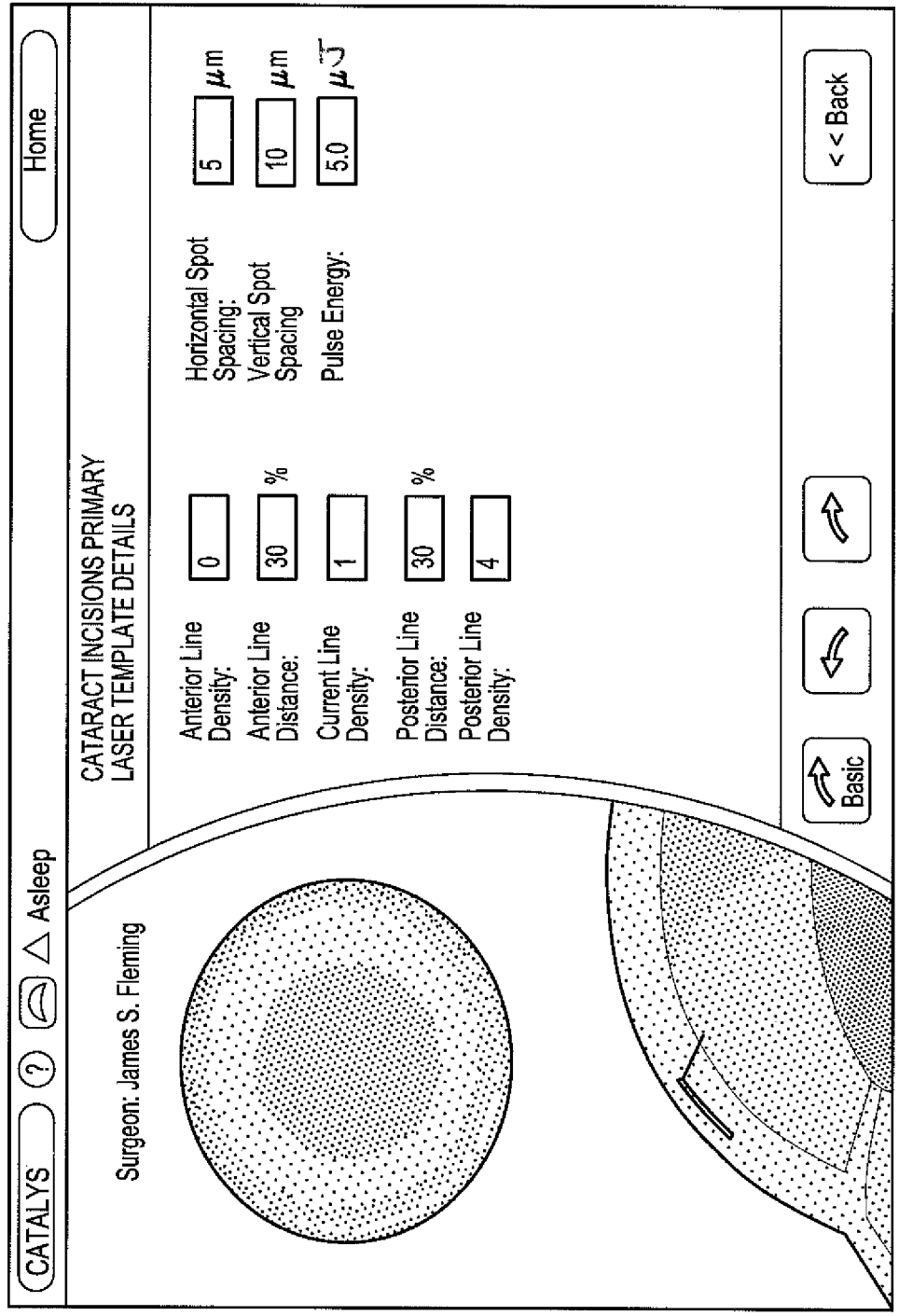
Figure 30:
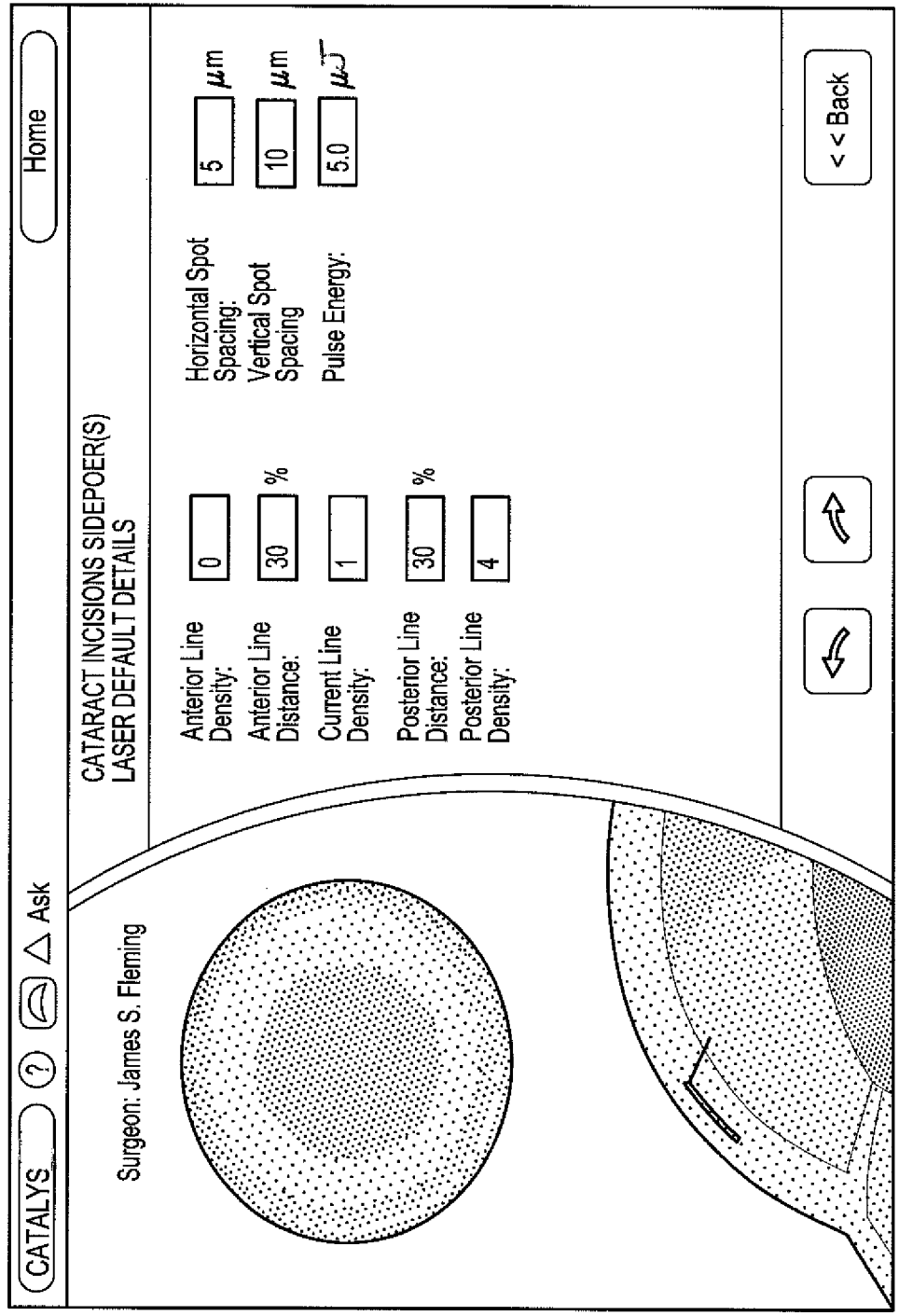

From the Surgeon Template Screen for the selected surgeon, pressing the ⚏ (create template) tab 228 for the desired treatment causes the corresponding Template Screen to be displayed. The template name that is entered in the NAME field 229 on this screen will display in a drop-down list on the Treatment Planning Screen for the selected treatment. Pressing the COPY button 230 is used to create a copy of the template. Pressing the X button 231 is used to delete the template. Pressing the DETAILS 234 button returns to the Template Details Screen. FIG. 22 shows an example capsulotomy (basic) template screen. FIG. 23 shows an example capsulotomy template details screen. Pressing the BACK button 226 returns to the Surgeon Template Screen. FIG. 24 shows an example lens fragmentation (basic) template screen. FIG. 25 shows an example lens fragmentation template details screen. FIG. 26 shows an example cataract incisions (basic) template screen. FIG. 27 shows an example cataract incision primary geometric template details screen. FIG. 28 shows an example cataract incisions sideport(s) geometric template details screen. FIG. 29 shows an example cataract incisions primary laser template details screen. FIG. 30 shows an example cataract incisions sideport(s) laser template details screen.

Figure 31:
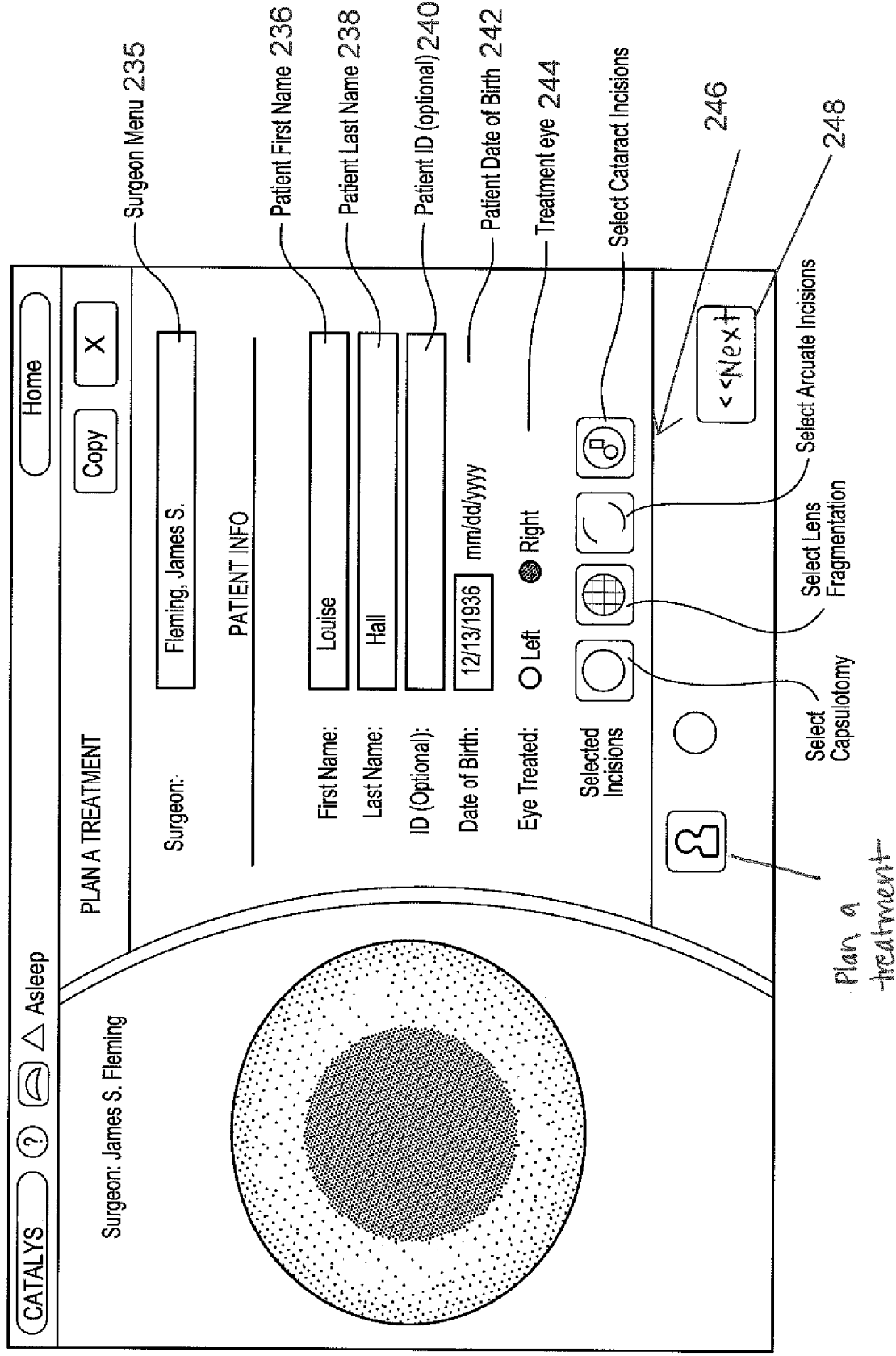

Pressing the ⚏ (create treatment plan) tab 232 on the Home Screen is used to access a Plan a Treatment Screen, an example of which is shown in FIG. 31. From the Plan a Treatment Screen, basic treatment information can be entered, and navigation to other screens can be accomplished. Treatment settings can be selected prior to coupling the patient's eye to the patient interface 52. All treatment parameters can be verified before proceeding with the treatment.

In many embodiments, the following information must be entered on the Plan a Treatment Screen before proceeding with treatment planning: surgeon name 235, patient first and last name 236, 283, patient ID 240 (optional), patient date of birth 242, treatment eye 244, and selected incision(s) 246. After entering the required information, pressing the NEXT button 248 is used to proceed to the treatment parameter selection screens.

Figure 32:
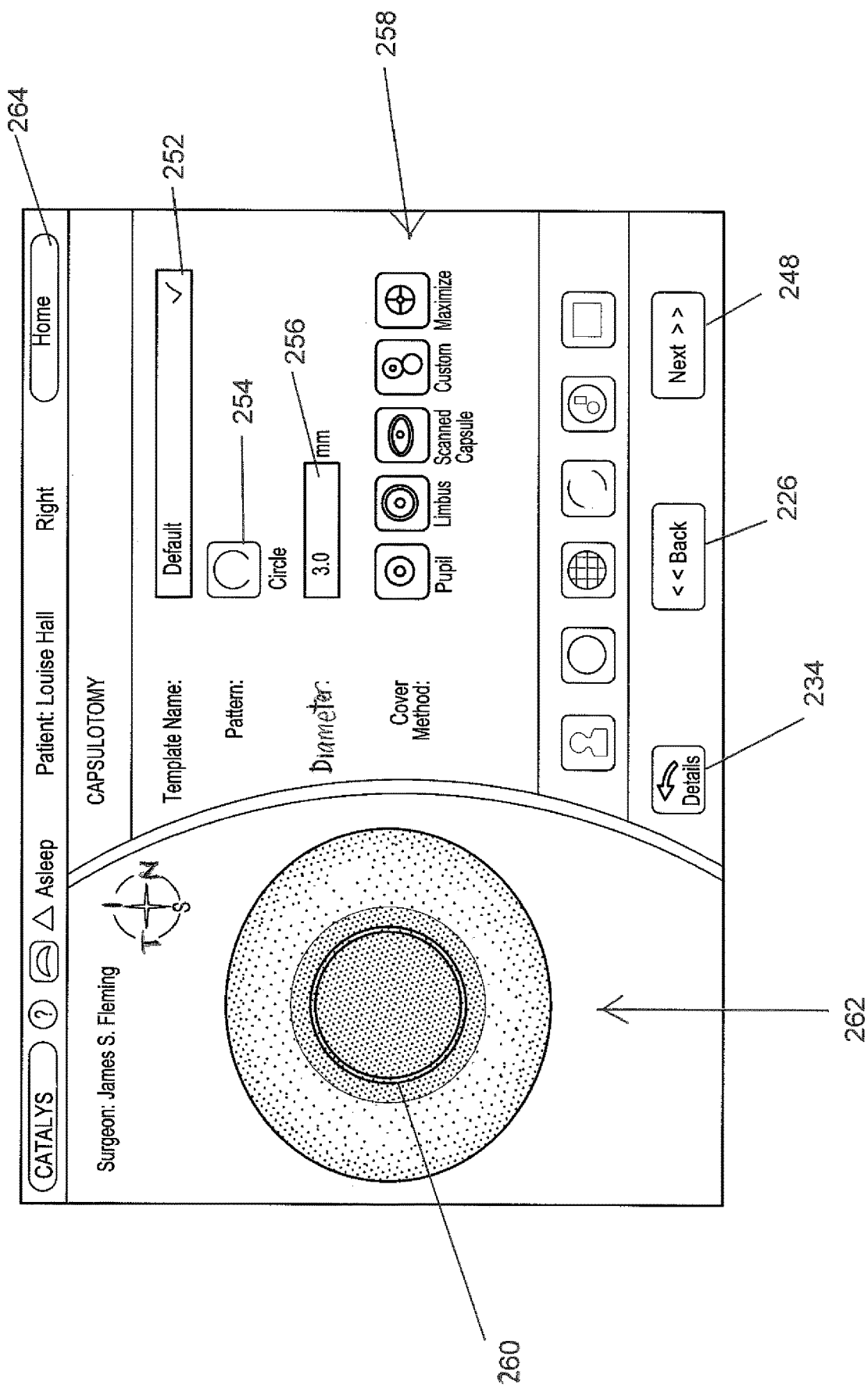

FIG. 32 shows a Capsulotomy (Basic) Screen used to select basic treatment parameter values for a capsulotomy incision. The Capsulotomy (Basic) Screen can be accessed in any of the following ways: pressing the NEXT button 248 on the Plan a Treatment Screen; pressing the BASIC button 250 on the Capsulotomy Details Screen; pressing the BACK button 226 on the (Basic) Screen for the next treatment in the sequence; and selecting the Quick Navigation Bar Capsulotomy Icon on the Plan a Treatment Screen, the Lens Fragmentation, Arcuate Incisions, or Cataract Incisions (Basic) Screen; or the Treatment Summary Screen. From the Capsulotomy (Basic) Screen, a person can select the following parameters:

Template Name 252

Pattern 254: "Circular" is currently the only pattern option although others can be implemented Diameter 256: capsulotomy circular opening diameter Center Method 258:
"Pupil" uses the identified pupil to center the capsulotomy.
"Limbus" uses the identified limbus to center the capsulotomy.
"Scanned Capsule" uses the data from the ranging subsystem 46 for the anterior and posterior lens surfaces, and the line connecting the centers of the spheres fitted to these surfaces, to center the capsulotomy.
"Custom" allows a user to drag the touchscreen image to the desired location within the safety zone when in the treatment screens. Dragging is not available during capsulotomy planning.
"Maximized" uses the identified pupil to center the capsulotomy and to maximize the capsulotomy diameter.

Figure 33:
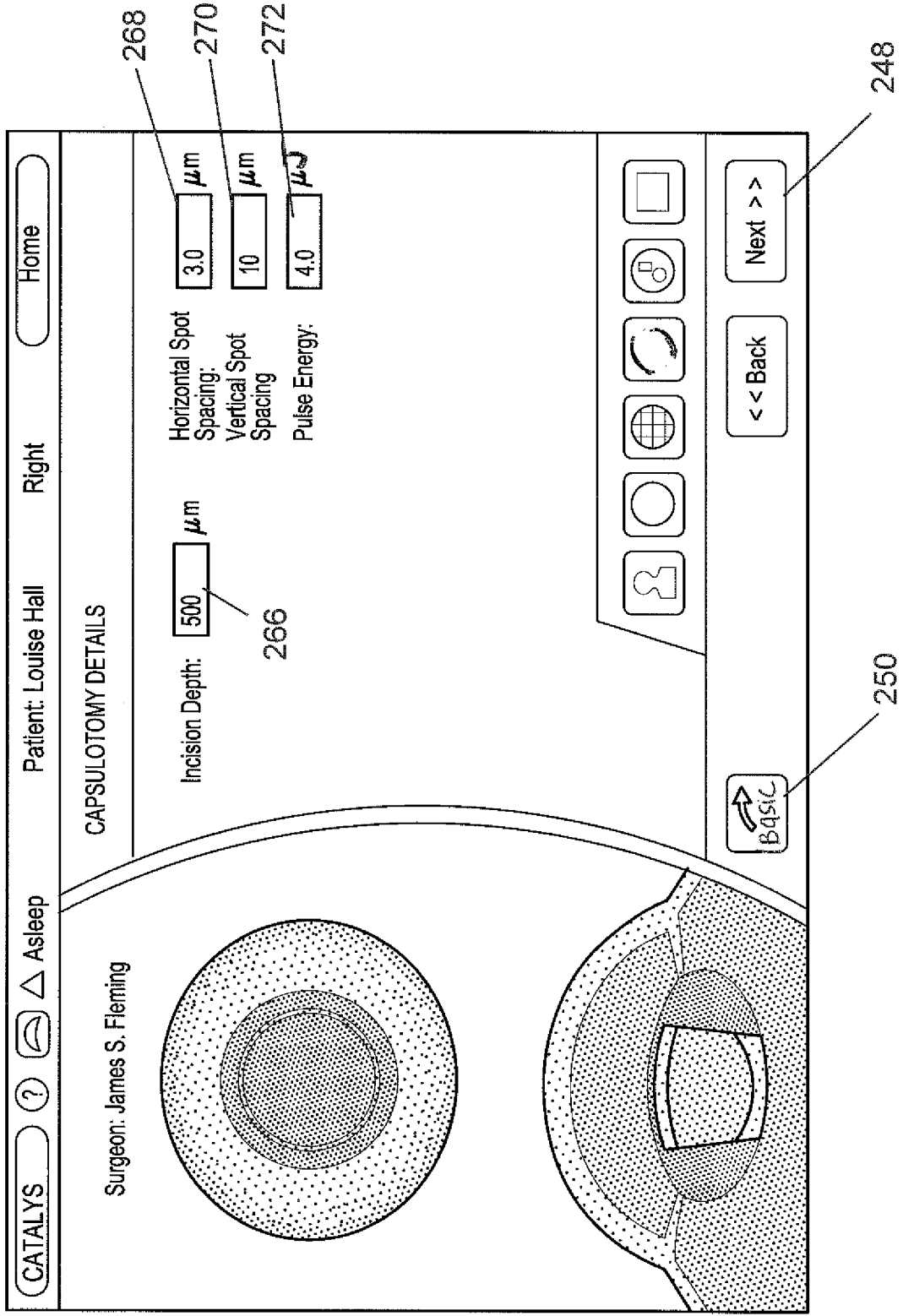

Once valid settings have been selected, the selected diameter 260 displays in the center of an eye model 262, as shown in FIG. 32. The planning screens typically shown an anterior view of the eye model and/or a cross-sectional view of the eye model. Details of the selected incisions are typically shown on the eye model so as to provide the user with a visual representation of the selected treatment parameter relative to a representation of an eye. Pressing the DETAILS button 234 proceeds to the Capsulotomy Details Screen, an example of which is shown in FIG. 33. Pressing the BACK button 226 returns to the Plan a Treatment Screen. Pressing the NEXT button 248 proceeds to the (Basic) Screen for the next treatment in the sequence. If, however, the only treatment selected on the Plan a Treatment Screen is the capsulotomy treatment, pressing the NEXT button 248 on the Capsulotomy (Basic) Screen will return directly to the Treatment Plan Summary Screen. If the HOME button 264 on the Capsulotomy (Basic) Screen is pressed, the current treatment parameters will be saved.

The Capsulotomy Details Screen is used to specify detail parameter values for the capsulotomy incision. To access the Capsulotomy Details Screen, the DETAILS button 234 is pressed on the Capsulotomy (Basic) Screen or the Quick Navigation Bar Capsulotomy Icon on the Lens Fragmentation, Arcuate Incisions, or Cataract Incisions Primary or Sideport(s) Details Screen.

Figure 34:
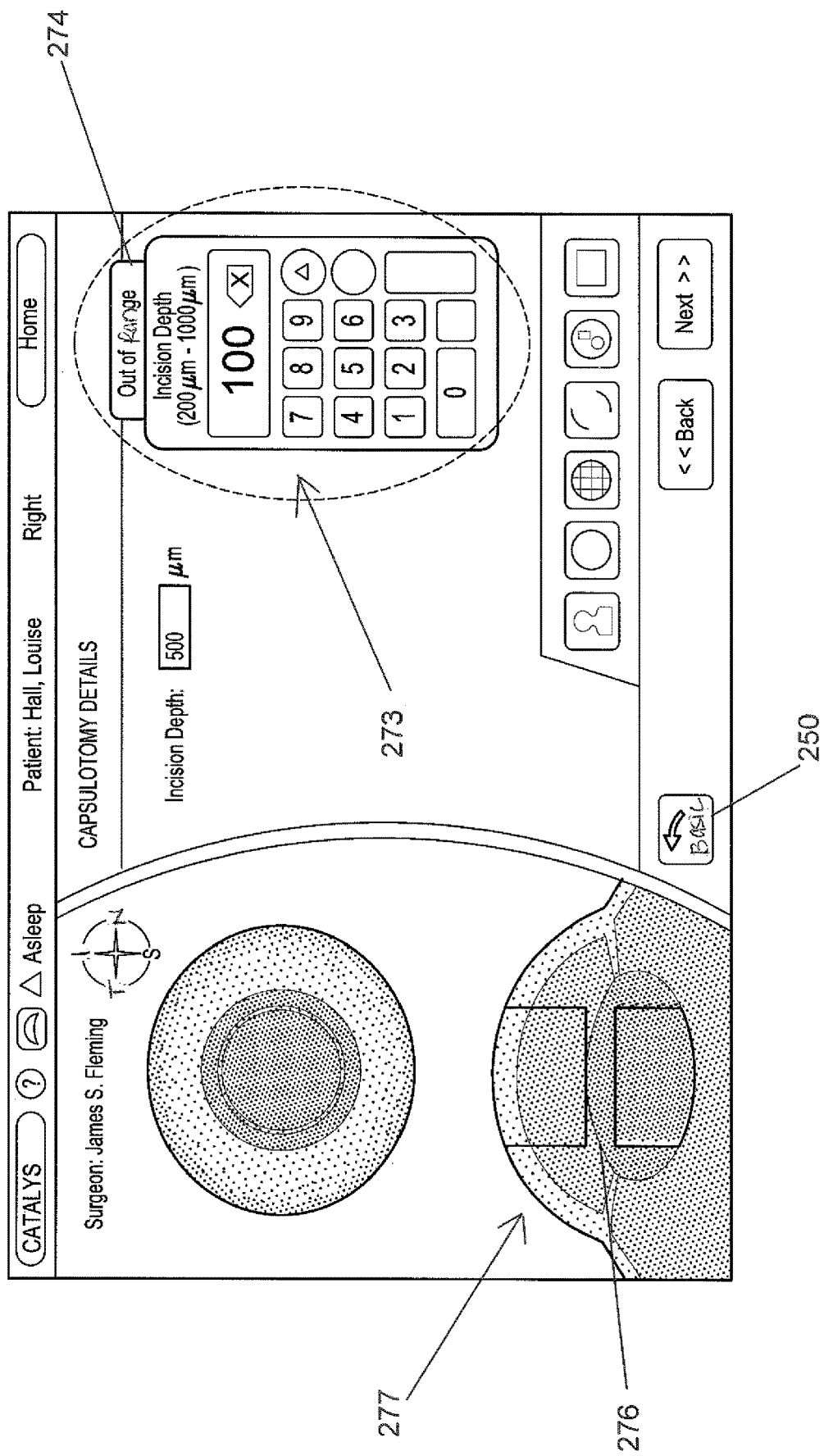

From the Capsulotomy Details Screen, a user can select incision depth 266, horizontal spot spacing 268, vertical spot spacing 270, and pulse energy 272. The incision depth 266 is the axial extent of the capsulotomy cylinder pattern centered on the detected lens anterior surface. The horizontal spot spacing 268 is the lateral spot-to-spot spacing. The vertical spot spacing 270 is the axial spot-to-spot spacing. And the pulse energy 272 is the energy delivered per pulse. FIG. 34 shows an entry key pad 273 that displays for entering incision depth upon selecting incision depth from the Capsulotomy Details Screen. If a parameter value is entered that is outside an acceptable range, an "out of range" error 274 displays as shown in FIG. 34. Once valid settings have been chosen, the incision depth 276 is displayed in the lower eye model 277, as shown in FIG. 34. Pressing the BASIC button 250 returns to the Capsulotomy (Basic) Screen. Then, pressing the BACK button 226 returns to the Plan a Treatment Screen. Alternatively, pressing the NEXT button 248 proceeds to the (Basic) Screen for the next treatment in the sequence. If, however, the only treatment selected on the Plan a Treatment Screen is the capsulotomy treatment, pressing the NEXT button 248 on the Capsulotomy (Basic) Screen will return directly to the Treatment Plan Summary Screen. If the HOME button 264 on the Capsulotomy (Basic) Screen is pressed, the current treatment parameters will be saved.

Figure 35:
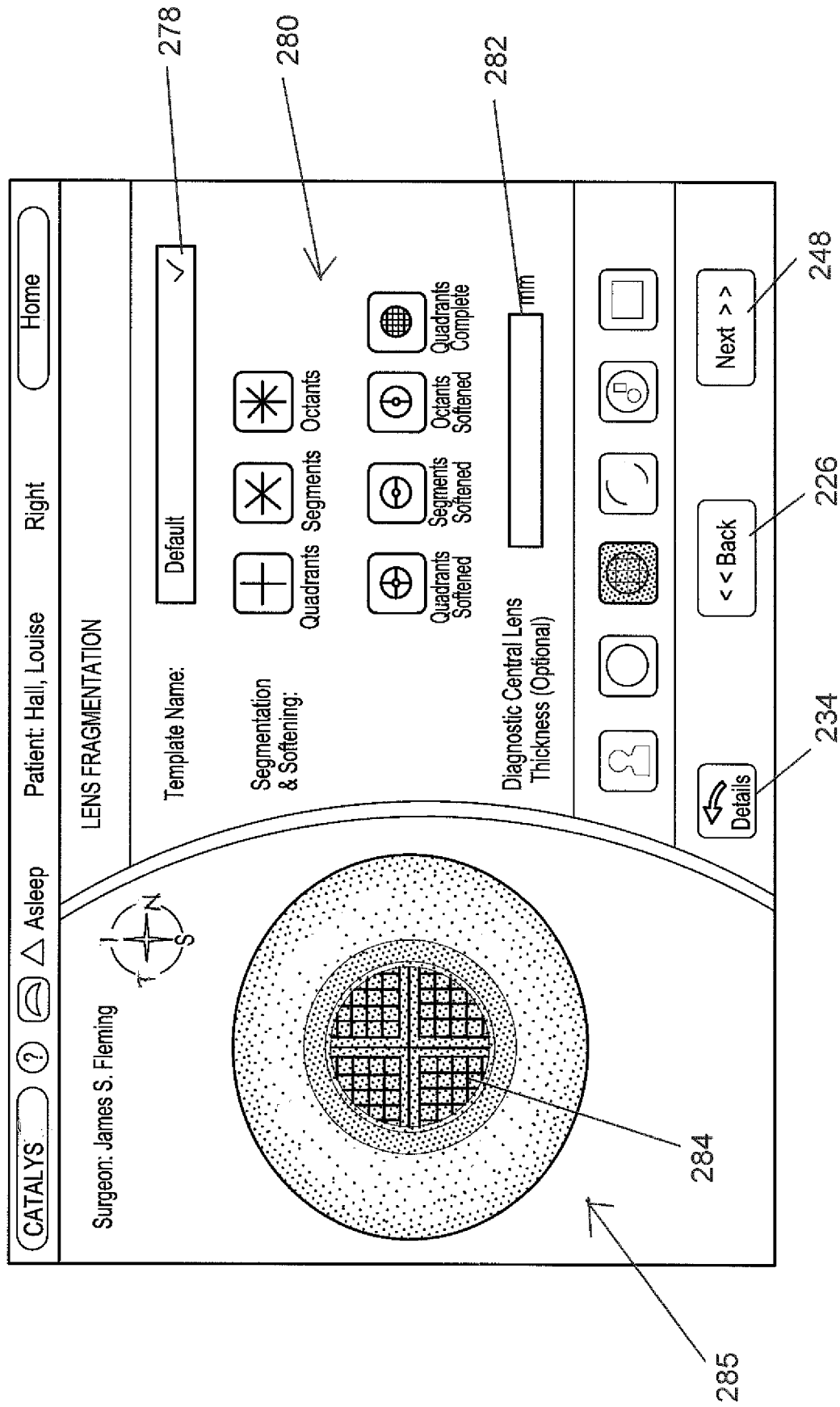

The Lens Fragmentation (Basic) Screen (an example of which is shown in FIG. 35) is used to control the fragmentation of the crystalline lens nucleus. The Lens Fragmentation (Basic) Screen can be accessed in any of the following ways:
  Press the NEXT button 248 on the Capsulotomy (Basic) or Details Screen (if the user selected the capsulotomy treatment) or on the Plan a Treatment Screen (if the user did not select the capsulotomy treatment).
  Press the BASIC button 250 on the Lens Fragmentation Details Screen.
  Select Quick Navigation Bar Lens Fragmentation Icon on the Plan a Treatment Screen; the Capsulotomy, Arcuate Incisions, or Cataract Incisions (Basic) Screen; or the Treatment Summary Screen.

Figure 36:
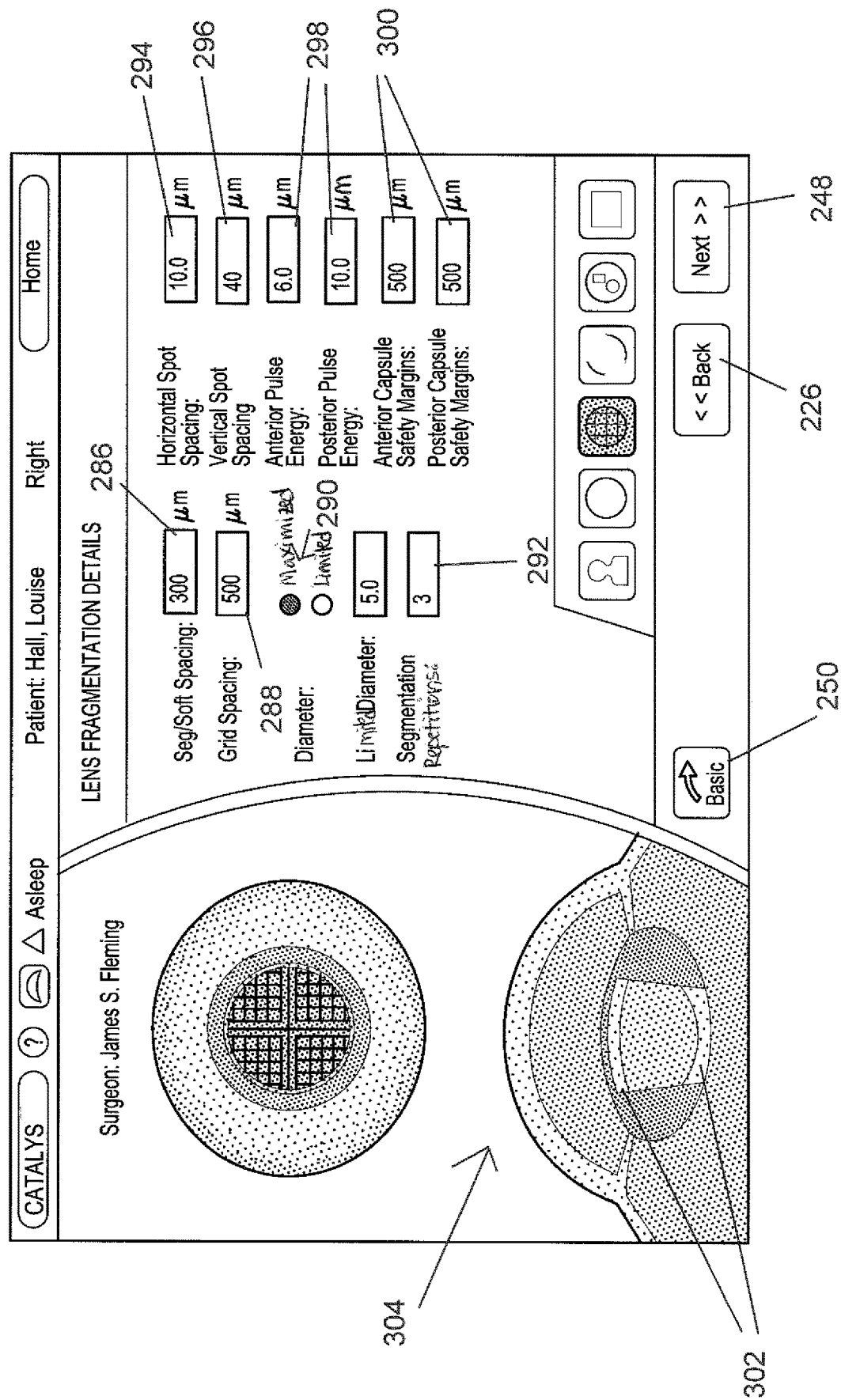

From the Lens Fragmentation (Basic) Screen, a user can select the following parameters:
  Template Name 278
  Segmentation 280: lens fragmentation pattern, with or without softening
    Lens softening adds cross-hatch patterns to the spaces between the lens segments defined in the pattern type selection.
  Diagnostic central lens thickness 282 (optional): thickness of diagnostic lens Once valid settings have been chosen, the selected fragmentation pattern 284 displays in the center of the eye model 285, as shown in FIG. 35. Pressing the DETAILS button 234 proceeds to the Lens Fragmentation Details Screen, an example of which is shown in FIG. 36. Pressing the BACK button 226 returns to the Capsulotomy (Basic) Screen. Pressing the NEXT button 248 proceeds to the Treatment Plan Summary Screen or to the (Basic) Screen for the next treatment in the sequence.

The Lens Fragmentation Details Screen is used to specify detailed parameter values used to control the fragmentation of the lens. To access the Lens Fragmentation Details Screen, the DETAILS button 234 is pressed on the Lens Fragmentation (Basic) Screen or the Quick Navigation Bar Lens Fragmentation icon on the Capsulotomy, Arcuate Incisions, or Cataract Incisions Primary or Sideport(s) Details Screen is pressed. From the Lens Fragmentation Details Screen, a user can select the following parameters:

Seg-Soft Spacing 286: distance between segmentation lines and initial softening cross-hatch pattern lines
  Grid Spacing 288: distance between successive softening cross-hatch pattern lines
  Diameter 290 (Maximized or Limited): diameter for maximum allowed lens fragmentation pattern; if maximized is selected, diameter is given by the detected iris; if limited is selected, size will be given by the smaller of either the detected iris or the limited diameter specified
  Segmentation Repetitions 292: number of times the treatment laser passes over the pattern
  Horizontal Spot Spacing 294: lateral spot-to-spot spacing
  Vertical Spot Spacing 296: axial spot-to-spot spacing
  Anterior/Posterior Capsule Safety Margin 298: safety distances between lens fragmentation incisions and anterior/posterior capsule surfaces
  Anterior/Posterior Pulse Energy 300: system varies pulse energy between these values as pattern is delivered, moving from posterior to anterior Similar to other screens of the GUI, parameter values can be entered by pressing the corresponding portion of the touch-screen control panel 12. Once valid settings have been chosen, anterior and posterior safety zones 302 are displayed in the lower eye model 304, as shown in FIG. 36. Pressing the BASIC button returns to the Lens Fragmentation (Basic) Screen. Pressing the BACK button 226 returns to the (Basic) Screen for the previous treatment in the sequence. Pressing the NEXT button 248 proceeds to the (Basic) Screen for the next treatment in the sequence.

Figure 37:
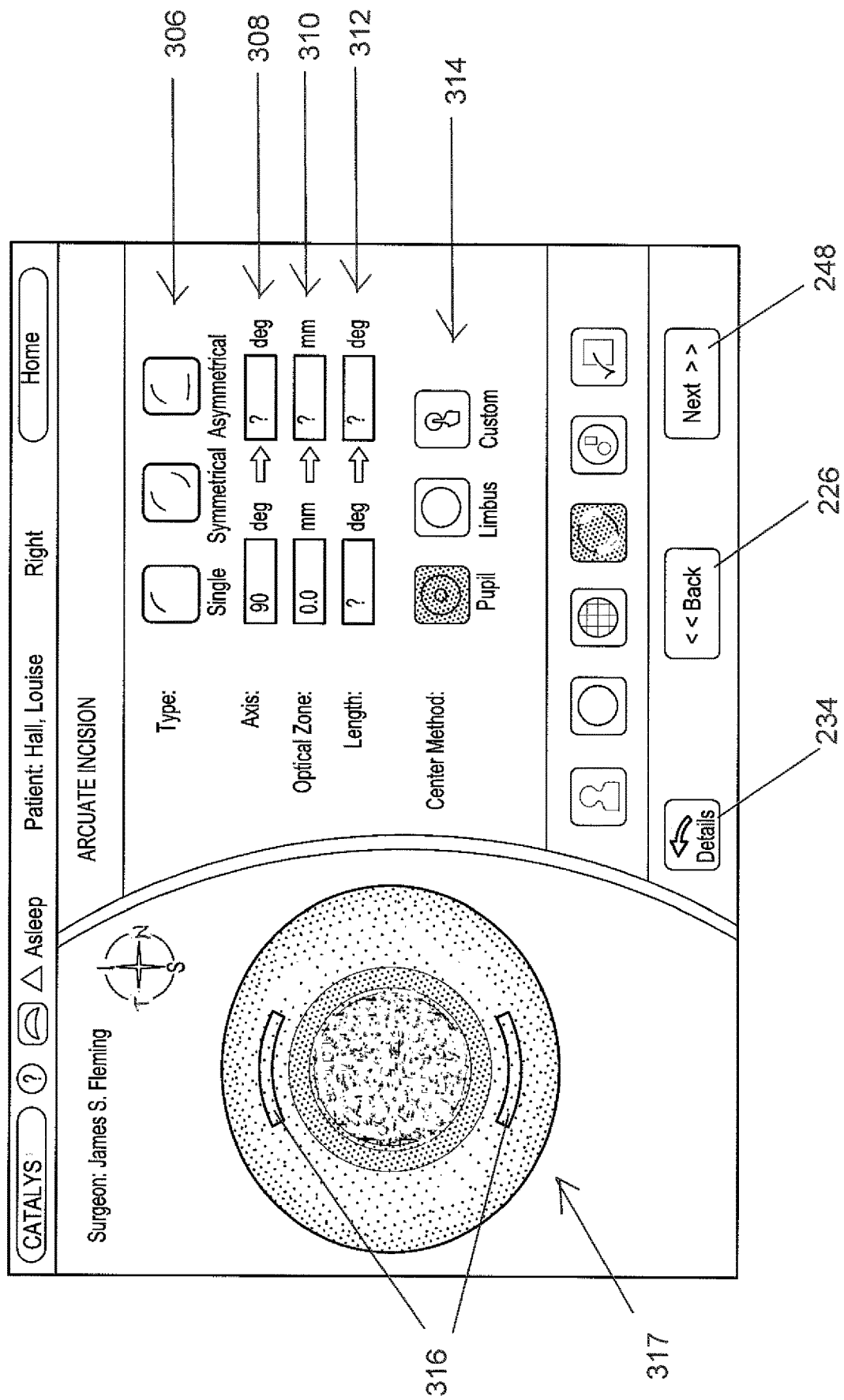

FIG. 37 shows the Arcuate Incisions (Basic) Screen. The Arcuate Incisions (Basic) Screen is used to control the formation of one or more arcuate incisions in the cornea. The Arcuate Incisions (Basic) Screen can be accessed in any of the following ways:
  Pressing the NEXT button 248 on the Lens Fragmentation (Basic) or Details Screen (if the lens fragmentation procedure was selected), on the Capsulotomy (Basic) or Details screen (if the capsulotomy procedure was selected and the lens fragmentation procedure was not selected), or on the Plan a Treatment Screen (if neither of the capsulotomy or lens fragmentation procedures were selected).
  Pressing the (BASIC) button 250 on the Arcuate Incisions Details Screen.
  Selecting the Quick Navigation Bar Arcuate Incisions Icon on the Plan a Treatment Screen; the Capsulotomy, Lens Fragmentation, or Cataract Incisions (Basic) Screen; or the Treatment Summary Screen.

From the Arcuate Incisions (Basic) Screen, a user can select the following parameters:
  Type 306: Single, Symmetric, or Asymmetric
  Axis 308
  Optical Zone 310: twice the radius from the lateral center of the eye (as determined with the user-selected centering method) to the cornea anterior penetrating point of the arcuate incision. In the case of intrastromal arcuate incisions, the optical zone is twice the radius from the center of the eye to the point where the incision would intersect the cornea anterior if the incision were extended.
  Length 312: length of the incision(s)
  Center Method 314:
    "Pupil" uses the identified pupil to center the incision.
    "Limbus" uses the identified limbus to center the incision.

"Custom" allows the user to drag the touchscreen image to the desired location within the safety zone when in the treatment screens. Dragging is not available during arcuate incision planning.

Once valid settings have been chosen, the selected arcuate incisions pattern 316 displays in the center of the eye model 317, as shown in FIG. 37. Pressing the DETAILS button 234 proceeds to the Arcuate Incisions Details Screen, an example of which is shown in FIG. 34. Pressing the BACK button 226 returns to the (Basic) Screen for the previous procedure in the sequence. Pressing the NEXT button 248 proceeds to the (Basic) Screen for the next procedure in the sequence.

To access the Arcuate Incisions Details Screen (example shown in FIG. 38), the DETAILS button 234 on the Arcuate Incisions (Basic) Screen is pressed or the Quick Navigation Bar Arcuate Incisions Icon on the Capsulotomy, Lens Fragmentation, or Cataract Incisions Primary or Sideport(s) Details Screen is pressed. From the Arcuate Incisions Details Screen, a user can select the following parameters:
  Penetration Type 318: Anterior Penetrating or Intrastromal
  Depth Unit 320: Percent or Microns
  Uncut Anterior/Posterior Percentage 322
  Side Cut Angle 324: angle at which incision is made to cornea
  Horizontal Spot Spacing 326: lateral spot-to-spot spacing
  Vertical Spot Spacing 328: axial spot-to-spot spacing
  Pulse Energy 330: energy delivered per pulse
  Anterior/Central Line Density 332
  Anterior Line Distance 334

Figure 38:
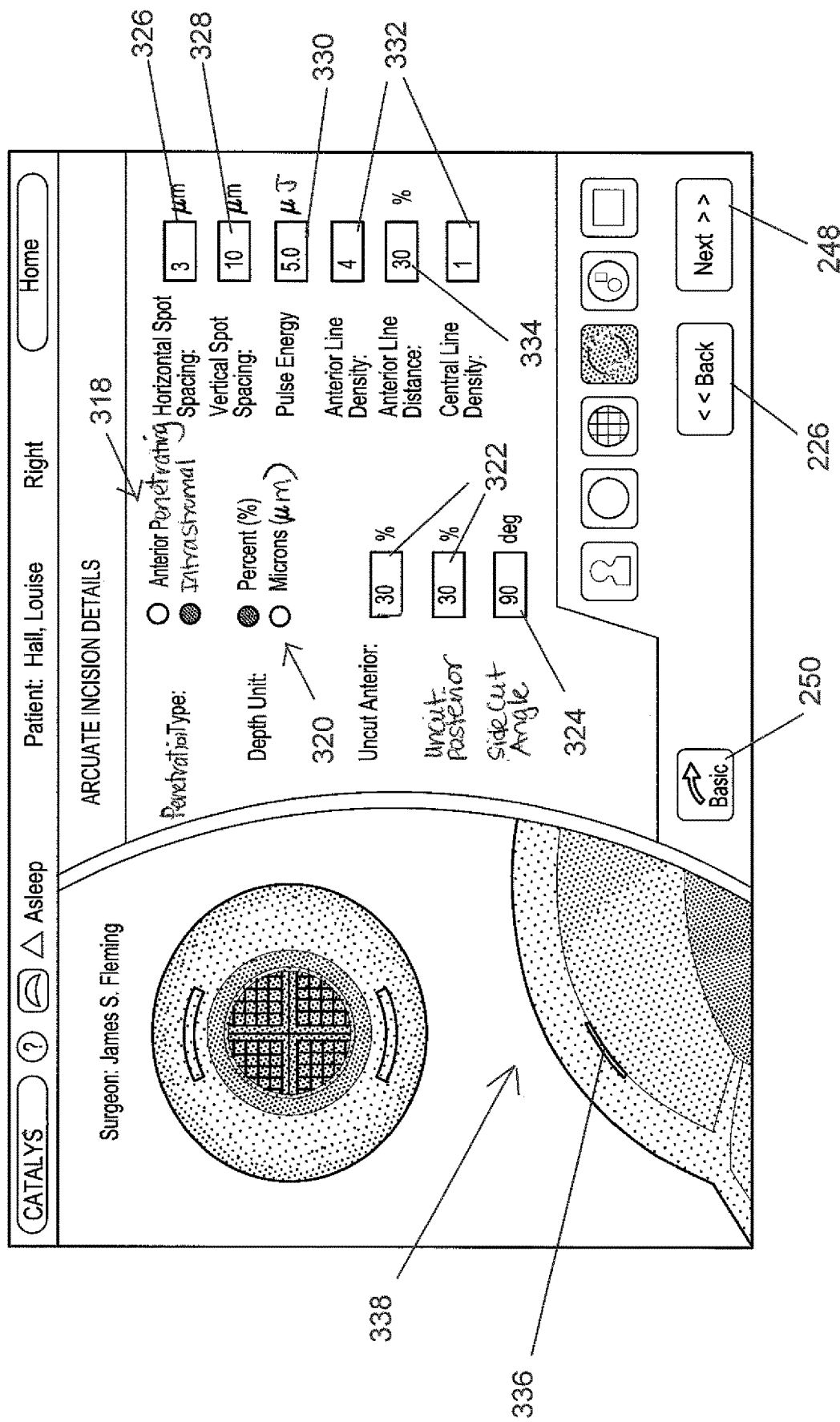

Once valid settings have been chosen, the side cut angle 336 and uncut anterior and posterior percentages are displayed in the lower eye model 338, as shown in FIG. 38. Pressing the BASIC button returns to the Arcuate Incisions (Basic) Screen. Pressing the BACK button 226 returns to the (Basic) Screen for the previous procedure in the sequence. Pressing the NEXT button 248 proceeds to the (Basic) Screen for the next procedure in the sequence.

Figure 39:
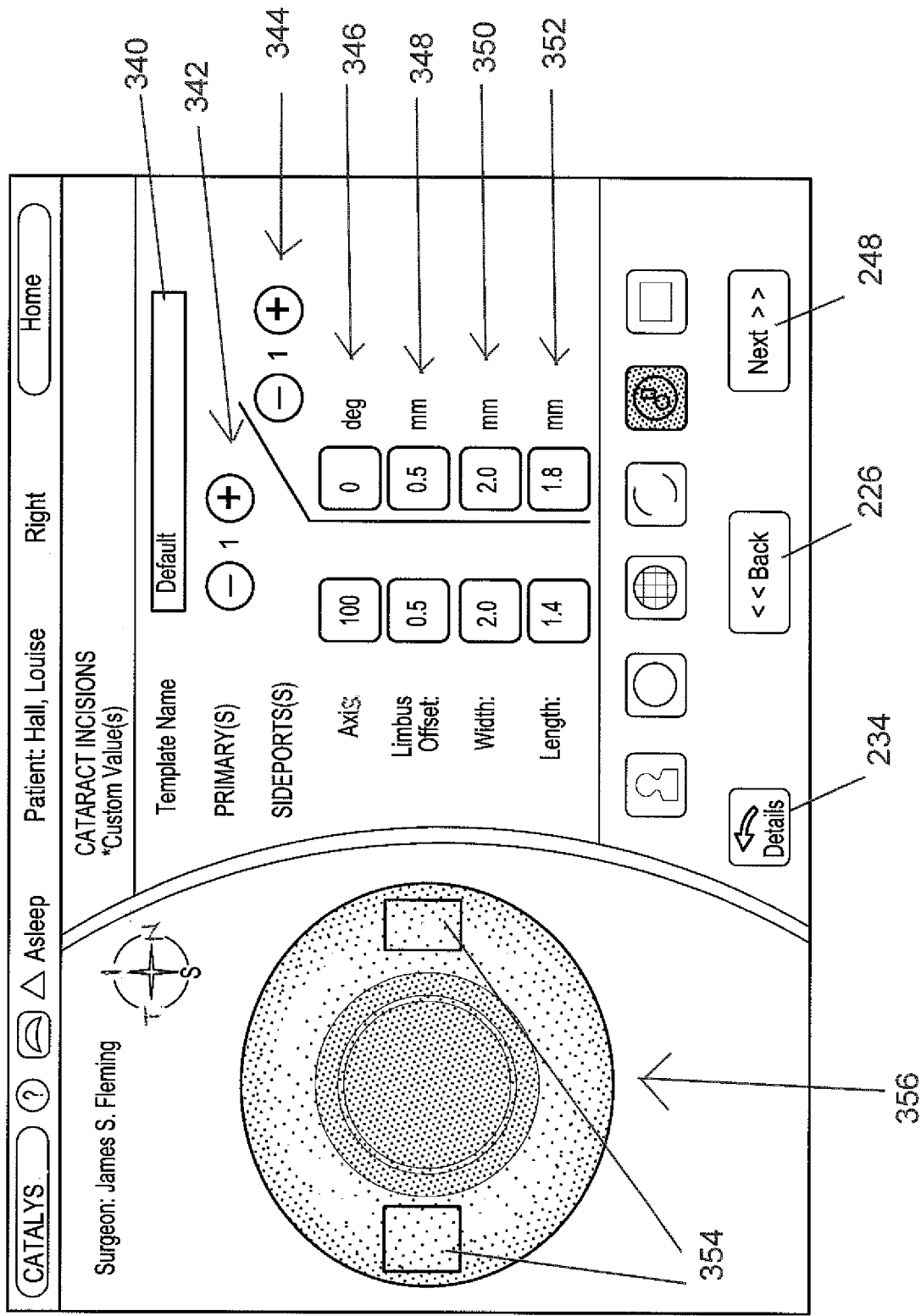

FIG. 39 shows an example of a Cataract Incisions (Basic) Screen. The Cataract Incisions (Basic) Screen is used to control the formation of access incisions in the cornea through which cataract surgical instruments are inserted to gain access to remove the fragmented crystalline lens nucleus. The Cataract Incisions (Basic) Screen can be accessed in any of the following ways:
  By pressing the NEXT button 248 on the Arcuate Incisions (Basic) or Details Screen (if the arcuate incisions procedure has been selected), on the Lens Fragmentation (Basic) or Details Screen (if the lens fragmentation procedure has been selected and the arcuate incisions procedure has not been selected), on the Capsulotomy (Basic) or Details screen (if the capsulotomy procedure has been selected and but the lens fragmentation or arcuate incisions procedure has not been selected), or on the Plan a Treatment Screen (if the capsulotomy, lens fragmentation, or arcuate incisions procedure has not been selected).
  By press the BASIC button 250 on any of the Cataract Incisions Details Screens.
  By select the Quick Navigation Bar Cataract Incisions Icon on the Plan a Treatment Screen; the Capsulotomy, Lens Fragmentation, or Arcuate Incisions (Basic) Screen; or the Treatment Summary Screen.

Figure 40:
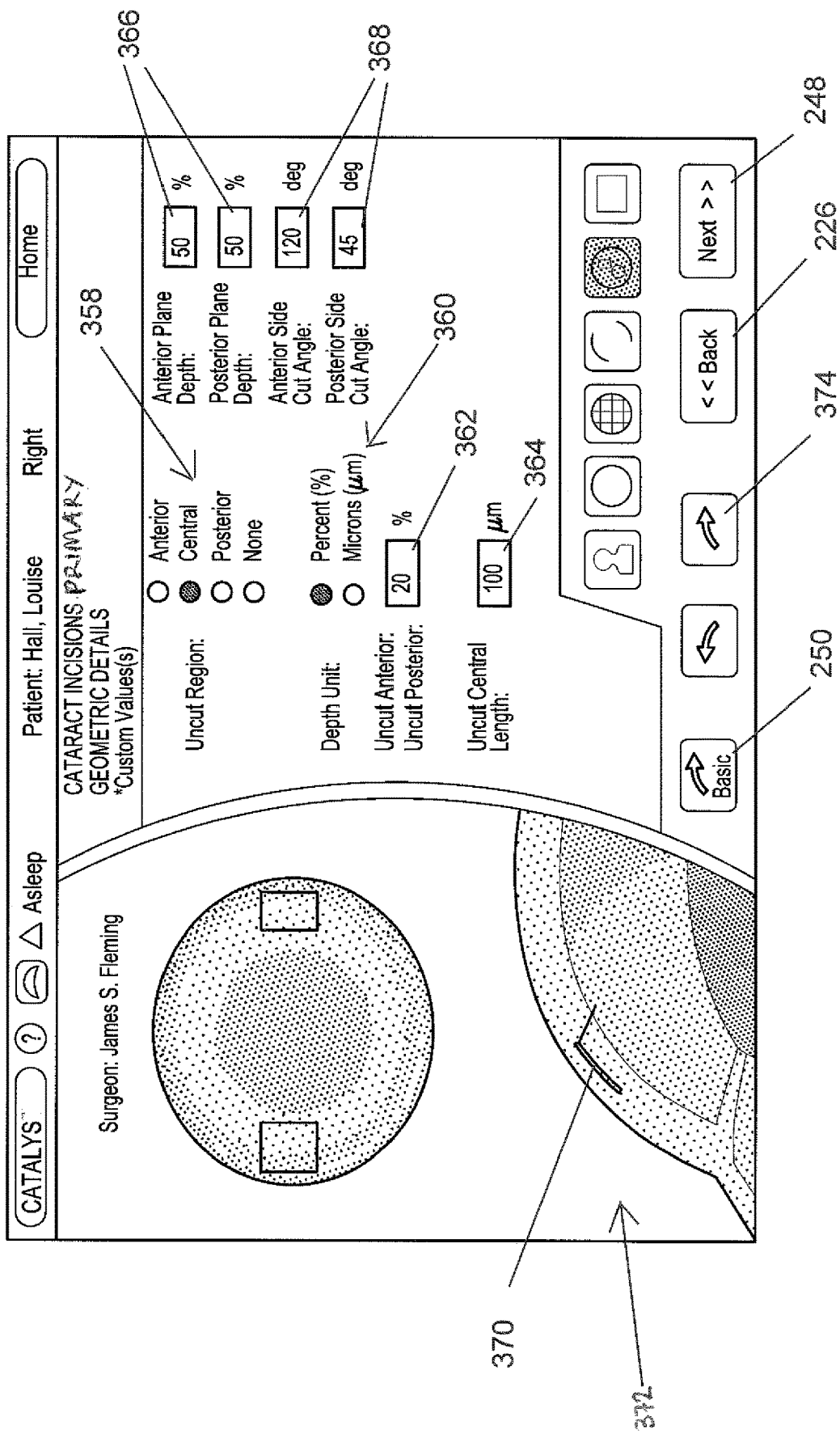

From the Cataract Incisions (Basic) Screen, a user can select the following parameters:
  Template Name 340
  Number of Primary Incisions 342 (1 or 2)
  Number of Sideport Incisions 344 (0 to 5)
  Axis of Primary/Sideport Incision(s) 346
  Limbus Offset of Primary/Sideport Incision(s) 348
  Width of Primary/Sideport Incision(s) 350: width of the cut from an en face view
  Length of Primary/Sideport Incision(s) 352: length of the cut from an en face view Once valid settings have been chosen, the selected cataract incision pattern 354 displays in the center of the eye model 356, as shown in FIG. 39. Pressing the DETAILS button 234 proceeds to the Cataract Incisions Primary Geometric Details Screen, an example of which is shown in FIG. 40. Pressing the BACK button 226 returns to the (Basic) Screen for the previous procedure in the sequence. Pressing the NEXT button 248 proceeds to the Treatment Plan Summary Screen.

To access the Cataract Incisions Primary Geometric Details Screens, the DETAILS button 234 on the Cataract Incisions (Basic) Screen is pressed or the Quick Navigation Bar Cataract Incisions Icon on the Capsulotomy, Lens Fragmentation, or Arcuate Incisions Details Screen is selected. From the Cataract Incisions Primary Geometric Details Screen, a person can select the following parameters:
  Uncut Region 358: Anterior, Central, Posterior, or None
  Depth Unit 360: Percent or Microns
  Uncut Anterior/Posterior Percentage 362
  Uncut Central Length 364
  Anterior/Posterior Plane Depth 366
  Anterior/Posterior Side Cut Angle 368

Figure 41:
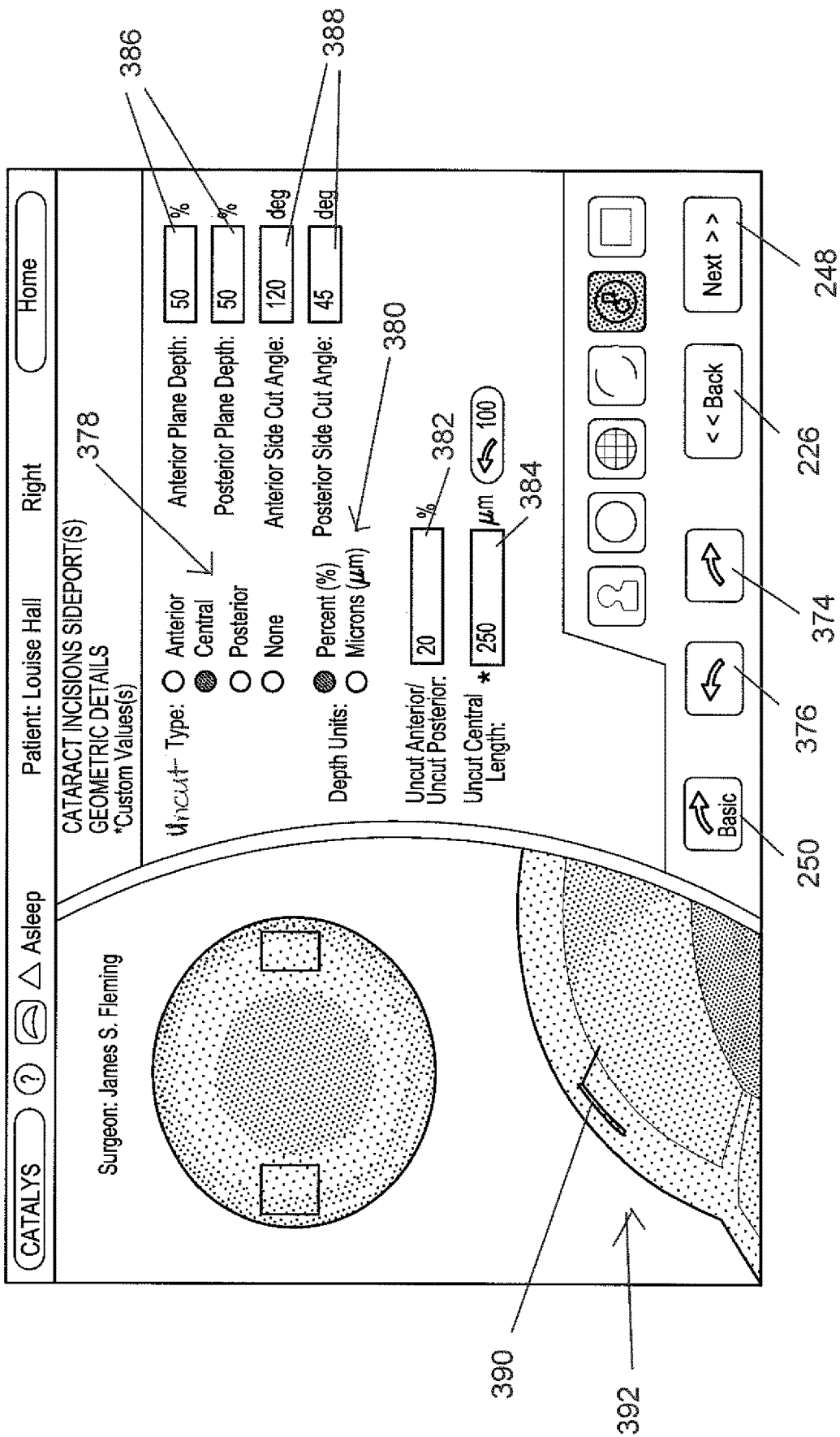

Once valid settings have been chosen, the anterior and posterior side cut angles and uncut central length 370 are displayed in the lower eye model 372, as shown in FIG. 40. Pressing the ▓ button 374 proceeds to the Cataract Incisions Sideport(s) Geometric Details Screen, an example of which is shown in FIG. 41. Pressing the BASIC button 250 returns to the Cataract Incisions (Basic) Screen. Pressing the BACK button 226 returns to the (Basic) Screen for the previous procedure in the sequence. Pressing the NEXT button 248 proceeds to the Treatment Plan Summary Screen.

To access the Cataract Incisions Sideport(s) Geometric Details Screens, the ▓ button 374 on the Cataract Incisions Primary Geometric Details Screen or the ▓ button 376 on the Cataract Incisions Primary Laser Details Screen is pressed. From the Cataract Incisions Sideport(s) Geometric Details Screen, a person can select the following parameters:
  Uncut Type 378: Anterior, Central, Posterior, or None
  Depth Unit 380: Percent or Microns
  Uncut Anterior/Posterior Percentage 382
  Uncut Central Length 384
  Anterior/Posterior Plane Depth 386
  Anterior/Posterior Side Cut Angle 388

Figure 42:
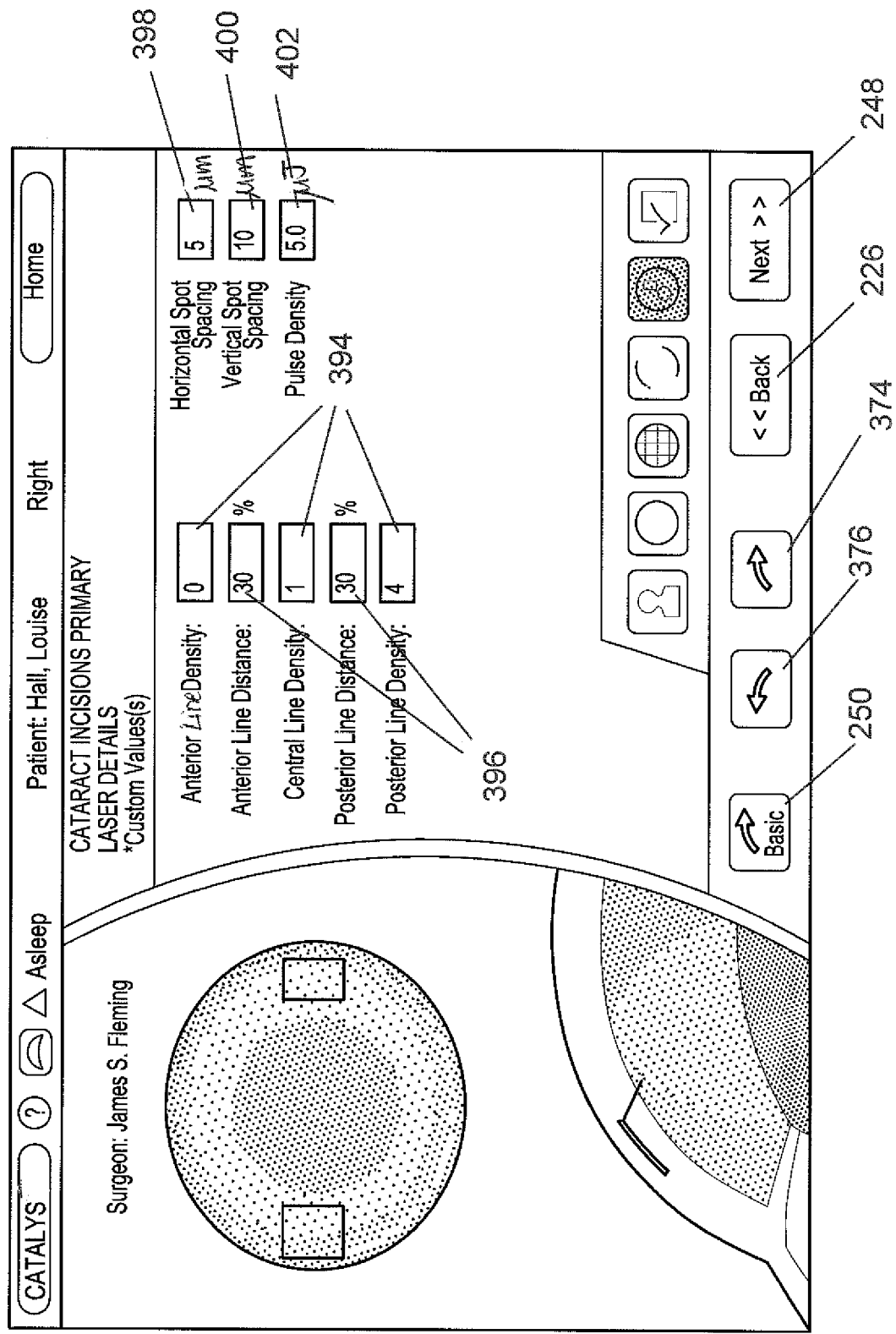

Once valid settings have been chosen, the anterior and posterior side cut angles and uncut central length 390 are displayed in the lower eye model 392, as shown in FIG. 41. Pressing the ▓ button 374 proceeds to Cataract Incisions Primary Laser Details Screen, an example of which is shown in FIG. 42. Pressing the ▓ button 376 returns to the Cataract Incisions Primary Geometric Details Screen. Pressing the BASIC button 250 returns to the Cataract Incisions (Basic) Screen. Pressing the BACK button 226 returns to the (Basic) Screen for the previous procedure in the sequence. Pressing the NEXT button 248 proceeds to the Treatment Plan Summary Screen.

Figure 43:
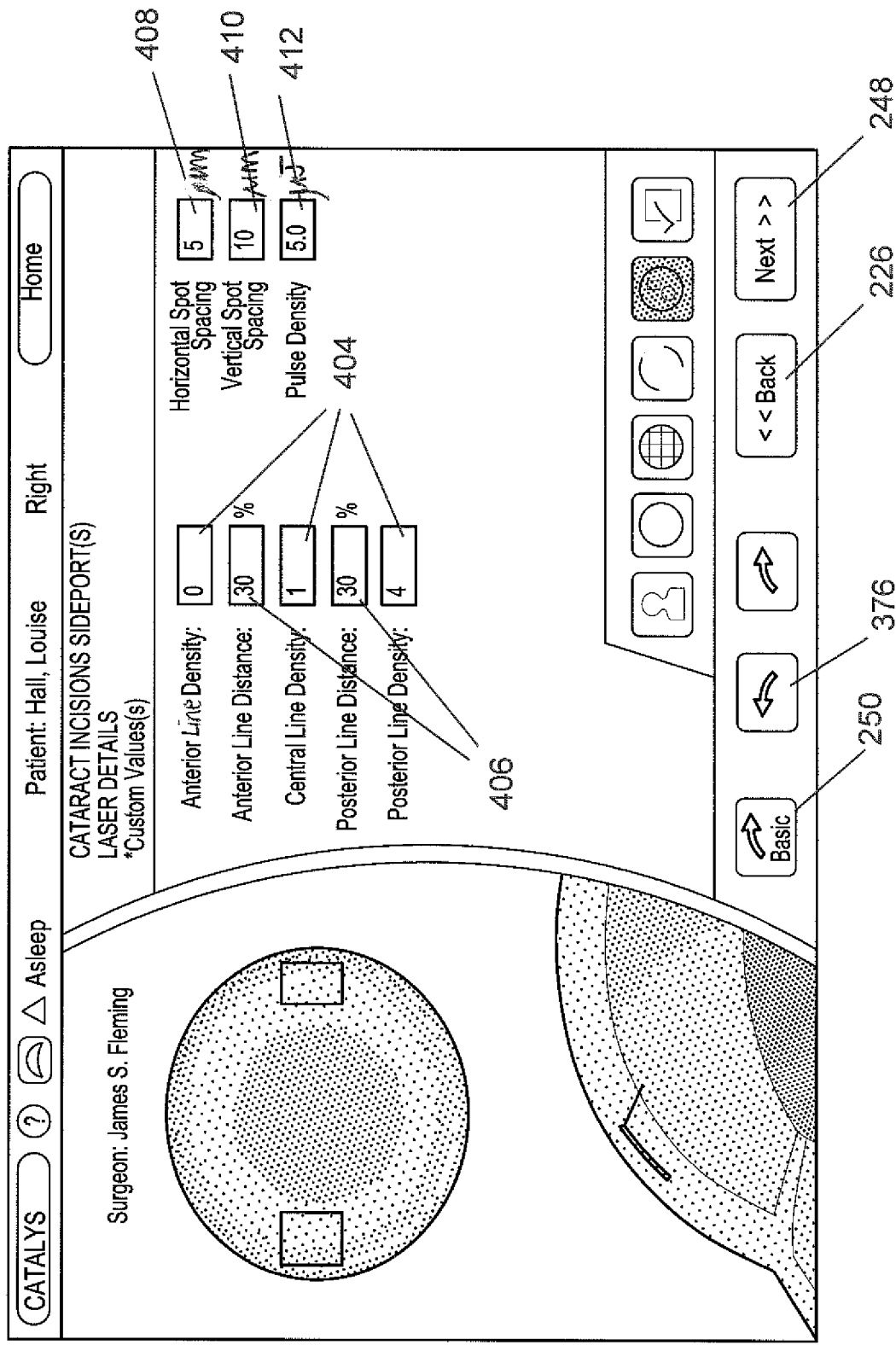

To access the Cataract Incisions Primary Laser Details Screens, the ▓ button 374 on the Cataract Incisions Sideport(s) Geometric Details Screen or the ▓ button 376 on the Cataract Incisions Sideport(s) Laser Details Screen is pressed. From the Cataract Incisions Primary Laser Details Screen, a person can select the following parameters:

Anterior/Central/Posterior Line Density 394
Anterior/Posterior Line Distance 396
Horizontal Spot Spacing 398: lateral spot-to-spot spacing
Vertical Spot Spacing 400: axial spot-to-spot spacing
Pulse Energy 402: energy delivered per pulse Pressing the  button 374 proceeds to Cataract Incisions Sideport(s) Laser Details Screen, an example of which is shown in FIG. 43. Pressing the  button 376 returns to the Cataract Incisions Sideport(s) Geometric Details Screen. Pressing the BASIC button 250 returns to the Cataract Incisions (Basic) Screen. Pressing the BACK button 226 returns to the (Basic) Screen for the previous procedure in the sequence. Pressing the NEXT button 248 proceeds to the Treatment Plan Summary Screen.

To access the Cataract Incisions Sideport(s) Laser Details Screens, the  button 374 on the Cataract Incisions Primary Laser Details Screen is pressed. From the Cataract Incisions Sideport(s) Laser Details Screen, a person can select the following parameters:

Anterior/Central/Posterior Line Density 404
Anterior/Posterior Line Distance 406
Horizontal Spot Spacing 408: lateral spot-to-spot spacing
Vertical Spot Spacing 410: axial spot-to-spot spacing
Pulse Energy 412: energy delivered per pulse Pressing the  button 376 returns to the Cataract Incisions Primary Laser Details Screen. Pressing the BASIC button 250 returns to the Cataract Incisions (Basic) Screen. Pressing the BACK button returns 226 to the (Basic) Screen for the previous procedure in the sequence. Pressing the NEXT button 248 proceeds to the Treatment Plan Summary Screen.

Figure 44:
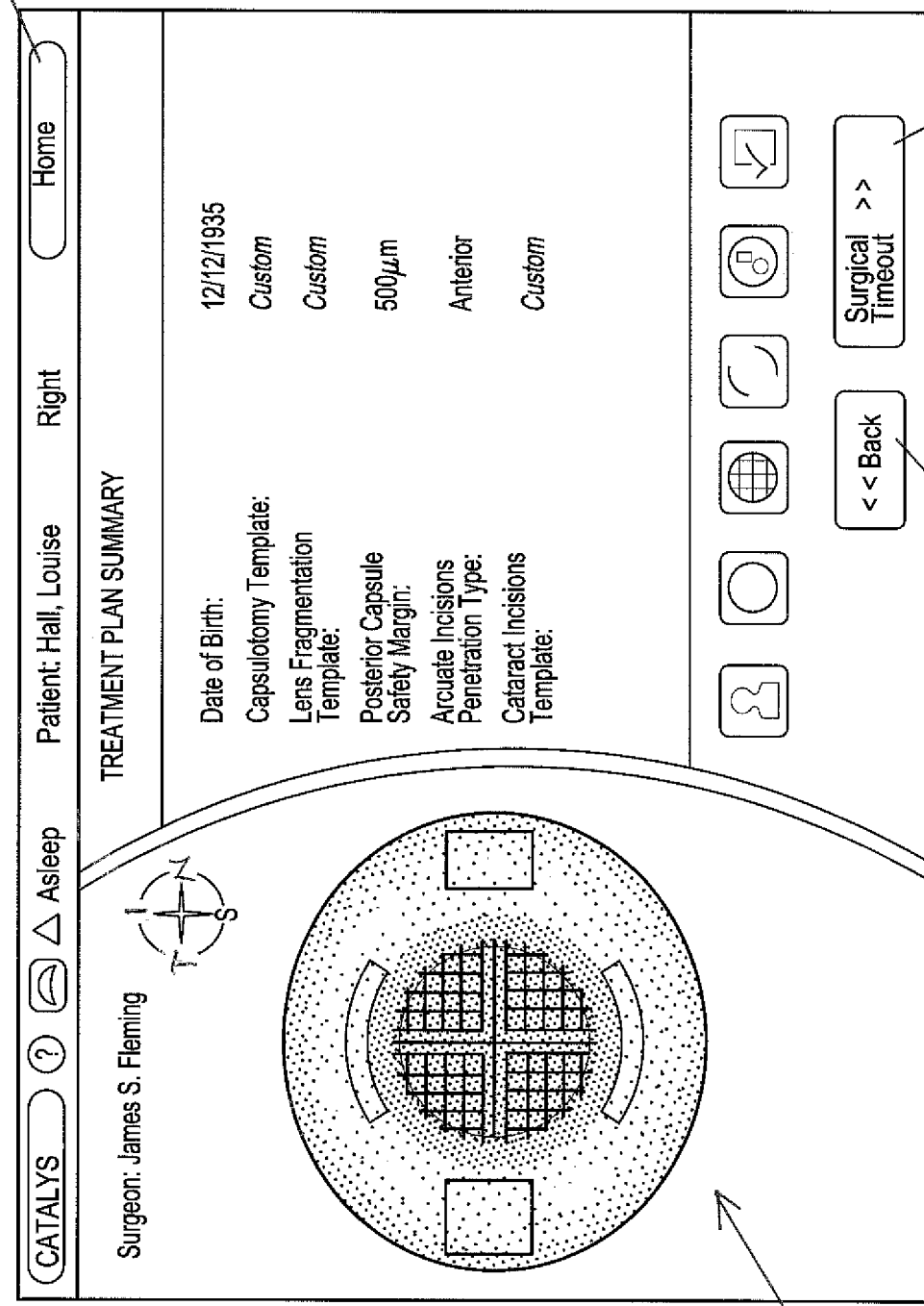

After the desired treatment parameters have been selected, pressing the NEXT button 248 on the (Basic) or Details Screen for the last treatment in the sequence or pressing the Quick Navigation Bar Treatment Summary Icon on the Patient Info, Capsulotomy, Lens Fragmentation, Arcuate Incisions or Cataract Incisions Screen proceeds to the Treatment Plan Summary Screen, an example of which is shown in FIG. 44. The Treatment Plan Summary Screen provides an overview of the current treatment plan, including a graphical representation 414 of the selected treatment parameters.

After verifying the treatment plan summary, pressing the HOME button 416 returns to the Home Screen. To make changes to the treatment plan, pressing the BACK button 226 returns to the (Basic) Screen for the last treatment in the sequence, or pressing the Quick Navigation Bar icon for the desired treatment returns to the (Basic) Screen for that treatment.

Figure 45:
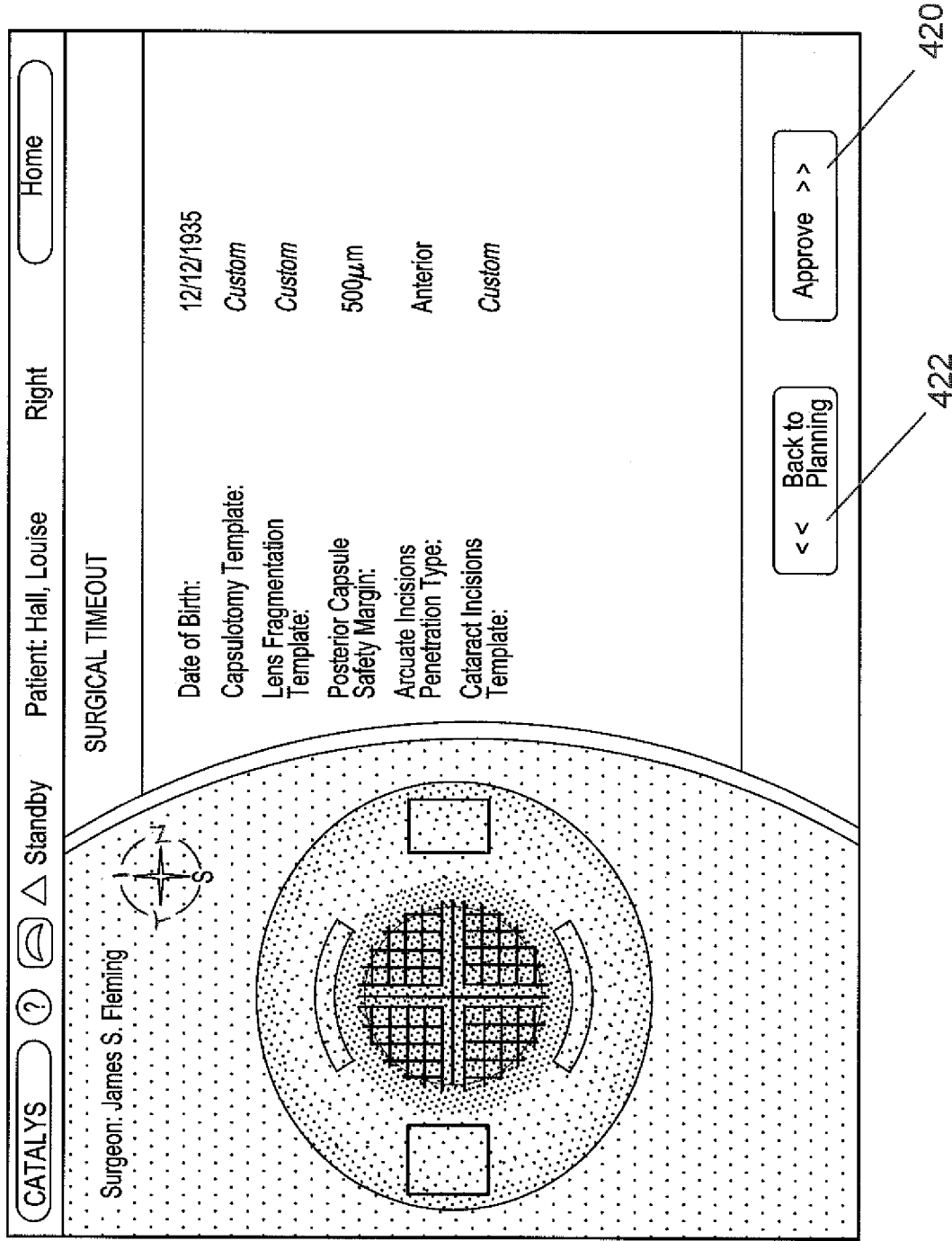

FIG. 45 shows an example Surgical Timeout Screen. After selecting a treatment plan from the Home Screen and pressing the SURGICAL TIMEOUT button 418 on the Treatment Summary Screen, the Surgical Timeout Screen displays. The Surgical Timeout Screen provides a opportunity to verify that the patient details and treatment parameters are correct. After verifying that the patient details and treatment parameters are correct, pressing the APPROVE button 420 proceeds to patient docking screens. If any information on the Surgical Timeout Screen is incorrect, pressing the Home button returns to the Home Screen. Alternatively, the BACK TO PLANNING 422 button can be pressed to edit the Treatment Plan.

Figure 46:
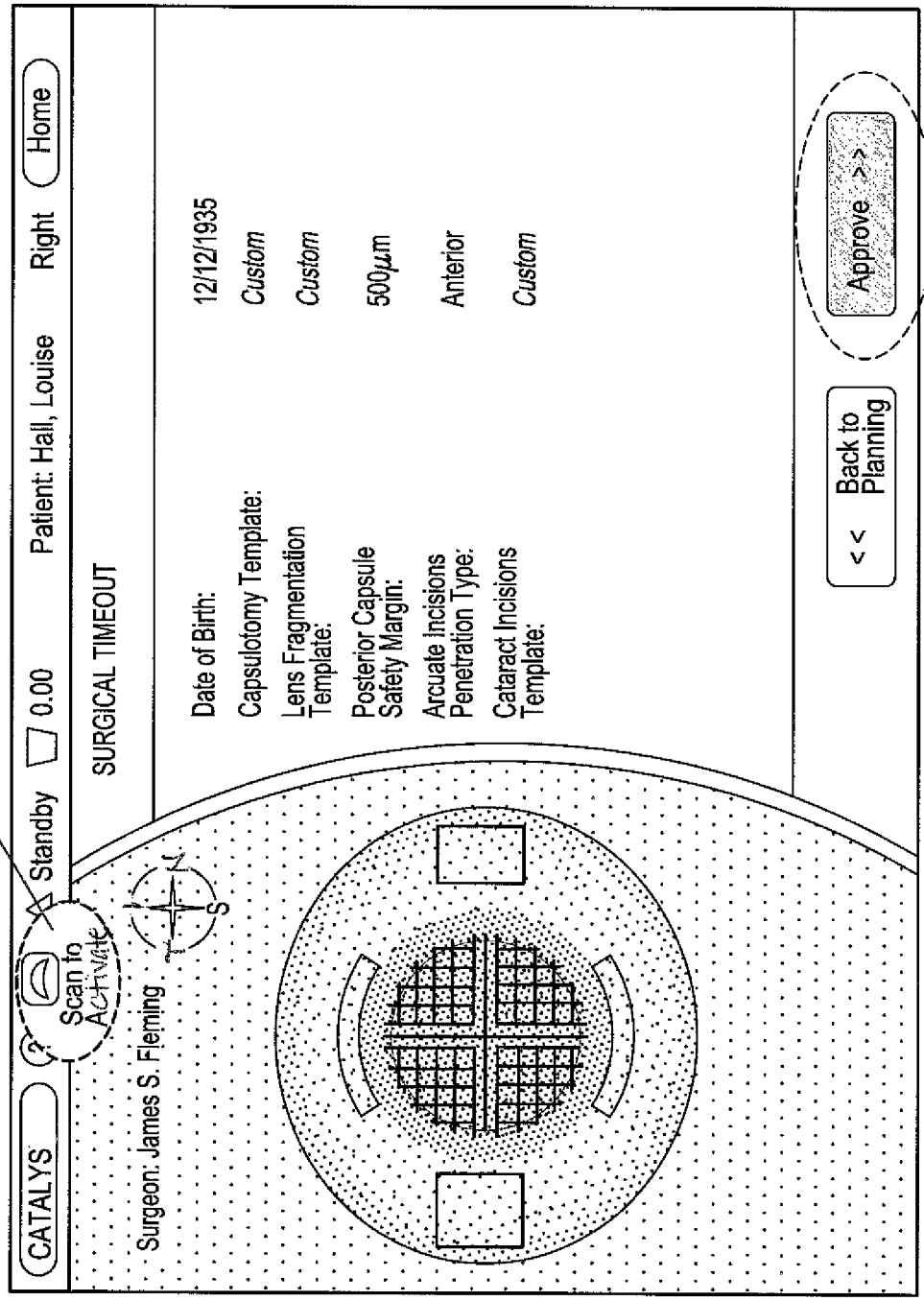

In many embodiments, the laser eye surgery system 2 is configured to require authorization for a treatment before performing the treatment. In many embodiments, the patient interface 52 includes single use components that are replaced prior to each treatment. Such single use components can include an RFID activation tag that is scanned via a suitable RFID reader, such as the patient interface radio frequency identification (RFID) reader 20. Other suitable known activation approaches can also be used, such as known activation approaches using network communication. The activation tag included with the single use patient interface components can be scanned before enabling proceeding to the patient docking screens. If the activation tag has not been scanned, "Scan to Activate" 424 displays at the top of the screen and the APPROVE button 420 is disabled, as shown in FIG. 46.

Figure 47:
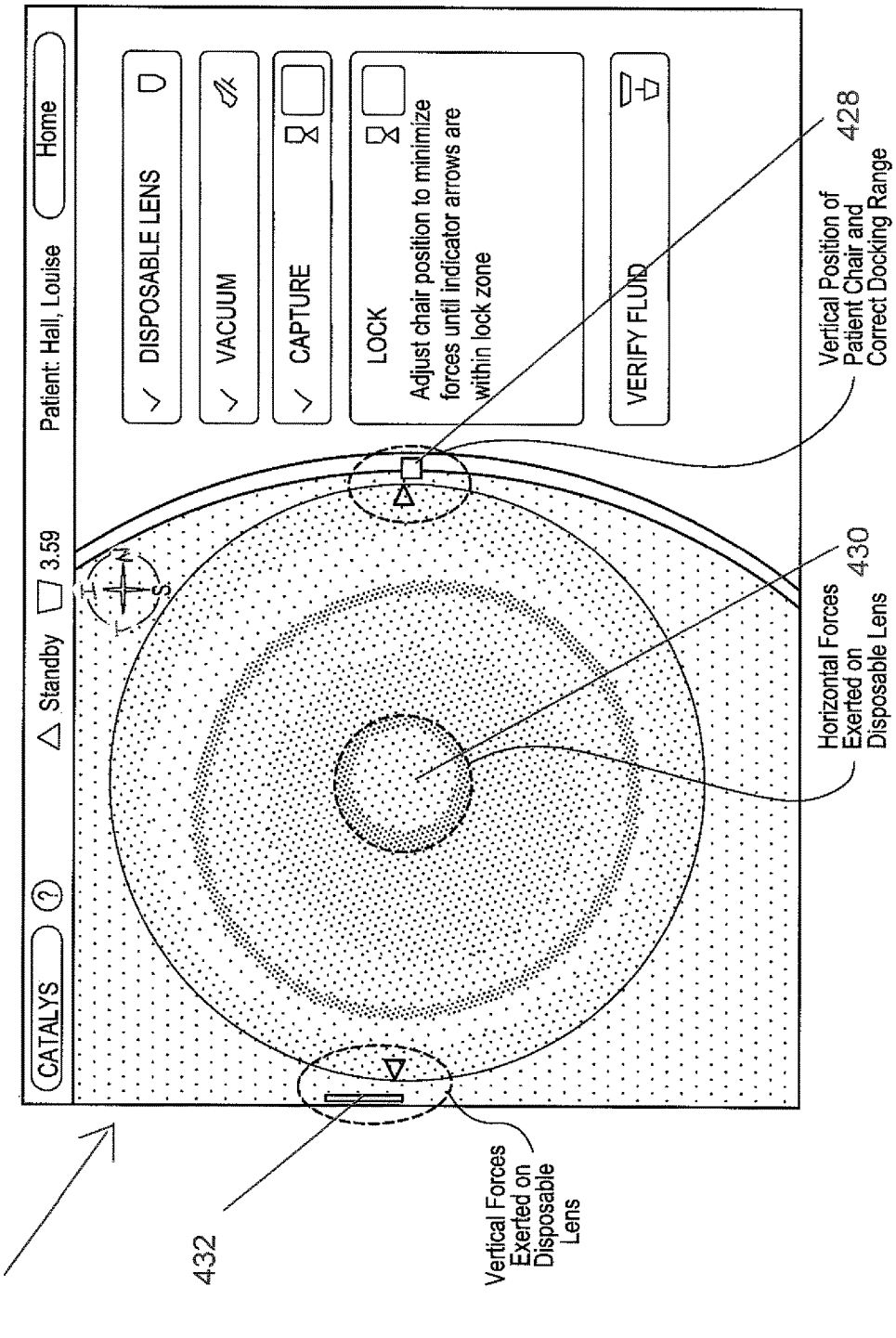

After verifying the information on the Surgical Timeout Screen, scanning the activation tag included with the single use patient interface components, and pressing the APPROVE button 420, the patient docking screens guide the user through the patient docking procedure. The patient docking screens, an example of which is shown in FIG. 47, display live video of the patient's eye 426 on the left side of the screen and display prompts for each step of the docking process with instructions on the right side of the screen. Also displayed on the left side of the screen, overlaid on top of the video, are three indicators that are used to aid in the docking process. The arrow and acceptable vertical zone 428 on the right side of the video indicate the vertical position of the patient chair and when it is in the correct range for certain steps of the docking process. The line centered on top of the video and the different colored zones 430, which change depending on the current step of the docking process, indicate the horizontal forces being exerted on the disposable lens. The arrow on the left of the video and the different colored zones 432, which change depending on the current step of the docking process, indicate the vertical forces being exerted on the disposable lens.

Figure 48:
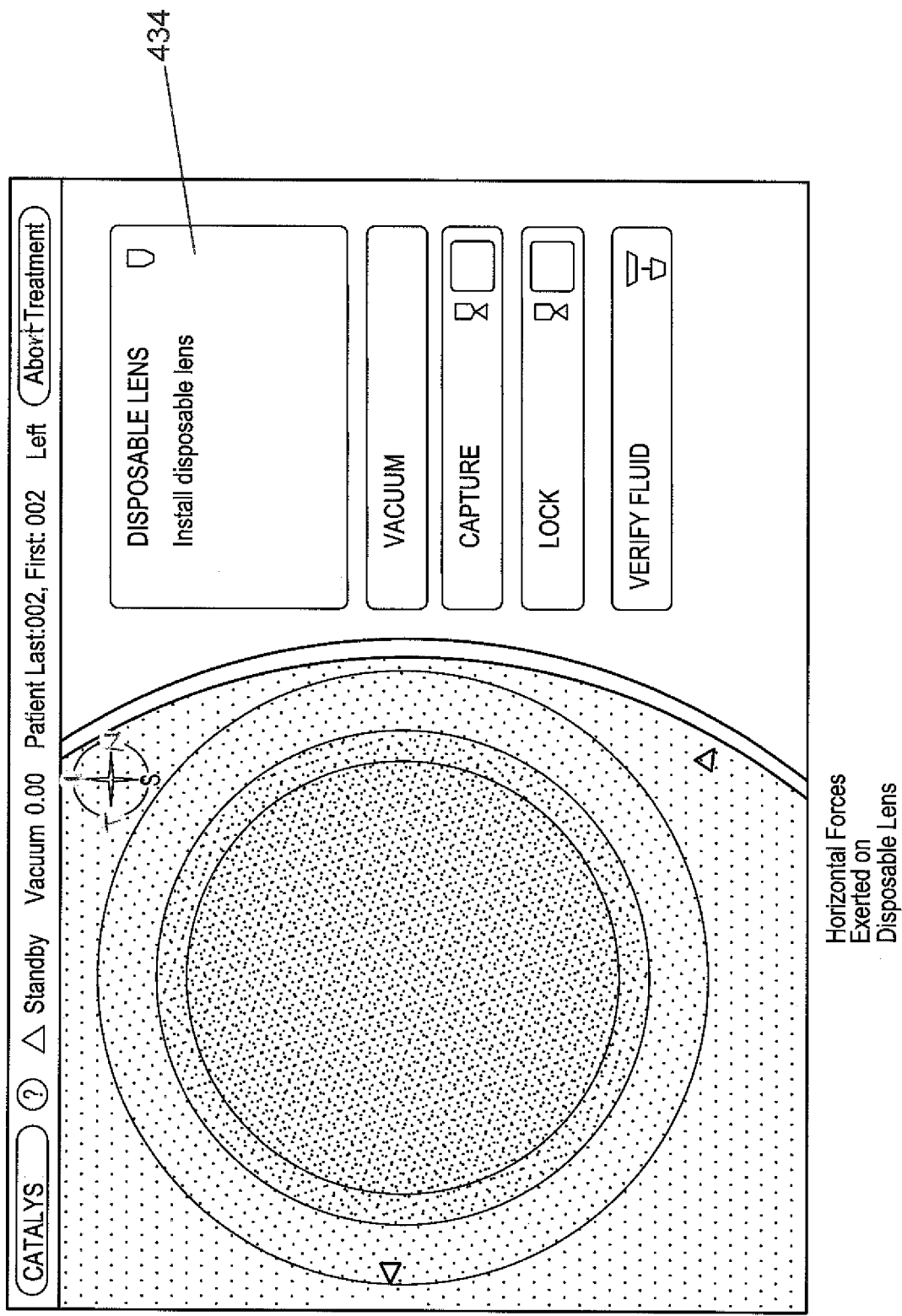
Figure 49:
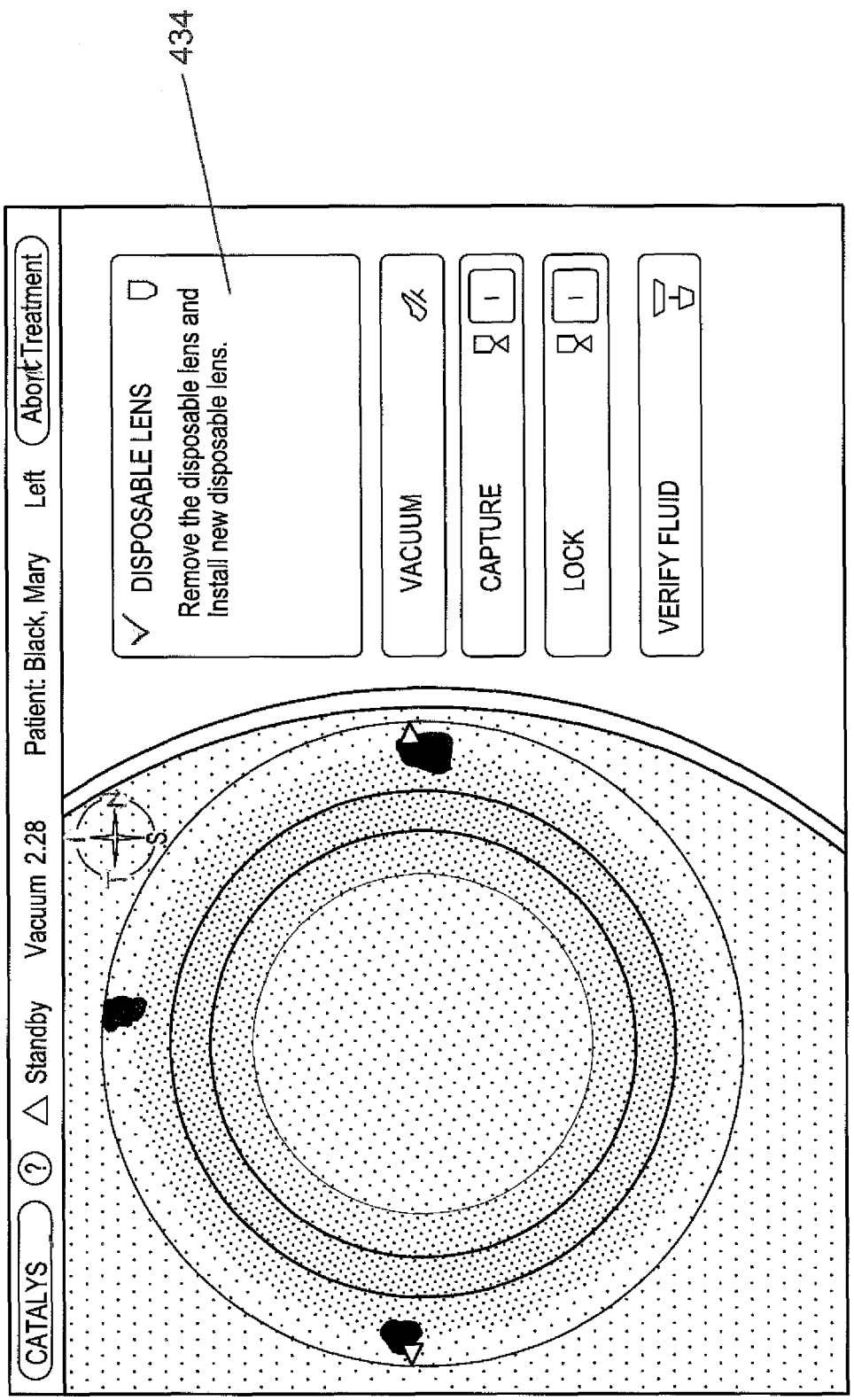

When the initial patient docking screen displays, the Disposable Lens panel 434 is open, as shown in FIG. 48. As indicated in the Disposable Lens panel 434, the user is prompted to install a new disposable lens on the system if not already installed. If the system detects that the disposable lens has not been replaced from a previous treatment, the user will be prompted to remove the old disposable lens and install a new disposable lens, as shown in FIG. 49.

Figure 50:
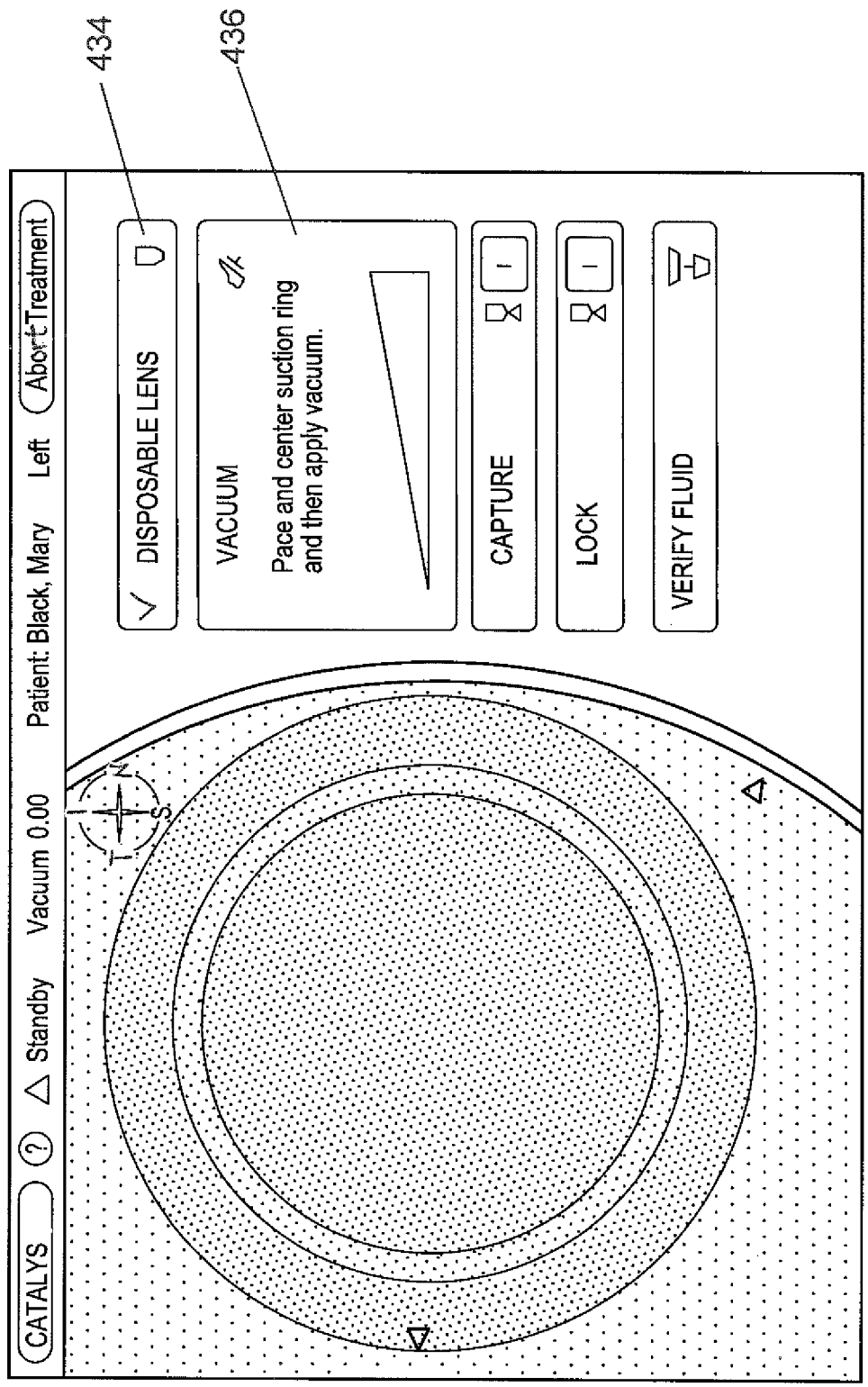

As shown in FIG. 50, when the system detects that a new disposable lens has been properly installed, a check mark displays in the Disposable Lens panel 434, and the Vacuum panel 436 opens. After the system verifies installation of the disposable lens, the Vacuum panel 436 opens. The open Vacuum panel 436 includes instructions to the user to place and center the suction ring of the patient interface 52 on the patient's eye, and then apply patient vacuum. In many embodiments, an audio sound will play repeatedly while the system is attempting to apply vacuum and a success or failure sound will alert the user if the application of vacuum has succeeded or failed.

Figure 51:
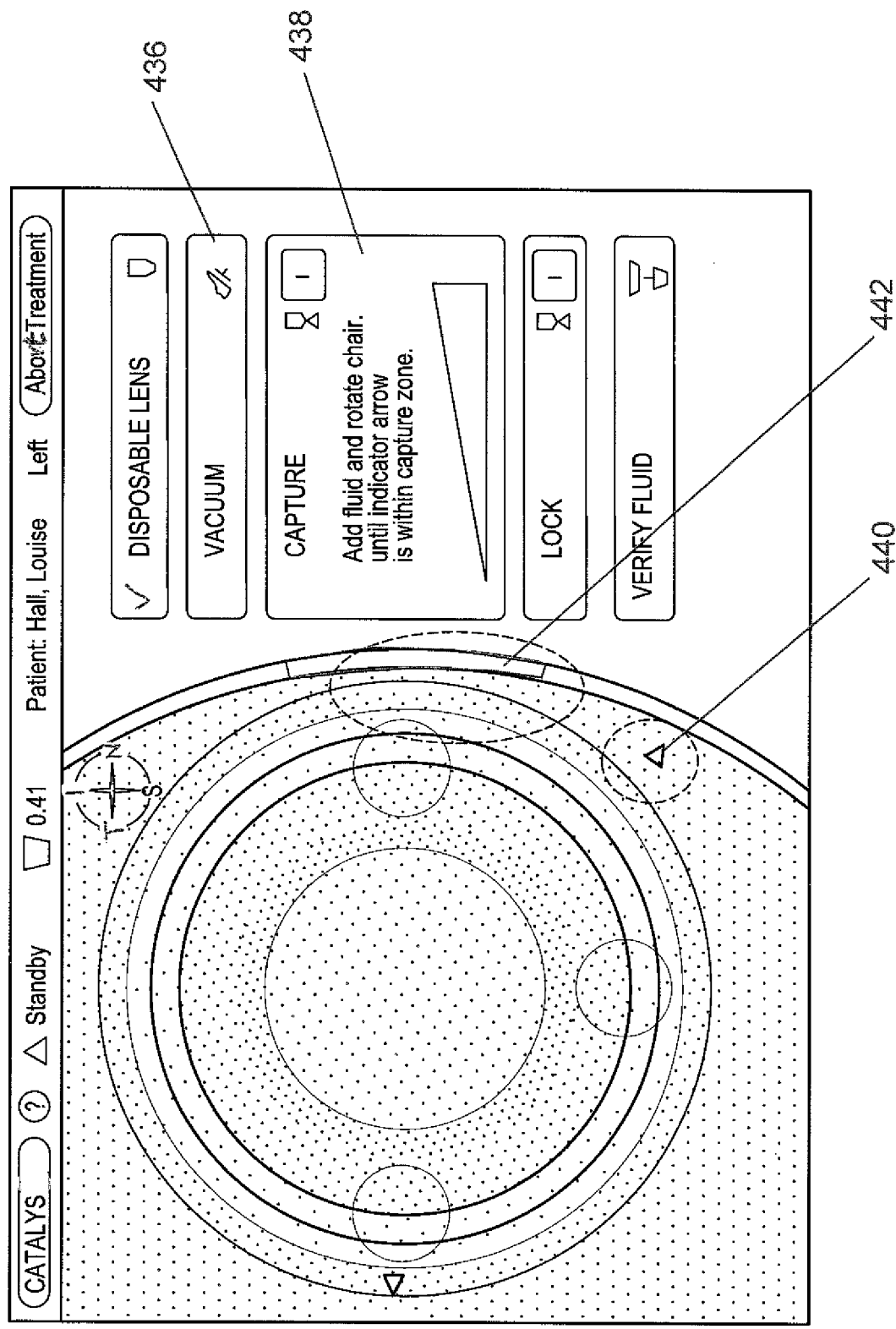
Figure 52:
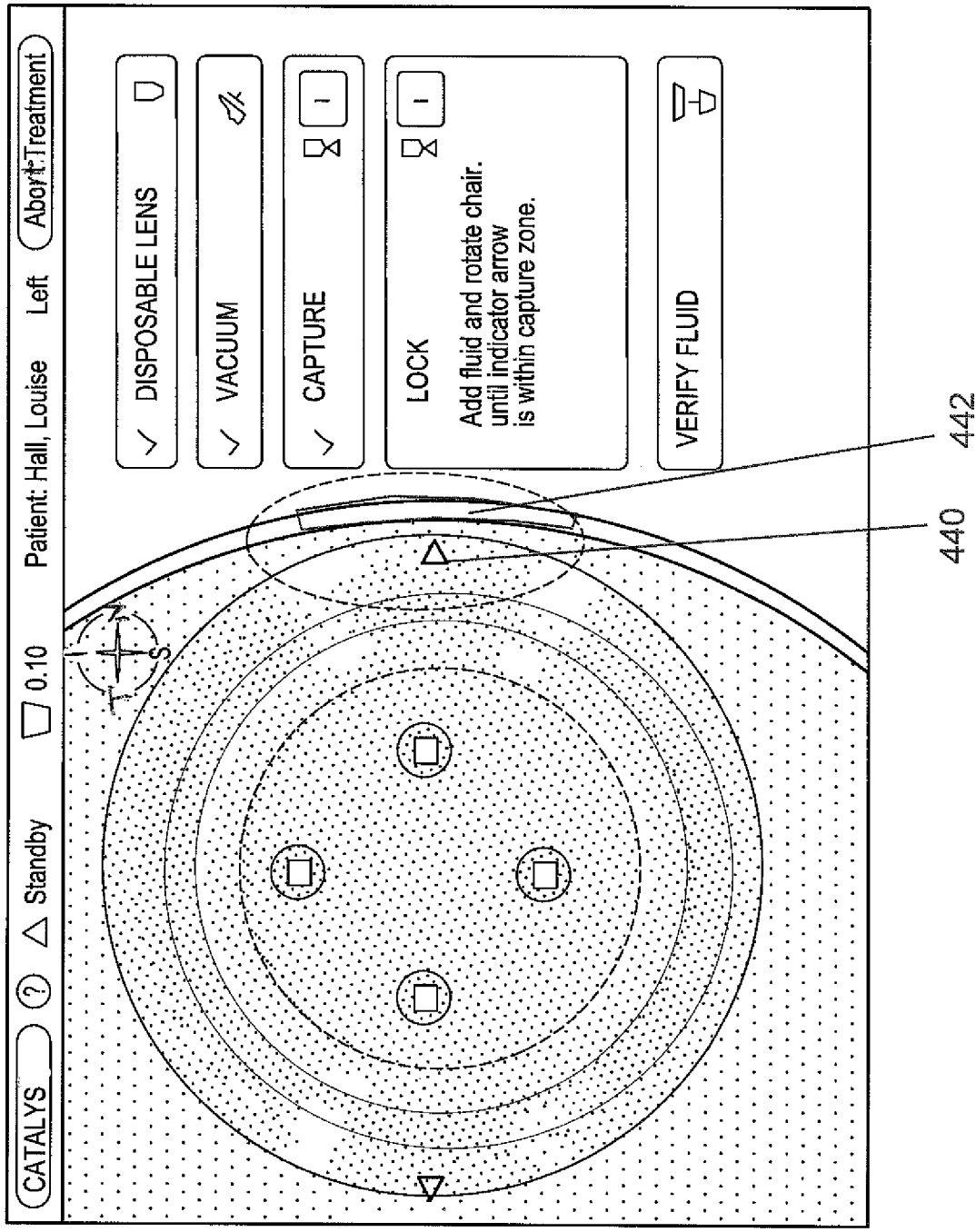

As shown in FIG. 51, when the system detects that the suction ring has been placed and patient vacuum applied, a check mark displays in the Vacuum panel 436, and the Capture panel 438 opens. The open Capture panel 438 includes instructions to rotate the surgical chair to the treatment position and use the joystick to raise the chair until the indicator arrow 440 on the right is within the Capture Zone 442. The indicator arrow corresponds to the position of the chair and must be within the green Capture Zone in order to enable the CAPTURE button. In FIG. 51, the indicator arrow 440 is outside the Capture Zone 442 and indicates that the patient chair must be raised to place the indicator arrow 440 within the Capture Zone 442 so as to engage the suction ring to the disposable lens. FIG. 52 shows the indicator arrow 440 within the Capture Zone 442 and engagement between the suction ring and the disposable lens.

Figure 53:
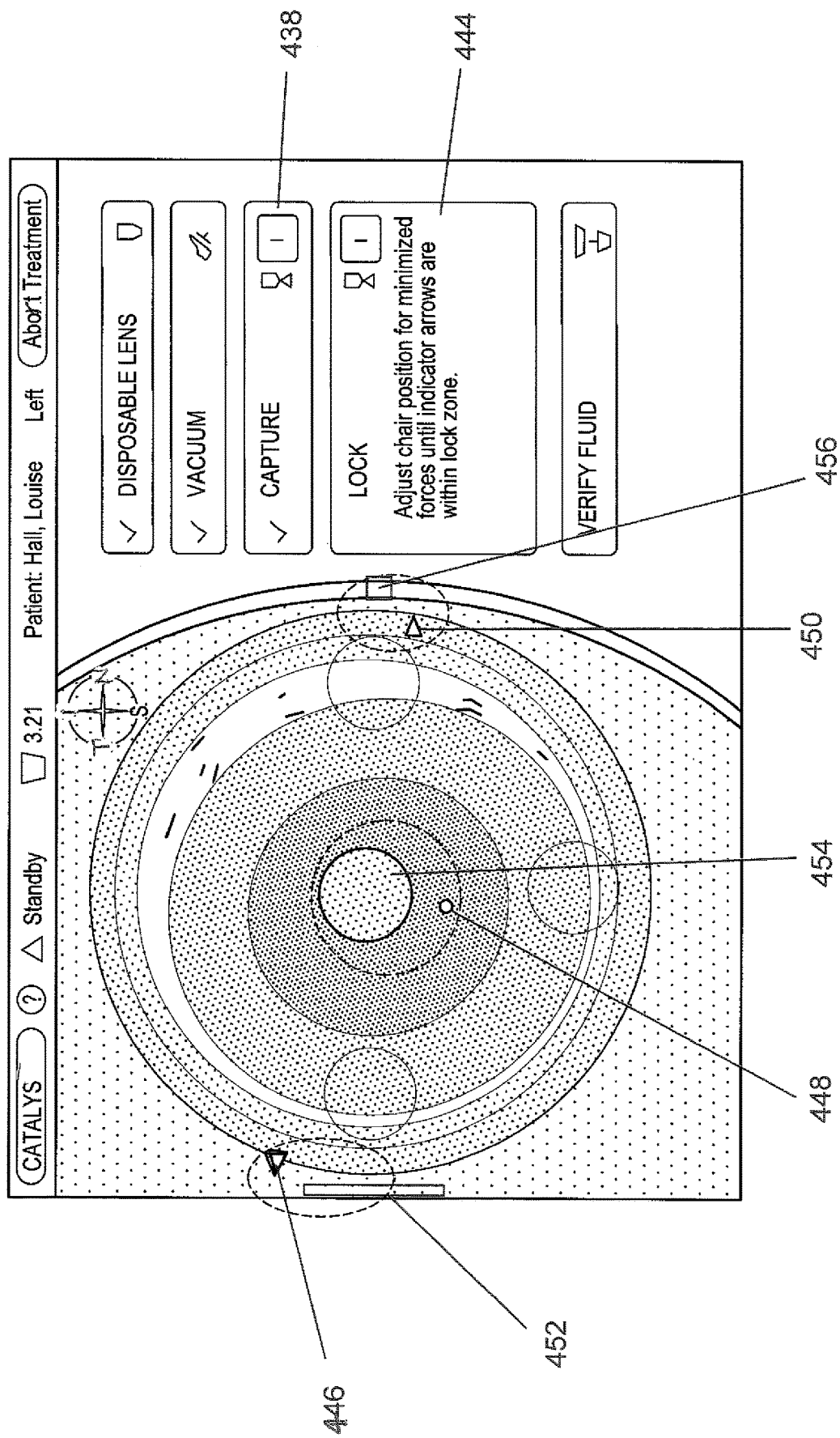
Figure 54:
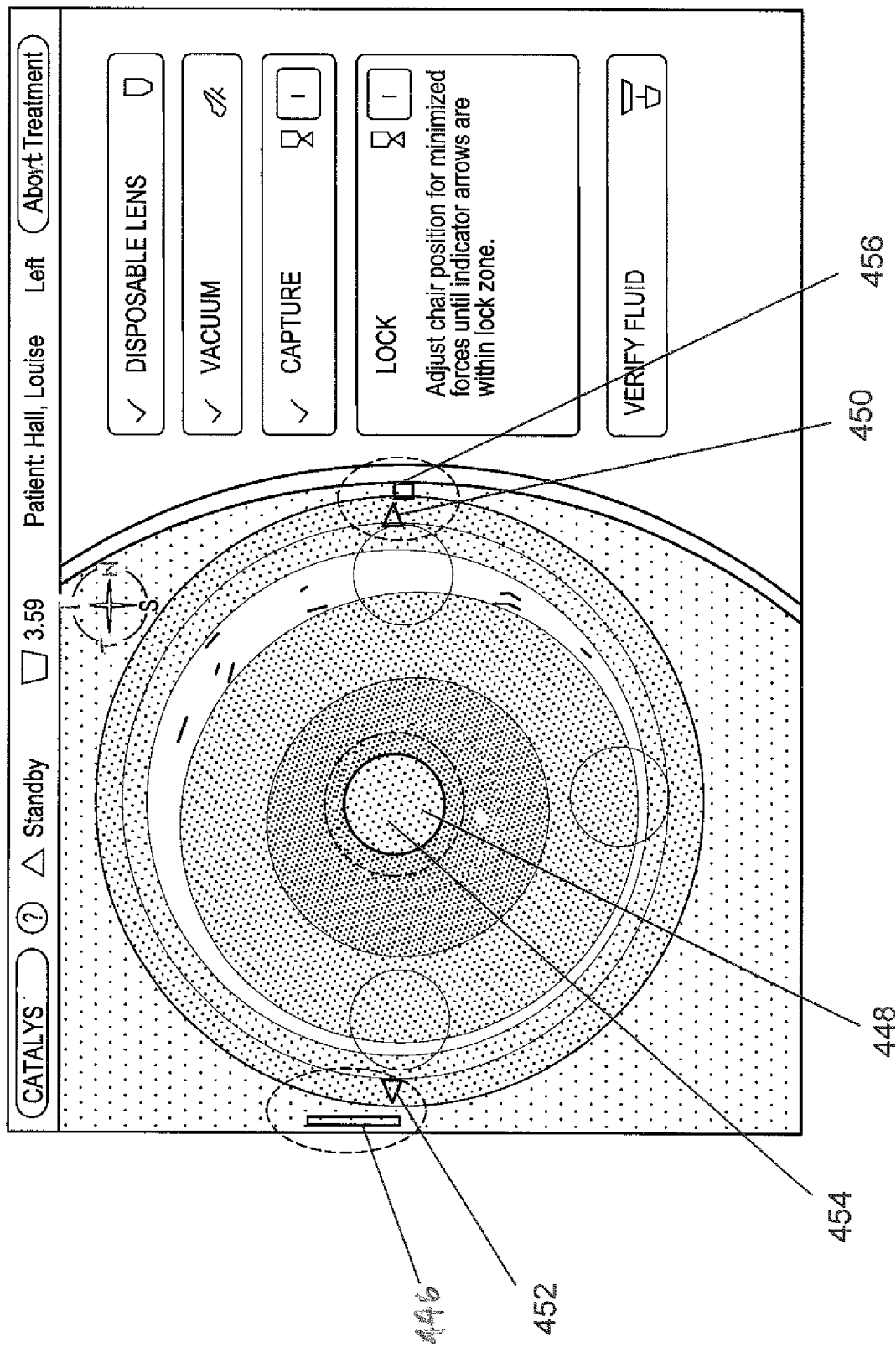

When the indicator arrow 440 on the right side of the video is within the Capture Zone 442, pressing the CAPTURE button activates vacuum to capture the suction ring in the disposable lens. When the system detects that the suction ring has been captured, a check mark displays in the Capture panel 438, and the Lock panel 444 opens, as shown in FIG. 53. An audio sound will play repeatedly while the system is attempting to capture the suction ring and a success or failure sound will alert the user if the capture has succeeded or failed. The open Lock panel 444 displays instructions to use the patient chair joystick 38 to adjust the surgical chair until all three indicators 446, 448, 450 (i.e., the vertical green bar on the left, circular green area over the video, and vertical green bar on the right) are within their respective Lock Zones 452, 454, 456, as shown in FIG. 54.

Figure 55:
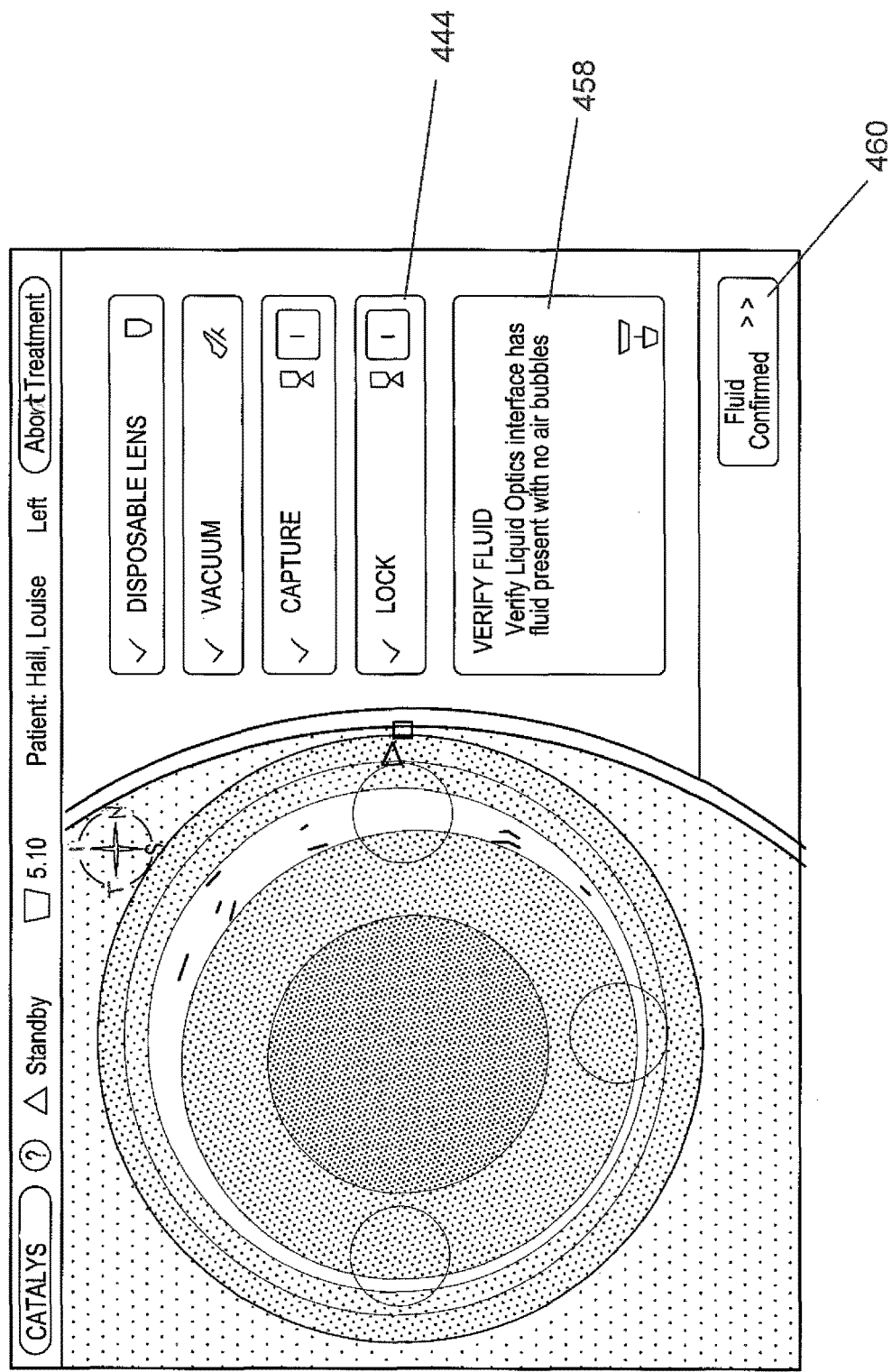

When the white indicator arrows 446, 448, 450 are within the Lock Zones 452, 454, 456 they will turn green, indicating that the Lock button should be pressed. Pressing the lock button activates a locking mechanism in the patient interface 52 that fixes the vertical position of the suction ring relative to the system. When the system detects that the lock has been secured, a check mark displays in the Lock panel 444, and the Verify Fluid panel 458 opens, as shown in FIG. 55. When the disposable lens, vacuum, capture, and lock steps have all been completed, the horizontal and vertical force indicators (indicator to the left of the video and in the center of the video) will minimize to the upper left corner of the video for the rest of the treatment process. The Verify Fluid panel 458 displays instructions to check the video image 426 of the patient's eye to ensure that the suction ring is completely filled with sterile buffered saline solution and that no air bubbles are present. The video image 426 should appear sharp and clear when the suction ring is completely filled with sterile buffered saline solution and no air bubbles are present.

After verifying that the video image 426 of the patient's eye is sharp and clear, the FLUID CONFIRMED button 460 is pressed to initiate scanning of the eye by the ranging subsystem 46. A check mark will appear next to the Verify Fluid panel 458 after pressing the FLUID CONFIRMED button 460. The force indicators will also change from only showing a red band, to showing yellow, orange and red bands, indicating different severity levels of forces being exerted by the patient on the disposable lens. In summary, after capturing and locking the patient; verifying that the video image 426 of the eye is sharp and clear; and pressing the FLUID CONFIRMED button 460 on the final Docking Screen, an Arcuate/Cataract Incisions Adjustment Screen or Lens Group Adjustment Screen displays, and scanning of the eye 43 by the ranging subsystem 46 begins automatically.

Figure 56:
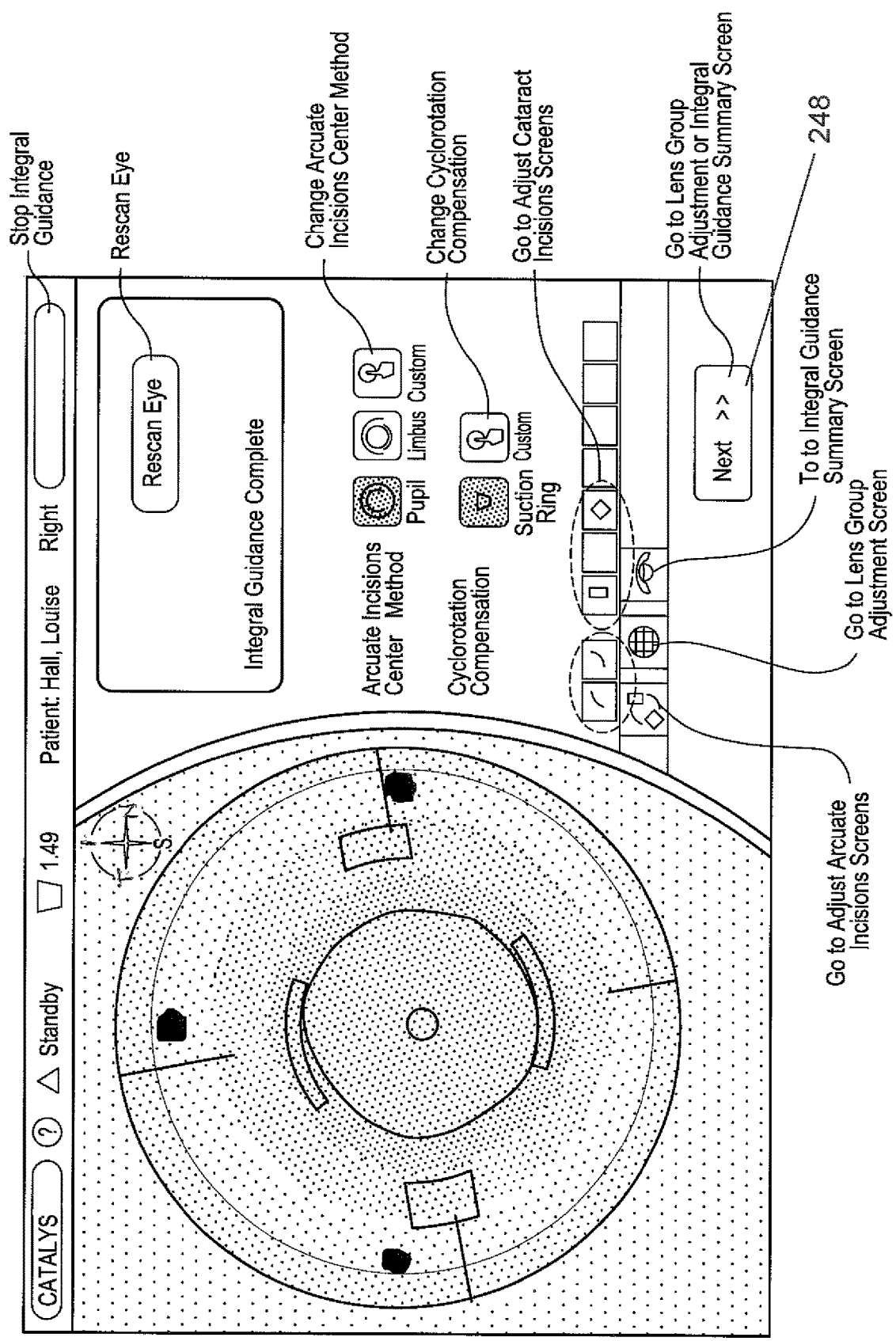

If arcuate and/or cataract incisions have been selected, the Arcuate/Cataract Incisions Adjustment Screen, as shown in FIG. 56, displays after pressing the FLUID CONFIRMED button 460 on the final Docking Screen. From the Arcuate/Cataract Incisions Adjustment Screen, the user can:

Monitor the progress of scanning of the eye by the ranging subsystem 46
Stop scanning of the eye by the ranging subsystem 46
Rescan the eye with the ranging subsystem 46
View a graphical display of selected treatment parameters
Change the Arcuate Incisions Center Method
Change the Cyclorotation Compensation
Navigate to the Adjust Arcuate Incisions and Adjust Cataract Incisions Screens to adjust treatment parameters
Accept the scan and proceed to the Lens Group Adjustment Screen (if the user selected capsulotomy or lens fragmentation) or the Integral Guidance® Summary Screen (if the user did not select capsulotomy or lens fragmentation)

When scanning of the eye by the ranging subsystem 46 is complete, "Integral Guidance® Complete" displays on the screen. If desired, the treatment parameters can be adjusted and the eye can be re-scanned. When satisfied with the scan of the eye 43 by the ranging subsystem 46, pressing the NEXT button 248 proceeds to the Lens Group Adjustment or Scanning Summary Screen.

Figure 57:
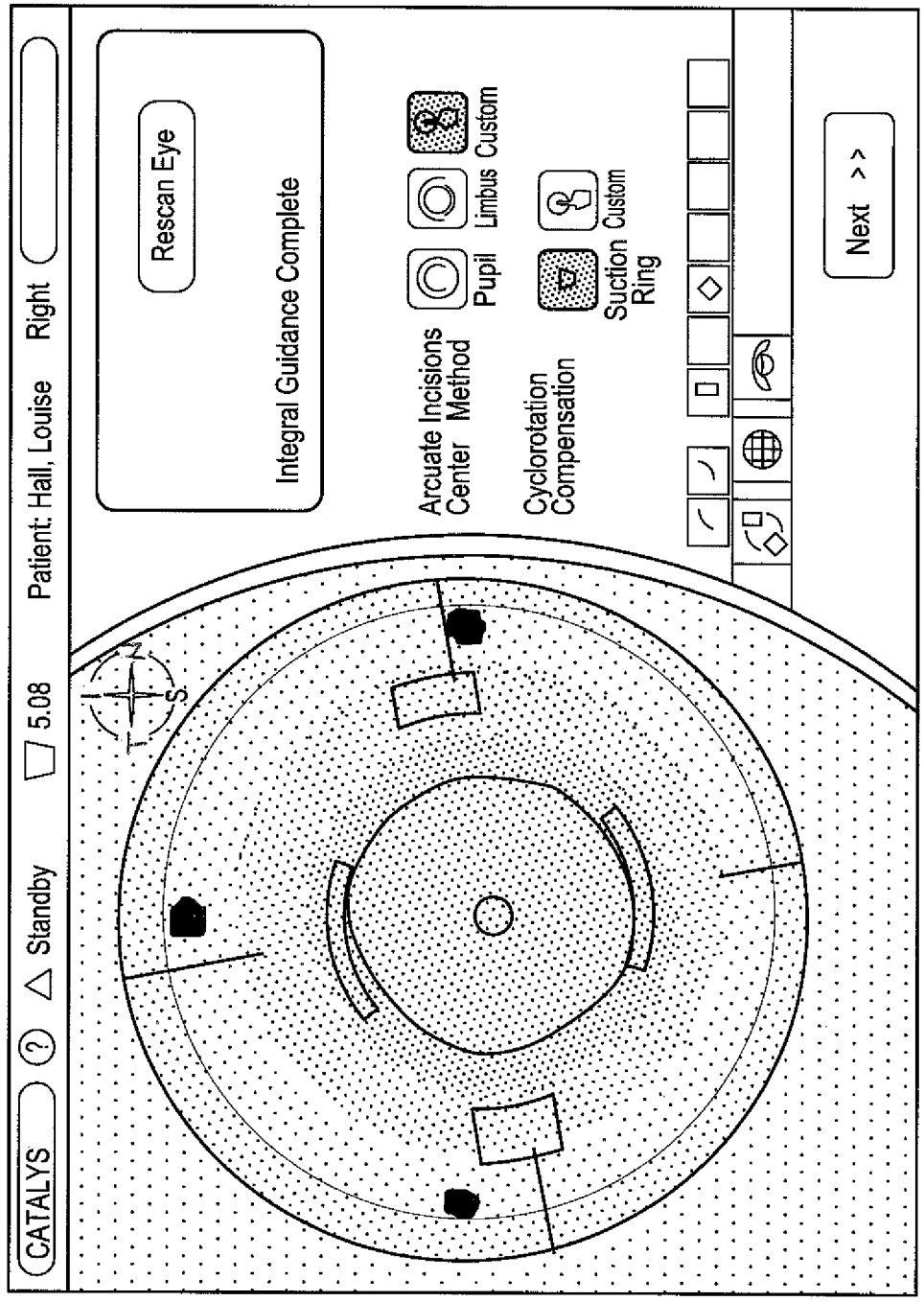
Figure 58:
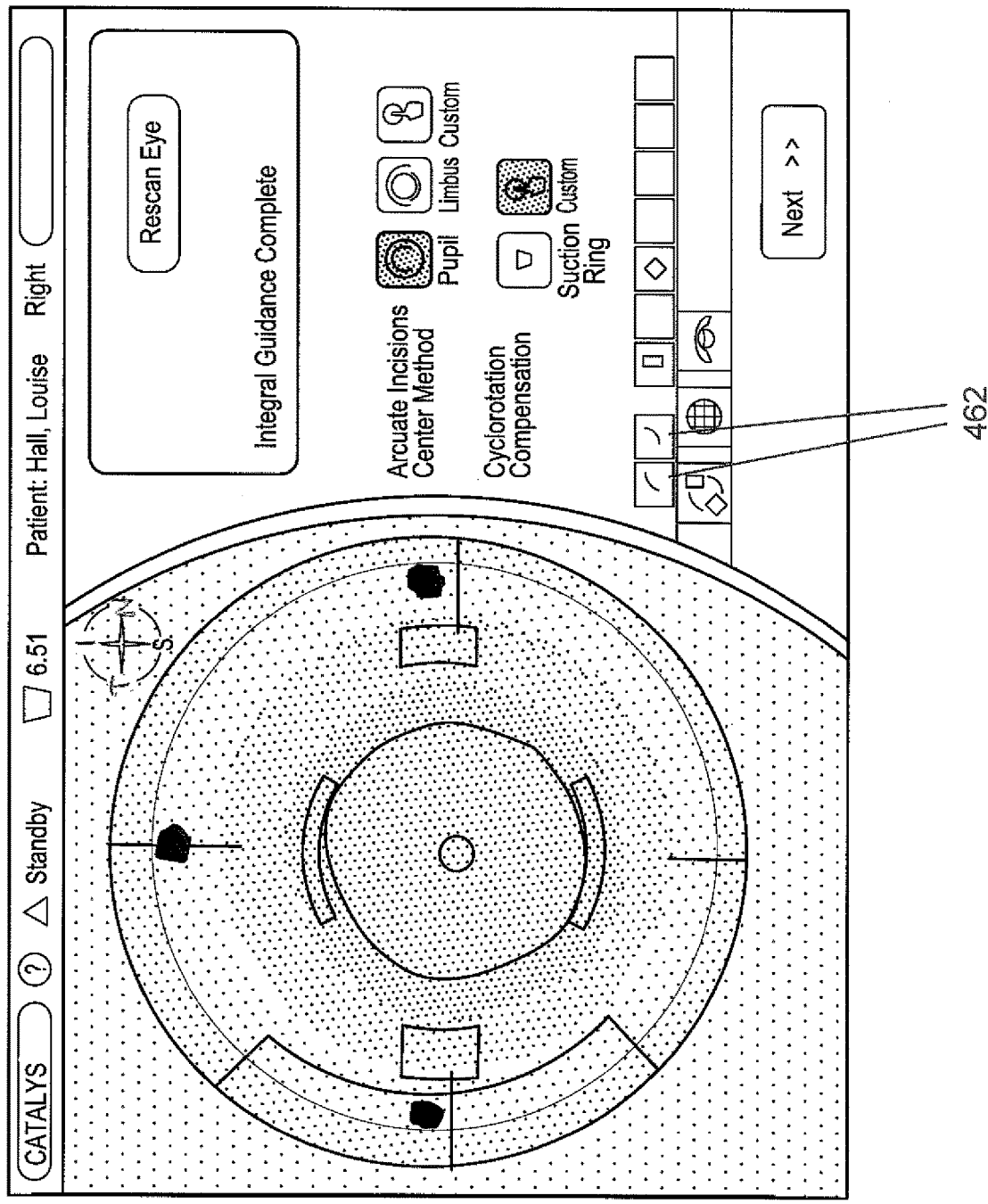

If custom arcuate incisions center method is selected, as shown in FIG. 57, the user can use the touchscreen 12 to drag and move the center of the arcuate incisions. Cyclorotation compensation adjustments are available for all corneal incisions, with the same cyclorotation compensation angle applied to all corneal incisions in a given treatment plan. The cyclorotation compensation adjustment can be selected as either suction ring position based or manually adjusted by the user. For suction ring-based cyclorotation compensation, the rotation angle of the patient suction ring is detected and used as the cyclorotation compensation angle. If the custom cyclorotation compensation method is selected, the cyclorotation compensation angle can be adjusted within the range of −45° to +45°. For example, the user can touch and drag the orientation indicators to adjust the cyclorotation compensation angle to a desired angle, such as from the orientation shown in FIG. 57 to the orientation shown in FIG. 58.

Figure 59:
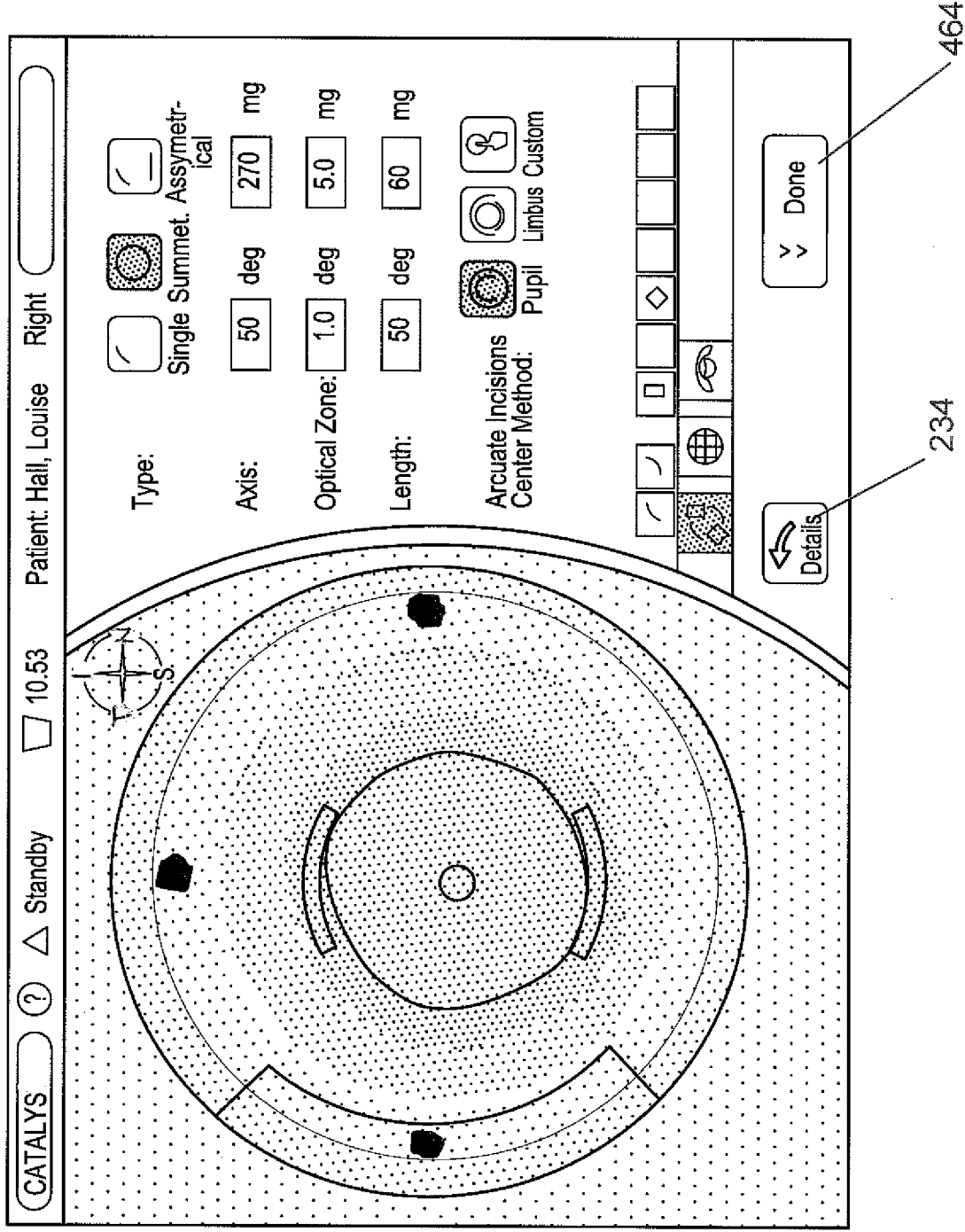
Figure 60:
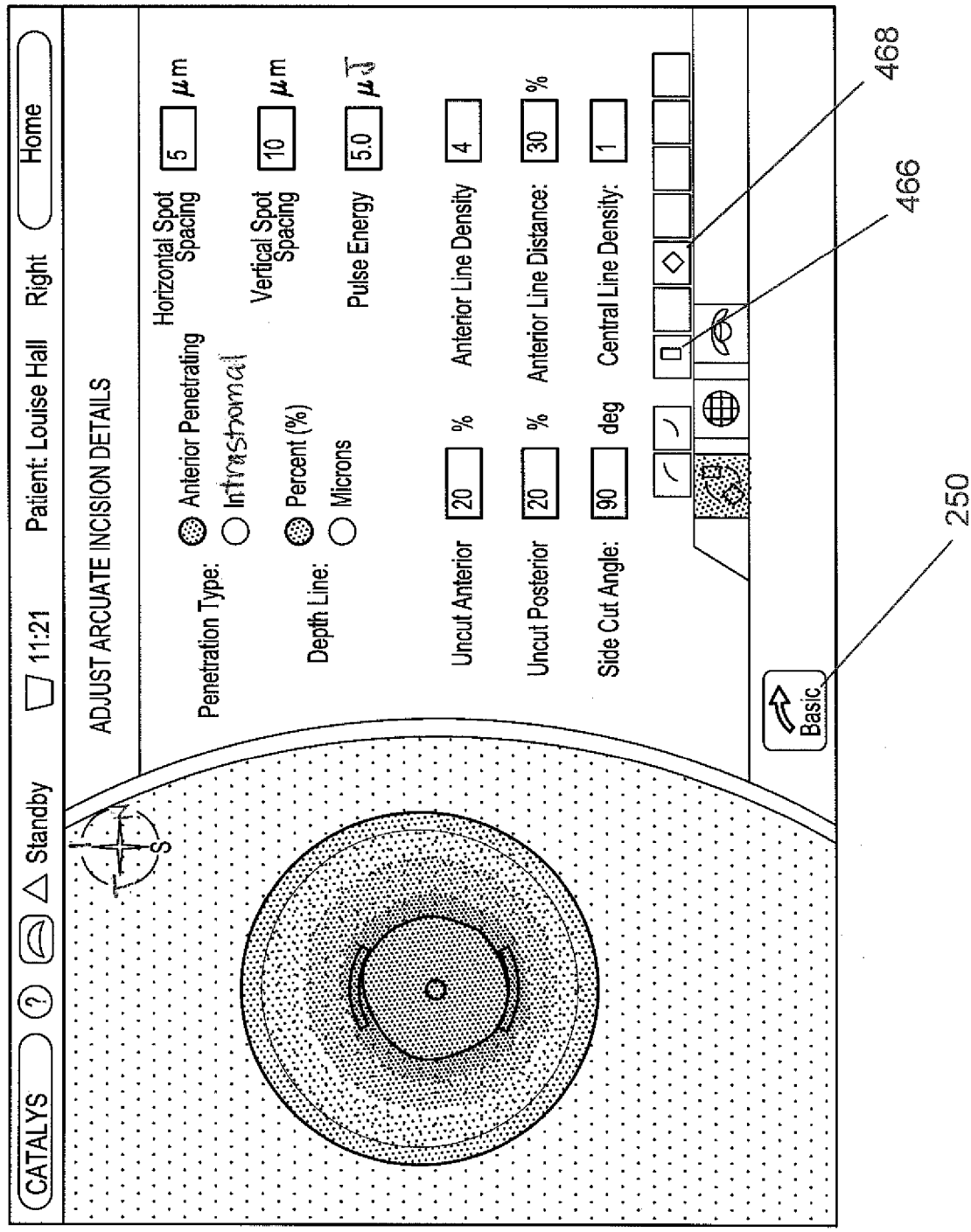

To adjust the arcuate incisions parameters after the scanning of the eye 43 by the ranging subsystem 46, pressing the ■ or ■ button 462 on the Arcuate/Cataract Incisions Adjustment Screen proceeds to the Adjust Arcuate Incisions (Basic) Screen, an example of which is shown in FIG. 59. The user can selectively adjust the parameters on the Adjust Arcuate Incisions (Basic) Screen, and then press the DETAILS button 234 to proceed to the Adjust Arcuate Incisions Details Screen, an example of which is shown in FIG. 60, or the DONE button 464 to return to the Arcuate/Cataract Incisions Adjustment Screen. The user can selectively adjust parameters on the Adjust Arcuate Incisions Details Screen, and then press the BASIC button 250 to return to the Adjust Arcuate Incisions (Basic) Screen or the ■ or ■ button 466, 468 to proceed to the Adjust Cataract Incisions (Basic) Screen.

Figure 61:
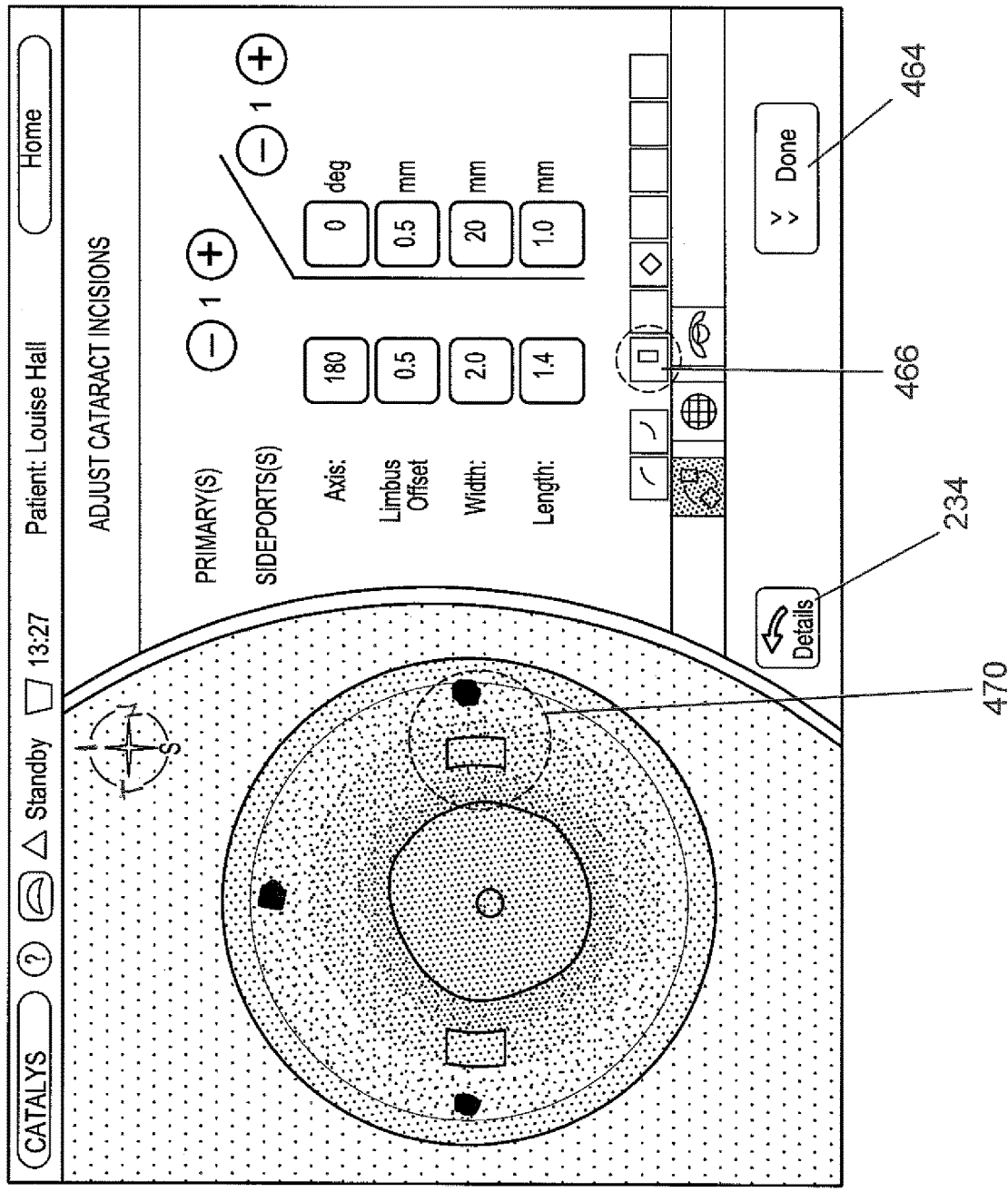
Figure 62:
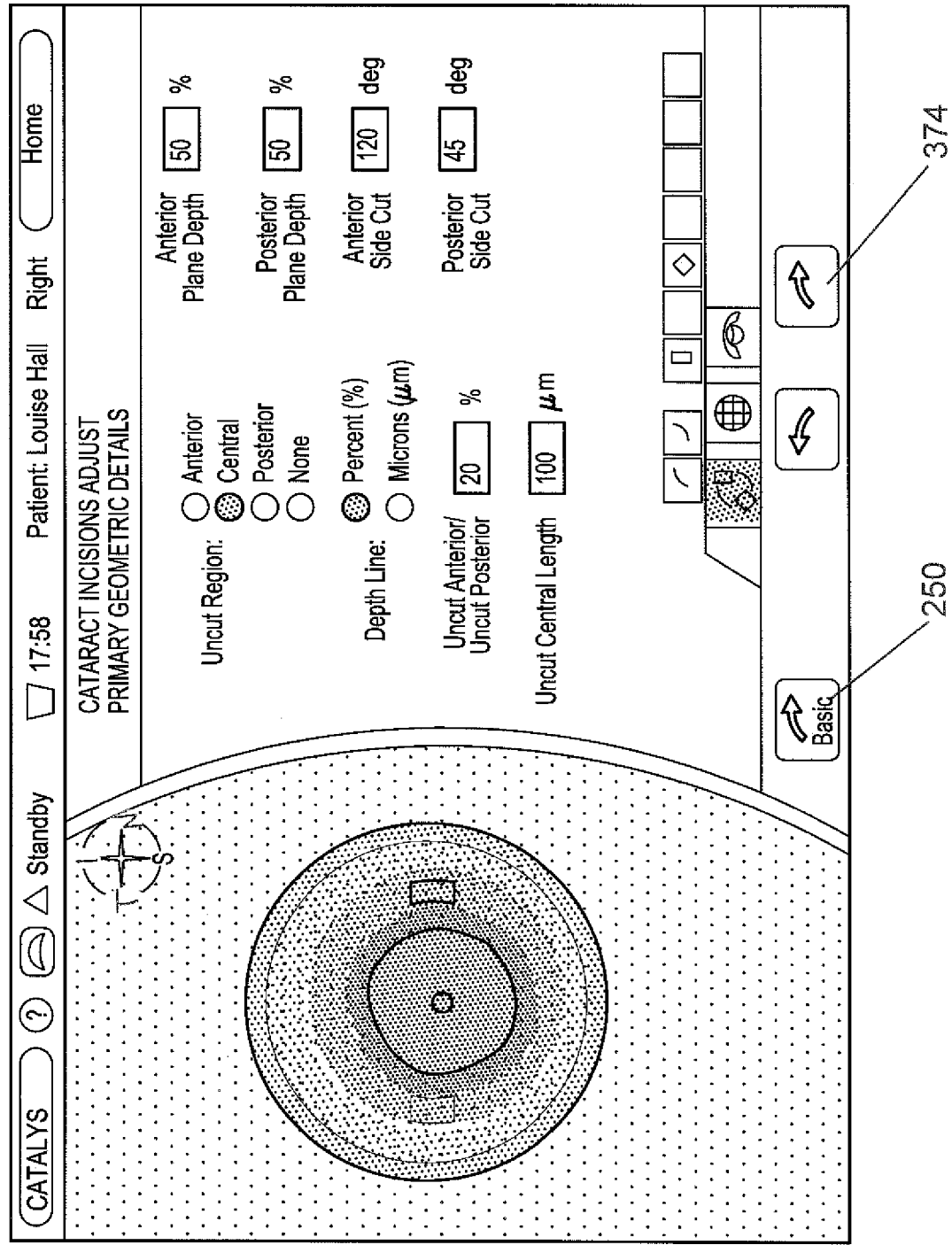

To adjust the cataract incisions parameters after the scanning of the eye 43 by the ranging subsystem 46, pressing the ■ or ■ button on the Arcuate/Cataract Incisions Adjustment Screen or Adjust Arcuate Incisions (Basic) or Details Screen proceeds to the Adjust Cataract Incisions (Basic) Screen. The ■ icons represent the primary incisions, and the ■ icons represent the sideport incisions. The number of icons displayed depends on the number of primary and sideport incisions selected on the Cataract Incisions (Basic) Screen. The user may press any ■ or ■ icon to proceed to the Adjust Cataract Incisions (Basic) Screen. The image displayed in orange in the eye model on the left of the Adjust Cataract Incisions (Basic) Screen, however, depends on which icon is selected. In FIG. 61, the primary incision icon 466 is selected, and the image 470 highlighted in the eye model represents the primary incision. The user can selectively adjust the parameters on the Adjust Cataract Incisions (Basic) Screen, and then press the DETAILS button 234 to proceed to the Cataract Incisions Adjust Primary Geometric Details Screen, an example of which is shown in FIG. 62, or the DONE button 464 to return to the Arcuate/Cataract Incisions Adjustment Screen.

Figure 63:
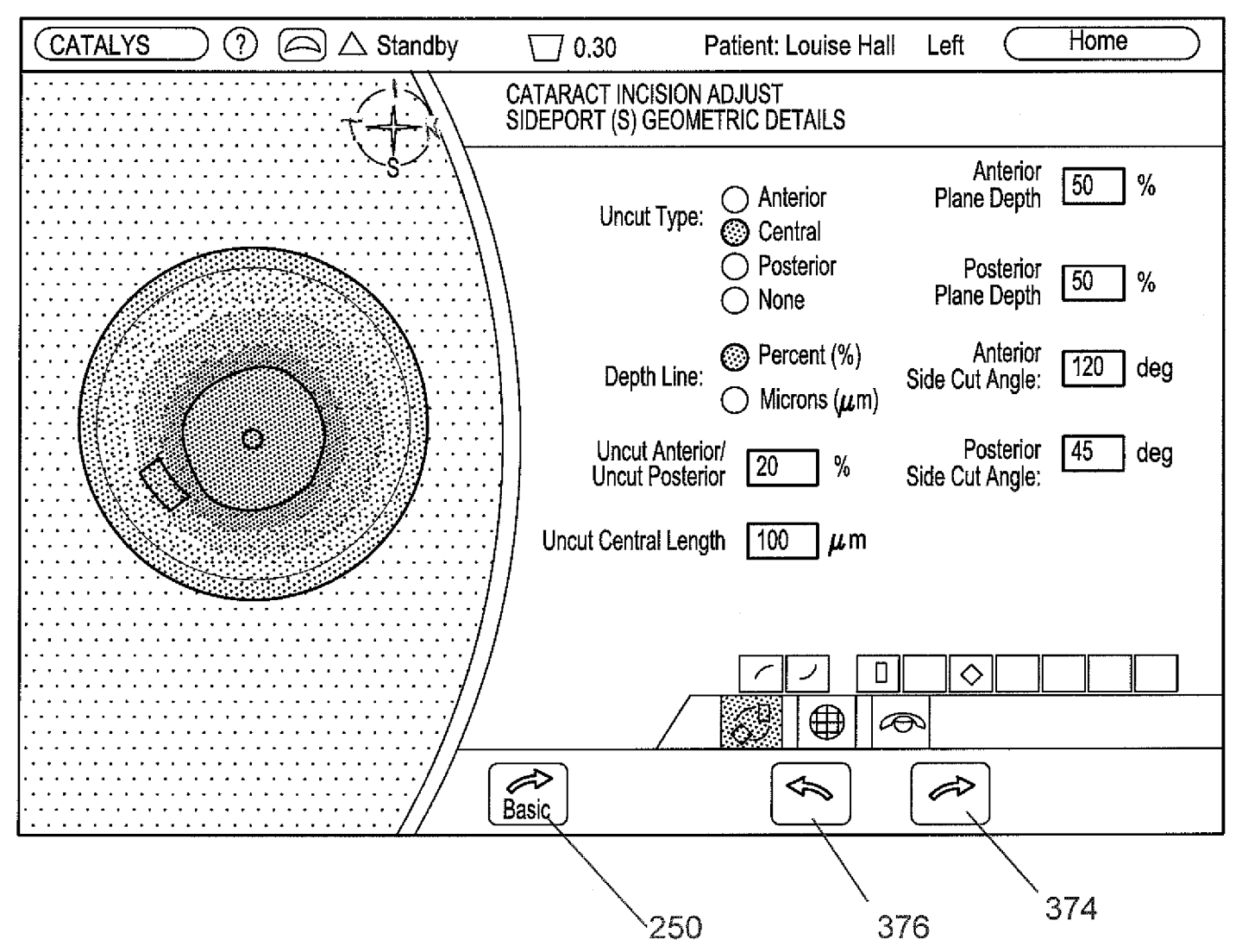

After selectively adjusting parameters on the Cataract Incisions Adjust Primary Geometric Details Screen, the user can press the ■ button 374 to go to the Cataract Incisions Adjust Sideport(s) Geometric Details Screen, an example of which is shown in FIG. 63, or the BASIC button 250 to return to the Adjust Cataract Incisions (Basic) Screen.

Figure 64:
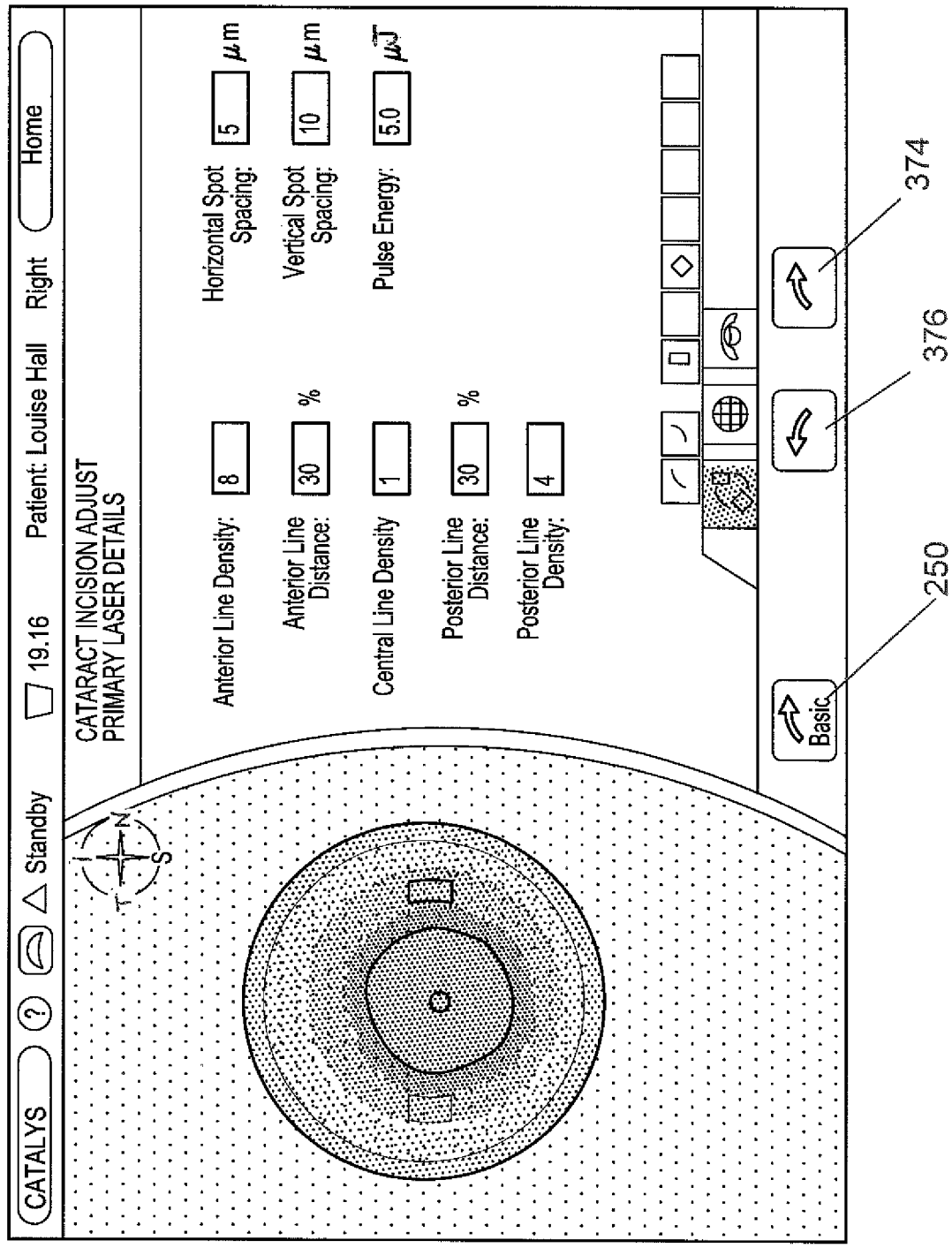

After selectively adjusting parameters on the Cataract Incisions Adjust Sideport(s) Geometric Details Screen, the user can press the ■ button 374 to go to the Cataract Incisions Adjust Primary Laser Details Screen, an example of which is shown in FIG. 64, the ■ button 376 to go to the Cataract Incisions Adjust Primary Geometric Details Screen, or the BASIC button 250 to return to the Adjust Cataract Incisions (Basic) Screen.

Figure 65:
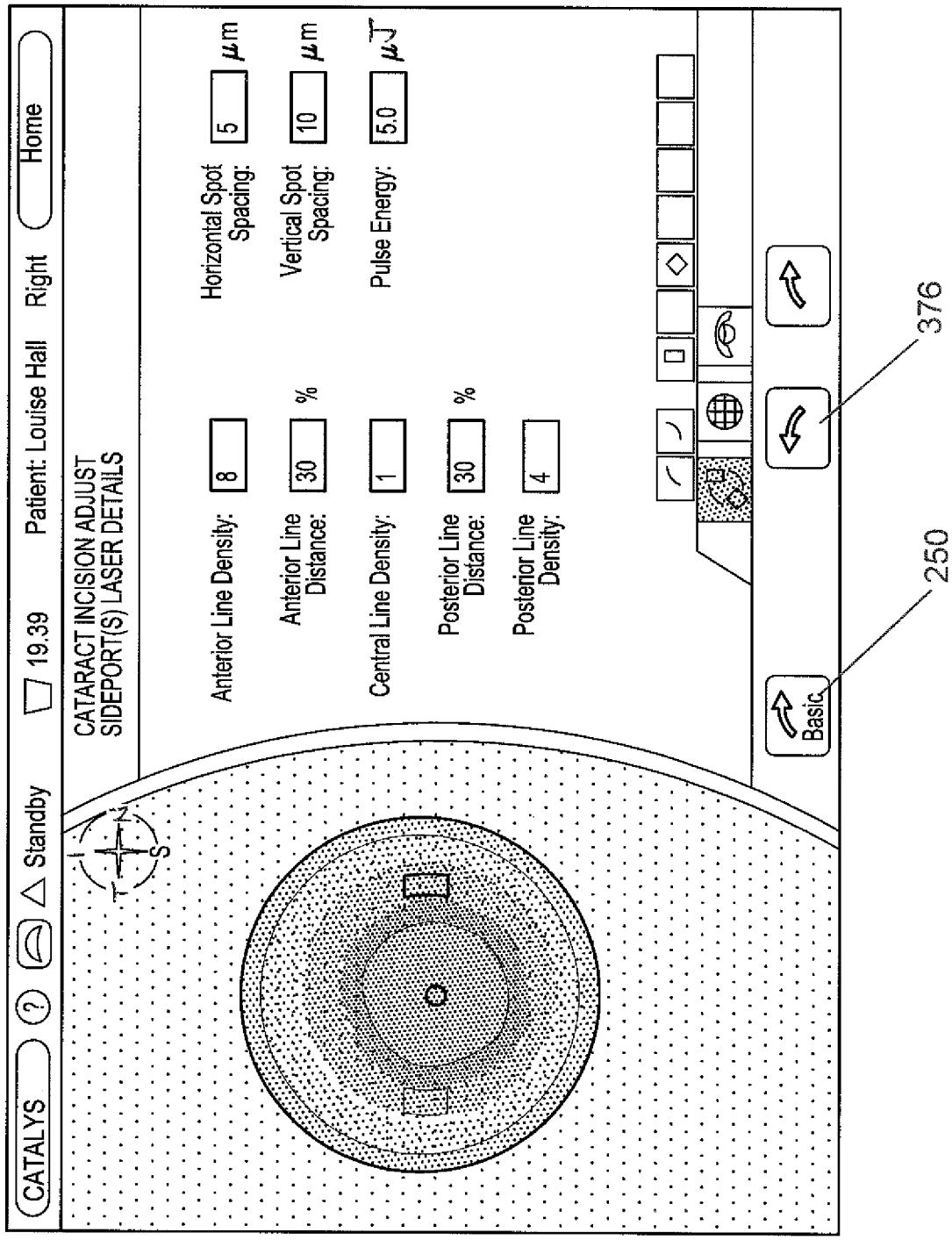

After selectively adjusting parameters on the Cataract Incisions Adjust Primary Laser Details Screen, the user can press the ■ button 374 to go to the Cataract Incisions Adjust Sideport(s) Laser Details Screen, an example of which is shown in FIG. 65, the ■ button 376 to go to the Cataract Incisions Adjust Sideport(s) Geometric Details Screen, or the BASIC button 250 to return to the Adjust Cataract Incisions (Basic) Screen. After selectively adjusting parameters on the Cataract Incisions Adjust Sideport(s) Laser Details Screen, the user can press the ■ button 376 to go to the Cataract Incisions Adjust Primary Laser Details Screen or the BASIC button 250 to return to the Adjust Cataract Incisions (Basic) Screen.

Figure 66:
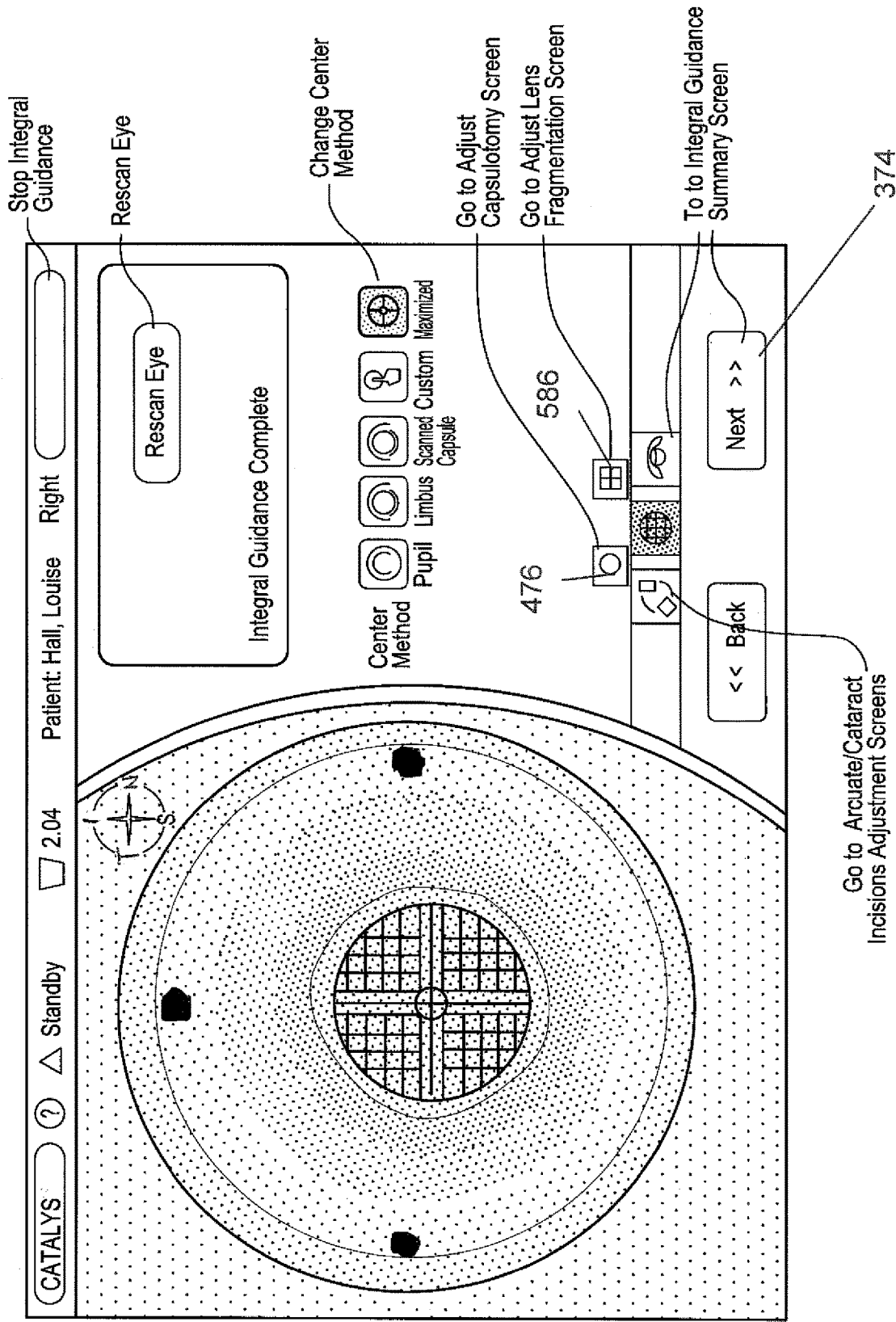
Figure 67:
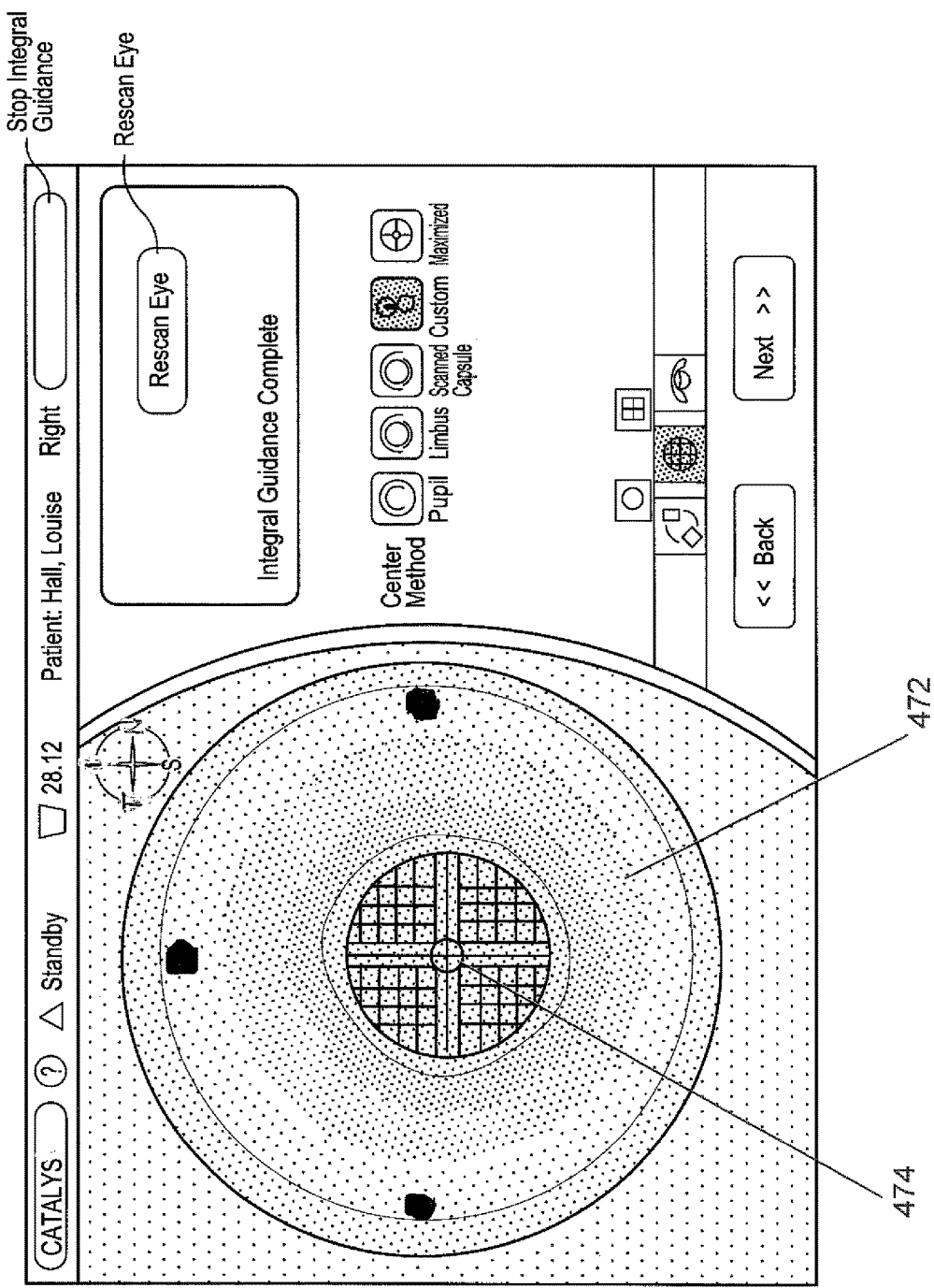

After selectively adjusting parameters on the Adjust Arcuate Incisions and Adjust Cataract Incisions Screens and pressing the NEXT button 248 on the Arcuate/Cataract Incisions Adjustment Screen, the Lens Group Adjustment Screen displays, examples of which is shown in FIGS. 66 and 67. The user can also access the Lens Group Adjustment Screen by pressing the Quick Navigation Bar Lens Group Adjustment Screen Icon. From the Lens Group Adjustment Screen, the user can:

Monitor the progress of scanning of the eye by the ranging subsystem 46
Stop scanning of the eye by the ranging subsystem 46
Rescan the eye with the ranging subsystem 46
View a graphical display of selected treatment parameters
Change the center method
Maximize the capsulotomy diameter (automatically centers on pupil)
Navigate to the Adjust Capsulotomy and Adjust Lens Fragmentation Screens to adjust treatment parameters
Navigate to the Arcuate/Cataract Incisions Adjustment Screen
Accept the scan and proceed to the Integral Guidance® Summary Screen If custom center method is selected, the user can use the touchscreen 12 to drag and move the center of the capsulotomy. When dragging the center of the capsulotomy, the area 472 (displayed in red in many embodiments) represents the capsulotomy iris safety zone. If the user drags the capsulotomy outside of this boundary, the system will not allow treatment. To move the center of the capsulotomy, the user touches near the center point and drags to move the custom center 474.

Figure 68:
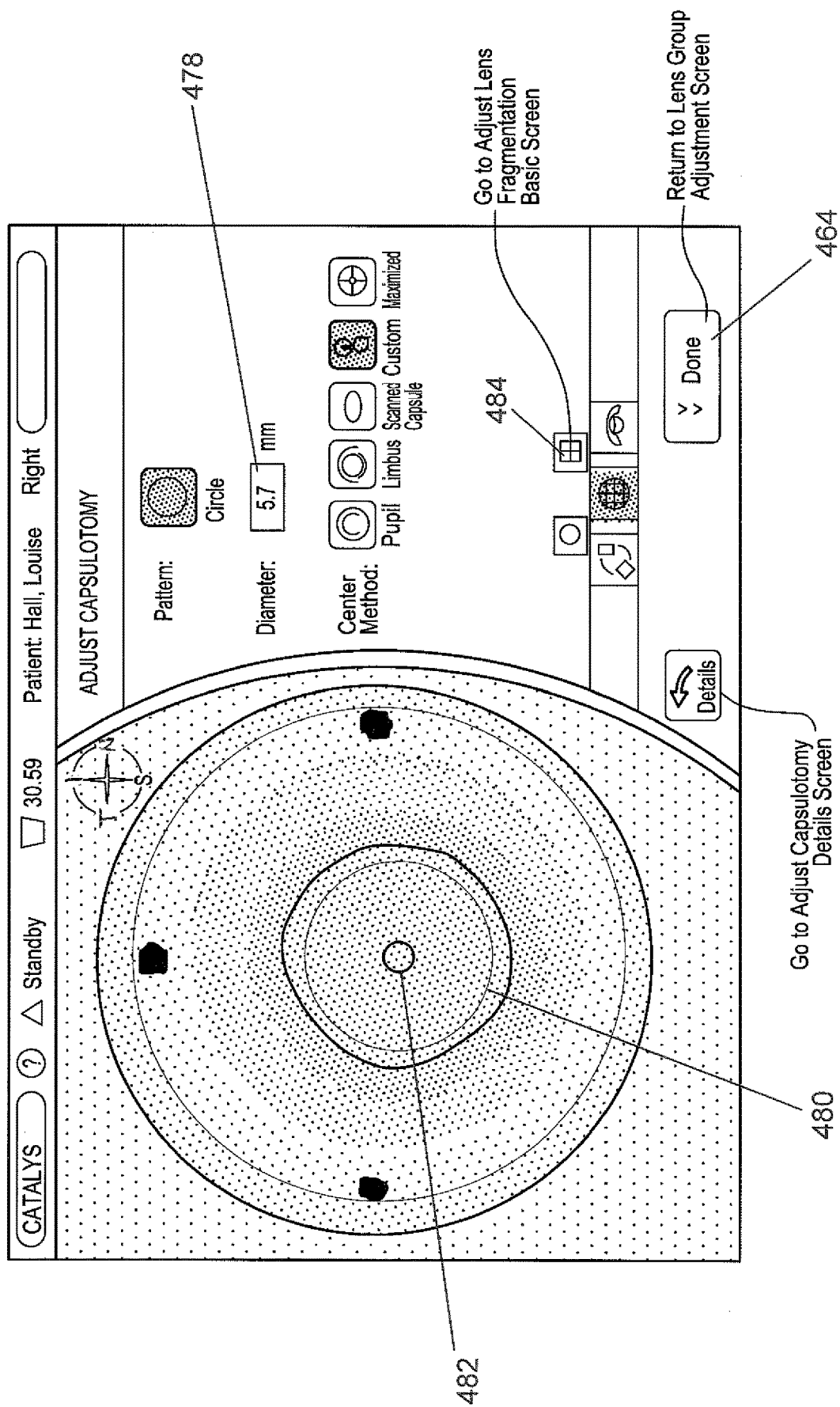
Figure 69:
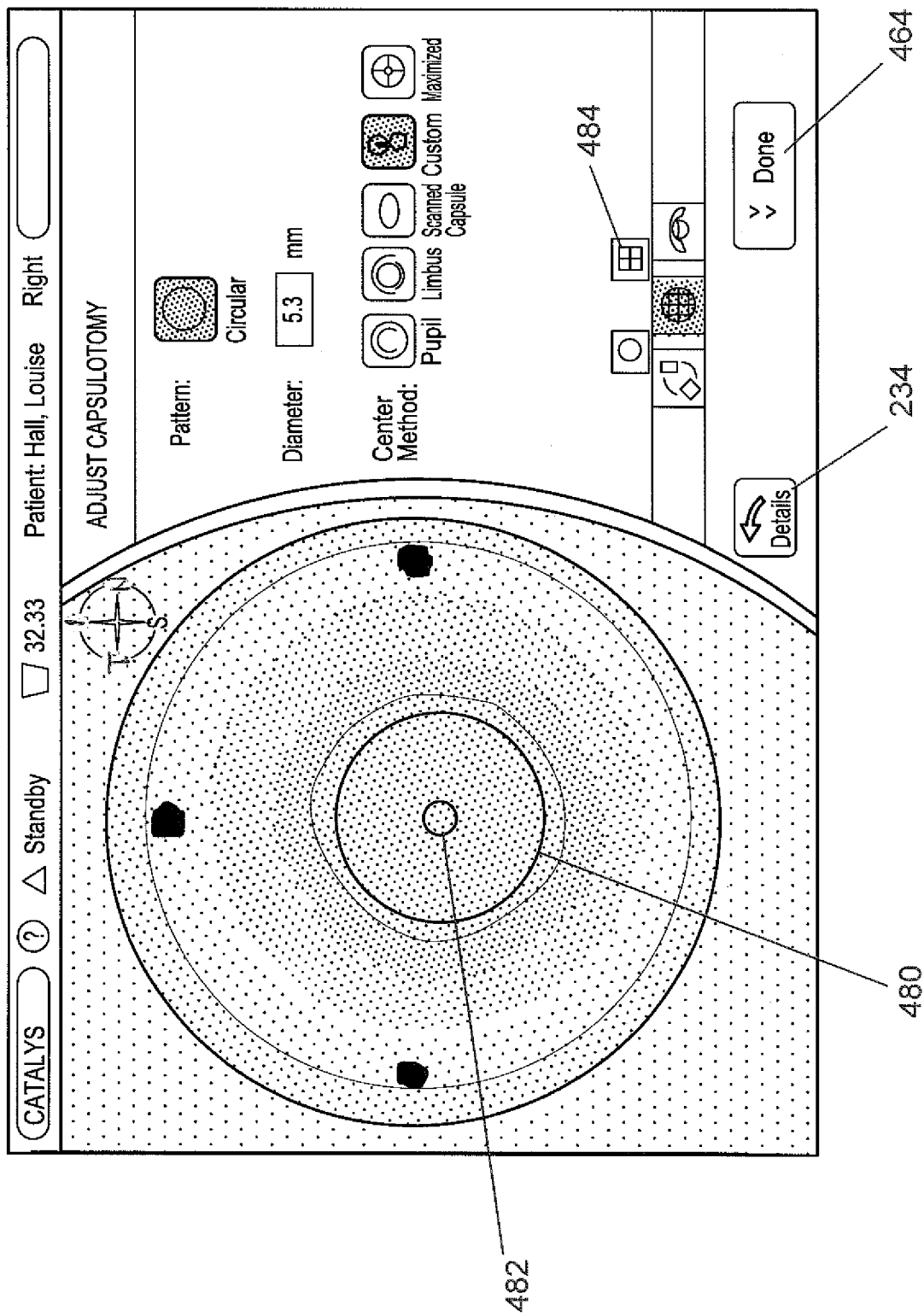

To selectively adjust the capsulotomy parameters after the scan of the eye 43 by the ranging subsystem 46, the user can press the ■ button 476 on the Lens Group Adjustment Screen to go to the Adjust Capsulotomy (Basic) Screen, an example of which is shown in FIG. 68. Capsulotomy diameter can be adjusted by changing the value in the Diameter field 478 or by pressing and dragging the capsulotomy video overlay 480. Dragging the overlay 480 away from the center 482 increases the diameter, and dragging the overlay 480 toward the center 482 decreases the diameter, for example, from the diameter shown in FIG. 68 to the diameter shown in FIG. 69.

Figure 70:
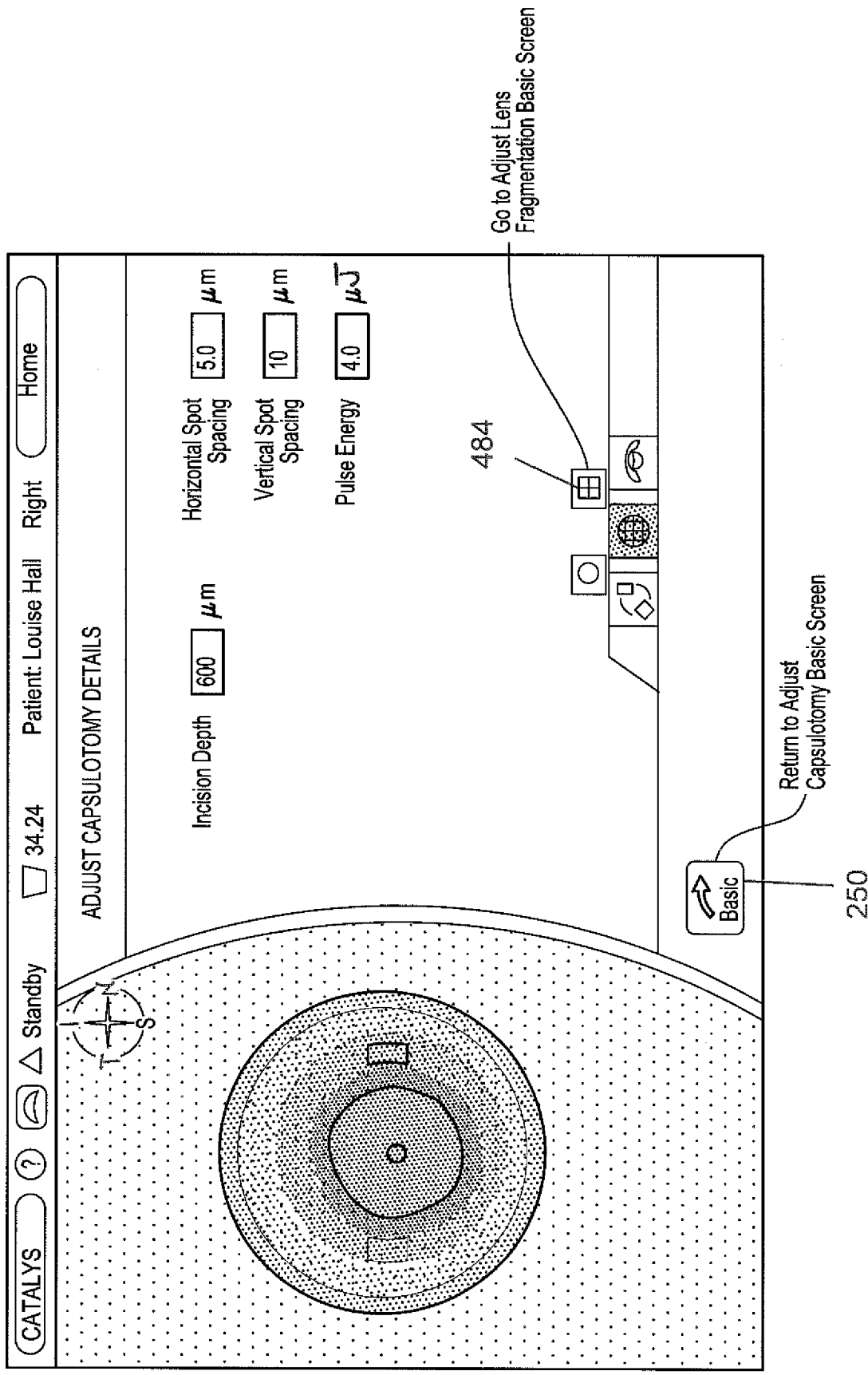

After selectively adjusting parameters on the Adjust Capsulotomy (Basic) Screen, the user can press the DETAILS button to proceed to the Adjust Capsulotomy Details Screen, an example of which is shown in FIG. 70. The user can press the ■ button 484 to go to the Adjust Lens Fragmentation (Basic) Screen or press the DONE button 464 to return to the Lens Group Adjustment Screen. After selectively adjusting parameters on the Adjust Capsulotomy Details Screen, the user can press the BASIC button 250 to return to the Adjust Capsulotomy (Basic) Screen or press the ■ button 484 to go to the Adjust Lens Fragmentation (Basic) Screen.

Figure 71:
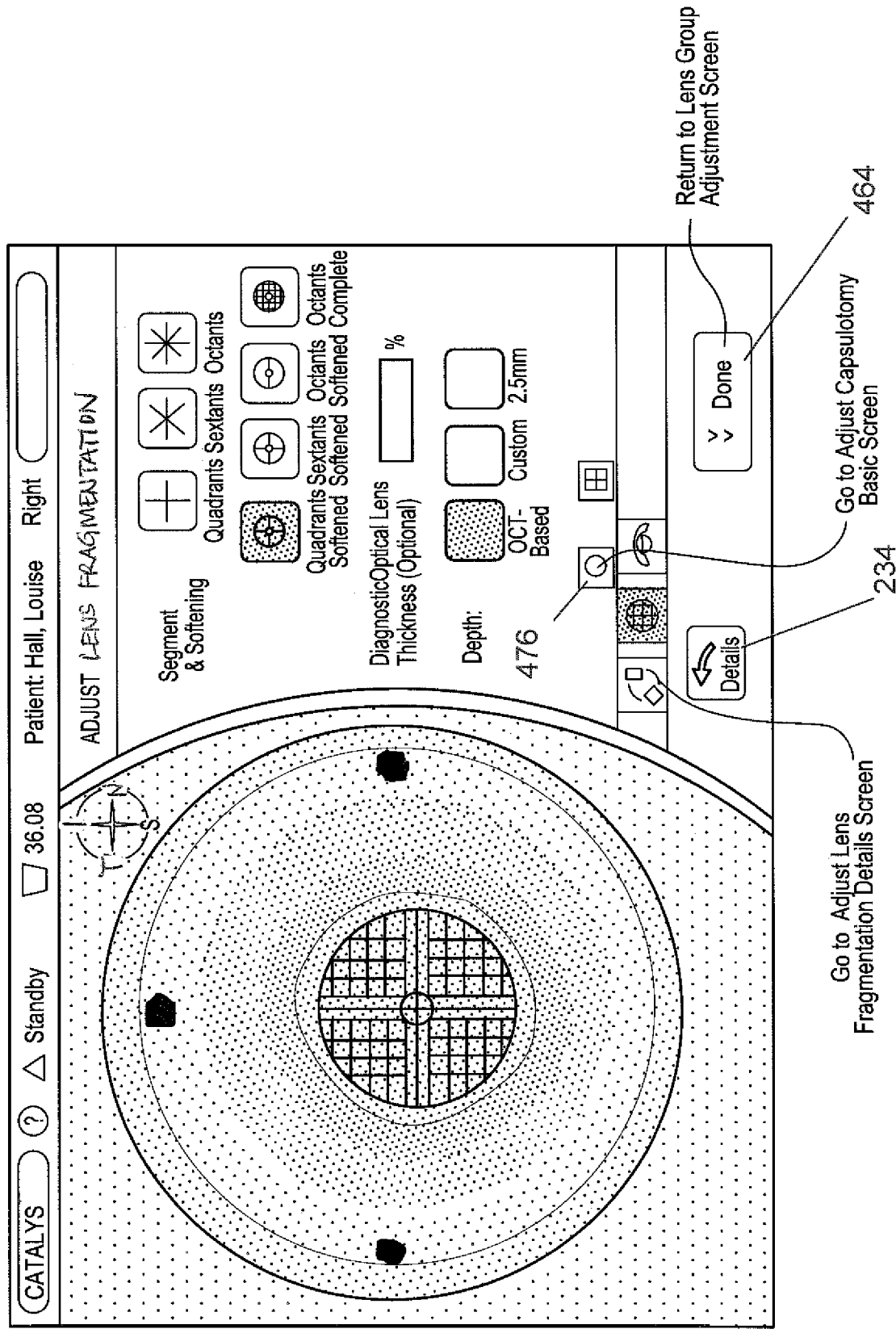
Figure 72:
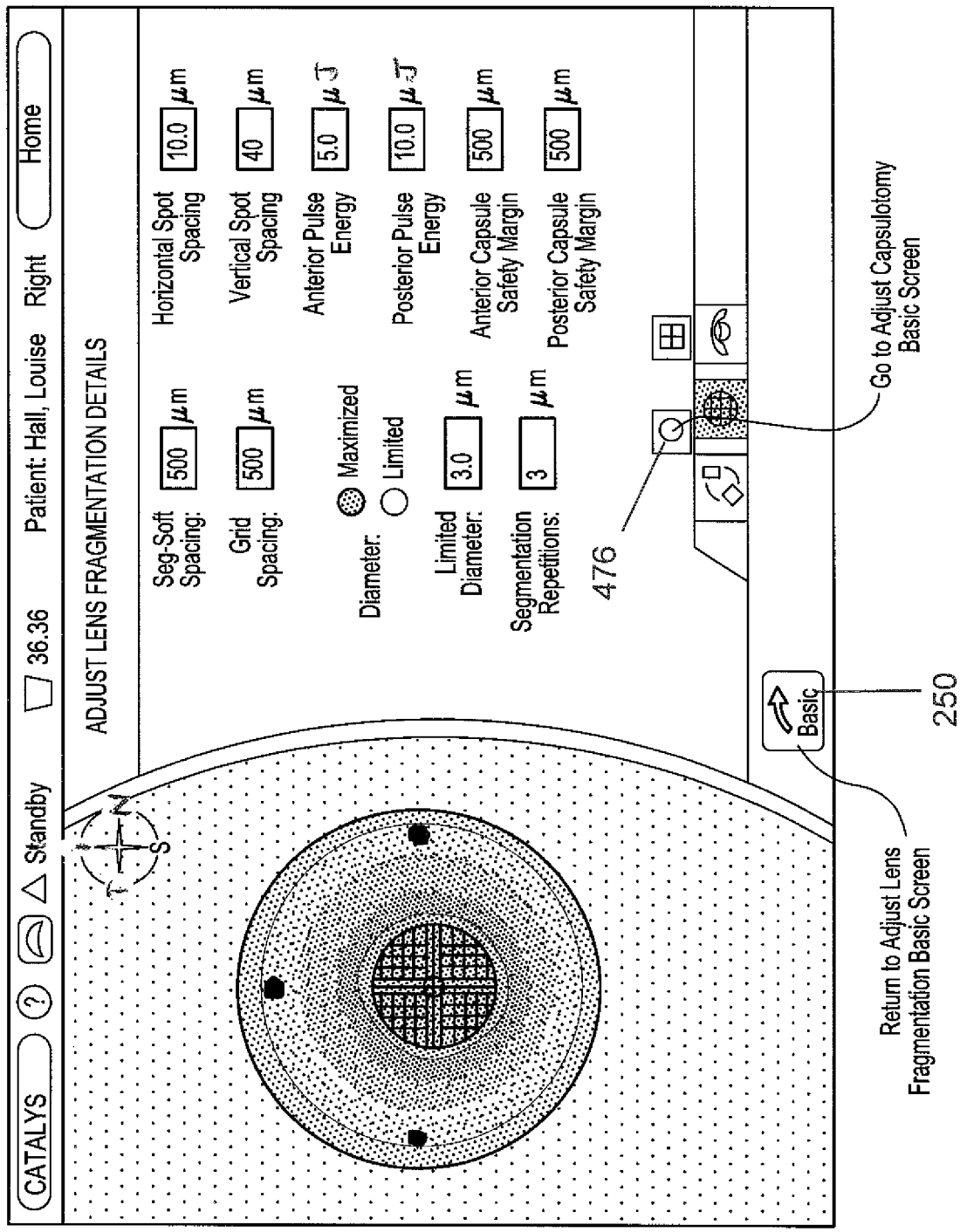

To adjust the lens fragmentation parameters after the scan of the eye 43 by the ranging subsystem 46, the user can press the ■ button 484 on the Lens Group Adjustment Screen or Adjust Capsulotomy (Basic) Screen to go to the Adjust Lens Fragmentation (Basic) Screen, an example of which is shown in FIG. 71. After selectively adjusting parameters on the Adjust Lens Fragmentation (Basic) Screen, the user can press the DETAILS button 234 to proceed to the Adjust Lens Fragmentation Details Screen, an example of which is shown in FIG. 72. The user can press the ■ button 476 to go to the Adjust Capsulotomy (Basic) Screen or press the DONE button 464 to return to the Lens Group Adjustment Screen. After selectively adjusting parameters on the Adjust Lens Fragmentation Details Screen, the user can press the BASIC button 250 to return to the Adjust Lens Fragmentation (Basic) Screen or press the ■ button 476 to go to the Adjust Capsulotomy (Basic) Screen.

Figure 73:
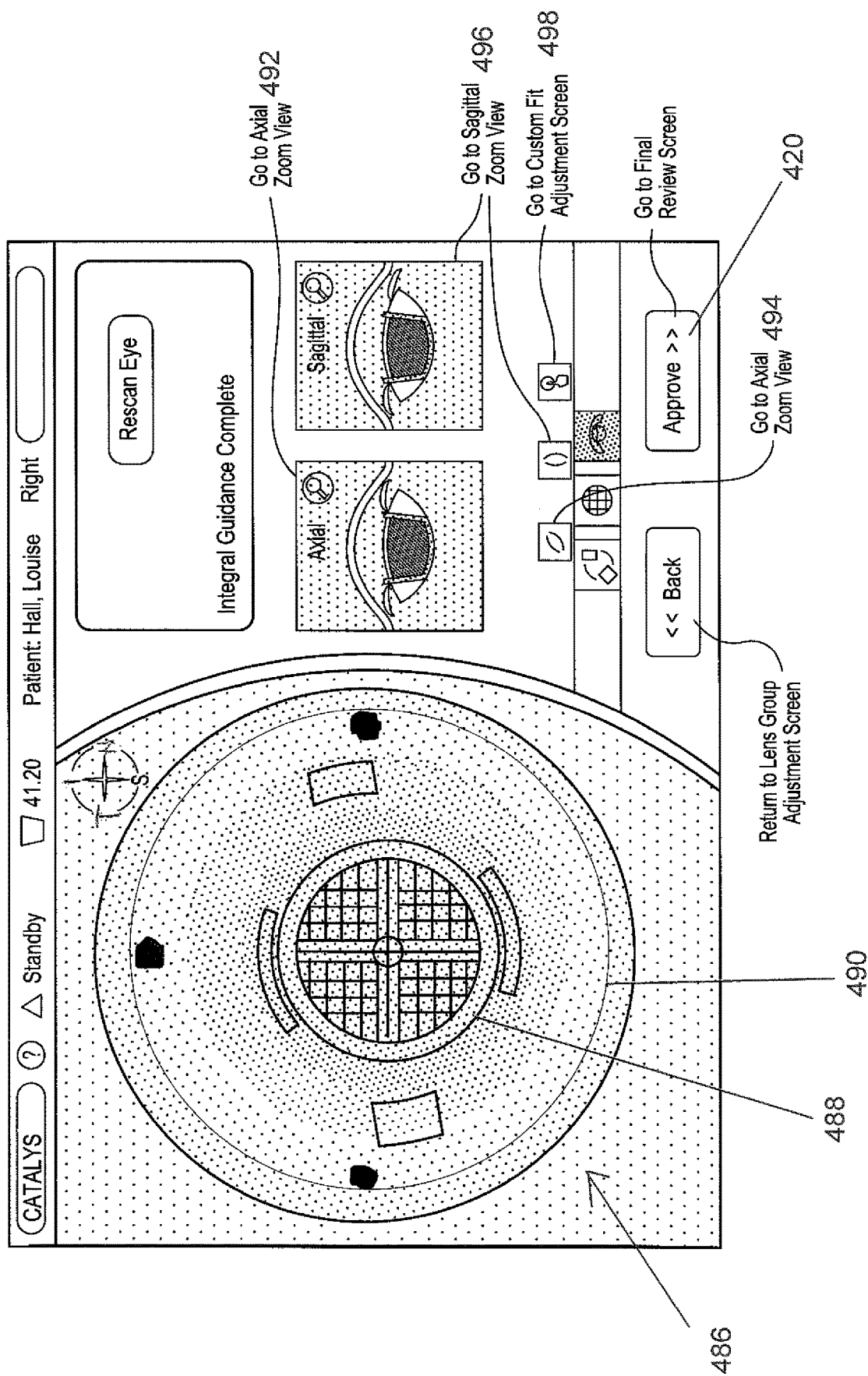
Figure 74:
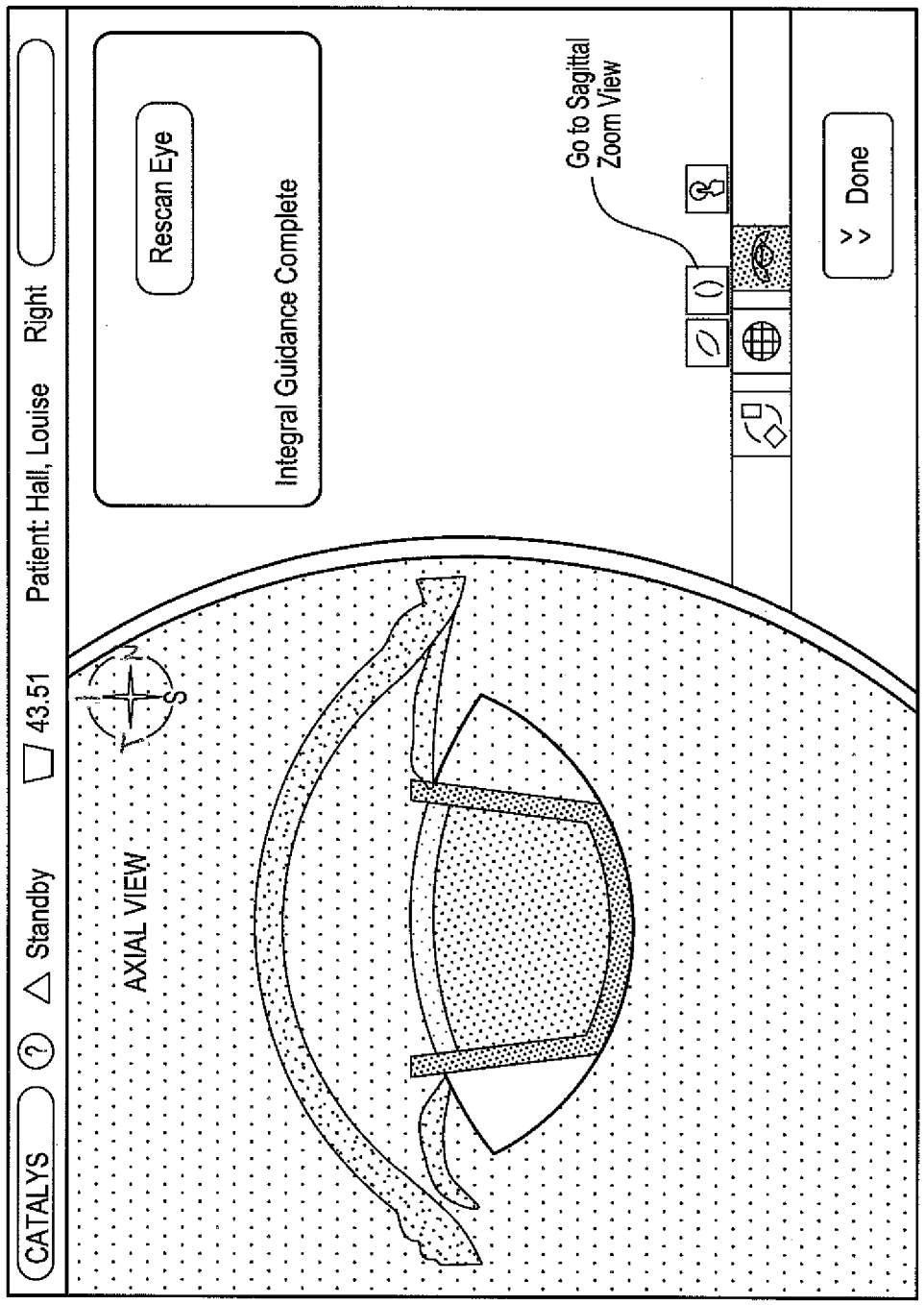
Figure 75:
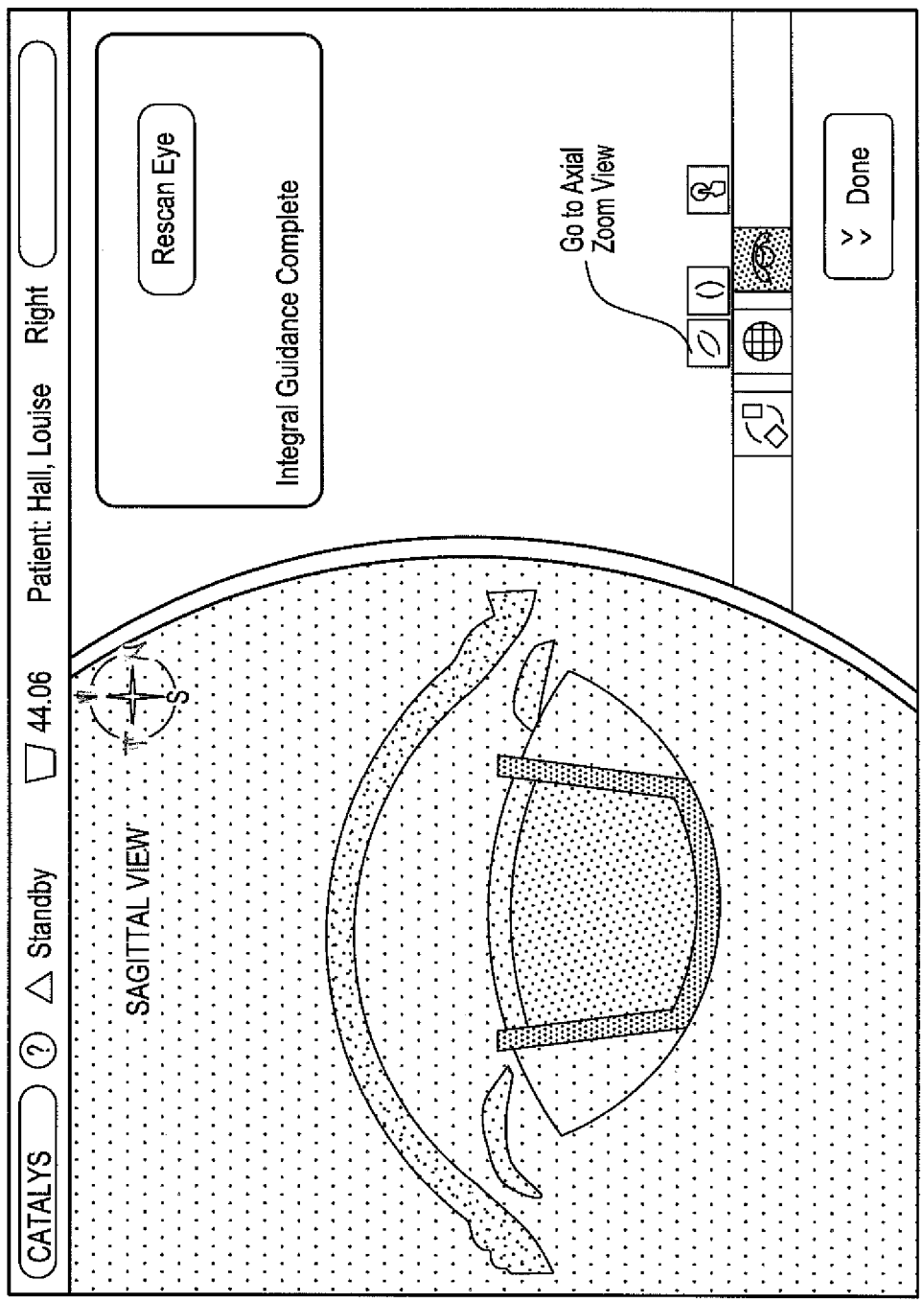

When the results of the scan of the eye 43 by the ranging subsystem 46 shown on the Lens Group Adjustment Screen are acceptable, the user can press the NEXT button 248 to proceed to a Scanning Summary Screen, an example of which is shown in FIG. 73. The Scanning Summary Screen displays a graphical representation 486 of the selected treatment parameters, including circles representing the Pupil 488 and/or Limbus 490 if either or both were used as the centering method for the capsulotomy and arcuate incisions. The user can verify that the graphical representation of all the optical surfaces (e.g., cornea anterior surface, cornea posterior surface, lens capsule anterior surface, lens capsule posterior surface, iris) identified by the laser eye surgery system 2 are accurate relative to the spatial disposition of the corresponding internal portions of the eye as located by the ranging subsystem 46. The user can press the axial (left) image 492 or ■ button 494 to go to the Axial Zoom View Screen, an example of which is shown in FIG. 74, or the sagittal (right) image or ■ button 496 to go to the Sagittal Zoom View Screen, an example of which is shown in FIG. 75.

Figure 76:
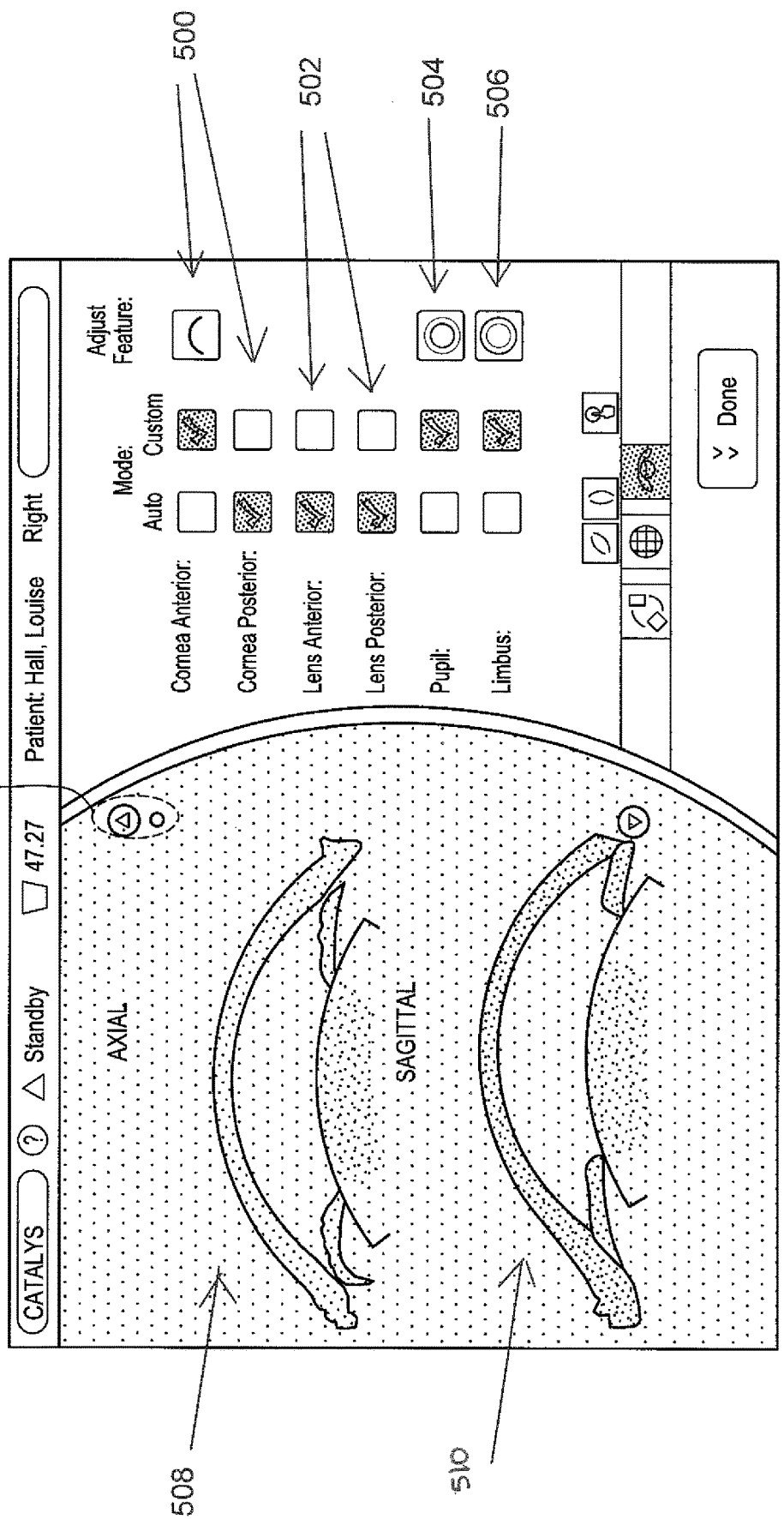

The user can manually adjust identified surfaces by pressing the ■ button 498 to go to the Custom Fit Adjustment Screen, an example of which is shown in FIG. 76. From the Custom Fit Adjustment Screen, the user can custom adjust the identified surfaces of the:

Cornea Anterior/Posterior 500
Lens Anterior/Posterior 502
Pupil 504
Limbus 506

On the Custom Fit Adjustment Screen the user can select between using the automatically detected ocular surfaces ("Auto") and custom fitting the ocular surfaces ("Custom") by selecting the check mark ☑ button under the desired column for each ocular surface. If custom fitting has been selected, an additional button will appear to the right of the check marks underneath the "Adjust Feature" column. Pressing the Adjust Feature button for a particular ocular surface will allow the user to custom fit that ocular surface. Both the axial 508 and sagittal 510 cross-section images of the scanned anterior portions of the patient's eye 43 are shown in a split-screen view on the left of the example Custom Fit Adjustment Screen. If none of the Adjust Feature buttons are selected, the currently selected set (i.e., combination of custom and automatic fits for each surface) of ocular surfaces is shown. When selecting a surface to custom fit by pressing the Adjust Feature button for that surface, only that feature will be shown on the images.

Figure 77:
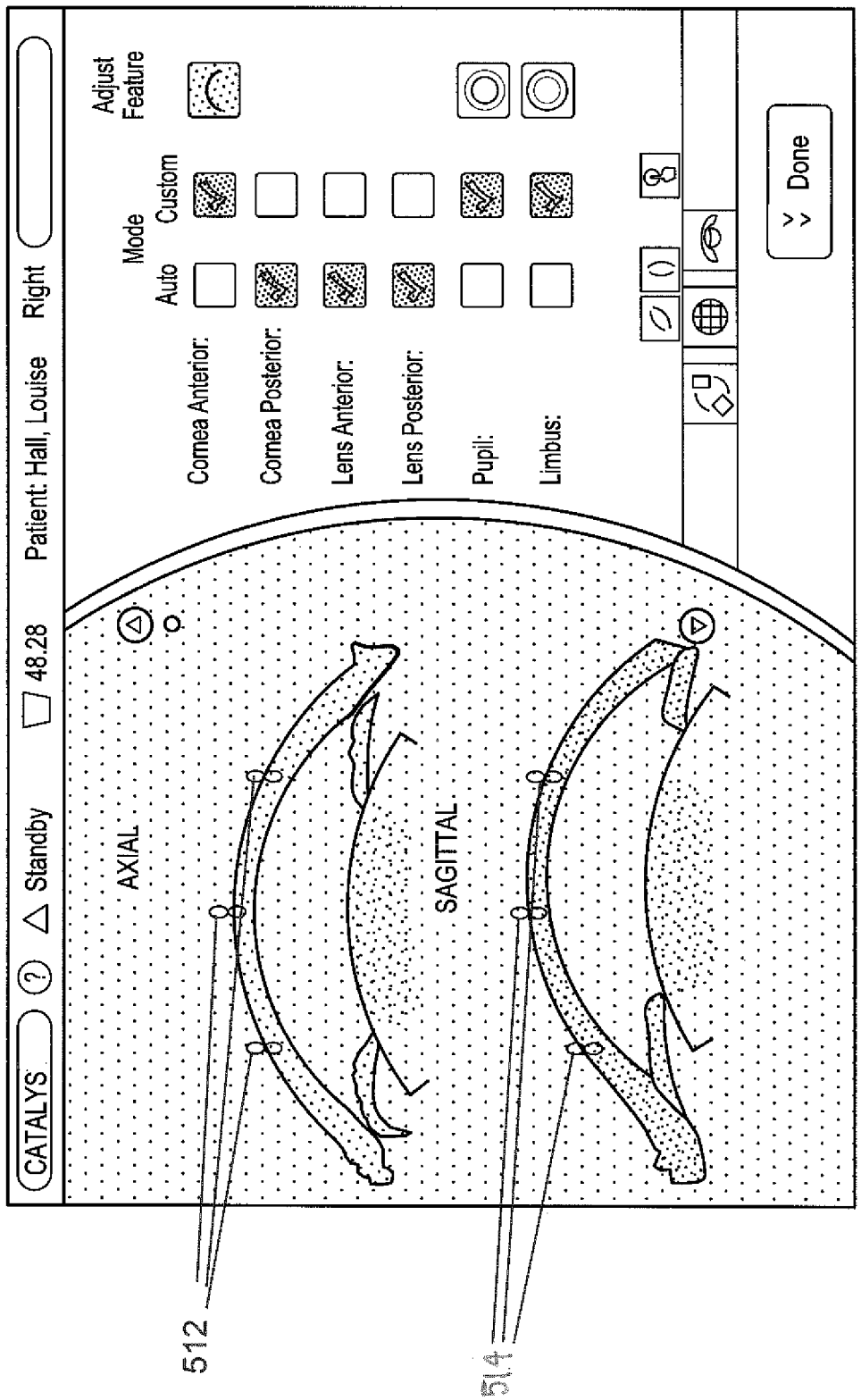

When custom fitting the Cornea Anterior, Cornea Posterior, Lens Anterior, or Lens Posterior surfaces, Slider Icons ▮ 512, 514 will also appear for custom fitting the surface, such as in FIG. 77, which shows an example Custom Fit Cornea Anterior Screen. The Slider Icons 512, 514 can be moved by touching and dragging the Slider Icons. Moving the middle slider on each image moves all three sliders on that particular image. When moving the slider, the highlighted surface disappears to allow accurate positioning of each slider over the image.

Custom fitting of a particular ocular surface using the Slider Icons 512, 514 can proceed in any suitable fashion. For example, the user can start the custom fit by moving the middle sliders to the ocular surface of the respective scanned structure (e.g., cornea, lens capsule) of the patient's eye 43 for both axial and sagittal images. Next, the user can move the two side sliders to the surface for both images. When all six sliders 512, 514 are on the ocular surface, custom fit for the particular surface is complete. The process can be repeated if the fit is not satisfactory. To view all of the ocular surfaces again, the Adjust Feature button is de-selected.

Figure 78:
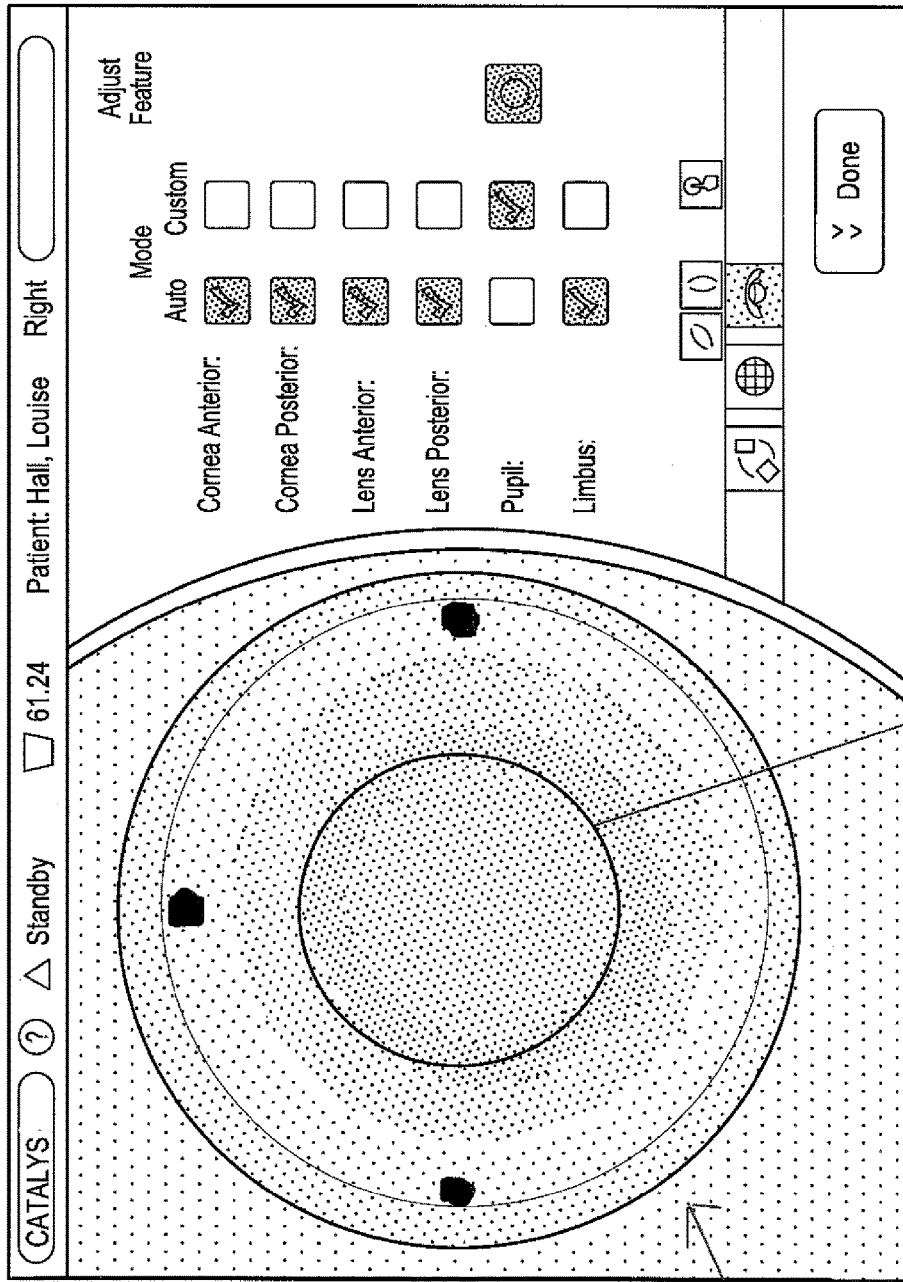

When custom fitting is enabled for the Pupil and Limbus surfaces and the respective Adjust Feature button is selected, the image of the eye 516 is shown from the anterior. To adjust this feature, the user can move the selected area by pressing inside the marked area 518 and moving to an area of the user's choice. To increase or decrease the size of the circle 518, the user can touch on or outside the circle 518 (FIG. 78 shows an example Custom Fit Pupil Screen) and slide the user's finger away from or toward the center of the circle. To show both the Pupil and Limbus fits, the currently selected Adjust Feature button is de-selected.

Figure 79:
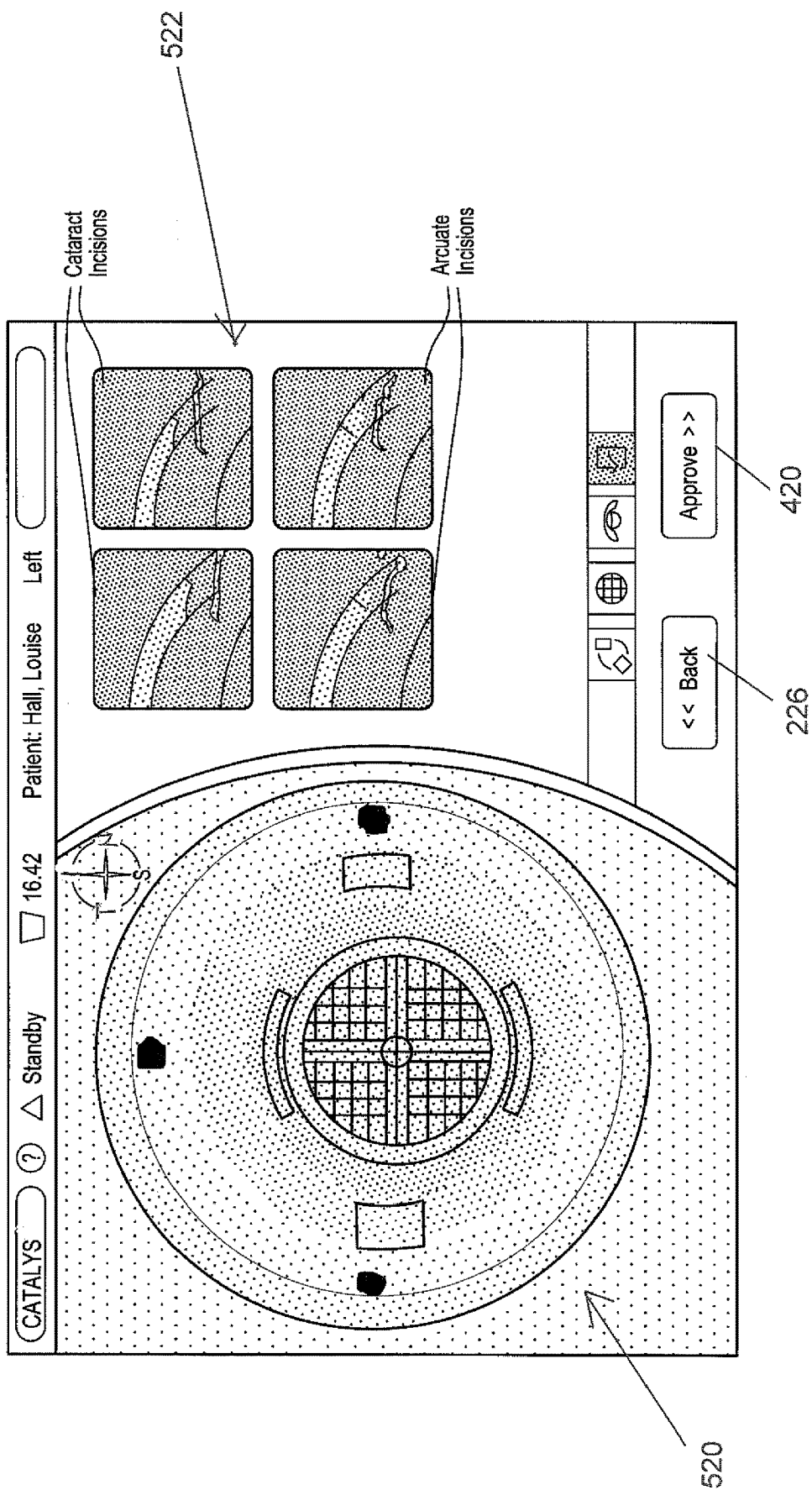
Figure 80:
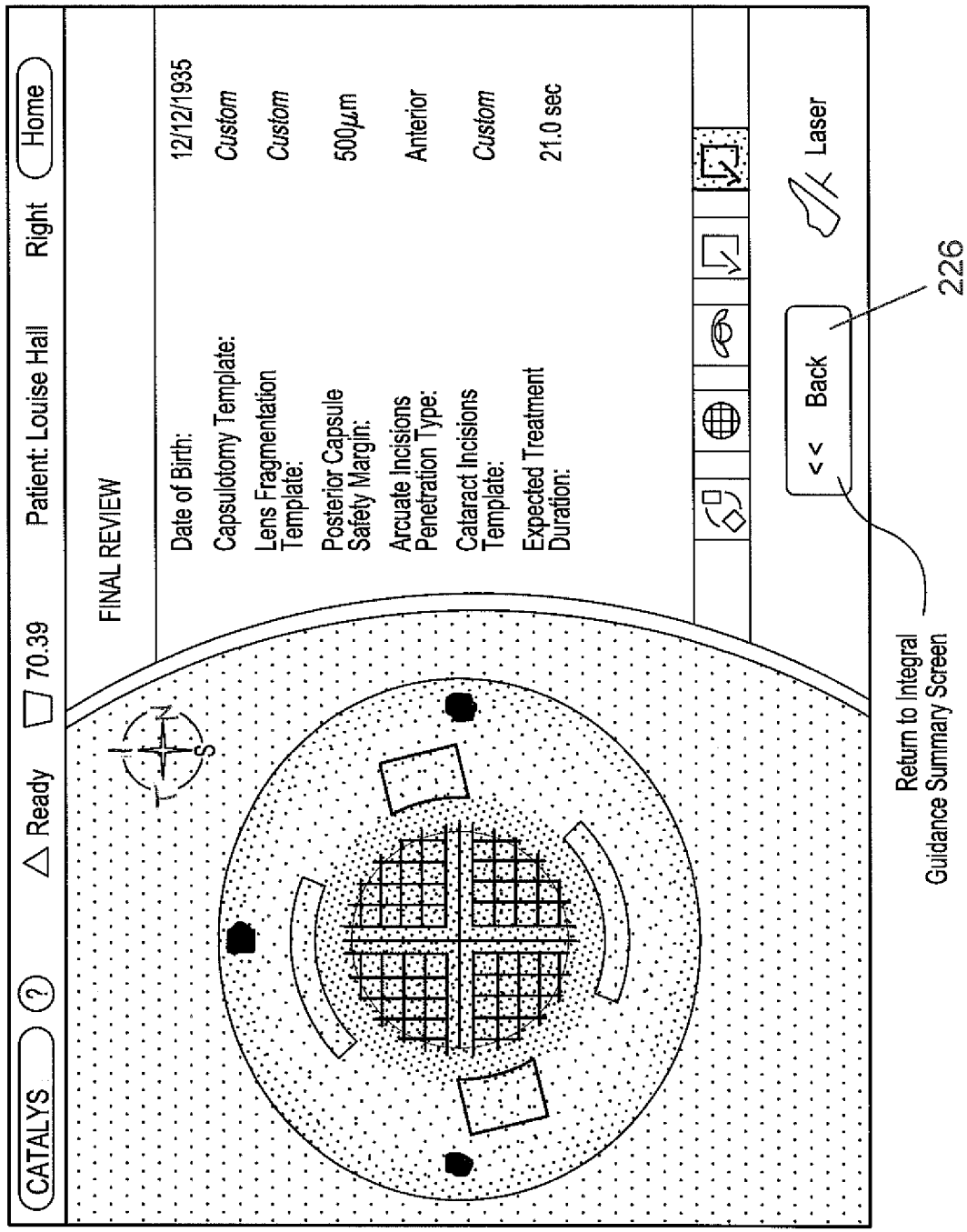

After verifying that the graphical representation on the Scanning Summary Screen is accurate, the user can press the APPROVE button 420 to proceed to the Arcuate/Cataract Incisions Review Screen, an example of which is shown in FIG. 79. The user can verify that the graphical representations of the arcuate and/or cataract incisions (both the anterior 520 and cross-sectional 522 views) are accurate and represent the selected treatment plan. If desired, the user can press the BACK button 226 to return to the Scanning Summary Screen. Otherwise, the user can press the APPROVE button 420 to proceed to the Final Review Screen, an example of which is shown in FIG. 80.

The Final Review Screen allows the user to perform a final review of treatment parameters before initiating laser treatment. If desired, the user can press the BACK button 226 to return to the Arcuate/Cataract Incisions Review Screen. Otherwise, the user can press the laser footswitch 10 to initiate laser treatment.

Figure 81:
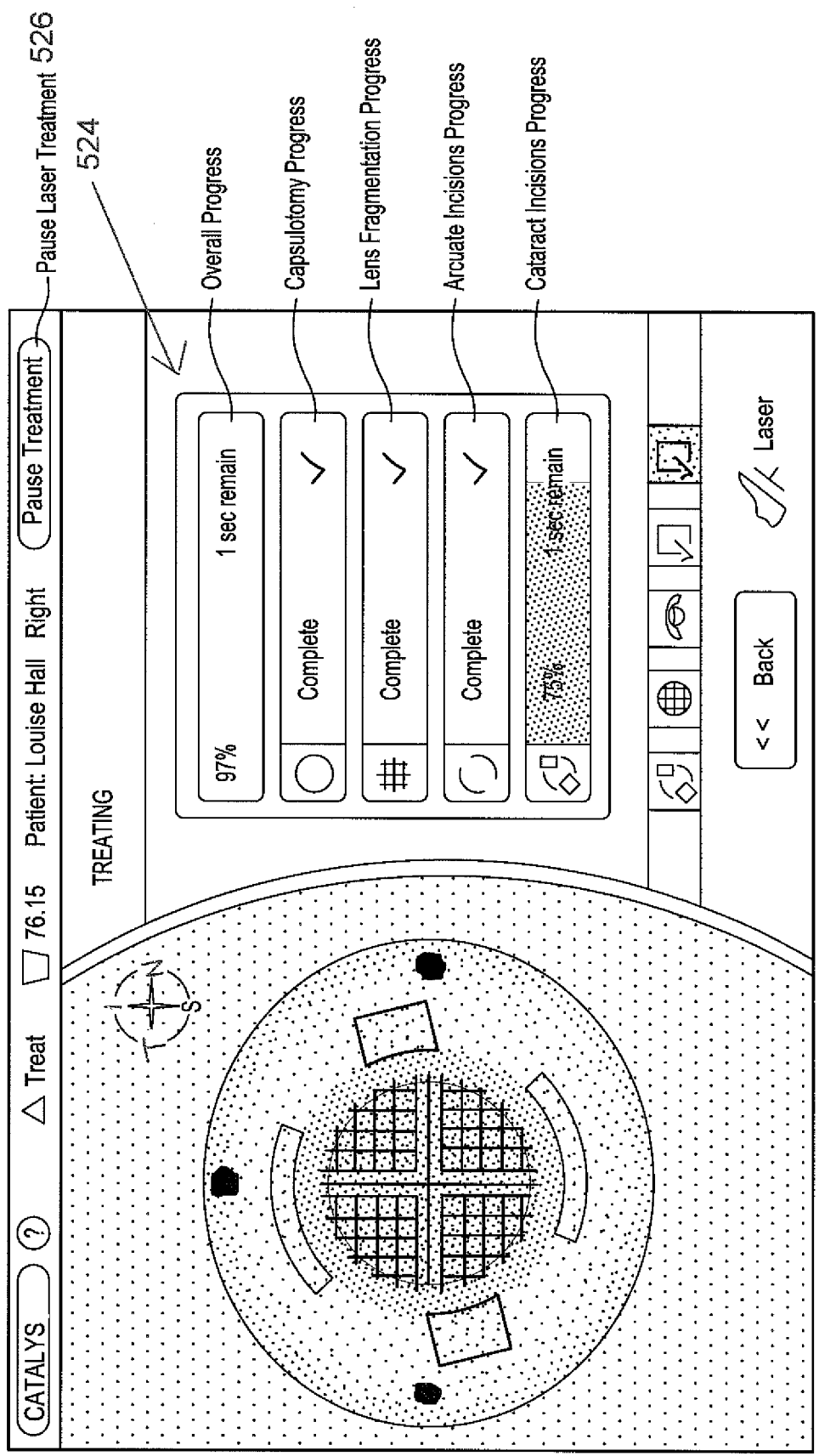

After initiating laser treatment, the Treatment Progress Screen, an example of which is shown in FIG. 81, displays. Separate progress bars 524 track the percentage treatment and time elapsed for the overall treatment, as well as the capsulotomy, lens fragmentation, arcuate incisions, and/or cataract incisions treatments. Adjacent to each progress bar is a count-down timer that displays the remaining treatment time. Laser treatment can be paused at any time by pressing the PAUSE TREATMENT button 526 on the control panel or by releasing the laser footswitch 10. When laser treatment is paused, a "Clearable Error" message displays, and the user must press the OK button to acknowledge and clear the error. To resume laser treatment, the user releases the laser footswitch 10 and then presses it again.

Figure 82:
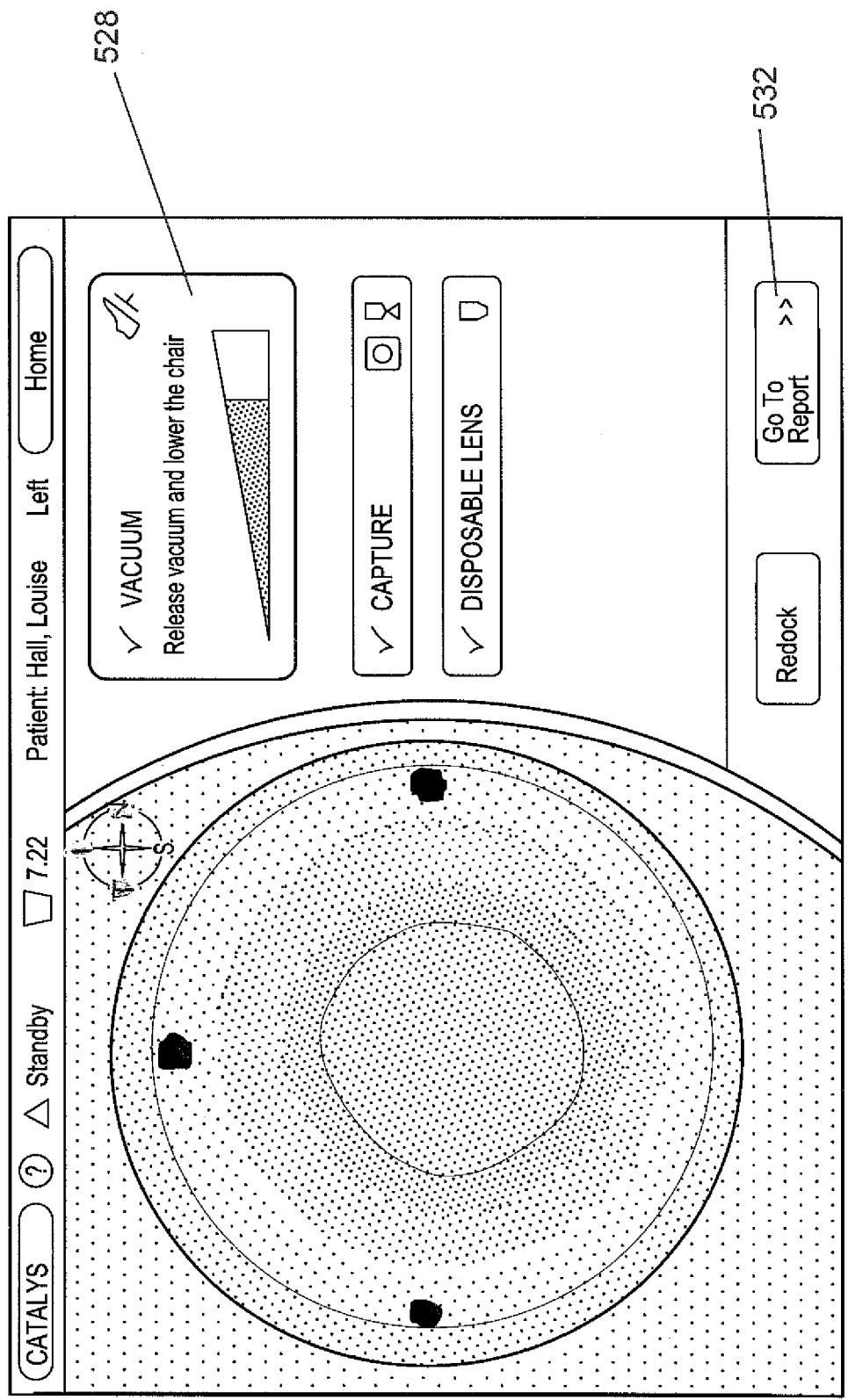

When laser treatment is complete, the system automatically proceeds to Undocking Screens. The Undocking Screens guide the user through the patient release procedure after laser treatment is complete or after the user has begun undocking the patient. When the initial Undocking Screen displays, the Vacuum panel 528 is open as shown in FIG. 82. The open Vacuum panel 528 displays instructions to release patient vacuum and lower the surgical chair.

Figure 83:
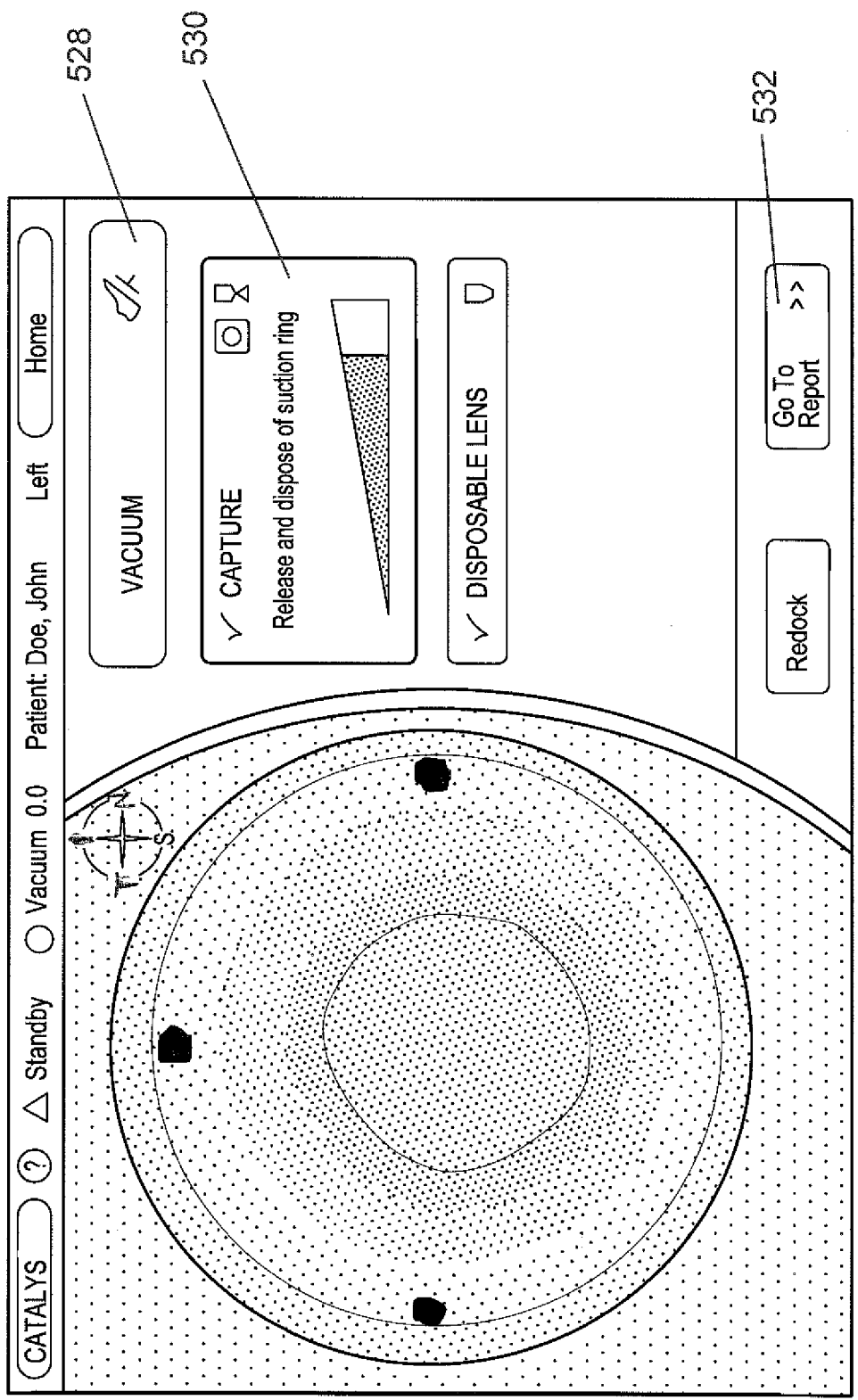

When the system detects that patient vacuum has been released and the surgical chair lowered, the check mark disappears in the Vacuum panel 528, and the Capture panel 530 opens as shown in FIG. 83. The Capture panel 530 displays instructions to release and dispose of the suction ring. The user can either continue with the patient release procedure, or the user can press the GO TO REPORT button 532 to skip to the Treatment Report Summary Screen.

Figure 84:
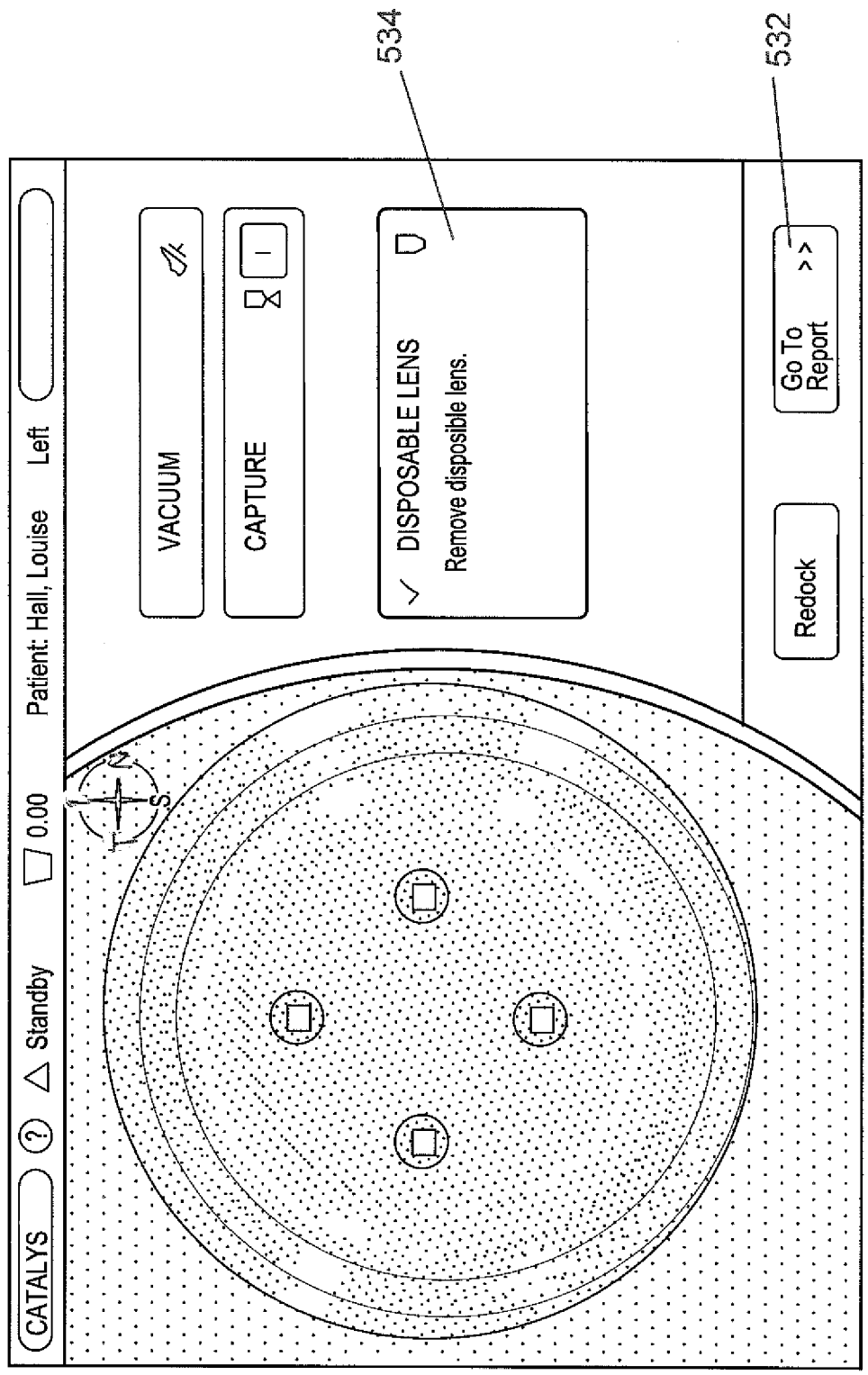

After the system verifies that patient vacuum has been released and the surgical chair lowered, the Disposable Lens panel 534 opens as shown in FIG. 84. The Disposable Lens panel 534 displays instructions to remove the disposable lens. After removing the disposable lens, the user can press the GO TO REPORT button 532 to proceed to the Treatment Report Summary Screen.

Figure 85:
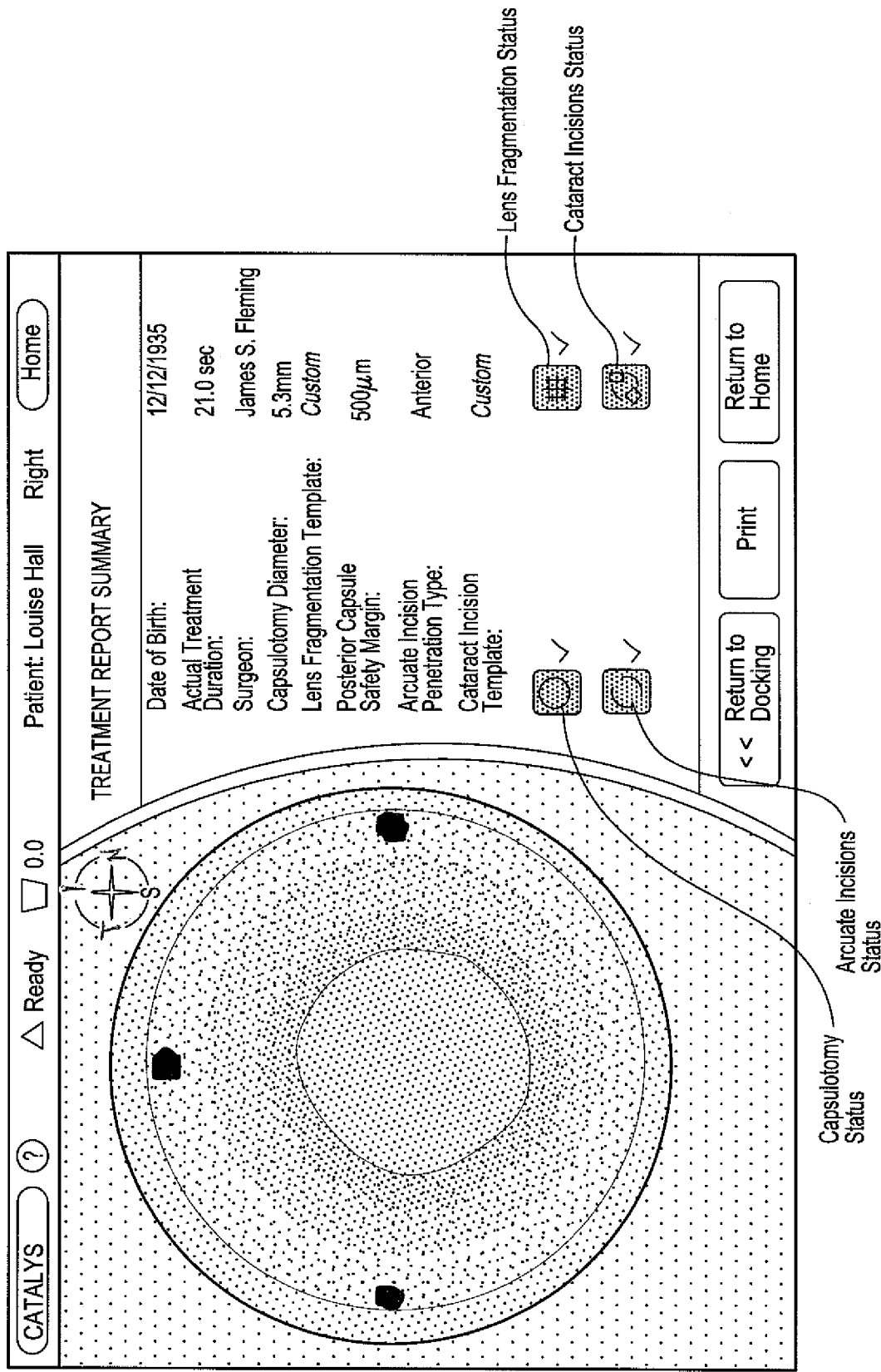

From any of the three Undocking Screens, the user can press the GO TO REPORT button 532 to access the Treatment Report Summary Screen, an example of which is shown in FIG. 85. If treatment was successfully completed, a check mark displays next to the icon(s) for the completed treatments(s).

Capsulotomy Parameters

Figure 86:
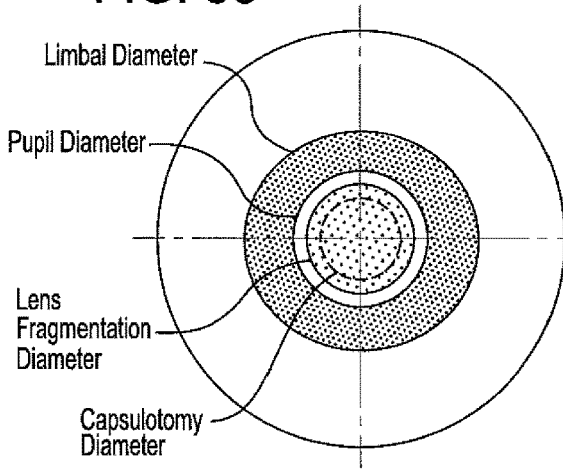
FIGS. 86 and 87 illustrate aspects of a capsulotomy incision of the anterior portion of the lens capsule, in accordance with many embodiments.
Figure 87:
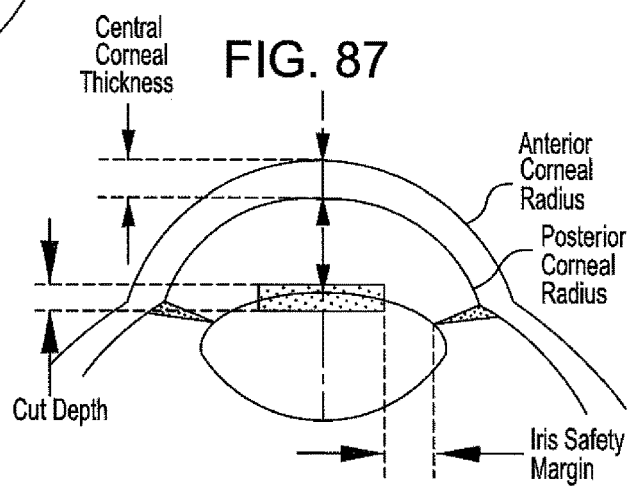

Capsulotomy parameters, including cut dimensions, laser settings and applicable safety margins, are illustrated in FIGS. 86 and 87 and summarized in Tables 3 and 4.

TABLE 3

User-Adjustable Capsulotomy Parameters

| Feature | Default | Range | Step Size | Units |
| --- | --- | --- | --- | --- |
| Pattern | Circle | N/A | N/A | N/A |
| Cut Depth | 600 | 200-1000 | 200 | µm |
| Diameter | N/A | 2.0-8.0 | 0.1 | mm |
| Horizontal Spot Spacing | 5 | 3-10 | 1 | µm |
| Vertical Spot Spacing | 10 | 5-50 | 5 | µm |
| Laser Pulse Energy | 4 | 1-10 | 0.5 | µJ |

TABLE 4

Capsulotomy Safety Margins

| Feature | Value | Units |
|---|---|---|
| Iris | 500 | μm |
| Corneal | 500 | μm |

Lens Fragmentation Parameters

Figure 88:
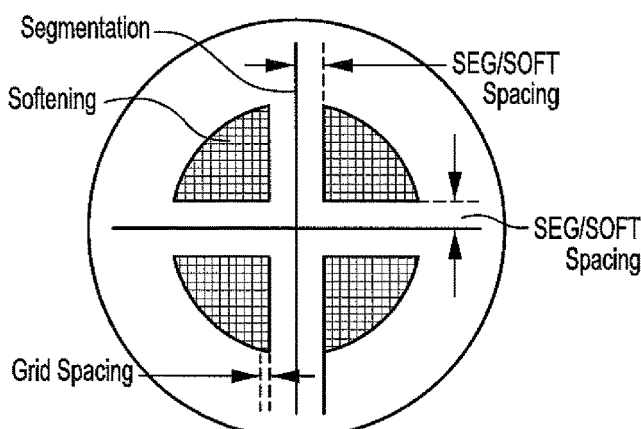
FIGS. 88 and 89 illustrate aspects of lens fragmentation incisions, in accordance with many embodiments.
Figure 89:
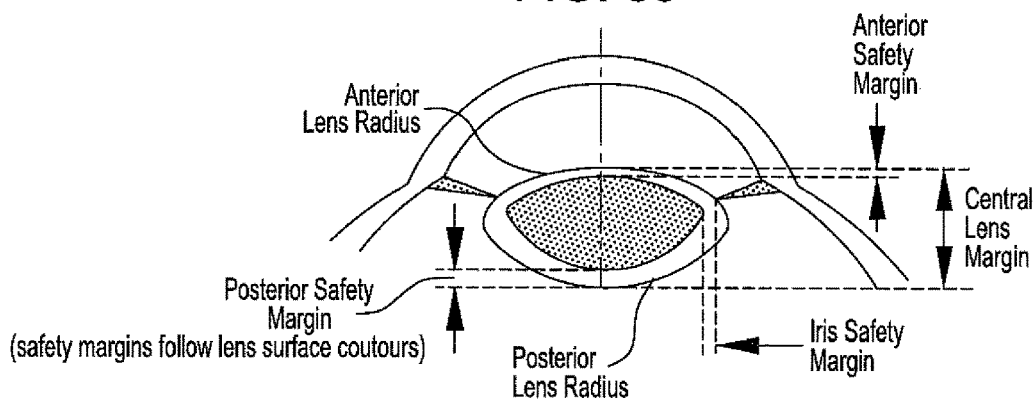

Lens Fragmentation parameters, including cut dimensions for lens segmentation and softening, laser settings, and applicable safety margins, are illustrated in FIGS. 88 and 89 and summarized in Tables 5, 6, and 7.

TABLE 5

Lens Fragmentation Icons

| Patterns | Description |
|---|---|
| ▨ | Lens Segmentation: Quadrants (2 intersecting lines) |
| ▨ | Lens Segmentation: Sextants (3 intersecting lines) |
| ▨ | Lens Segmentation: Octants (4 intersecting lines) |
| ▨ | Lens Softening: Quadrants |
| ▨ | Lens Softening: Sextants |
| ▨ | Lens Softening: Octants |
| ▨ | Quadrants Complete |

TABLE 6

User-Adjustable Lens Fragmentation Parameters

| Feature | Default | Range | Step Size | Units |
|---|---|---|---|---|
| Diameter | * | 3.0-10.0 | 0.5 | mm |
| Horizontal Spot Spacing | 10 | 5-25 | 2.5 | μm |
| Vertical Spot Spacing | 40 | 10-100 | 10 | μm |
| Pulse Energy, Anterior** | 8 | 1-10 | 0.5 | μJ |
| Pulse Energy, Posterior** | 10 | 1-10 | 0.5 | μJ |
| Seg-Soft Spacing | 500 | 100-1500 | 100 | μm |
| Grid Spacing | 500 | 100-2000 | 100 | μm |

*Default diameter is defined by available pupil diameter—2*safety margin.
**Pulse energy to vary stepwise (linear) from posterior to anterior, if different

TABLE 7

Lens Fragmentation Safety Margins

| Feature | Default | Range | Step Size | Units |
|---|---|---|---|---|
| Iris | 500 | N/A | N/A | μm |
| Anterior *** | 500 | 200-1000 | 100 | μm |
| Posterior *** | 500 | 500-1000 | 100 | μm |

*** Safety margins follow lens surface contours.

Arcuate and Cataract Incision Parameters

Figure 90:
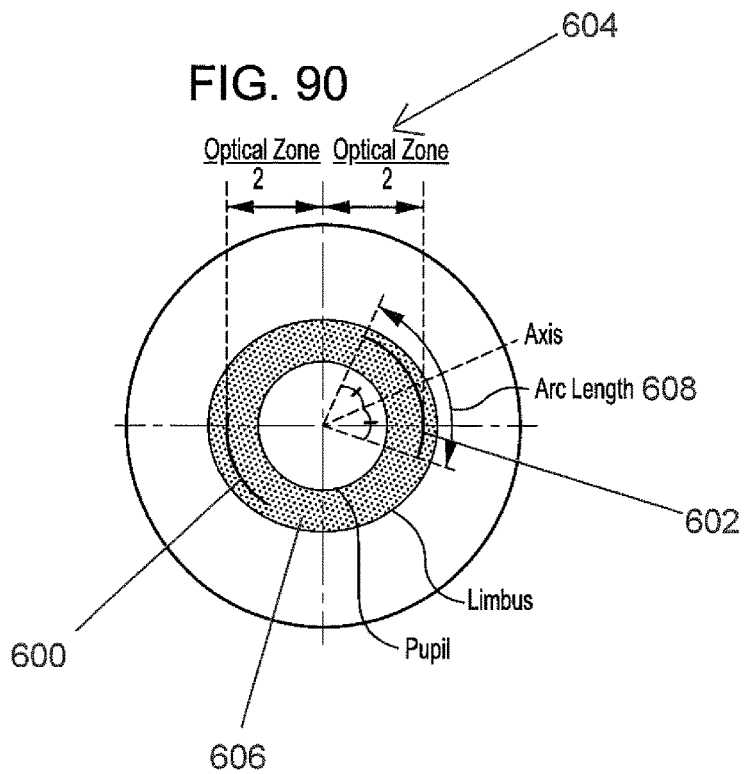
FIGS. 90 through 92 illustrate aspect of arcuate incisions of a cornea, in accordance with many embodiments.

FIG. 90 shows an en face view of arcuate incisions 600, 602 within the optical zone 604 of the cornea 606 that can be formed using the system 2. The optical zone 604 is user-adjustable within the range of 2 mm-11 mm. For asymmetric arcuate incisions, the optical zone 604 is independently adjustable for each incision. Arc length 608 is user-adjustable within the range of 10°-120°.

Figure 91:
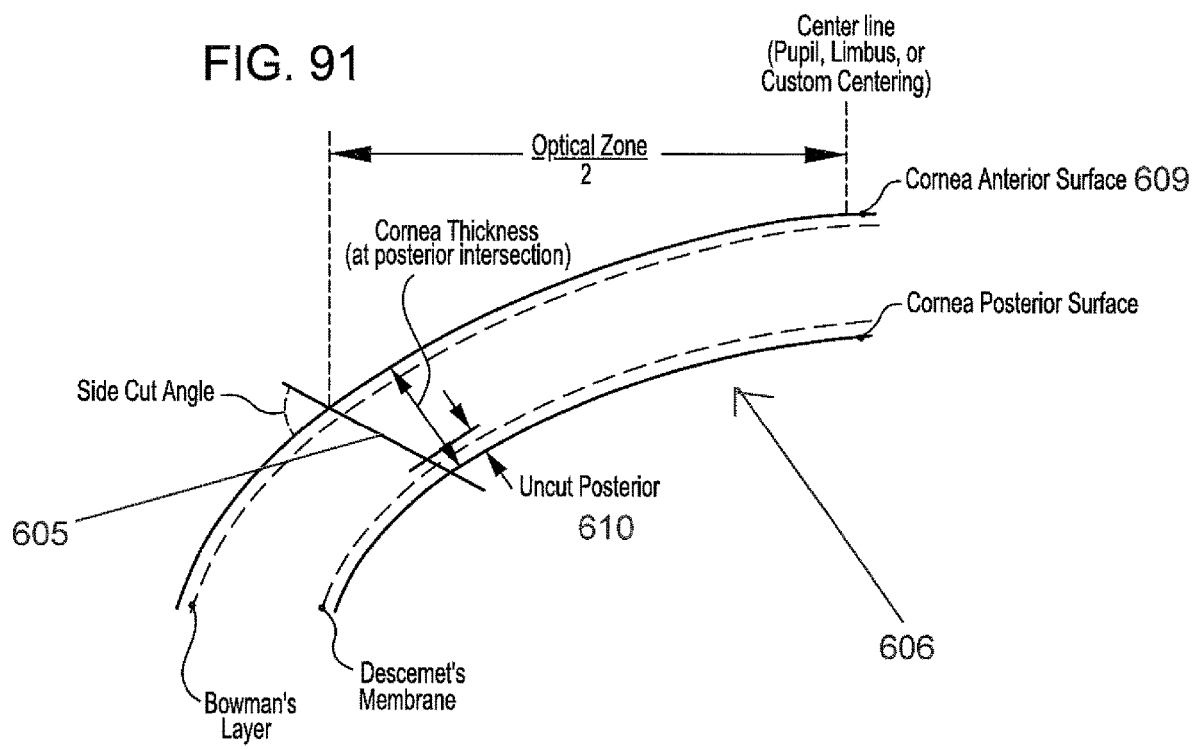
Figure 92:
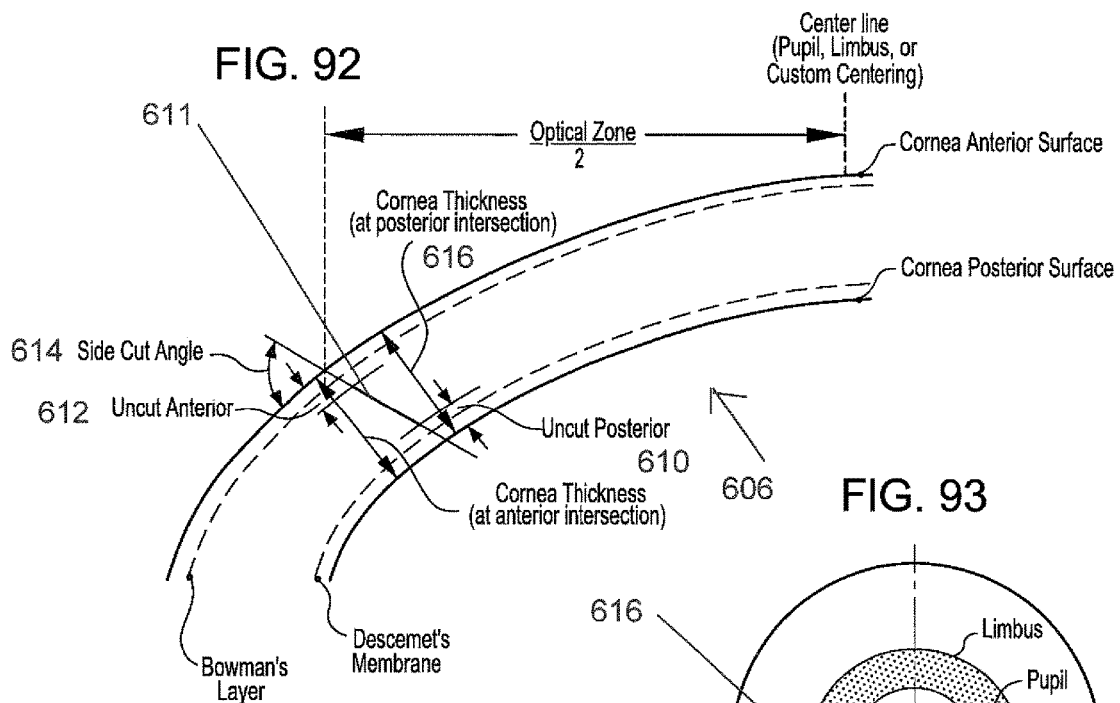

FIG. 91 shows a cross-sectional view of an arcuate incision 605 in the cornea 606 that can be formed using the system 2 and that penetrates the cornea anterior surface 609 and has an uncut posterior portion 610. FIG. 92 shows a cross-sectional view of an arcuate intrastromal incision 611 in the cornea 606 that can be formed using the system 2. The arcuate intrastromal incision 611 has an uncut anterior portion 612 and an uncut posterior portion 610. Side cut angle 614 is user-adjustable within the range of 30°-150°. Uncut posterior and anterior portions 610, 612 are user-adjustable within the range of 100 μm-250 μm or 20%-50% of the cornea thickness. Cornea thickness is measured at the projected intersection of the incision with the cornea anterior/posterior measured at 90° to anterior/posterior cornea surface regardless of what side cut angle 614 is chosen.

Figure 93:
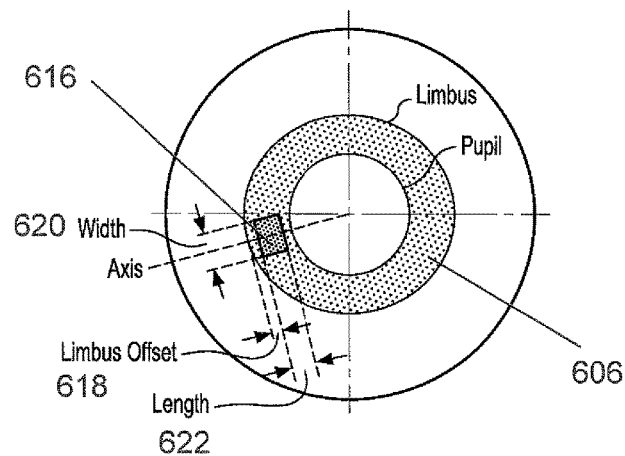
FIGS. 93 through 98 illustrate aspects of primary cataract incisions of a cornea, in accordance with many embodiments.
Figure 94:
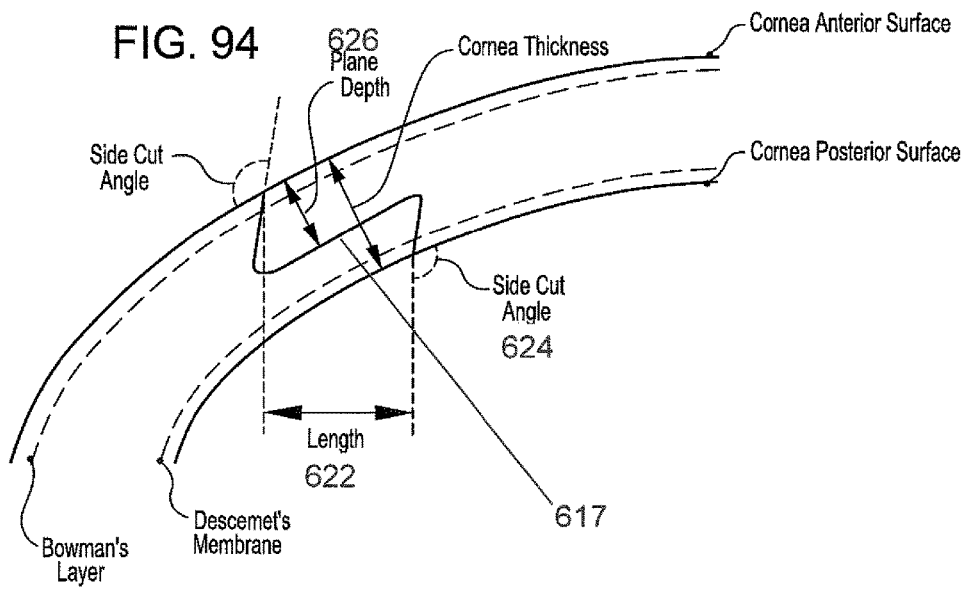
Figure 95:
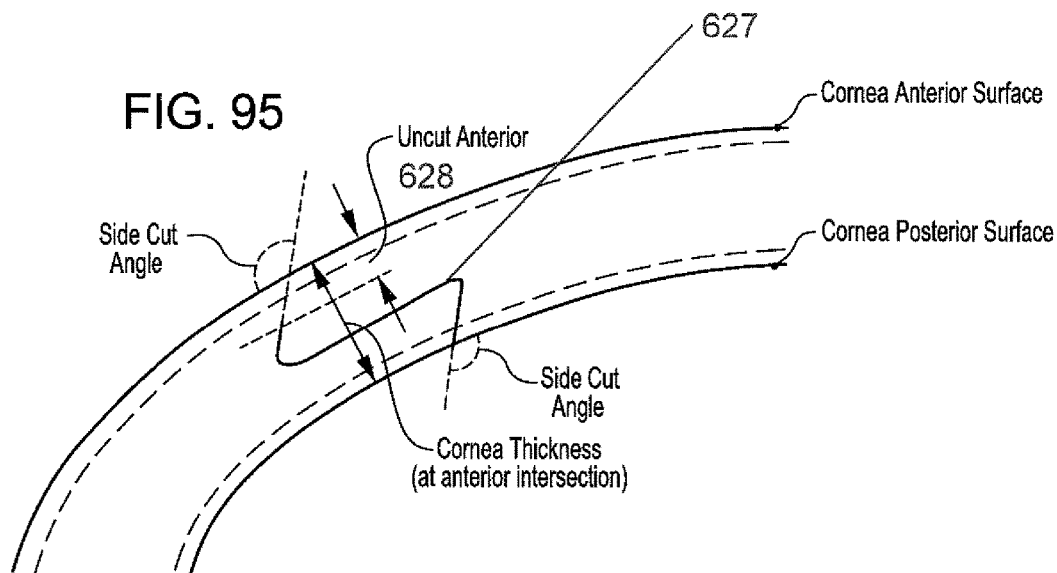
Figure 96:
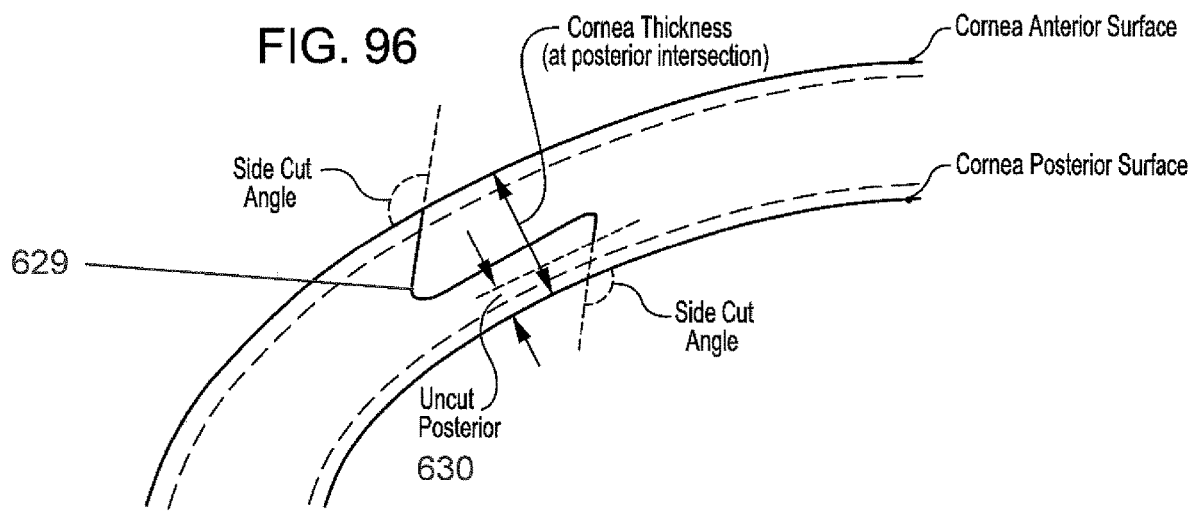
Figure 97:
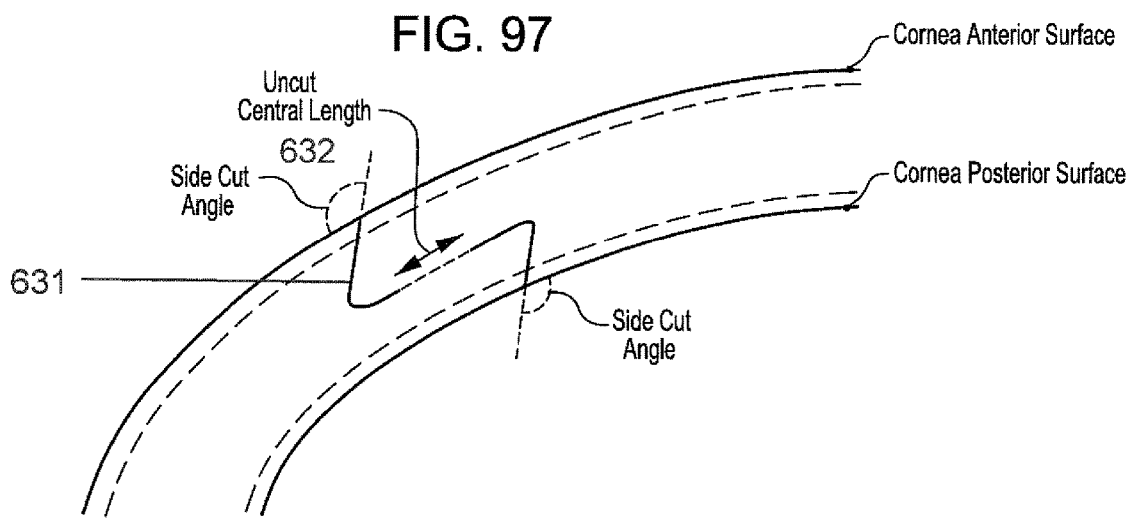
Figure 98:
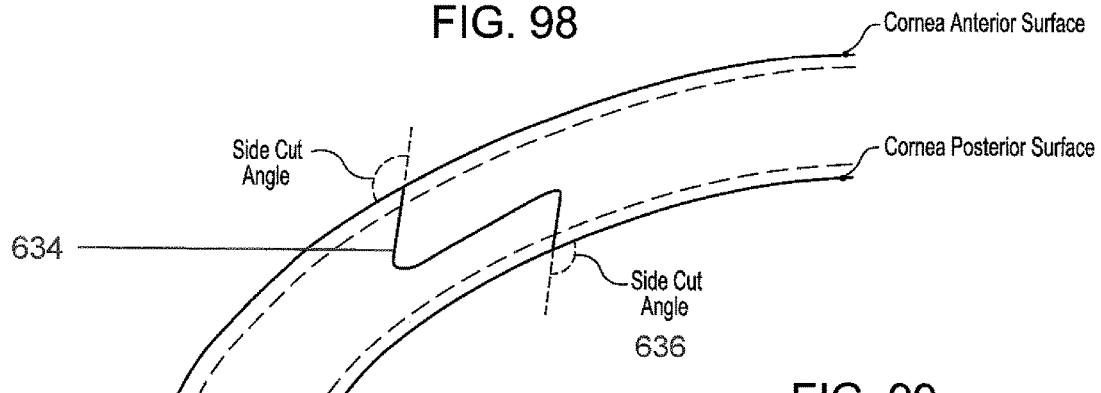

FIG. 93 shows an en face view of a primary cataract incision 616 in the cornea 606 that can be formed using the system 2. The primary cataract incision 616 provides access to surgical tools used to, for example, remove the fragmented crystalline lens nucleus and insert an IOL. FIG. 94 shows a cross-sectional view of a primary cataract incision 617 of the cornea 606 that can be formed using the system 2. Limbus offset 618 is user-adjustable within the range of 0.0 mm-5.0 mm. Width 620 is user-adjustable within the range 0.2 mm-6.5 mm. Length 622 is user-adjustable within the range of 0.5 mm-3.0 mm. Side Cut Angle 624 is user-adjustable within the range of 30°-150°. Plane depth 626 is user-adjustable within the range of 125 μm-375 μm or 25%-75% of the cornea thickness. Length 622 is defined as the en face view distance between the projected incision intersection with the cornea anterior and the cornea posterior. FIG. 95 shows a cross-sectional view of a primary cataract incision 627 that includes an uncut anterior portion 628. FIG. 96 shows a cross-sectional view of a primary cataract incision 629 that includes an uncut posterior portion 630. FIG. 97 shows a cross-sectional view of a primary cataract incision 631 that includes an uncut central length 632. And FIG. 98 shows a cross-sectional view of a primary cataract incision 634 that includes no uncut portion. Side Cut Angle 636 is user-adjustable within the range of 30°-150°. Uncut central length 632 is user-adjustable within the range of 25 μm-1000 μm.

Figure 99:
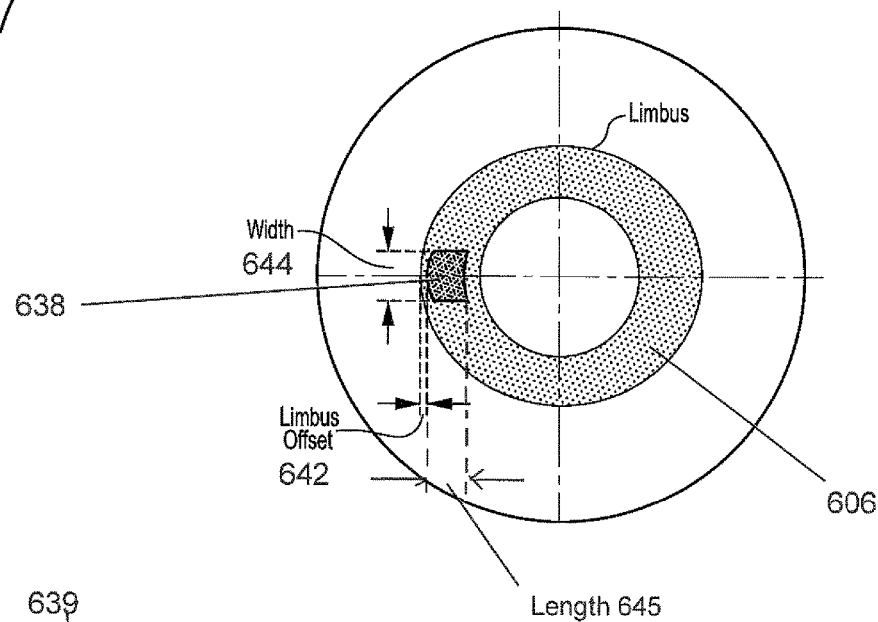
FIGS. 99 through 103 illustrate aspects of sideport cataract incisions of a cornea, in accordance with many embodiments.
Figure 100:
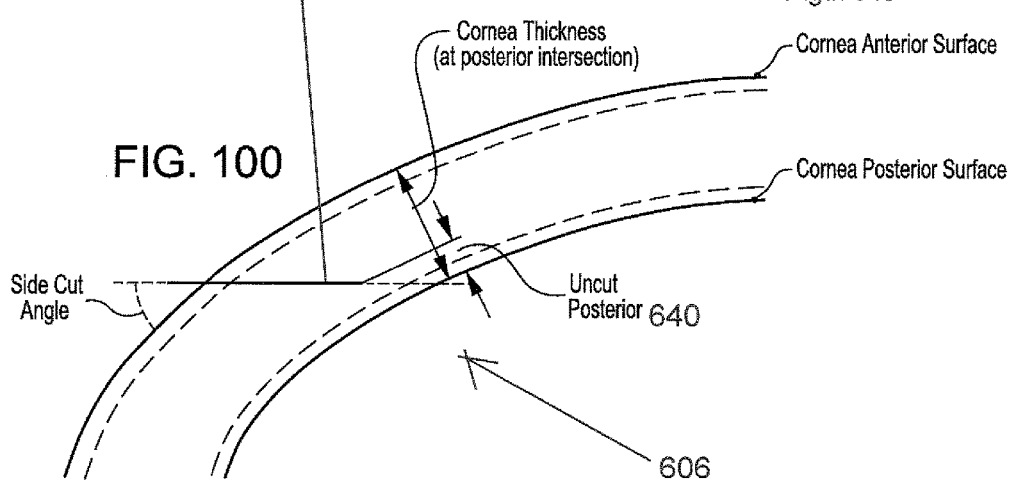
Figure 101:
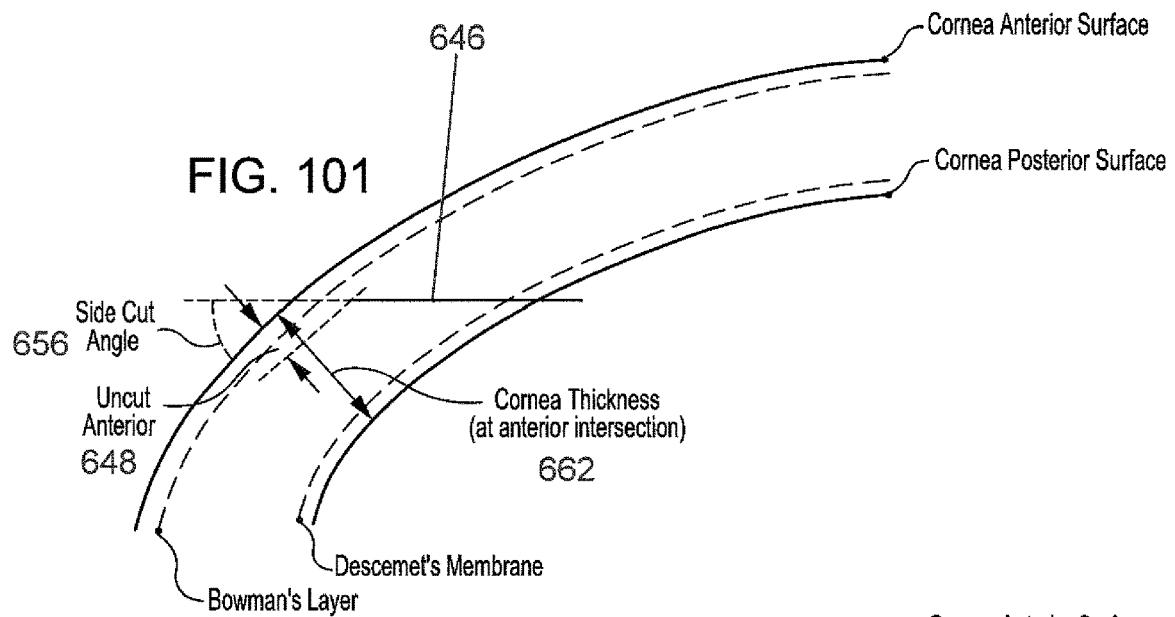
Figure 102:
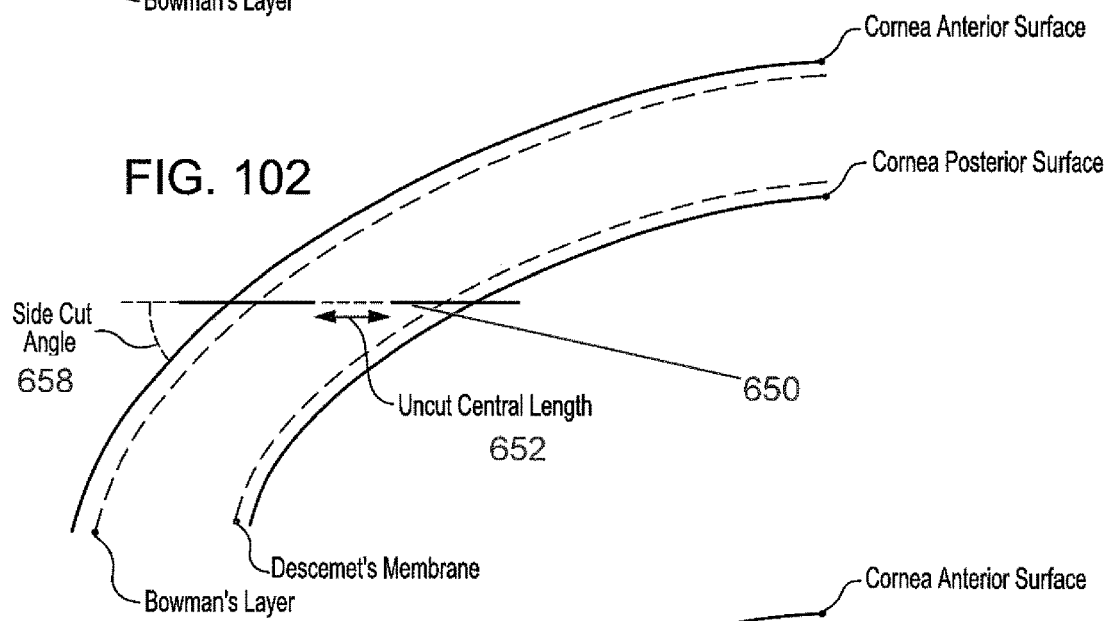
Figure 103:
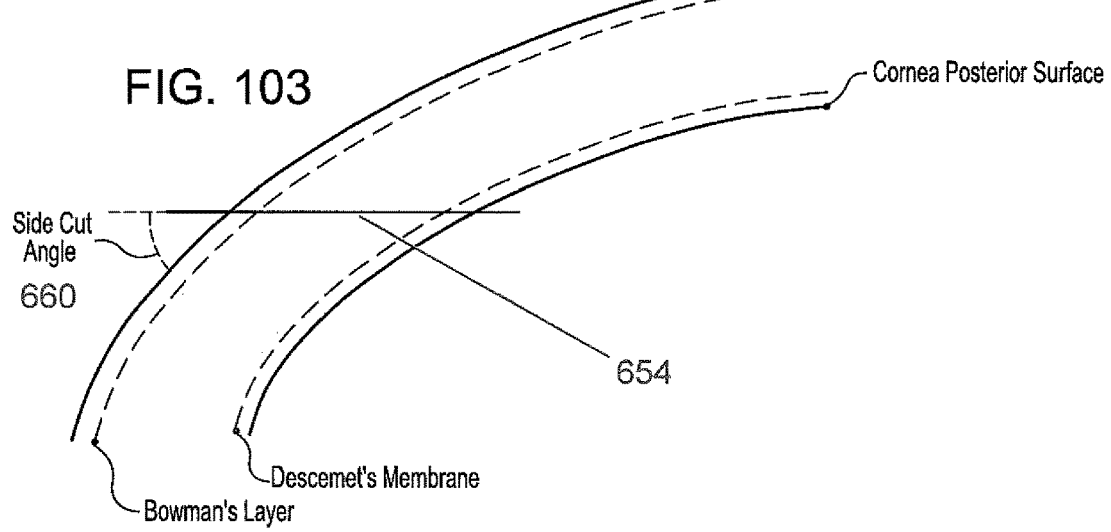

FIG. 99 shows an en face view of a sideport cataract incision 638 in the cornea 606 that can be formed using the system 2. The sideport cataract incision 638 provides access for surgical tools used, for example, to assist in the removal of the fragmented crystalline lens. FIG. 100 shows a cross-sectional view of a sideport cataract incision 639 of the cornea 606 that has an uncut posterior portion 640 and can be formed using the system 2. Limbus offset 642 is user-adjustable within the range of 0.0 mm-5.0 mm. Width 644 is user-adjustable within the range 0.2 mm-6.5 mm. Length 645 is user-adjustable within the range of 0.5 mm-3.0 mm. FIG. 101 shows a cross-sectional view of a sideport cataract incision 646 that includes an uncut anterior portion 648. FIG. 102 shows a cross-sectional view of a sideport cataract incision 650 that includes an uncut central length 652. And FIG. 103 shows a cross-sectional view of a sideport cataract incision 654 that includes no uncut portion. Side Cut Angle 656, 658, 660 is user-adjustable within the range of 30°-150°. Uncut central length 652 is user-adjustable within the range of 100 μm-250 μm or 20%-50% of the cornea thickness. Cornea thickness 662 is measured at the projected intersection location of the incision with the cornea anterior/posterior measured at 90° to the anterior/posterior cornea surface regardless of what side cut angle is chosen.

Figure 104A:
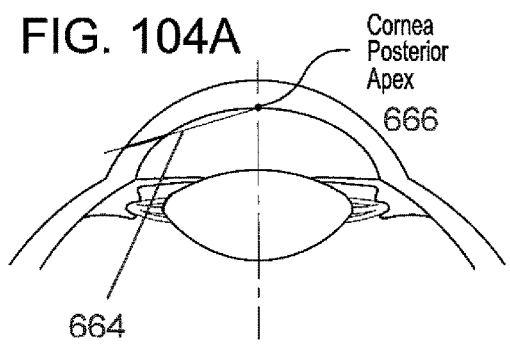
FIGS. 104A through 104D illustrate alignments for sideport cataract incisions of the cornea, in accordance with many embodiments.
Figure 104C:
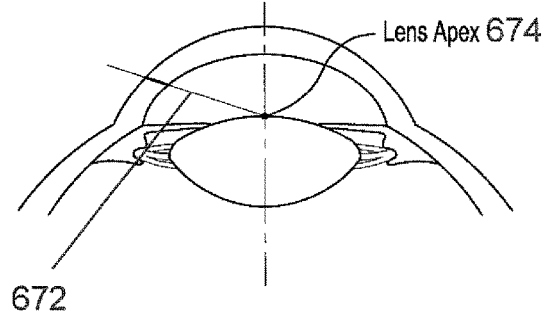
Figure 104B:
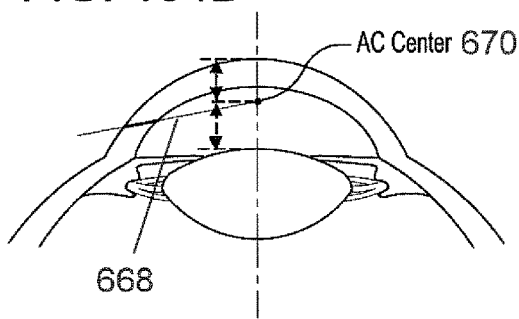
Figure 104D:
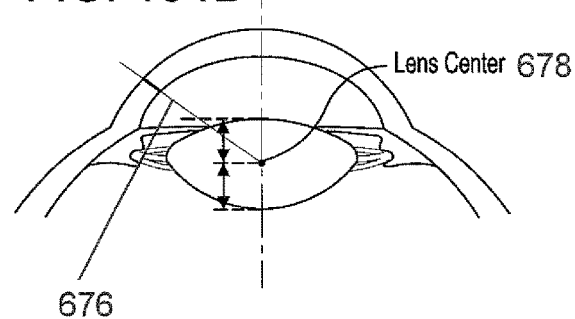

FIGS. 104A, 104B, 104C, and 104D illustrate side cut angle methods for sideport cataract incisions. FIG. 104A illustrates aligning the sideport cataract incision 664 with the cornea posterior apex 666. FIG. 104B illustrates aligning the sideport cataract incision 668 with the anterior chamber center 670. FIG. 104C illustrates aligning the sideport cataract incision 672 with the lens apex 674. And FIG. 104D illustrates aligning the sideport cataract incision 676 with the lens center 679.

Figure 105:
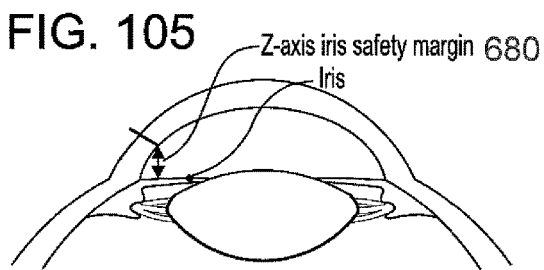
FIG. 105 illustrates a z-axis iris safety margin for all corneal incisions, in accordance with many embodiments.
Figure 106:
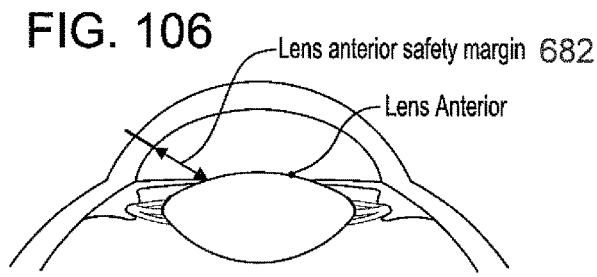
FIG. 106 illustrates a lens anterior safety margin for all corneal incisions, in accordance with many embodiments.

FIG. 105 illustrates a z-axis iris safety margin 680 for all corneal incisions. And FIG. 106 illustrates a lens anterior safety margin 682 for all corneal incisions.

Table 8 contains user-adjustable parameters for arcuate incisions. Table 9 contains user-adjustable parameters for primary cataract incisions. Table 10 contains user-adjustable parameters for sideport cataract incisions.

TABLE 8

User-adjustable parameters for arcuate incisions.

| Feature | Default* | Range | Increment | Step Size | Units |
|---|---|---|---|---|---|
| Incision Type | N/A | Single, Symmetric, Asymmetric | N/A | 0.5 | N/A |
| Axis** | N/A | 0-360 | 1 | 2.5 | ° |
| Optical Zone** | N/A | 2-11 | 0.1 | 10 | mm |
| Arc Length** | N/A | 10-120 | 1 | 0.5 | ° |
| Centering Method | N/A | Pupil, Limbus, Custom | N/A | 0.5 | N/A |
| Penetration Type | Anterior | Anterior or Intrastromal | N/A | N/A | N/A |
| Depth Units | Percentage | Percentage or Absolute | N/A | N/A | N/A |
| Uncut Anterior*** | 20% | 20-50% | 1 | 2 | % |
|  | 100 | 100-250 | 1 | 10 | μm |
| Uncut Posterior | 20% | 20-50% | 1 | 2 | % |
|  | 100 | 100-250 | 1 | 10 | μm |
| Side Cut Angle | 90 | 30-150 | 1 | 5 | ° |
| Horizontal Spot Spacing | 10 | 5-50 | 1 | 5 | μm |
| Vertical Spot Spacing | 20 | 10-50 | 1 | 5 | μm |
| Pulse Energy | 5 | 3-10 | 0.1 | 0.5 | μJ |

*Parameters do not have default values; user must select each parameter.
**Independently adjustable parameters for asymmetric incisions.
***Not applicable for anterior penetrating.

TABLE 9

User-adjustable parameters for primary cataract incisions.

| Feature | Default* | Range | Increment | Step Size | Units |
|---|---|---|---|---|---|
| Axis | N/A | 0-360 | 1 | 5 | ° |
| Limbus Offset | N/A | 0.0-5.0 | 0.1 | 0.1 | mm |
| Width | 2.2 | 0.2-6.5 | 0.1 | 0.1 | mm |
| Length | 2.2 | 0.5-3.0 | 0.1 | 0.1 | mm |
| Uncut Region | Central | Anterior, Central, Posterior, None | N/A | N/A | N/A |
| Depth Units | Percentage | Percentage or Absolute | N/A | N/A | N/A |
| Uncut Anterior/ | 20% | 20-50% | 1% | 5% | % |
| Uncut Posterior | 100 | 100-250 | 1 | 25 | μm |
| Uncut Central Length* | 100 | 25-1000 | 1 | 25 | μm |
| Plane Depth | 50% | 25-75% | 1% | 5% | % |
|  | 250 | 125-375 | 1 | 50 | μm |
| Side Cut Angle | 120 | 30-150 | 1 | 5 | ° |
| Horizontal Spot Spacing | 10 | 5-50 | 1 | 5 | μm |
| Vertical Spot Spacing | 20 | 10-50 | 1 | 5 | μm |
| Pulse Energy | 5 | 3-10 | 0.1 | 0.5 | μJ |

*If the uncut central length is longer than the length parameter, then the uncut central length will be set as equal to the length parameter.

TABLE 10

User-adjustable parameters for sideport cataract incisions.

| Feature | Default* | Range | Increment | Step | Units |
|---|---|---|---|---|---|
| Number of Incisions | N/A | 0-6 | 1 | 1 | N/A |
| Axis* | N/A (0) | 0-360 | 1 | 5 | ° |
| Limbus Offset* | N/A (1.0) | 0.0-5.0 | 0.1 | 0.1 | mm |
| Width* | N/A (0.5) | 0.2-6.5 | 0.1 | 0.1 | mm |
| Uncut Type | Central | Anterior, Central, Posterior, None | N/A | N/A | N/A |
| Uncut Units | Percentage | Percentage or Absolute | N/A | N/A | N/A |
| Uncut Length | 20% | 20-50% | 1% | 2% | % |
| (Anterior, Posterior, | 100 | 100-250 | 1 | 10 | μm |
| Side Cut Angle Type | Lens Apex | Cornea Posterior Apex, AC Center, Lens Apex, Lens Center, Custom | N/A | N/A | N/A |
| Custom Side Cut Angle | 90 | 30-150 | 1 | 5 | ° |

TABLE 10-continued

User-adjustable parameters for sideport cataract incisions.

| Feature | Default* | Range | Increment | Step | Units |
|---|---|---|---|---|---|
| Horizontal Spot Spacing | 10 | 5-50 | 1 | 5 | µm |
| Vertical Spot Spacing | 20 | 10-50 | 1 | 5 | µm |
| Pulse Energy | 5 | 3-10 | 0.1 | 0.5 | µJ |

*Individually adjustable for each sideport cataract incision.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for planning and performing a laser surgery procedure on an eye having a cornea, a pupil, and a lens, the cornea having an anterior surface and a posterior surface, the lens being disposed within a lens capsule having an anterior portion and a posterior portion, the system comprising:
   a treatment lase delivery system including a laser source configured to produce a treatment beam that includes a plurality of laser pulses;
   an integrated optical system that includes an imaging assembly containing at least one optical lens and operatively coupled to the treatment laser delivery system for the treatment beam such that the imaging assembly and the treatment laser delivery system share at least one common optical element, the integrated optical system being configured to locate at least a portion of the corneal anterior surface and at least a portion of the corneal posterior surface;
   a patient interface configured to couple the eye with the integrated optical system so as to constrain the position of the eye relative to the integrated optical system;
   a display device; and
   a controller operatively coupled with the display device, the laser source, and the integrated optical system; the controller being configured to:
      generate, relative to the integrated optical system, a spatial disposition of the corneal anterior surface and a spatial disposition of the corneal posterior surface by using the integrated optical system to locate at least portions of the corneal anterior and posterior surfaces;
      generate a spatial disposition of an incision to be formed in the cornea using the spatial dispositions of the corneal anterior and posterior surfaces and at least one corneal incision parameter, the at least one corneal incision parameter including a first numerical parameter that defines an amount of an uncut anterior region of the cornea and/or a second numerical parameter that defines an amount of an uncut posterior region of the cornea, the incision being a two-dimensional surface, wherein the corneal incision extends partially through the cornea so as to leave the uncut anterior or posterior region of the cornea aligned with one or more cut portions of the corneal incision, the corneal incision and the uncut anterior or posterior region of the cornea defining an access path for a cataract surgery instrument;
      display a composite image on the display device, the composite image including an image representative of the spatial dispositions of the corneal anterior and posterior surfaces and an image representing the corneal incision, and display the first and/or the second numerical parameter on the display device; and
      operate the a treatment lase delivery system to deliver the treatment beam into the eye to form the incision in the cornea.

2. The system of claim 1, wherein the at least one corneal incision parameter includes a corneal incision line density parameter to control amount of overlap between adjacent lines of laser pulse focus points that will be used to form the corneal incision.

3. The system of claim 1, further comprising a user input device, the controller being further configured to:
   alter the at least one corneal incision parameter in response to user input via the user input device;
   generate a spatial disposition of an altered incision of the cornea using the generated corneal anterior and posterior spatial dispositions and the altered corneal incision parameter; and
   display a second composite image on the display device, the second composite image including an image representative of the generated spatial dispositions of the corneal anterior and posterior surfaces and an image representing the altered corneal incision.

4. The system of claim 1, wherein the integrated optical system is configured to locate at least a portion of the anterior portion of the lens capsule, the controller being further configured to:
   generate a spatial disposition of at least a portion of the anterior portion of the lens capsule by using the integrated optical system to locate at least a portion of the anterior portion of the lens capsule;
   generate a spatial disposition of a capsulotomy incision of the anterior portion of the lens capsule using the generated spatial disposition of the anterior portion of the lens capsule and at least one capsulotomy parameter; and
   display a third composite image on the display device, the third composite image including an image representative of the generated spatial disposition of the anterior portion of the lens capsule and an image representing the capsulotomy incision.

5. The system of claim 4, further comprising a user input device, the controller being further configured to:
   alter the at least one capsulotomy parameter in response to user input via the user input device;

generate a spatial disposition of an altered capsulotomy incision of the anterior portion of the lens capsule using the generated anterior lens capsule spatial disposition and the altered capsulotomy parameter; and display a fourth composite image on the display device, the fourth composite image including an image representative of the generated spatial disposition of the anterior portion of the lens capsule and an image representing the altered capsulotomy incision.

6. The system of claim 4, wherein the integrated optical system is configured to locate at least a portion of the posterior portion of the lens capsule, the controller being further configured to:

generate a spatial disposition of at least a portion of the posterior portion of the lens capsule by using the integrated optical system to locate at least the portion of the posterior portion of the lens capsule;

generate a spatial disposition of a lens fragmentation incision pattern of the lens using the generated spatial disposition of the posterior portion of the lens capsule and at least one lens fragmentation parameter; and display a fifth composite image on the display device, the fifth composite image including an image representative of the generated spatial dispositions of the anterior and posterior portions of the lens capsule and an image representing the lens fragmentation incision pattern.

7. The system of claim 6, further comprising a user input device, the controller being further configured to:

alter the at least one lens fragmentation parameter in response to user input via the user input device;

generate a spatial disposition of an altered lens fragmentation incision pattern using the generated spatial dispositions of the anterior and posterior portions of the lens capsule and the altered at least one lens fragmentation parameter; and display a sixth composite image on the display device, the sixth composite image including an image representative of the generated spatial dispositions of the corneal anterior and posterior surfaces and an image representing the altered lens fragmentation incision pattern.

8. The system of claim 1, wherein the composite image includes an image representative of a spatial disposition of an anterior portion of the lens capsule and an image representing a capsulotomy incision, and at least one capsulotomy parameter for generating the spatial disposition of the capsulotomy incision includes a capsulotomy line density parameter to control amount of overlap between adjacent lines of laser pulse focus points that will be used to form the capsulotomy incision.

9. The system of claim 1, wherein the composite image includes an image representative of a spatial dispositions of the anterior and posterior portions of the lens capsule and an image representing the lens fragmentation incision pattern, wherein at least one lens fragmentation parameter for generating the spatial disposition of the lens fragmentation incision pattern includes a lens fragmentation line density parameter to control amount of overlap between adjacent lines of laser pulse focus points that will be used to form the lens fragmentation incision pattern.

10. The system of claim 9, the controller being further configured to:

generate a spatial disposition a safety volume within the lens, the incision pattern not overlapping the safety volume, the safety volume separating the lens fragmentation incision pattern from the anterior and posterior portions of the lens capsule and separating the lens fragmentation pattern transverse to the pupil such that a maximum transverse width of the lens fragmentation pattern is less than a diameter of the pupil; and display a safety volume image that includes a representation of the safety volume.

11. The system of claim 9, wherein the controller is further configured to:

prior to coupling the eye to the integrated optical system, generate a spatial disposition a safety volume within the lens, the incision pattern not overlapping the safety volume, the safety volume separating the lens fragmentation incision pattern from the anterior and posterior portions of the lens capsule and separating the lens fragmentation pattern transverse to the pupil such that a maximum transverse width of the lens fragmentation pattern is less than a diameter of the pupil; and display a safety volume image that includes a representation of the safety volume.

\* \* \* \* \*